US009561991B2

United States Patent
(12) United States Patent
Zong et al.

(10) Patent No.: US 9,561,991 B2
(45) Date of Patent: Feb. 7, 2017

(54) PROCESS AND APPARATUS FOR CO-PRODUCING CYCLOHEXANOL AND ALKANOL

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Baoning Zong, Beijing (CN); Dongqiang Ma, Beijing (CN); Langyou Wen, Beijing (CN); Bin Sun, Beijing (CN); Keyong Yang, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 0 days.

(21) Appl. No.: 14/429,189

(22) PCT Filed: Sep. 17, 2013

(86) PCT No.: PCT/CN2013/001100
§ 371 (c)(1),
(2) Date: Mar. 18, 2015

(87) PCT Pub. No.: WO2014/044020
PCT Pub. Date: Mar. 27, 2014

(65) Prior Publication Data

US 2015/0274620 A1 Oct. 1, 2015

(30) Foreign Application Priority Data

Sep. 18, 2012 (CN) .......................... 2012 1 0347119
Sep. 18, 2012 (CN) .......................... 2012 1 0347463
(Continued)

(51) Int. Cl.
*C07D 201/02* (2006.01)
*B01J 23/10* (2006.01)
(Continued)

(52) U.S. Cl.
CPC .............. *C07C 29/149* (2013.01); *B01J 23/80* (2013.01); *B01J 23/83* (2013.01); *B01J 23/835* (2013.01);
(Continued)

(58) Field of Classification Search
CPC .... C07C 29/149; C07C 67/04; C07C 2101/04; B01J 23/80; B01J 23/83; B01J 23/835; B01J 45/002; C07D 223/10
(Continued)

(56) References Cited

U.S. PATENT DOCUMENTS 4,339,604 A * 7/1982 van Geem .............. C07C 45/34
568/357
4,595,786 A 6/1986 Waller
(Continued)

FOREIGN PATENT DOCUMENTS

CN 86105765 A 1/1987
CN 1038273 A 12/1989
(Continued)

OTHER PUBLICATIONS

McClellan et al, The Hydrogenation of Aryl Esters, Journal of American Chemical Society, 1941, 63, p. 484-487.*
(Continued)

*Primary Examiner* — T. Victor Oh
(74) *Attorney, Agent, or Firm* — Novick, Kim & Lee, PLLC; Allen Xue

(57) ABSTRACT

This invention relates to a process for co-producing cyclohexanol and alkanol, including a cyclohexene esterification step and a cyclohexyl ester hydrogenation step. This invention further relates to a process for further producing cyclo-
(Continued)

Figure 1:
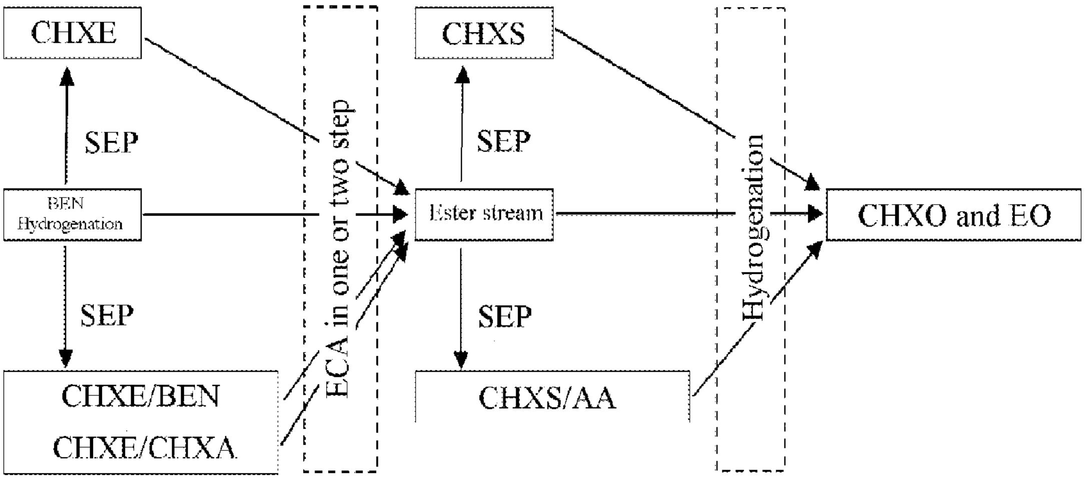

hexanone or caprolactam, starting from the co-producing process, and an apparatus for co-producing cyclohexanol and alkanol. The process for co-producing cyclohexanol and alkanol of this invention is environment-friendly, with low production cost and highly improved atom economy.

12 Claims, 14 Drawing Sheets

(30) Foreign Application Priority Data

| | | |
|---|---|---|
| Sep. 18, 2012 | (CN) | 2012 1 0348062 |
| Sep. 18, 2012 | (CN) | 2012 1 0348078 |
| Dec. 20, 2012 | (CN) | 2012 1 0559160 |
| Dec. 20, 2012 | (CN) | 2012 1 0559175 |
| Dec. 20, 2012 | (CN) | 2012 1 0559915 |
| Dec. 20, 2012 | (CN) | 2012 1 0559981 |
| Dec. 20, 2012 | (CN) | 2012 1 0560215 |
| Dec. 20, 2012 | (CN) | 2012 1 0560237 |
| Dec. 20, 2012 | (CN) | 2012 1 0560665 |
| Jan. 5, 2013 | (CN) | 2013 1 0001078 |
| Jan. 5, 2013 | (CN) | 2013 1 0001152 |

(51) Int. Cl.

| | |
|---|---|
| ***B01J 23/06*** | (2006.01) |
| ***C07C 45/00*** | (2006.01) |
| ***C07C 29/20*** | (2006.01) |
| ***C07C 29/149*** | (2006.01) |
| ***C07C 67/04*** | (2006.01) |
| ***B01J 23/80*** | (2006.01) |
| ***B01J 23/83*** | (2006.01) |
| ***B01J 23/835*** | (2006.01) |
| ***C07D 223/10*** | (2006.01) |

(52) U.S. Cl.
CPC ............. *C07C 45/002* (2013.01); *C07C 67/04* (2013.01); *C07D 223/10* (2013.01); *C07C 2101/14* (2013.01)

(58) Field of Classification Search
USPC ......... 540/534; 502/303, 342, 343; 568/361, 568/835
See application file for complete search history.

(56) References Cited

U.S. PATENT DOCUMENTS

| | | | | |
|---|---|---|---|---|
| 4,598,061 A * | 7/1986 | Schneider | B01J 23/80 502/302 |
| 5,254,721 A | 10/1993 | Inoue et al. | |
| 5,334,779 A * | 8/1994 | Kuo | B01J 23/80 568/830 |
| 5,403,962 A * | 4/1995 | Schneider | B01J 23/8892 502/241 |
| 2010/0112397 A1* | 5/2010 | Takatsu | B01J 23/80 429/423 |

FOREIGN PATENT DOCUMENTS

| | | |
|---|---|---|
| CN | 1072405 A | 5/1993 |
| CN | 1138018 A | 12/1996 |
| CN | 1289638 A | 4/2001 |
| CN | 1414933 A | 4/2003 |
| CN | 1639090 A | 7/2005 |
| CN | 101796001 A | 8/2010 |
| CN | 101851151 A | 10/2010 |
| CN | 102146019 A | 8/2011 |
| CN | 102149661 A | 8/2011 |
| CN | 103254038 A | 8/2013 |
| WO | 2009/131769 A1 | 10/2009 |

OTHER PUBLICATIONS

G. D. Yadav et al. "Selective synthesis of perfumery grade cyclohexyl esters from cyclohexene and carboxylic acids over ion exchange resins: an example of 100% atom economy" Green Chemistry, Apr. 2000, pp. 71-77.
Qin Li et al. "Use of a Solid Acid Catalyst in the Esterification Reaction Between an Olefin and a Carboxylic Acid" Industrial Catalysis, 2007, vol. 15, pp. 67-69.
Sen Dong et al. "Synthesis of cyclohexyl acetate by catalytic action of cation exchange resin" China Surfactant Detergent & Cosmetics, Aug. 2012, vol. (42), No. 4, pp. 285-287.
Huaibin Zhang et al., "Catalytic Property of Zeolites in Hydration Reaction of Cyclohexene", Journal of Fuel Chemistry and Technology, vol. 23 No. 4, Dec. 1995.

* cited by examiner

PROCESS AND APPARATUS FOR CO-PRODUCING CYCLOHEXANOL AND ALKANOL

TECHNICAL FIELD

This invention relates to a process for producing cyclohexanol, more specifically, to a process for co-producing cyclohexanol and alkanol. This invention further relates to a process for further producing cyclohexanone or caprolactam, starting from the process for producing cyclohexanol. This invention further relates to an apparatus for co-producing cyclohexanol and alkanol.

BACKGROUND ART

Cyclohexanol and alkanols for example ethanol, represent important chemicals and organic solvents in the organic chemical industry.

Cyclohexanol is mainly used in a dehydrogenation for producing cyclohexanone, while cyclohexanone represents a main intermediate for further producing nylon 6 and nylon 66. Since the birth of nylon, big chemical companies all around the world have been dedicated to identifying an industrial source for cyclohexanol or cyclohexanone. In 1980s, the Japan asahi kasei company developed a process for producing cyclohexanol by hydration of cyclohexene (cyclohexene hydration process). However, the process suffers from the following problems: (1) the direct hydration of cyclohexene is thermodynamically restricted, and cyclohexene is only slightly soluble in water, for this reason, the hydration reaction mainly occurs at the interface between the two phases, causing the cyclohexene hydration reaction to proceed at a rather slow speed with a low single-pass conversion; Even if a supersiliceous ZSM-5 catalyst is used, and two slurry reactors in series are used with a residence time of 2 h, the single-pass conversion of cyclohexene reaches merely 12.5%; Such a low single-pass conversion necessitates separation of a massive amount of unreacted cyclohexene from the product stream and recycling of same, which results in huge energy consumption; (2) cyclohexene with a high purity should be used as the feed stock, otherwise the dilution by other components will result in more amount of mass to be recycled and more lowered reaction efficiency; Cyclohexene is produced from a partial hydrogenation of benzene, whose product stream contains a significantly amount of cyclohexane and benzene other than cyclohexene. The boiling point of the three is much close to one another, and therefore purification of cyclohexene is much difficult, which necessarily renders much higher purification cost; (3) the process involves a complicate reaction system consisted of an aqueous phase, an oil phase and a solid catalyst phase, which necessitates strong stirring for the formation of an emulsion system throughout which aqueous droplets and oil droplets are sufficiently dispersed, so as for cyclohexene to be adsorbed onto the surface of the catalyst, and also necessitates well separation of the catalyst from the oil phase at the sedimentation section, all of which complicate the operation, and lead to severe loss of the catalyst.

Ethanol has been produced on an industrial scale mainly by the direct ethylene hydration method, while for some countries with plentiful agricultural by-products, the fermentation method prevails as the process for producing ethanol. The fermentation method suffers from the problem of severe pollution, and further, is criticized for food consumption, and therefore is not suitable for a country with a huge population and less arable land. The direct ethylene hydration method is rather demanding in terms of reaction conditions, which needs elevated temperatures and high pressures. Further, the price of ethylene is much influenced by the international oil price fluctuations, and for a country lacking of oil resources, the direct ethylene hydration method for producing ethanol has to face some cost pressure.

Therefore, there is still a need in the prior art for a process for producing cyclohexanol, especially a process for co-producing cyclohexanol and alkanol (for example ethanol), which is capable of co-producing cyclohexanol and alkanol (for example ethanol) with a more simplified production procedure and at a relatively lowered production cost, and further overcoming the problems associated with the prior art.

Invention Summary

The present inventors, on the basis of the prior art, found that if at two steps, i.e. a cyclohexene esterification step and a cyclohexyl ester hydrogenation step, are involved in a process, it will be possible for said process to co-produce cyclohexanol and alkanol (for example ethanol) with a more simplified production procedure and at a relatively lowered production cost, and the aforesaid problems encountered by the prior art can be solved, and then this invention is achieved.

Specifically, this invention relates to the following aspects.

1. A process for co-producing cyclohexanol and alkanol, characterized by, including the following steps:

(1) a step of reacting a cyclohexene source with at least one carboxylic acid in the presence of an addition esterification catalyst to conduct an addition esterification reaction, to produce an addition esterification product containing a carboxylic acid cyclohexyl ester, wherein the at least one carboxylic acid is represented by the formula R—COOH, and the group R is hydrogen or a $C_{1-23}$ straight or branched alkyl, preferably a $C_{1-6}$ straight or branched alkyl, more preferably a $C_{1-3}$ straight or branched alkyl, most preferably methyl, the cyclohexene source has a cyclohexene content of 20 mol % or more, 35 mol % or more, 20 to 80 mol %, 20 to 60 mol %, 40 to 80 mol %, 80 to 95 mol % or 95 mol % or more; and (2) a step of reacting the addition esterification product with hydrogen gas in the presence of a hydrogenation catalyst to conduct a hydrogenation reaction, whereby producing cyclohexanol and an alkanol at the same time, wherein the alkanol is represented by the formula R—$CH_2$—OH, and the group R is as defined in the carboxylic acid, most preferably methyl.

2. The process according to any one of the preceding aspects, further including the following Step (A), Step (A)+Step (B), Step (C), Step (C)+Step (D) or any combination thereof:

(A) a step of reacting benzene with hydrogen gas in the presence of a partial hydrogenation catalyst to conduct a partial hydrogenation reaction, to obtain a cyclohexene-containing hydrogenation product as the cyclohexene source;

(B) a step of subjecting the hydrogenation product obtained from Step (A) to a further separation, to obtain cyclohexene, a mixture of cyclohexene and benzene or a mixture of cyclohexene and cyclohexane as the cyclohexene source;

(C) a step of subjecting cyclohexane in the presence of a partial dehydrogenation catalyst to a partial dehydrogenation, to obtain a cyclohexene-containing partial dehydrogenation product as the cyclohexene source;

(D) a step of subjecting the partial dehydrogenation product obtained from Step (C) to a further separation, to obtain cyclohexene or a mixture of cyclohexene and cyclohexane as the cyclohexene source.

3. The process according to any one of the preceding aspects, further including the following Step (I), Step (II), Step (III) or any combination thereof:

(I) a step of recovering and recycling to Step (A) benzene and/or hydrogen gas isolated from any step in the process for co-producing cyclohexanol and alkanol;

(II) a step of recovering and recycling to Step (C) cyclohexane isolated from any step in the process for co-producing cyclohexanol and alkanol;

(III) a step of recovering and dehydrogenating in the presence of a dehydrogenation catalyst cyclohexane isolated from any step in the process for co-producing cyclohexanol and alkanol, to obtain benzene and hydrogen gas, and recycling the obtained benzene and/or hydrogen gas to Step (A).

4. The process according to any one of the preceding aspects, wherein the addition esterification catalyst is one or more selected from the group consisting of solid acid catalysts, preferably one or more selected from the group consisting of solid acid catalysts having an acidity function (Hammett function) H0 of −8 or less (preferably −12 or less, more preferably −13 or less), more preferably one or more selected from the group consisting of strong-acid ion exchange resins (preferably one or more selected from the group consisting of sulfonic acid type ion exchange resins, more preferably one or more selected from the group consisting of macroporous sulfonic acid type ion exchange resins and halogen modified sulfonic acid type ion exchange resins), a heteropolyacid (for example, one or more selected from the group consisting of a heteropolyacid having a keggin structure, a heteropolyacid having a Dawson structure, a heteropolyacid having an Anderson structure, a heteropolyacid having a Silverton structure, acid salts of the heteropolyacid, the heteropolyacid/carrier and acid salts of the heteropolyacid/carrier, preferably one or more selected from the group consisting of a heteropolyacid having a keggin structure, acid salts of a heteropolyacid having a keggin structure, a heteropolyacid having a keggin structure/carrier and acid salts of a heteropolyacid having a keggin structure/carrier, more preferably one or more selected from the group consisting of 12-phosphotungstic acid or 12-phosphotungstic acid/carrier, 12-sillicontungstic acid or 12-sillicontungstic acid/carrier, 12-molybdophosphoric acid or 12-molybdophosphoric acid/carrier, 12-molybdovanadophosphoric acid or 12-molybdovanadophosphoric acid/carrier, acid salts of the heteropolyacid and acid salts of the heteropolyacid/carrier, more preferably one or more selected from the group consisting of acid phosphotungstic acid cesium salt ($Cs_{2.5}H_{0.5}P_{12}WO_{40}$) and acid phosphotungstic acid cesium salt/carrier; the carrier, for example, is one or more selected from the group consisting of silica and activated carbon) and a zeolite type molecular sieve (preferably one or more selected from the group consisting of a H-beta zeolite type molecular sieve, a fluorine and/or phosphorus modified H-beta zeolite type molecular sieve, a HY zeolite type molecular sieve, a fluorine and/or phosphorus modified HY zeolite type molecular sieve, a HZSM-5 zeolite type molecular sieve and a fluorine and/or phosphorus modified HZSM-5 zeolite type molecular sieve).

5. The process according to any one of the preceding aspects, wherein the hydrogenation catalyst is one or more selected from the group consisting of a copper based catalyst (more preferably one or more selected from the group consisting of a zinc-containing copper based catalyst and a chromium-containing copper based catalyst), a ruthenium based catalyst (preferably one or more selected from the group consisting of $Ru/Al_2O_3$ and $Ru—Sn/Al_2O_3$) and a noble metal based catalyst (preferably one or more selected from the group consisting of $Pt/Al_2O_3$, $Pd—Pt/Al_2O_3$ and Pd/C), preferably a copper based catalyst.

6. The process according to any one of the preceding aspects, wherein the copper based catalyst comprises (preferably consists of) the following components: (a) copper oxide; (b) zinc oxide; (c) a metal oxide, wherein the metal is one or more selected from the group consisting of aluminium, gallium, tin, titanium, zirconium, chromium, molybdenum, tungsten, manganese, rhenium, lanthanide metals and actinide metals, preferably one or more selected from the group consisting of aluminium, gallium, tin, titanium, zirconium, chromium, molybdenum, tungsten, manganese, rhenium, lanthanum and cerium; and a component (d) one or more selected from the group consisting of alkali metal hydroxides and alkaline earth metal hydroxides, preferably one or more selected from the group consisting of KOH, NaOH and barium hydroxide, wherein expressed as parts by weight, the ratio of the component (a):the component (b):the component (c):the component (d) is 5 to 60:10 to 50:5 to 60:0.2 to 2, preferably 10 to 50:15 to 45:15 to 55:0.2 to 2, more preferably 30 to 45:20 to 35:20 to 50:0.5 to 1.5.

7. The process according to any one of the preceding aspects, wherein the copper based catalyst is produced in line with a process including the following steps:

(1) by a coprecipitation method, producing a composite metal oxide, wherein the composite metal oxide comprises (preferably consists of) the following components: (a) copper oxide; (b) zinc oxide; and (c) a metal oxide, wherein the metal is one or more selected from the group consisting of aluminium, gallium, tin, titanium, zirconium, chromium, molybdenum, tungsten, manganese, rhenium, lanthanide metals and actinide metals, preferably one or more selected from the group consisting of aluminium, gallium, tin, titanium, zirconium, chromium, molybdenum, tungsten, manganese, rhenium, lanthanum and cerium, wherein expressed as parts by weight, the ratio of the component (a):the component (b):the component (c) is 5 to 60:10 to 50:5 to 60, preferably 10 to 50:15 to 45:15 to 55, more preferably 30 to 45:20 to 35:20 to 50; and (2) by an impregnation method, introducing into the composite metal oxide a component (d) one or more selected from the group consisting of alkali metal hydroxides and alkaline earth metal hydroxides (preferably one or more selected from the group consisting of KOH, NaOH and barium hydroxide), such that expressed as parts by weight, the ratio of the component (a):the component (b):the component (c):the component (d) is 5 to 60:10 to 50:5 to 60:0.2 to 2, preferably 10 to 50:15 to 45:15 to 55:0.2 to 2, more preferably 30 to 45:20 to 35:20 to 50:0.5 to 1.5.

8. The process according to any one of the preceding aspects, wherein the ratio by molar of the at least one carboxylic acid to the cyclohexene source (based on cyclohexene) is 0.2 to 20:1, preferably 1.2 to 4:1, more preferably 1.2 to 3:1, and Step (1) is conducted in line with the following Manner (1), Manner (2) or any combination thereof, preferably Manner (2) or a combination of Manner (1) and Manner (2), more preferably a combination wherein Manner (1) firstly and then Manner (2) is conducted, according to Manner (1), the reactor is a tank reactor, a fixed bed reactor, a fluidized bed reactor, a boiling bed reactor or any combination thereof in parallel, preferably a tubular fixed bed reactor, more preferably a shell and tube reactor, the reaction temperature is from 50 to 200 degrees Celsius, preferably 60 to 120 degrees Celsius, the reaction pressure is from the normal pressure to 10 MPa, preferably from the normal pressure to 1 MPa, when the addition esterification reaction is conducted in a continuous manner, the liquid feed space velocity is from 0.5 to 20 $h^{-1}$, preferably 0.5 to 5 $h^{-1}$, more preferably 1 to 5 $h^{-1}$, when the addition esterification reaction is conducted in a batchwise manner, the reaction duration is from 0.1 to 10 h, preferably 0.2 to 2 h;

according to Manner (2), the reactor is a reactive rectification tower, preferably a tray tower, a packing tower or any combination thereof in parallel, the theoretical plate number thereof is from 10 to 150, preferably 30 to 100, the operation pressure is from −0.0099 MPa to 5 MPa, preferably from the normal pressure to 1 MPa, the temperature in the addition esterification catalyst bed loading area is from 40 to 200 degrees Celsius, preferably 50 to 200 degrees Celsius, more preferably 60 to 120 degrees Celsius, the reflux ratio is from 0.1:1 to full reflux, preferably 0.1 to 100:1, more preferably 0.5 to 10:1, the addition esterification catalyst is disposed onto 5 to 30 plates (preferably 8 to 20 plates) located between a position corresponding to ⅓ of the theoretical plate number and a position corresponding to ⅔ of the theoretical plate number, and relative to the total packed volume of the addition esterification catalyst, the liquid feed space velocity is from 0.1 to 20 $h^{-1}$, preferably 0.2 to 20 $h^{-1}$, more preferably 0.5 to 5 $h^{-1}$.

9. The process according to any one of the preceding aspects, wherein Step (2) is conducted under reaction conditions wherein the reactor is a tank reactor, a fixed bed reactor, a boiling bed reactor, a fluidized bed reactor or any combination thereof in parallel, preferably a tubular fixed bed reactor, more preferably a shell and tube reactor, the reaction temperature is from 150 to 400 degrees Celsius, preferably 200 to 300 degrees Celsius, the reaction pressure is from the normal pressure to 20 MPa, preferably from the normal pressure to 10 MPa, more preferably 4 to 10 MPa, the ratio by molar of hydrogen gas to the addition esterification product (based on the carboxylic acid cyclohexyl ester) is 1 to 1000:1, preferably 5 to 100:1, when the hydrogenation reaction is conducted in a continuous manner, the liquid feed space velocity is from 0.1 to 20 $h^{-1}$, preferably 0.2 to 2 $h^{-1}$, when the hydrogenation reaction is conducted in a batchwise manner, the reaction duration is from 0.2 to 20 h, preferably 0.5 to 5 h, more preferably 1 to 5 h.

10. The process according to any one of the preceding aspects, further comprising prior to the hydrogenation reaction between the addition esterification product and hydrogen gas, subjecting the addition esterification product to a separation, to obtain carboxylic acid cyclohexyl ester or a mixture of carboxylic acid cyclohexyl ester and carboxylic acid as the addition esterification product, preferably to obtain the carboxylic acid cyclohexyl ester as the addition esterification product, and/or, prior to the hydrogenation reaction between the addition esterification product and hydrogen gas, reacting the addition esterification product with hydrogen gas in the presence of a carboxylic acid hydrogenation catalyst to conduct a carboxylic acid hydrogenation reaction, so as to convert any free carboxylic acid contained in the addition esterification product into an alkanol.

11. The process according to any one of the preceding aspects, wherein the carboxylic acid hydrogenation catalyst consists of a main active component 0.1 to 30 wt %, an auxiliary agent 0.1 to 25 wt % and remaining amount of carrier, wherein the main active component is one or more selected from the group consisting of platinum, palladium, ruthenium, tungsten, molybdenum and cobalt, the auxiliary agent is one or more selected from the group consisting of tin, chromium, aluminium, zinc, calcium, magnesium, nickel, titanium, zirconium, rhenium, lanthanum, thorium and gold, the carrier is one or more selected from the group consisting of silica, alumina, titania, zirconia, activated carbon, graphite, carbon nano-tube, calcium silicate, zeolite and aluminium silicate, and/or, the carboxylic acid hydrogenation reaction is conducted under reaction conditions wherein the reactor is a tank reactor, a fixed bed reactor, a boiling bed reactor, a fluidized bed reactor or any combination thereof in parallel, preferably a tubular fixed bed reactor, more preferably a shell and tube reactor, the reaction temperature is from 100 to 400 degrees Celsius, preferably 180 to 300 degrees Celsius, the reaction pressure is from 0.1 to 30 MPa, preferably 2 to 10 MPa, the ratio by molar of hydrogen gas to the free carboxylic acid is from 1 to 500:1, preferably 5 to 50:1, when the carboxylic acid hydrogenation reaction is conducted in a continuous manner, the liquid feed space velocity is from 0.1 to 5 $h^{-1}$, preferably 0.2 to 2 $h^{-1}$, when the carboxylic acid hydrogenation reaction is conducted in a batchwise manner, the reaction duration is from 0.5 to 20 h, preferably 1 to 5 h.

12. The process according to any one of the preceding aspects, wherein the carboxylic acid and/or the cyclohexene source isolated from any step in the process for co-producing cyclohexanol and alkanol is recovered and recycled to Step (1), and/or, hydrogen gas isolated from any step in the process for co-producing cyclohexanol and alkanol is recovered and recycled to Step (2).

13. A process for producing cyclohexanone, characterized by, comprising:

producing cyclohexanol in line with the process according to any one of the preceding aspects, and using the obtained cyclohexanol to produce cyclohexanone.

14. A process for producing caprolactam, characterized by, comprising:

producing cyclohexanone in line with the process according to any one of the preceding aspects, and using the obtained cyclohexanone to produce caprolactam.

15. An apparatus for co-producing cyclohexanol and alkanol, characterized by, including a hydrogenation reaction unit A, an optional hydrogenation product separation unit A, an addition esterification reaction unit, an optional addition esterification product separation unit, a hydrogenation reaction unit B and a hydrogenation product separation unit B, wherein, in the hydrogenation reaction unit A, benzene reacts with hydrogen gas in the presence of a partial hydrogenation catalyst to conduct a partial hydrogenation reaction, to obtain a cyclohexene-containing hydrogenation product;

in the hydrogenation product separation unit A, the hydrogenation product obtained from the hydrogenation reaction unit A is subject to a separation, to obtain cyclohexene, a mixture of cyclohexene and benzene or a mixture of cyclohexene and cyclohexane;

in the addition esterification reaction unit, the hydrogenation product obtained from the hydrogenation reaction unit A and/or cyclohexene, the mixture of cyclohexene and benzene or the mixture of cyclohexene and cyclohexane obtained from the hydrogenation product separation unit A reacts with a carboxylic acid in the presence of an addition esterification catalyst to conduct an addition esterification reaction, whereby producing an addition esterification product containing a carboxylic acid cyclohexyl ester;

in the addition esterification product separation unit, the addition esterification product obtained from the addition esterification reaction unit is subject to a separation, to obtain carboxylic acid cyclohexyl ester or a mixture of carboxylic acid cyclohexyl ester and carboxylic acid;

in the hydrogenation reaction unit B, the addition esterification product obtained from the addition esterification reaction unit and/or carboxylic acid cyclohexyl ester or the mixture of carboxylic acid and carboxylic acid cyclohexyl ester obtained from the addition esterification product separation unit reacts with hydrogen gas in the presence of a hydrogenation catalyst to conduct a hydrogenation reaction, whereby producing a hydrogenation product containing cyclohexanol and an alkanol; and in the hydrogenation product separation unit B, the hydrogenation product obtained from the hydrogenation reaction unit B is subject to a separation, to obtain cyclohexanol and an alkanol.

Technical Effects

According to this invention, for example, the following technical effects can be obtained.

According to the process for co-producing cyclohexanol and alkanol of this invention, the single-pass selectivity and the single-pass conversion in the cyclohexene esterification step and the cyclohexyl ester hydrogenation step are both high, with little by-products, especially both the single-pass selectivity and the single-pass conversion of the cyclohexyl ester hydrogenation step are close to 100%, and for this reason, the process is characterized by much higher single-pass selectivity and much higher single-pass conversion as a whole, for example, much greater than that observed with the process for producing cyclohexanol developed by the asahi kasei company, and as compared with the prior art, is characterized by low cyclohexanol production cost and highly improved atom economy.

The process for co-producing cyclohexanol and alkanol according to this invention, is characterized by low hydrogen consumption, little wastes emission throughout the whole process, and as compared with the prior art, is highly environmental friendly and highly atom economical.

The process for co-producing cyclohexanol and alkanol according to this invention, with mild reaction conditions throughout the process, as compared with the prior art, is characterized by much higher production safety.

The process for co-producing cyclohexanol and alkanol according to this invention, involves use of a reactive rectification tower alone or in combination to conduct the addition esterification reaction of cyclohexene, whereby significantly improving the single-pass conversion of cyclohexene (up to 99% or more), and at the same time, significantly simplifying separation of the esterification product, and as compared with the prior art, is characterized by significantly lowered cyclohexanol production cost and highly improved atom economy.

The process for co-producing cyclohexanol and alkanol according to this invention, in the cyclohexene esterification step, the reaction procedure is simple, with much less by-reactions, and less vulnerable to impurities, and for this reason, the present process is less demanding to the purity of the cyclohexene feed stock, such that a crude product thereof (with a cyclohexene content of as less as, for example, 20 mol %) may be used as the feed stock. For example, this invention has for the first time in this field found that, the present process for co-producing cyclohexanol and alkanol can even use the product stream from a benzene partial hydrogenation as such as the feed stock without an absolute necessity of purification or separation thereof beforehand, which is complicate or expensive, and as compared with the prior art, is characterized by significantly lowered production cost.

According to the process for co-producing cyclohexanol and alkanol according to this invention, by a benzene partial hydrogenation to obtain the cyclohexene source, cyclohexane as a by-product from this benzene partial hydrogenation can be converted again into benzene by dehydrogenation at a relatively higher conversion and selectivity, such that the whole procedure consisting of the benzene partial hydrogenation, the cyclohexene esterification and the cyclohexyl ester hydrogenation exhibits a carbon utilization approximating to 100%.

According to the process for co-producing cyclohexanol and alkanol according to this invention, cyclohexanol is produced, and at the same time, an alkanol (especially ethanol), which is more economically valuable as compared with the carboxylic acid feed stock, is co-produced. In co-production of these more valuable alkanols (for example, ethanol), there is no need to separate the carboxylic acid from the carboxylic acid cyclohexyl ester, but rather to hydrogenate the unreacted carboxylic acid and the carboxylic acid cyclohexyl ester at the same time so as to obtain cyclohexanol and a further amount of alkanols, especially when a reactive rectification tower is used to conduct the esterification reaction, a further merit of e.g. lowering the operation temperature of the reactive rectification tower, generates.

According to the process for co-producing cyclohexanol and alkanol according to this invention, the reaction system is simple, with a simple and convenient operation, and as compared with the prior art, the cyclohexanol production cost and the maintenance cost of the production apparatus can be significantly reduced.

FIGURE DESCRIPTION

FIG. 1 schematically illustrates the general flow diagram of the process for co-producing cyclohexanol and alkanol of this invention.

FIG. 2 to FIG. 16 schematically illustrate the flow diagram of each specific embodiment of the process for co-producing cyclohexanol and alkanol of this invention.

In the figures, the abbreviation "ECA" stands for "esterification by carboxylic acid", "CHXE" stands for "cyclohexene", "CHXA" for "cyclohexane", "CHXS" for "cyclohexyl ester", "CHXO" for "cyclohexanol", "AA" for "acetic acid", "BEN" for "benzene", "EO" for "ethanol", "HG" for "hydrogen gas", "HBM" for "high boiling materials", "SEP" for "separation", "ACXS" for "acetic acid cyclohexyl ester", "AERS" for "addition esterification reaction system", "EPSS" for "esterification product separation system", "EHRS" for "ester hydrogenation reaction system", and "HPSS" for "hydrogenation product separation system".

SPECIFIC MODE TO CARRY OUT THIS INVENTION

This invention will be described in details hereinafter with reference to the following specific embodiments. However, it should be noted that the protection scope of this invention should not be construed as limited to these specific embodiments, but rather determined by the attached claims.

In the context of this invention, unless otherwise specified, a hydrocarbyl or hydrocarbyl derivative group having 3 or more carbon atoms (for example, propyl, propoxy, butyl, butane, butene, butenyl, hexane or the like) without the prefix "n-" shares the same meaning as that with the prefix "n-". for example, propyl generally refers to n-propyl, while butyl generally refers to n-butyl, unless otherwise specified.

Every document cited herein, comprising any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention.

In the context of this invention, when an expression like "conventionally known in this field" or "conventionally used in the prior art" or the like is used to describe/define an item like a material, a process, a part, an apparatus or a device, it means that this item (1) has been well known for a similar purpose in this field before this application, or (2) has not been that much well known for a similar purpose in this field before this application but gets well known for a similar purpose in this field after this application.

In the context of this specification, unless otherwise specified, for any item or content not expressively described herein, one may refer to that conventionally known in this field without any change or modification. Further, any embodiment described herein can be freely combined with one or more of other embodiment(s) herein described, and the thus obtained combination is still identified as a part of the original disclosure or description of this specification rather than a new content, unless this combination is obviously unreasonable to a person skilled in the art.

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined. That is to say that, unless otherwise indicated, all ranges disclosed herein are to be understood to encompass any and all subranges subsumed therein.

In the context of this specification, unless otherwise specified, by selectivity, it refers to the single-pass selectivity, while by conversion, it refers to the single-pass conversion.

In the context of this specification, the term "cyclohexene source" refers to any reaction feed stock that can be used in the cyclohexene esterification step of this invention as the source of cyclohexene (i.e. providing cyclohexene), including an industrial pure product of cyclohexene (with a cyclohexene content of, for example, 95 mol % or more), an industrial crude product of cyclohexene (with a cyclohexene content of, for example, at least 80 mol % and at most 95 mol %) or a cyclohexene-containing industrial mixed product (with a cyclohexene content of, for example, at least 20 mol % and at most 80 mol %) or the like. According to the cyclohexene esterification step of this invention, the reaction procedure is simple, with less by-reactions, the esterification reaction is less vulnerable to impurities, and for this reason, this step is less demanding to the purity of the cyclohexene source. Under this circumstance, in the context of this specification, the term "cyclohexene source" further covers a cyclohexene-containing industrial waste or industrial by-product, for example, a cyclohexene-containing waste gas (for example, that obtained from a prior art cyclohexene hydration method) and a cyclohexene-containing off-gas (for example, as a by-product from the chemical synthesis industry) or the like. Generally speaking, any cyclohexene source, especially the industrial waste or by-product, can be used as such without the need of being subject to a purification or edulcoration treatment in advance, as long as it contains an impurity whose nature or amount does not significantly hinder the cyclohexene esterification step of this invention (for example, leading to a reduction in the single-pass conversion of cyclohexene by no more than 5%). These impurities are identified as chemically inert to the cyclohexene esterification step of this invention, for example, there may be exemplified nitrogen gas, rare gas, carbon dioxide, benzene, hydrogen gas or cyclohexane and the like, referred to in this specification as inert diluent. Of course, it will be very easy for a person skilled in the art to by a simple experiment (for example, by determining the reduction in the single-pass conversion of cyclohexene) to determine whether an industrial waste or industrial by-product contains an impurity whose nature or at an amount that may significantly hinder the cyclohexene esterification step of this invention, whereby identifying whether this can be used as such for the co-producing process of this invention. Further, if needed, it is also acceptable for a person skilled in the art to, by any means conventionally known in this field, lower the content of an impurity of this type in an industrial waste or industrial by-product to a level that will not significantly hinder the co-producing process of this invention, and if needed, increase the content of cyclohexene in an industrial waste or industrial by-product to a level more favorable to the co-producing process of this invention (for example, by concentration, to increase the content of cyclohexene to the level of 20 mol % or more, relatively to the total amount of the industrial waste or industrial by-product).

Unless otherwise specified, percents, parts or ratios or the like mentioned in this specification are all on a weight basis.

This invention relates to a process for co-producing cyclohexanol and alkanol, which comprises at least (1) a cyclohexene esterification step and (2) a cyclohexyl ester hydrogenation step.

The cyclohexene esterification step is described in details as follows.

According to the cyclohexene esterification step of this invention, a cyclohexene source reacts with at least one carboxylic acid in the presence of an addition esterification catalyst to conduct an addition esterification reaction, to produce an addition esterification product containing a carboxylic acid cyclohexyl ester.

According to this invention, by "addition esterification reaction", it refers to a reaction wherein a carboxylic acid adds to the ethylenic bond of cyclohexene to produce a carboxylic acid cyclohexyl ester.

According to this invention, the at least one carboxylic acid may be represented by the formula R—COOH, wherein the group R represents hydrogen or a $C_{1-23}$ straight or branched alkyl.

According to this invention, the group R is preferably a $C_{1-9}$ straight or branched alkyl, preferably a $C_{1-6}$ straight or branched alkyl, more preferably a $C_{1-3}$ straight or branched alkyl, most preferably methyl.

According to this invention, as the carboxylic acid, one kind or a mixture of two or more kinds at any ratio therebetween could be used. Preference is given to one or more selected from the group consisting of formic acid, acetic acid, propionic acid and n-butyric acid, most preferably acetic acid as the carboxylic acid.

According to this invention, the cyclohexene source has a cyclohexene content generally in the range of: 20 mol % or more, 35 mol % or more, 20 to 80 mol %, 20 to 60 mol %, 40 to 80 mol %, 80 to 95 mol %, or 95 mol % or more.

According to this invention, the cyclohexene source may further comprise remaining amount of the aforesaid inert diluent. As the inert diluent, it is preferably benzene, cyclohexane or any combination thereof at any ratio therebetween.

According to this invention, as the cyclohexene source, it is preferably an industrial pure product of cyclohexene (with a cyclohexene content of, for example, 95 mol % or more), an industrial crude product of cyclohexene (with a cyclohexene content of, for example, at least 80 mol % and at most 95 mol %) or a cyclohexene-containing industrial mixed product (with a cyclohexene content of, for example, at least 20 mol % and at most 80 mol %), especially the cyclohexene-containing industrial mixed product. The cyclohexene source may be conventionally produced or commercially available as an industrial product.

According to this invention, as the cyclohexene-containing industrial mixed product, for example, there may be exemplified (1) a cyclohexene-containing hydrogenation product obtained from a partial hydrogenation reaction between benzene and hydrogen gas in the presence of a partial hydrogenation catalyst (also referred to as benzene partial hydrogenation product stream), or a pure product of cyclohexene, a mixture of cyclohexene and benzene or a mixture of cyclohexene and cyclohexane obtained by subjecting the hydrogenation product to a further separation, or (2) a cyclohexene-containing partial dehydrogenation product obtained from a partial dehydrogenation of cyclohexane in the presence of a partial dehydrogenation catalyst (also referred to as cyclohexane partial dehydrogenation product stream), or a pure product of cyclohexene or a mixture of cyclohexene and cyclohexane obtained by subjecting the partial dehydrogenation product to a further separation.

In this context, the process for co-producing cyclohexanol and alkanol according to this invention, prior to the cyclohexene esterification step, may optionally further comprise any one of the following Step (A), Step (A)+Step (B), Step (C), Step (C)+Step (D) or any combination thereof:

(A) reacting benzene with hydrogen gas in the presence of a partial hydrogenation catalyst to conduct a partial hydrogenation reaction (benzene partial hydrogenation), to obtain a cyclohexene-containing hydrogenation product as the cyclohexene source;

(B) subjecting the hydrogenation product obtained from Step (A) to a further separation, to obtain cyclohexene, a mixture of cyclohexene and benzene or a mixture of cyclohexene and cyclohexane as the cyclohexene source;

(C) subjecting cyclohexane in the presence of a partial dehydrogenation catalyst to a partial dehydrogenation (cyclohexane partial dehydrogenation), to obtain a cyclohexene-containing partial dehydrogenation product as the cyclohexene source;

(D) subjecting the partial dehydrogenation product obtained from Step (C) to a further separation, to obtain cyclohexene or a mixture of cyclohexene and cyclohexane as the cyclohexene source.

According to this invention, there is no specific limitation as to how to conduct the benzene partial hydrogenation (Step (A)) and the cyclohexane partial dehydrogenation (Step (C)) and the subsequent separations (Step (B) or Step (D)) or the like, any method known in this field can be used as such.

According to this invention, as a preferred embodiment, in Step (A), the liquid phase method can be used in a manner conventionally known in this field to conduct the benzene partial hydrogenation. As the partial hydrogenation catalyst to be used in Step (A), it is preferably a ruthenium based catalyst, more preferably a ruthenium based catalyst containing cobalt and/or zinc. This kind of catalyst may be produced in a manner conventionally known in this field by a method, for example, involving coprecipitating or impregnating onto a carrier.

According to Step (A), the cyclohexene-containing hydrogenation product (also referred to as benzene partial hydrogenation product stream) is generally a mixture of cyclohexane, cyclohexene and benzene, which may be used as the cyclohexene source of this invention as such.

According to this invention, in Step (B), any method known in the prior art can be used to separate cyclohexene (also referred to as pure product of cyclohexene), a mixture of cyclohexene and benzene or a mixture of cyclohexene and cyclohexane from the benzene partial hydrogenation product stream, which may be used as such as the cyclohexene source of this invention. As the separation method, for example, there may be exemplified extractive rectification or azeotropic rectification, preferably extractive rectification. According to the extractive rectification, N-methyl-2-pyrrolidone, N,N-dimethyl acetamide, adiponitrile, malonic acid dimethyl ester, succinic acid dimethyl ester, ethylene glycol or sulfolane and so on may be used as the extractant.

According to this invention, as the extractive rectification, for example, there may be exemplified a method wherein the benzene partial hydrogenation product stream is introduced into an extractive rectification tower at the middle part, N,N-dimethyl acetamide is introduced at the upper part of the tower, from the tower top there is obtained a cyclohexane stream (i.e. a pure product of cyclohexane) or a mixed stream of cyclohexane and cyclohexene (i.e. a mixture of cyclohexane and cyclohexene). Depending on the separation at the tower top, when from the tower bottom there is obtained a solution containing cyclohexene, benzene and N,N-dimethyl acetamide, the solution is then introduced into the rectification tower for a further separation, and from the tower top there may be obtained a mixed stream of cyclohexene and benzene (i.e. a mixture of cyclohexene and benzene), or when from the tower bottom there is obtained a solution containing benzene and N,N-dimethyl acetamide, the solution is then introduced into the rectification tower for a further separation, and from the tower top there may be obtained a benzene stream (i.e. a pure product of benzene), from the rectification tower bottom there is obtained N,N-dimethyl acetamide. The mixed stream of cyclohexane and cyclohexene is introduced into a rectification tower, to the upper part of the tower there is introduced N,N-dimethyl acetamide, from the tower top there is obtained a cyclohexane stream (i.e. a pure product of cyclohexane), from the tower bottom there is obtained a mixed stream of cyclohexene and N,N-dimethyl acetamide, the stream from the tower bottom is introduced into a next stage rectification tower to separate cyclohexene therefrom, from the tower top there is obtained a cyclohexene stream (i.e. a pure product of cyclohexene), from the tower bottom there is obtained a N,N-dimethyl acetamide stream. The mixed stream of cyclohexene and benzene is introduced into a rectification tower, to the upper part of the tower there is introduced N,N-dimethyl acetamide, from the tower top there is obtained a cyclohexene stream (i.e. a pure product of cyclohexene), from the tower bottom there is obtained a mixed stream of benzene and N,N-dimethyl acetamide, the stream from the tower bottom is introduced into a next stage rectification tower to separate benzene therefrom, from the tower top there is obtained a benzene stream (i.e. a pure product of benzene), from the tower bottom there is obtained a N,N-dimethyl acetamide stream. Herein, the benzene stream may be recycled as a part of the reaction feed stock to Step (A), while the cyclohexane stream may be discharged as the by-product or recycled as a part of the reaction feed stock to Step (C).

According to this invention, depending on the operation in Step (A) or Step (B), the benzene partial hydrogenation product stream, the mixture of cyclohexene and benzene or the mixture of cyclohexene and cyclohexane may have a cyclohexene content of generally at least 20 mol %, 35 mol % or 40 mol %, at most 60 mol % or 80 mol %, while the pure product of cyclohexene may have a cyclohexene content of generally 95 mol % or more or even higher.

According to this invention, as an embodiment, in Step (C), in a manner conventionally known in this field, for example, cyclohexane is subject to an oxidative dehydrogenation to conduct a cyclohexane partial dehydrogenation.

According to this invention, in Step (D), any method known in the prior art can be used to separate cyclohexene (also referred to as pure product of cyclohexene) or the mixture of cyclohexene and cyclohexane from the cyclohexene partial dehydrogenation product stream, which may be used as such as the cyclohexene source of this invention.

According to this invention, as the addition esterification catalyst, for example, there may be exemplified an acid catalyst, for example, a liquid acid catalyst, specifically for example, an inorganic acid like phosphoric acid or sulphuric acid, or an organic acid like methyl benzene sulfonic acid, amino sulfonic acid, or a solid acid catalyst. As the addition esterification catalyst, from the standpoints of reducing apparatus corrosion and improving separation of the catalyst from the esterification product, it is preferably a solid acid catalyst, especially a solid acid catalyst having an acidity function (Hammett function) H0 of −8 or less (preferably −12 or less, more preferably −13 or less). As the solid acid catalyst, it is more preferably a strong-acid ion exchange resin, a heteropolyacid or a zeolite type molecular sieve. As the solid acid catalyst, one kind or a mixture of two or more kinds at any ratio therebetween could be used.

According to this invention, as the strong-acid ion exchange resin, it is preferably a sulfonic acid type ion exchange resin, more preferably a macroporous sulfonic acid type ion exchange resin (a macroporous sulfonic acid type polystyrene-divinylbenzene resin) or a halogen modified sulfonic acid type ion exchange resin. These strong-acid ion exchange resins are readily commercially available, or can be produced in line with a classic literature process. According to a general process for producing the macroporous sulfonic acid type polystyrene-divinylbenzene resin, a mixture of styrene and divinylbenzene is dropwised introduced under high speed stirring into an aqueous phase system containing a dispersant, an initiator, a porogenic agent to conduct a suspension polymerization, and then the resultant small polymer spheres (base spheres) are separated from the system, removing therefrom the porogenic agent by a solvent, and then subject to a sulfonation reaction with dichloroethane as the solvent and concentrated sulfuric acid as the sulfonating agent, and at the end, subject to a treatment like filtration and washing, to obtain the final product. Further, it is possible to into the skeleton of a strong-acid ion exchange resin a halogen atom like fluorine, chlorine, bromine, so as to further increase the temperature resistance and the acidity of the resin. A halogen modified sulfonic acid type ion exchange resin of this type can be obtained by at least two ways, wherein according to the first way, into the benzene ring on the skeleton of a sulfonated styrene resin, there is introduced a halogen atom like chlorine. In this connection, the strong electron withdrawing ability of a halogen element will stabilize the benzene ring, and further increase the acidity of the sulfonic acid group on the benzene ring, whereby providing the resin catalyst an acidity function (Hammett function) H0 of ≤−8, and the resistance against use at 150 degrees Celsius or more for a long term, which type of resin is commercially available as for example, Amberlyst 45 resin (from the ROHM & HASS company), D008 resin (from the Hebei Jizhong Chemical plant, China); According to the second way, any hydrogen atom on the skeleton of a resin is totally replaced by fluorine. In this connection, due to the strong electron withdrawing ability of fluorine, the resin is provided with a ultra strong acidity and a ultra high heat resistance, with an acidity function (Hammett function) H0 of less than −12, and a heat resistance against 250 degrees Celsius or more. The high temperature resistive strong-acid resin of this kind is typically the Nafion resin (from the DuPont company). As the strong-acid ion exchange resin, one kind or a mixture of two or more kinds at any ratio therebetween could be used.

According to this invention, as the heteropolyacid (with an acidity function H0 of generally less than −13.15), for example, there may be exemplified a heteropolyacid having a keggin structure, a heteropolyacid having a Dawson structure, a heteropolyacid having an Anderson structure, a heteropolyacid having a Silverton structure, acid salts of the heteropolyacid, the heteropolyacid/carrier and acid salts of the heteropolyacid/carrier, preferably a heteropolyacid having a keggin structure, acid salts of a heteropolyacid having a keggin structure, a heteropolyacid having a keggin structure/carrier and acid salts of a heteropolyacid having a keggin structure/carrier. it is preferred that, these heteropolyacids can be used at a temperature of 300 degrees Celsius or more for a long term, and may have a specific surface area (by the BET method) of generally 100 $m^2/g$ or more. As the heteropolyacid, one kind or a mixture of two or more kinds at any ratio therebetween could be used.

In the context of this specification, the expression "##/carrier" in connection with the heteropolyacid means "supporting ## onto the carrier so as to obtain a supported ## on the carrier". As the carrier used herein, for example, there may be exemplified silica, activated carbon or a combination thereof.

According to this invention, as the heteropolyacid, specifically for example, there may be exemplified 12-phosphotungstic acid or 12-phosphotungstic acid/carrier, 12-sillicontungstic acid or 12-sillicontungstic acid/carrier, 12-molybdophosphoric acid or 12-molybdophosphoric acid/carrier, 12-molybdovanadophosphoric acid or 12-molybdovanadophosphoric acid/carrier, acid salts of the heteropolyacid and acid salts of the heteropolyacid/carrier, preferably acid phosphotungstic acid cesium salt ($Cs_{2.5}H_{0.5}P_{12}WO_{40}$) and acid phosphotungstic acid cesium salt/carrier. As the heteropolyacid, one kind or a mixture of two or more kinds at any ratio therebetween could be used.

According to this invention, as the zeolite type molecular sieve, for example, there may be exemplified H-beta zeolite type molecular sieve, a fluorine and/or phosphorus modified H-beta zeolite type molecular sieve, a HY zeolite type molecular sieve, a fluorine and/or phosphorus modified HY zeolite type molecular sieve, a HZSM-5 zeolite type molecular sieve or a fluorine and/or phosphorus modified HZSM-5 zeolite type molecular sieve, preferably a fluorine and/or phosphorus modified H-beta zeolite type molecular sieve, a fluorine and/or phosphorus modified HY zeolite type molecular sieve or a fluorine and/or phosphorus modified HZSM-5 zeolite type molecular sieve. As the zeolite type molecular sieve, one kind or a mixture of two or more kinds at any ratio therebetween could be used.

According to this invention, in the cyclohexene esterification step, the ratio by molar of the at least one carboxylic acid to the cyclohexene source (based on cyclohexene) is generally from 0.2 to 20:1, preferably 1.2 to 4:1, more preferably 1.2 to 3:1, but not limiting thereto.

According to this invention, as the way to conduct the cyclohexene esterification step, for example, there may be exemplified the following Manner (1) and Manner (2), wherein from the standpoint of significantly improving the single-pass conversion of cyclohexene, it is preferably Manner (2) or a combination of Manner (1) and Manner (2).

According to Manner (1), the addition esterification reaction is conducted in one or more addition esterification reactor. As the addition esterification reactor, for example, there may be exemplified a tank reactor, a fixed bed reactor, a fluidized bed reactor, a boiling bed reactor or any combination thereof in parallel, preferably a tubular fixed bed reactor, more preferably a shell and tube reactor.

According to Manner (1), the addition esterification reactor may be operated in a bathwise manner or a continuous manner. A tubular fixed bed reactor is characterized by low production cost and simple operation, and for this reason, is preferred by this invention. The fixed bed reactor may be operated under an adiabatic or isothermal condition. As the adiabatic reactor, a cylinder reactor may be used, wherein the catalyst is fixed into the reactor, the outer wall of the reactor is heat insulated. In this connection, the addition esterification reaction is an exothermal reaction, and for this reason, it is necessary to adjust the concentration of the reactant so as to control the temperature increase in the reactor bed, or a part of the reaction product is cooled and then recycled to the reactor inlet so as to dilute the reactant. As the isothermal reactor, a shell and tube reactor may be used, wherein the catalyst is fixed in the tube, while the shell is cooled by cooling water so as to remove the heat generated from the reaction.

According to Manner (1), the reaction temperature of the addition esterification reaction is generally 50 to 200 degrees Celsius, preferably 60 to 120 degrees Celsius, but not limiting thereto.

According to Manner (1), the addition esterification reaction is conducted in liquid phase, and for this reason, the reaction pressure is so determined that the reaction necessarily presents as a liquid phase reaction. Generally speaking, the reaction pressure is from the normal pressure to 10 MPa, preferably from the normal pressure to 1 MPa, but not limiting thereto.

According to Manner (1), when the addition esterification reaction is conducted in a continuous manner, the liquid feed space velocity is generally 0.5 to 20 $h^{-1}$, preferably 0.5 to 5 $h^{-1}$, more preferably 1 to 5 $h^{-1}$, but not limiting thereto.

According to Manner (1), when the addition esterification reaction is conducted in a batchwise manner, the reaction duration is generally 0.1 to 10 h, preferably 0.2 to 2 h, but not limiting thereto.

According to Manner (1), the single-pass conversion of cyclohexene in the addition esterification reaction can generally reach 80% or more, while the single-pass selectivity to carboxylic acid cyclohexyl ester, for example acetic acid cyclohexyl ester, can reach 99% or more.

According to Manner (1), the addition esterification product obtained from the addition esterification reaction mainly comprises unreacted carboxylic acid and cyclohexene, and the carboxylic acid cyclohexyl ester as the reaction product, and further comprises any inert diluent originated from the cyclohexene source, for example, cyclohexane and benzene, which depends on the original composition of the cyclohexene source. The addition esterification product may be or may not be subject to a separation or purification, and introduced as such as the addition esterification product into the cyclohexyl ester hydrogenation step of this invention.

Or alternatively, it is preferred that, according to Manner (1), the addition esterification product may be subject to a separation by rectification in an esterification product separation system. Herein, the addition esterification product separation system may be provided in any manner conventionally known in this field with a rectification separation unit and/or an extractive rectification separation unit, while the detailed separation procedure depends on the original composition of the cyclohexene source. As a general rule, by the esterification product separation system, the addition esterification product is separated into a carboxylic acid stream and a carboxylic acid cyclohexyl ester stream (or a mixed stream of carboxylic acid and carboxylic acid cyclohexyl ester), and a C6 hydrocarbon stream. Herein, depending on the original composition of the cyclohexene source, the C6 hydrocarbon may refer to benzene, cyclohexane, cyclohexene, a mixture of cyclohexane and benzene, a mixture of cyclohexane and cyclohexene, a mixture of cyclohexene and benzene, or a mixture of cyclohexane, cyclohexene and benzene, optionally containing an additional inert diluent.

Specifically, the esterification product separation system may be provided with one or more C6 hydrocarbon/carboxylic acid removing tower. The addition esterification product is introduced into the C6 hydrocarbon/carboxylic acid removing tower for separation, the tower may be operated at the normal pressure, by controlling heating at the bottom, the reflux ratio, the top withdrawal and the bottom withdrawal, a mixed stream of C6 hydrocarbon and carboxylic acid is withdrawn from the top, a carboxylic acid cyclohexyl ester stream is withdrawn from the bottom. The obtained mixed stream of C6 hydrocarbon and carboxylic acid may be further separated by the following C6 hydrocarbon removing tower into a C6 hydrocarbon stream and a carboxylic acid stream. Or alternatively, the esterification product separation system may be provided with one or more C6 hydrocarbon removing tower and one or more carboxylic acid (for example, acetic acid) removing tower. The addition esterification product is firstly introduced into the C6 hydrocarbon removing tower for separation, the tower may be operated at the normal pressure operation, by controlling heating at the bottom, the reflux ratio, the top withdrawal and the bottom withdrawal, from the top there is withdrawn a C6 hydrocarbon stream, the stream withdrawn from the bottom of the C6 hydrocarbon removing tower is introduced into the carboxylic acid removing tower for separation, the tower may also be operated at the normal pressure, by controlling heating at the bottom, the reflux ratio, the top withdrawal and the bottom withdrawal, from the top there is withdrawn a carboxylic acid stream, from the bottom there is withdrawn a carboxylic acid cyclohexyl ester stream. The esterification product separation system may be further provided with one or more extractive rectification tower, the obtained C6 hydrocarbon stream is as needed further separated into a mixed stream of cyclohexane and benzene, a mixed stream of cyclohexene and benzene, a mixed stream of cyclohexane and cyclohexene, and a benzene stream, or further provided with two or more extractive rectification towers, the obtained C6 hydrocarbon stream is as needed further separated into a cyclohexane stream, a cyclohexene stream and a benzene stream. Optionally, the esterification product separation system may be further provided with one or more heavier components removing tower, the carboxylic acid cyclohexyl ester stream is introduced into the heavier components removing tower, and separated by rectification to further remove heavier components in the stream, to obtain a carboxylic acid cyclohexyl ester stream free of heavier components, while the separated heavier components as the by-product are discharged from the system.

According to Manner (1), if the obtained C6 hydrocarbon stream presents as a mixture, it may be subject to a hydrogenation to produce cyclohexane, or in line with the manner hereinbefore described, for example, to an extractive rectification, to separate therefrom a cyclohexene stream, a mixed stream of cyclohexene and benzene, a mixed stream of cyclohexene and cyclohexane, a benzene stream and a cyclohexane stream or the like as needed.

According to Manner (1), the obtained carboxylic acid cyclohexyl ester stream or mixed stream of carboxylic acid and carboxylic acid cyclohexyl ester (preferably the carboxylic acid cyclohexyl ester stream) as the addition esterification product is introduced into the cyclohexyl ester hydrogenation step of this invention, while the obtained carboxylic acid stream may be recycled as a part of the reaction feed stock to Manner (1). Further, the obtained mixed stream of cyclohexane and benzene or mixed stream of cyclohexene and benzene may be further subject to an extractive rectification so as to be separated into a cyclohexane stream, a benzene stream and a cyclohexene stream, the obtained cyclohexene stream, mixed stream of cyclohexene and benzene or mixed stream of cyclohexene and cyclohexane may be used as the cyclohexene source to the cyclohexene esterification step of this invention, the obtained benzene stream or mixed stream of cyclohexene and benzene may be recycled as a part of the reaction feed stock to Step (A), while the obtained cyclohexane stream is as the by-product discharged or recycled as a part of the reaction feed stock to Step (C).

According to Manner (1), especially, when the cyclohexene source has a cyclohexene content of 95 mol % or more or a pure product of cyclohexene is used as the cyclohexene source, the esterification product separation system may be merely provided with one or more rectification tower for removing the carboxylic acid (for example, acetic acid) and cyclohexene; or may be provided with one or more rectification tower for removing the carboxylic acid and cyclohexene and one or more rectification tower for removing heavier components. To this end, the addition esterification product is firstly introduced into the acid/cyclohexene removing tower for separation by rectification, the tower may be operated at the normal pressure, by controlling heating at the bottom, the reflux ratio, the top withdrawal and the bottom withdrawal, unreacted cyclohexene and carboxylic acid are withdrawn from the top and recycled back to the reaction system, from the bottom there is withdrawn the carboxylic acid cyclohexyl ester. If the carboxylic acid cyclohexyl ester product withdrawn from the bottom of the acid/cyclohexene removing tower contains a significantly amount of heavier components, the carboxylic acid cyclohexyl ester product is further needed to be introduced into the heavier components removing tower so as to remove heavier components, from the tower top of the heavier components removing tower to obtain a carboxylic acid cyclohexyl ester product with improved purity, while heavier components from the tower bottom are as the by-product discharged from the system.

According to Manner (2), the addition esterification reaction is conducted in one or more reactive rectification tower.

According to Manner (2), the reactive rectification tower is the same as a normal rectification tower in terms of configuration, generally consisted of a tower body, a condenser at the tower top, a reflux tank, a reflux pump, a bottom and a reboiler and so on. The tower may be a tray tower, a packing tower, or a combination thereof in parallel. A suitable tray tower includes a float valve tower, a sieve tower, a bubble cap tower or the like. The packing tower may be loaded with random packing, for example Pall ring packing, Dixon packing, saddle packing, cascade ring packing; or with structured packing, for example corrugated plating packing, corrugated wire mesh packing or the like.

According to Manner (2), inside the reactive rectification tower, there is loaded the addition esterification catalyst (for example, the solid acid catalyst). It has been well known to a person skilled in the art that, the catalyst is loaded into the reactive rectification tower such that the following two requirements are met: (1) providing sufficient pathways for both phases of liquid and vapor to pass through, or providing a relatively larger bed porosity (with a value of generally at least 50% or more) for both phases of liquid and vapor to counter currently pass through without causing a flooding issue; (2) exhibiting suitable mass transfer performance, so as for the reactant to be transferred from the fluid phase into the catalyst to conduct a reaction, and at the same time for the reaction product to be transferred out of the catalyst. The prior art teaches a lot about how to load a catalyst into a reactive rectification tower, all of which may be used in this invention. According to the prior art, a catalyst is loaded into a reaction tower in three ways as follows: (1) a first way of directly loading the catalyst into the tower as rectification packing, which mainly comprises mechanically mixing catalyst particles with a predetermined size and shape with rectification packing, or sandwiching the catalyst between different structured packings and forming the combination into an integrated packing, or forming the catalyst into the shape of rectification packing; (2) a second way of introducing the catalyst into a small container which is permeable to liquid and vapor and then loading same onto the tray of a reaction tower, or loading the catalyst into a downcomer of the reaction tower; (3) a third way of loading the catalyst in the form of fixed bed directly into a reaction tower, for the liquid phase to directly pass through the catalyst bed, with a pathway specifically designed for the vapor phase; According to this way, at the position wherein the catalyst is loaded, a catalyst bed and a rectification tower tray are alternatively arranged, liquid on a tower tray is through a downcomer and a redistributor introduced into the subsequent catalyst bed, with the addition reaction conducted in the bed, liquid at the lower part of a catalyst bed is through a liquid collector introduced into the subsequent tower tray.

According to Manner (2), the theoretical plate number of the reactive rectification tower is generally 10 to 150, preferably 30 to 100. it is preferred that, between the position corresponding to ⅓ of the theoretical plate number and that corresponding to ⅔ of the theoretical plate number, for example, between the position corresponding to a theoretical plate number of 10 and the position corresponding to a theoretical plate number of 120, preferably between the position corresponding to a theoretical plate number of 10 and the position corresponding to a theoretical plate number of 80, for example, there are selected 5 to 30 plates, preferably 8 to 20 plates, to load the addition esterification catalyst (for example, the solid acid catalyst), but not limiting thereto.

According to Manner (2), relative to the total packed volume of the addition esterification catalyst, the liquid feed space velocity is from 0.1 to 20 $h^{-1}$, preferably 0.2 to 20 $h^{-1}$, more preferably 0.5 to 5 $h^{-1}$ or 0.5 to 2 $h^{-1}$, but not limiting thereto.

According to Manner (2), the reactive rectification tower may be operated under reduced pressures, normal pressure and high pressure. Generally speaking, the operation pressure of the reactive rectification tower is from −0.0099 MPa to 5 MPa, preferably from the normal pressure to 1 MPa, but not limiting thereto.

The operation temperature of the reactive rectification tower depends on the pressure of the reactive rectification tower, and the temperature distribution of the reaction tower can be adjusted by adjusting the operation pressure of the reaction tower, such that the temperature of the catalyst loading area is remained at a value range within with the catalyst exhibits its activity. According to Manner (2), the temperature in the addition esterification catalyst bed loading area is generally 40 to 200 degrees Celsius, preferably 50 to 200 degrees Celsius or 50 to 180 degrees Celsius, more preferably 60 to 120 degrees Celsius or 60 to 150 degrees Celsius, but not limiting thereto.

It is necessary for the reflux ratio of the reactive rectification tower to at the same time meet the requirements of separation and reaction, generally speaking, increasing the reflux ratio will facilitate the separation performance and the reaction conversion, while at the same time, increase energy consumption of the process. According to Manner (2), if a pure product of cyclohexene and a carboxylic acid (for example, acetic acid) are used as the reaction feed stock, theoretically speaking, a full reflux may be used. However, when the reaction feed stock contains small amount of lighter impurities, it is advisable to discharge small amount of the tower top stream from the reactive rectification tower.

According to this invention, generally speaking, the reflux ratio of the reactive rectification tower is generally 0.1:1 to a full reflux, preferably 0.1 to 100:1, more preferably 0.5 to 10:1, but not limiting thereto.

According to Manner (2), an addition esterification reaction is conducted, and at the same time, a separation of the addition esterification product is conducted. Herein, the addition esterification product mainly comprises unreacted carboxylic acid and cyclohexene, and a carboxylic acid cyclohexyl ester as the reaction product, and further various inert diluents originated from the cyclohexene source, for example, cyclohexane and benzene or the like, which depends on the original composition of the cyclohexene source. Specifically, from the tower bottom of the reactive rectification tower there is obtained a carboxylic acid cyclohexyl ester stream or a mixed stream of carboxylic acid and carboxylic acid cyclohexyl ester, and depends on the separation at the tower bottom, from the top of the reactive rectification tower there is obtained a C6 hydrocarbon stream, or a mixed stream of carboxylic acid and C6 hydrocarbon. Herein, depending on the original composition of the cyclohexene source to be used, the C6 hydrocarbon may refer to benzene, cyclohexane, cyclohexene, a mixture of cyclohexane and benzene, a mixture of cyclohexane and cyclohexene, a mixture of cyclohexene and benzene, or a mixture of cyclohexane, cyclohexene and benzene, optionally containing an additional inert diluent. The mixed stream of carboxylic acid and C6 hydrocarbon may be subject to rectification and separated into a C6 hydrocarbon stream and a carboxylic acid stream. Specifically, the mixed stream is in a C6 hydrocarbon removing tower subject to a separation by rectification, wherein the tower may be operated at the normal pressure, by controlling heating at the bottom, the reflux ratio, the top withdrawal and the bottom withdrawal, from the top there is withdrawn a C6 hydrocarbon stream (for example, a cyclohexane stream or a mixed stream of cyclohexane and benzene), from the bottom there is withdrawn a carboxylic acid stream.

According to Manner (2), if the obtained C6 hydrocarbon stream presents as a mixture, it may be subject to a hydrogenation to produce cyclohexane, or in the manner hereinbefore described, for example, to an extractive rectification, and separate therefrom a cyclohexene stream, a mixed stream of cyclohexene and benzene, a mixed stream of cyclohexene and cyclohexane, a benzene stream and a cyclohexane stream or the like as needed.

According to Manner (2), the obtained carboxylic acid cyclohexyl ester stream or mixed stream of carboxylic acid and carboxylic acid cyclohexyl ester (preferably the carboxylic acid cyclohexyl ester stream) is as the addition esterification product introduced into the cyclohexyl ester hydrogenation step of this invention, while the obtained carboxylic acid stream may be recycled as a part of the reaction feed stock to Manner (2). Further, the obtained mixed stream of cyclohexene and cyclohexane or mixed stream of cyclohexene and benzene may be further subject to an extractive rectification and separated into a cyclohexane stream, a benzene stream and a cyclohexene stream, the obtained cyclohexene stream, mixed stream of cyclohexene and benzene or mixed stream of cyclohexene and cyclohexane may be used as the cyclohexene source to the cyclohexene esterification step of this invention, the obtained benzene stream or mixed stream of cyclohexene and benzene may be recycled as a part of the reaction feed stock to Step (A), while the obtained cyclohexane stream is as the by-product discharged or recycled as a part of the reaction feed stock to Step (C).

According to this invention, to conduct the cyclohexene esterification step, it is also possible to firstly conduct Manner (1), and then Manner (2). As a preferred combination thereof, for example, there may be exemplified a combination wherein an addition esterification reaction is firstly conducted in line with Manner (1) as aforesaid (herein the reaction in line with Manner (1) is also referred to as pre-esterification reaction), and then the obtained addition esterification product is used as such (or after removing a part or all of the carboxylic acid cyclohexyl ester therefrom) as the feed stock to conduct a further addition esterification reaction in line with Manner (2) as aforesaid (hereinafter referred to as Manner (3)). Herein, Manner (1) and Manner (2) may be conducted in the same manner as aforesaid respectively, and the addition esterification catalyst to be used in each case may be identical to or different from each other, and can be independently selected from the addition esterification catalysts given hereinbefore respectively.

The cyclohexyl ester hydrogenation step is described in details as follows.

According to the cyclohexyl ester hydrogenation step, the obtained (various) addition esterification products react with hydrogen gas in the presence of a hydrogenation catalyst to conduct a hydrogenation reaction, whereby producing at the same time cyclohexanol and an alkanol.

According to this invention, the alkanol is represented by the formula R—$CH_2$—OH, wherein the group R is as defined for the at least one carboxylic acid, most preferably methyl. As the alkanol, it is most preferably ethanol.

According to this invention, as the hydrogenation catalyst, for example, there may be exemplified a copper based catalyst, a ruthenium based catalyst and a noble metal based catalyst, preferably a copper based catalyst. As the catalyst, one kind or a mixture of two or more kinds at any ratio therebetween could be used.

According to this invention, as the ruthenium based catalyst, for example, there may be exemplified $Ru/Al_2O_3$ and Ru—$Sn/Al_2O_3$.

According to this invention, as the noble metal based catalyst, for example, there may be exemplified $Pt/Al_2O_3$, Pd—$Pt/Al_2O_3$ and Pd/C.

According to this invention, as the copper based catalyst, for example, there may be exemplified a zinc-containing copper based catalyst and a chromium-containing copper based catalyst, preferably a copper based catalyst comprising the following components, more preferably consisting of the following components:

(a) copper oxide;

(b) zinc oxide;

(c) a metal oxide, wherein the metal is one or more selected from the group consisting of aluminium, gallium, tin, titanium, zirconium, chromium, molybdenum, tungsten, manganese, rhenium, lanthanide metals and actinide metals, preferably selected from the group consisting of aluminium, gallium, tin, titanium, zirconium, chromium, molybdenum, tungsten, manganese, rhenium, lanthanum and cerium; and (d) one or more selected from the group consisting of alkali metal hydroxides and alkaline earth metal hydroxides, preferably one or more selected from the group consisting of KOH, NaOH and barium hydroxide.

According to this invention, it is preferred that in the copper based catalyst, expressed as parts by weight, the ratio of the component (a):the component (b):the component (c):the component (d) is 5 to 60:10 to 50:5 to 60:0.2 to 2, preferably 10 to 50:15 to 45:15 to 55:0.2 to 2, more preferably 30 to 45:20 to 35:20 to 50:0.5 to 1.5.

According to this invention, the copper based catalyst is generally reduced before use. Further, it is understood that in this field, a catalyst is generally sold and stored as a precursor, which precursor may not be used as such to catalyze a reaction, however is still called "catalyst" as a rule. The copper based catalyst of this invention (actually a precursor of the copper based catalyst) can exhibit a catalysis activity only after this reduction, which may be generally conducted by an operator of an industrial apparatus, which reduction has been well known by a person skilled in the art, and for this reason, detailed description thereof is omitted herein.

According to this invention, the copper based catalyst (i.e. the precursor) can be formed into various shapes as needed, for example, small spheres, or not formed, for example as powder.

According to this invention, the copper based catalyst may be produced by a process including the following Step (1a) and Step (2a).

Step (1a): by a coprecipitation method, producing a composite metal oxide, wherein the composite metal oxide comprises the following components, preferably consists of the following components: (a) copper oxide; (b) zinc oxide; and (c) a metal oxide, wherein the metal is one or more selected from the group consisting of aluminium, gallium, tin, titanium, zirconium, chromium, molybdenum, tungsten, manganese, rhenium, lanthanide metals and actinide metals, preferably selected from the group consisting of aluminium, gallium, tin, titanium, zirconium, chromium, molybdenum, tungsten, manganese, rhenium, lanthanum and cerium, wherein expressed as parts by weight, the ratio of the component (a):the component (b):the component (c) is 5 to 60:10 to 50:5 to 60, preferably 10 to 50:15 to 45:15 to 55, more preferably 30 to 45:20 to 35:20 to 50.

According to this invention, by coprecipitation, it refers to a method wherein two or more metal cations in a homogenous solution react with a precipitating agent, whereby precipitating these metal cations out of the solution to obtain a precipitation which is homogeneous in terms of composition, and the thus obtained precipitation mixture or solid solution precursor is subject to filtration, washing and calcination (thermally decomposing the precipitation mixture or solid solution precursor) to obtain the composite metal oxide.

According to this invention, the coprecipitation may be conducted in various manners, there may be exemplified a method wherein a solution containing metal cations is introduced into a precipitating agent solution, or that wherein a precipitating agent solution is introduced into a solution containing metal cations, or that wherein a solution containing metal cations and a precipitating agent solution is introduced into a solvent at the same time.

According to this invention, the coprecipitation, for example, may include the following steps:

(I) formulating the (aqueous) solution of each soluble metal salt and mixing same at a predetermined ratio therebetween, wherein the metal refers to (a) copper; (b) zinc; and (c) one or more metal selected from the group consisting of aluminium, gallium, tin, titanium, zirconium, chromium, molybdenum, tungsten, manganese, rhenium, lanthanide metals and actinide metals, preferably one or more metal selected from the group consisting of aluminium, gallium, tin, titanium, zirconium, chromium, molybdenum, tungsten, manganese, rhenium, lanthanum and cerium, the ratio therebetween is such that on the basis of the corresponding metal oxide, expressed as parts by weight, the ratio of metal (a):metal (b):metal (c) is 5 to 60:10 to 50:5 to 60, preferably 10 to 50:15 to 45:15 to 55, more preferably 30 to 45:20 to 35:20 to 50;

(II) at a temperature ranging from 15 degrees Celsius to 80 degrees Celsius, introducing the (aqueous) solution of a precipitating agent into the mixed solution obtained in Step (I), then adjusting the pH value to a value of 6 to 9, to produce a mixed precipitation, wherein the nature of the precipitating agent is determined such that the produced mixed precipitation can be thermally decomposed into a metal oxide; and (III) retaining the precipitation system of Step (II) at a temperature of 30 degrees Celsius to 80 degrees Celsius for 1 to 48 h, and then filtering and washing the mixed precipitation till the concentration of any metal cation in the filtrate is less than 100 ug/g, which is then dried at a temperature of 100 degrees Celsius to 200 degrees Celsius for 3 to 48 h, and then at a temperature of 250 degrees Celsius to 400 degrees Celsius calcinated for 3 to 48 h, to obtain a composite metal oxide in the form of powder.

In Step (I), by "soluble", it means that the concentration of the metal salt in a solution thereof (for example, solubility in water) is sufficient for producing a composite metal oxide with a predetermined composition. As the salt, for example, there may be exemplified nitrates, sulfates, hydrochlorides, acetates or hydrates of the metal.

In Step (II), preferably under stirring, into the mixed solution obtained from Step (I), there is introduced a (an aqueous) solution of the precipitating agent, which facilitates improving the homogeneity of the resultant catalyst.

According to this invention, as the precipitating agent, for example, there may be exemplified one or more of NaOH, KOH, sodium carbonate, potassium carbonate, ammonium carbonate, ammonia, urea, sodium oxalate, potassium oxalate and ammonium oxalate.

According to this invention, there is no specific limitation as to the concentration of the soluble metal salt and that of the precipitating agent in its solution, as long as it can lead to production of the composite metal oxide, which is free selectable to a person skilled in the art as needed.

According to this invention, to produce each solution, the soluble metal salt and/or the precipitating agent (and further alkali metal hydroxides and/or alkaline earth metal hydroxides hereinafter described) may be dissolved in water, or may be dissolved in a non-water solvent, for example, ethanol, or in a mixture of water and ethanol at any ratio therebetween, which is free selectable to a person skilled in the art.

Step (2a): by an impregnation method, introducing into the composite metal oxide produced by Step (1a) a component (d) one or more selected from the group consisting of alkali metal hydroxides and alkaline earth metal hydroxides, preferably one or more selected from the group consisting of KOH, NaOH and barium hydroxide, such that expressed as parts by weight, the ratio of the component (a):the component (b):the component (c):the component (d) is 5 to 60:10 to 50:5 to 60:0.2 to 2, preferably 10 to 50:15 to 45:15 to 55:0.2 to 2, more preferably 30 to 45:20 to 35:20 to 50:0.5 to 1.5.

According to this invention, as a way to conduct Step (2a), for example, there may be exemplified a method wherein the composite metal oxide obtained by Step (1a) is impregnated with the (aqueous) solution of an alkali metal hydroxide and/or an alkaline earth metal hydroxide (with a concentration of, for example, 0.5 to 5 wt %), and then filtered, dried and calcinated to obtain the copper based catalyst (precursor) of this invention.

According to this invention, preferably, in Step (2a), the impregnation temperature is from 30 degrees Celsius to 80 degrees Celsius, the impregnation duration is 1 to 48 h; the drying temperature is from 100 degrees Celsius to 200 degrees Celsius, the drying duration is 3 to 48 h; the calcination temperature is from 250 degrees Celsius to 400 degrees Celsius, the calcination duration is 3 to 48 h.

According to this invention, the alkali metal hydroxide and/or alkaline earth metal hydroxide is preferably one or more of KOH, NaOH and barium hydroxide.

According to this invention, the obtained copper based catalyst is in the form of powder, which may be molded into any desirable shape as needed. As aforesaid, the catalyst, no matter molded or un-molded, should be reduced in hydrogen gas atmosphere before exhibiting a hydrogenation activity. Herein, the reduction may present as an additional step for producing the catalyst before use, or may be conducted during the cyclohexyl ester hydrogenation step of this invention, preferably as an additional step for producing the catalyst before use.

According to this invention, the hydrogenation reaction may be conducted in one or more hydrogenation reactor. As the hydrogenation reactor, for example, there may be exemplified a tank reactor, a fixed bed reactor, a boiling bed reactor, a fluidized bed reactor or a combination thereof in parallel, preferably a tubular fixed bed reactor, more preferably a shell and tube reactor.

According to this invention, the hydrogenation reaction may be conducted in a continuous manner or a batchwise manner. A batchwise reaction generally involves a kettle as the reactor, wherein the addition esterification product and a hydrogenation catalyst are introduced into a kettle, supplied with hydrogen gas, to conduct the reaction at a predetermined temperature and pressure, upon completion of the reaction, the reaction product is discharged from the reactor, and then the product is separated, and then another batch of mass is introduced to conduct the reaction. A continuous hydrogenation reaction may involve a shell and tube tubular reactor, wherein the hydrogenation catalyst is fixed in the tube, while the shell is cooled by cooling water to remove heat generated from the reaction.

According to this invention, the reaction temperature of the hydrogenation reaction is generally 150 to 400 degrees Celsius, preferably 200 to 300 degrees Celsius.

According to this invention, the reaction pressure of the hydrogenation reaction is generally from the normal pressure to 20 MPa, preferably from the normal pressure to 10 MPa, more preferably 4 to 10 MPa.

According to this invention, in the hydrogenation reaction, the ratio by molar of hydrogen gas to the addition esterification product (based on the carboxylic acid cyclohexyl ester) is 1 to 1000:1, preferably 5 to 100:1.

According to this invention, when the hydrogenation reaction is conducted in a continuous manner, the liquid feed space velocity is from 0.1 to 20 $h^{-1}$, preferably 0.2 to 2 $h^{-1}$.

According to this invention, when the hydrogenation reaction is conducted in a batchwise manner, the reaction duration is from 0.2 to 20 h, preferably 0.5 to 5 h, more preferably 1 to 5 h.

According to this invention, the hydrogenation product obtained from the hydrogenation reaction is introduced into a hydrogenation product separation system for separation. Specifically, the hydrogenation product is introduced into a vapor liquid separating tank for vapor liquid separation, wherein the vapor phase mainly consists of hydrogen gas, and may further comprise various inert diluents originated from the cyclohexene source, for example, cyclohexane and benzene, which depends on the original composition of the cyclohexene source in the cyclohexene esterification step. The separated hydrogen gas is recycled after compressed by a compressor back to the hydrogenation reactor. The liquid phase mainly comprises the alkanol (for example, ethanol) and cyclohexanol, and may further comprise a certain amount of carboxylic acid alkanol ester (for example, carboxylic acid ethyl ester) and cyclohexanone, and at the same time may further comprise a certain amount of unreacted carboxylic acid cyclohexyl ester, and a small amount of heavy boiling materials (ketene dimer). The product of liquid phase may be separated by rectification and/or extractive separation.

According to this invention, the hydrogenation product is preferably separated by rectification. The rectification may be conducted in a continuous manner or in a batchwise manner, preferably the continuous manner. A continuous rectification necessarily involves a series of towers for separating various components. The separation may be conducted according to the order of the components to be separated, and a sequential separation is preferred by this invention.

According to this invention, before conducting the cyclohexyl ester hydrogenation step, it is optional to react the addition esterification product with hydrogen gas in the presence of a carboxylic acid hydrogenation catalyst to conduct a carboxylic acid hydrogenation reaction (referred to as carboxylic acid hydrogenation step), so as to convert in advance any free carboxylic acid (and any benzene) contained in the addition esterification product into an alkanol (and cyclohexane). The reaction product obtained from the carboxylic acid hydrogenation step (optionally after separating therefrom a part of or all of alkanol and/or cyclohexane) is still identified as addition esterification product, and can be used in the same manner as aforesaid to conduct the cyclohexyl ester hydrogenation step.

According to this invention, the carboxylic acid hydrogenation catalyst may be any catalyst conventionally used in this filed for producing the corresponding alcohol by a carboxylic acid hydrogenation, preferably, the carboxylic acid hydrogenation catalyst consists of a main active component 0.1 to 30 wt %, an auxiliary agent 0.1 to 25 wt % and the remaining amount of carrier.

According to this invention, the main active component is one or more selected from the group consisting of platinum, palladium, ruthenium, tungsten, molybdenum and cobalt.

According to this invention, the auxiliary agent is one or more selected from the group consisting of tin, chromium, aluminium, zinc, calcium, magnesium, nickel, titanium, zirconium, rhenium, lanthanum, thorium and gold.

According to this invention, the carrier is one or more selected from the group consisting of silica, alumina, titania, zirconia, activated carbon, graphite, carbon nano-tube, calcium silicate, zeolite and aluminium silicate.

According to this invention, the carboxylic acid hydrogenation step and the cyclohexyl ester hydrogenation step may be conducted in different reactors, or in different sections of the same reactor. For example, the carboxylic acid hydrogenation step may be conducted in an individual carboxylic acid hydrogenation reactor. As the carboxylic acid hydrogenation reactor, for example, there may be exemplified a tank reactor, a fixed bed reactor, a boiling bed reactor, a fluidized bed reactor or any combination thereof in parallel, preferably a tubular fixed bed reactor, more preferably a shell and tube reactor.

According to this invention, the reaction temperature of the carboxylic acid hydrogenation reaction is from 100 to 400 degrees Celsius, preferably 180 to 300 degrees Celsius.

According to this invention, the reaction pressure of the carboxylic acid hydrogenation reaction is from 0.1 to 30 MPa, preferably 2 to 10 MPa.

According to this invention, in the carboxylic acid hydrogenation reaction, the ratio by molar of hydrogen gas to the free carboxylic acid is 1 to 500:1, preferably 5 to 50:1.

According to this invention, when the carboxylic acid hydrogenation reaction is conducted in a continuous manner, the liquid feed space velocity is from 0.1 to 5 $h^{-1}$, preferably 0.2 to 2 $h^{-1}$.

According to this invention, when the carboxylic acid hydrogenation reaction is conducted in a batchwise manner, the reaction duration is from 0.5 to 20 h, preferably 1 to 5 h.

According to this invention, the process for co-producing cyclohexanol and alkanol may optionally further comprise the following Step (I), Step (II), Step (III) or any combination thereof. These steps may be conducted in a manner conventionally known in this field, and the description thereof in details is omitted herein.

Step (I): Benzene and/or hydrogen gas isolated from any step in the process for co-producing cyclohexanol and alkanol are recovered, and recycled to Step (A).

Step (II): Cyclohexane isolated from any step in the process for co-producing cyclohexanol and alkanol is recovered, and recycled to Step (C).

Step (III): Cyclohexane isolated from any step in the process for co-producing cyclohexanol and alkanol is recovered, and, for example, in a manner conventionally known in this field, in the presence of a dehydrogenation catalyst, subject to a dehydrogenation, to obtain benzene and hydrogen gas. And then, the obtained benzene and/or hydrogen gas are recycled to Step (A).

For Step (III), the reaction of cyclohexane by dehydrogenation to produce benzene is so easy to proceed that in the presence of a monofunctional dehydrogenation catalyst and under suitable reaction conditions, cyclohexane will be produced into benzene with high conversion and high selectivity. A person skilled in the art may refer to JP285001/87, WO2009/131769, or CN1038273 for a suitable procedure. Of course, a bi- or multi-functional catalyst may also be used, for example, a catalytic reforming catalyst having both dehydrogenation function and acidic function. There are at least two ways for this invention to convert cyclohexane by dehydrogenation into benzene, one of which is to establish a specific cyclohexane dehydrogenation apparatus, in the presence of a mono-functional or multi-functional dehydrogenation catalyst, to conduct the cyclohexane dehydrogenation; the other of which is to make use of the existing catalytic reforming apparatus, which may specifically treat cyclohexane or mix and treat cyclohexane and the catalytic reforming feed stock (for producing aromatics) simultaneously. It should be understood that, according to the prior art, the presence of benzene shows no unfavorable effect on the dehydrogenation of cyclohexane to produce benzene, and therefore this cyclohexane may contain benzene.

According to this invention, the process for co-producing cyclohexanol and alkanol may further optionally comprise the following steps or any combination thereof. These steps may be conducted in a manner conventionally known in this field, and the description thereof in details is omitted herein.

Step (IV): The carboxylic acid and/or the cyclohexene source isolated from any step in the process for co-producing cyclohexanol and alkanol is recovered, and recycled to the cyclohexene esterification step.

Step (V): Hydrogen gas isolated from any step in the process for co-producing cyclohexanol and alkanol is recovered, and recycled to the cyclohexyl ester hydrogenation step.

According to this invention, by taking the cyclohexanol produced as aforesaid as a feed, it is possible to produce cyclohexanone. In this context, this invention further relates to a process for producing cyclohexanone, including producing in line with the process of this invention cyclohexanol, and using the produced cyclohexanol as a starting material to produce cyclohexanone.

According to this invention, the production of cyclohexanone by using cyclohexanol as a starting material may be conducted in a manner conventionally known in this field, and description thereof in details is omitted herein.

According to this invention, by taking the cyclohexanone produced as aforesaid as a feed, it is possible to produce caprolactam. In this context, this invention further relates to a process for producing caprolactam, including producing in line with the process of this invention cyclohexanone, and using the produced cyclohexanone as a starting material to produce caprolactam.

According to this invention, the production of caprolactam by using cyclohexanone as a starting material may be conducted in a manner conventionally known in this field, and description thereof in details is omitted herein.

According to this invention, there further relates to an apparatus for co-producing cyclohexanol and alkanol, which apparatus is specialized for conducting the process for co-producing cyclohexanol and alkanol of this invention.

According to this invention, the apparatus for co-producing cyclohexanol and alkanol comprises a hydrogenation reaction unit A (benzene hydrogenation reactor), an optional hydrogenation product separation unit A, an addition esterification reaction unit (esterification reactor), an optional addition esterification product separation unit, a hydrogenation reaction unit B (ester hydrogenation reactor) and a hydrogenation product separation unit B (ester hydrogenation product separation unit), wherein, in the hydrogenation reaction unit A, benzene reacts with hydrogen gas in the presence of a partial hydrogenation catalyst to conduct a partial hydrogenation reaction, to obtain a cyclohexene-containing hydrogenation product (corresponding to Step (A));

in the hydrogenation product separation unit A, the hydrogenation product obtained from the hydrogenation reaction unit A is subject to a separation, to obtain cyclohexene, a mixture of cyclohexene and benzene or a mixture of cyclohexene and cyclohexane (corresponding to Step (B));

in the addition esterification reaction unit, the hydrogenation product obtained from the hydrogenation reaction unit A and/or cyclohexene, the mixture of cyclohexene and benzene or the mixture of cyclohexene and cyclohexane obtained from the hydrogenation product separation unit A, reacts with a carboxylic acid in the presence of an addition esterification catalyst to conduct an addition esterification reaction, to produce an addition esterification product containing carboxylic acid cyclohexyl ester (corresponding to the cyclohexene esterification step);

in the addition esterification product separation unit, the addition esterification product obtained from the addition esterification reaction unit is subject to a separation, to obtain carboxylic acid cyclohexyl ester or a mixture of carboxylic acid cyclohexyl ester and carboxylic acid;

in the hydrogenation reaction unit B, the addition esterification product obtained from the addition esterification reaction unit and/or the carboxylic acid cyclohexyl ester or the mixture of carboxylic acid cyclohexyl ester and carboxylic acid obtained from the addition esterification product separation unit reacts with hydrogen gas in the presence of a hydrogenation catalyst to conduct a hydrogenation reaction, to produce a hydrogenation product containing cyclohexanol and an alkanol (corresponding to the cyclohexyl ester hydrogenation step); and in the hydrogenation product separation unit B, the hydrogenation product obtained from the hydrogenation reaction unit B is subject to a separation, to obtain cyclohexanol and an alkanol.

It will be very easy for a person skilled in the art on the basis of the process of this invention as aforesaid, to determine how to connect different units and apparatus.

According to this invention, it is preferred that, the hydrogenation reaction unit A is provided with one or more reactor in parallel, which reactor may be a fixed bed reactor and/or a tank reactor.

According to this invention, it is preferred that, the addition esterification reaction unit is provided with one or more reactor X in parallel, which reactor X may be one or more of a tank reactor, a fixed bed reactor, a boiling bed reactor and a fluidized bed reactor, for conducting the cyclohexene esterification step according to Manner (1).

According to this invention, it is preferred that, the addition esterification reaction unit is provided with at least one reactive rectification tower, for conducting the cyclohexene esterification step according to Manner (2).

According to this invention, it is preferred that, upstream of the reactive rectification tower, one or more parallelly arranged reactor X (also referred to as pre-addition esterification reaction unit) is/are arranged in series, for conducting the cyclohexene esterification step according to Manner (3).

According to this invention, it is preferred that, the addition esterification product separation unit is provided with at least one rectification tower.

According to this invention, it is preferred that, the hydrogenation reaction unit B may be provided with one or more reactor arranged in parallel, which reactor may be one or more of a tank reactor, a fixed bed reactor, a boiling bed reactor and a fluidized bed reactor, preferably one or more shell and tube reactor arranged in parallel.

According to this invention, it is preferred that, the hydrogenation product separation unit B may be provided with at least one rectification tower.

According to this invention, the apparatus for co-producing cyclohexanol and alkanol may optionally further comprise at least one of the following recycling apparatus.

Recycling apparatus A: for recovering benzene and/or hydrogen gas obtained from any unit in the apparatus for co-producing cyclohexanol and alkanol, and recycling same to the hydrogenation reaction unit A.

Recycling apparatus B: for recovering carboxylic acid and/or cyclohexene obtained from any unit in the apparatus for co-producing cyclohexanol and alkanol, and recycling same to the addition esterification reaction unit.

Recycling apparatus C: for recovering hydrogen gas obtained from any unit in the apparatus for co-producing cyclohexanol and alkanol, and recycling same to the hydrogenation reaction unit B.

According to this invention, in the apparatus for co-producing cyclohexanol and alkanol, the addition esterification reaction unit may present as a reactor (for example, a tank reactor, a fixed bed reactor, a fluidized bed reactor, a boiling bed reactor or any combination thereof), a reactive rectification tower (with a theoretical plate number of for example, 10 to 150, preferably 30 to 100, preferably a tray tower or a packing tower) or any combination thereof, preferably the reactive rectification tower (for conducting the cyclohexene esterification step according to Manner (2)) or a combination in series of the reactor and the reactive rectification tower, more preferably a combination in series of the reactor and the reactive rectification tower, most preferably a combination in series wherein the reactor (herein also referred to as pre-addition esterification reactor)

is arranged upstream of the reactive rectification tower (for conducting the cyclohexene esterification step according to Manner (3)).

The invention is described more fully hereinafter with reference to the accompanying drawings, in which specific embodiments of the invention are shown. This invention may, however, be embodied in many different forms and should not be construed as limited to the embodiments set forth herein.

According to this specification, for different figures, reference numbers are independently provided, that is, each figure is provided with a unique set of reference number. Unless otherwise specified, the same reference number may not refer to the same element/feature or may not have the same meaning in different figures. It will be very easy for a person skilled in the art by referring to the following brief description on each figure, to cleary understand the specific embodiment represented by each figure without being distracted or interfered by the reference number.

Figure 2:
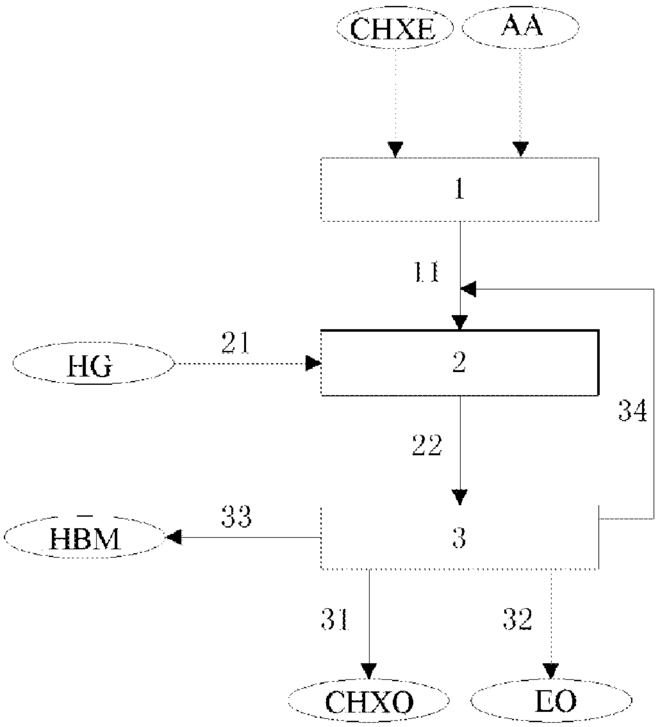

According to the embodiment of FIG. 2, cyclohexene and acetic acid are introduced into the esterification reactor 1, in the presence of an addition esterification catalyst, to conduct an addition esterification reaction, the addition esterification product stream via the line 11 is introduced into the ester hydrogenation reactor 2, in the presence of an ester hydrogenation catalyst, contacts with hydrogen gas to conduct an ester hydrogenation reaction, the ester hydrogenation product stream 22 is introduced into the ester hydrogenation product separation unit 3, upon separation to obtain the cyclohexanol stream 31, the ethanol stream 32, the high-boiling material stream 33, the acetic acid cyclohexyl ester stream 34, the cyclohexanol stream 31 and the ethanol stream 32 as the product are discharged from the apparatus, the high-boiling material stream 33 as the by-product is discharged from the apparatus, the acetic acid cyclohexyl ester stream 34 is recycled back to the ester hydrogenation reactor 2.

Figure 3:
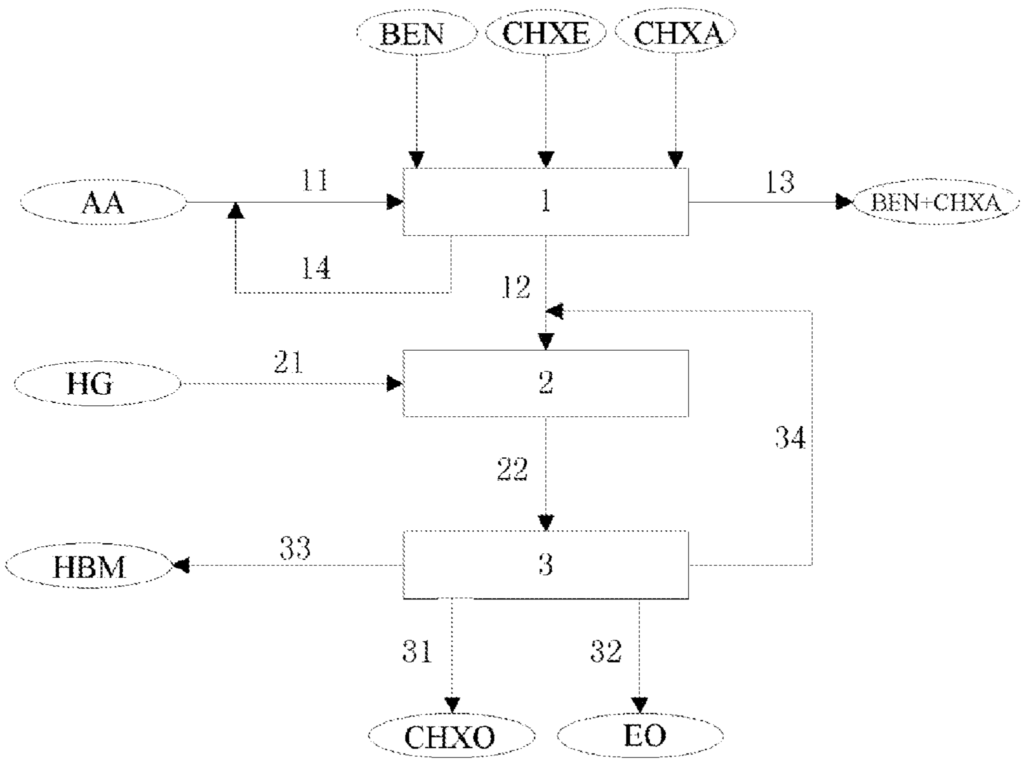

According to the embodiment of FIG. 3, a stream containing benzene and cyclohexane together with acetic acid are introduced into the reactive rectification tower 1, in the presence of an addition esterification catalyst, to conduct an addition esterification reaction, and at the same time, to separate the reaction product, whereby at the rectification section of the tower, obtaining the benzene/cyclohexane stream 13 and the acetic acid stream 14, the acetic acid stream is recycled back to the reactive rectification tower 1, from the tower bottom there is obtained the acetic acid cyclohexyl ester stream, via the line 12 is introduced into the ester hydrogenation reactor 2, in the presence of an ester hydrogenation catalyst, contacts with hydrogen gas to conduct an ester hydrogenation reaction, the ester hydrogenation product stream 22 is introduced into the ester hydrogenation product separation unit 3, upon separation to obtain the cyclohexanol stream 31, the ethanol stream 32, the high-boiling material stream 33 and the acetic acid cyclohexyl ester stream 34, the cyclohexanol stream 31 and the ethanol stream 32 as the product are discharged from the apparatus, the high-boiling material stream 33 as the by-product is discharged from the apparatus, the acetic acid cyclohexyl ester stream 34 is recycled back to the ester hydrogenation reactor 2.

Figure 4:
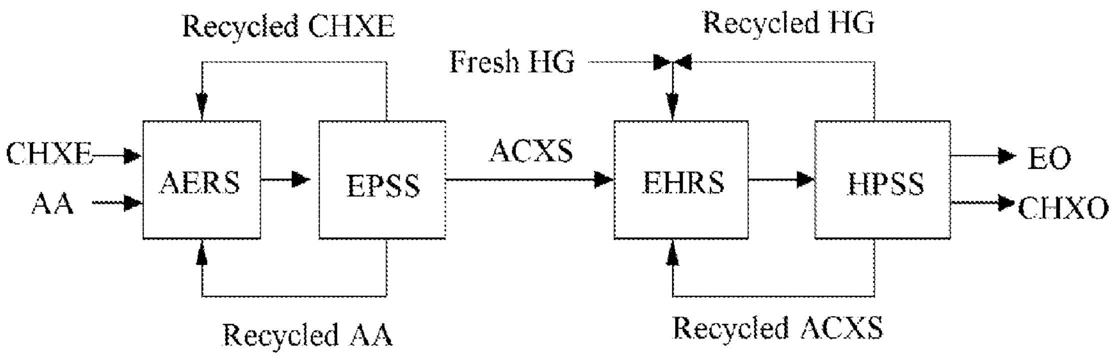

According to the embodiment of FIG. 4, cyclohexene and acetic acid are introduced into the addition esterification reaction system, in the presence of an addition esterification catalyst, to conduct an esterification reaction, the reaction product is introduced into the esterification product separation system, upon separation to obtain the acetic acid cyclohexyl ester stream, the cyclohexene stream and the acetic acid stream, the cyclohexene stream and the acetic acid stream are recycled back to the addition esterification reaction system, the acetic acid cyclohexyl ester stream is introduced into the ester hydrogenation reaction system, in the presence of an ester hydrogenation catalyst, contacts with hydrogen gas, to conduct the hydrogenation reaction of acetic acid cyclohexyl ester, the hydrogenation product is introduced into the hydrogenation product separation system, upon separation to obtain the cyclohexanol stream, the ethanol stream, the acetic acid cyclohexyl ester stream and the hydrogen gas stream, the cyclohexanol stream and the ethanol stream as the product are discharged from the apparatus, the acetic acid cyclohexyl ester stream and the hydrogen gas stream are recycled back to the ester hydrogenation reaction system.

Figure 5:
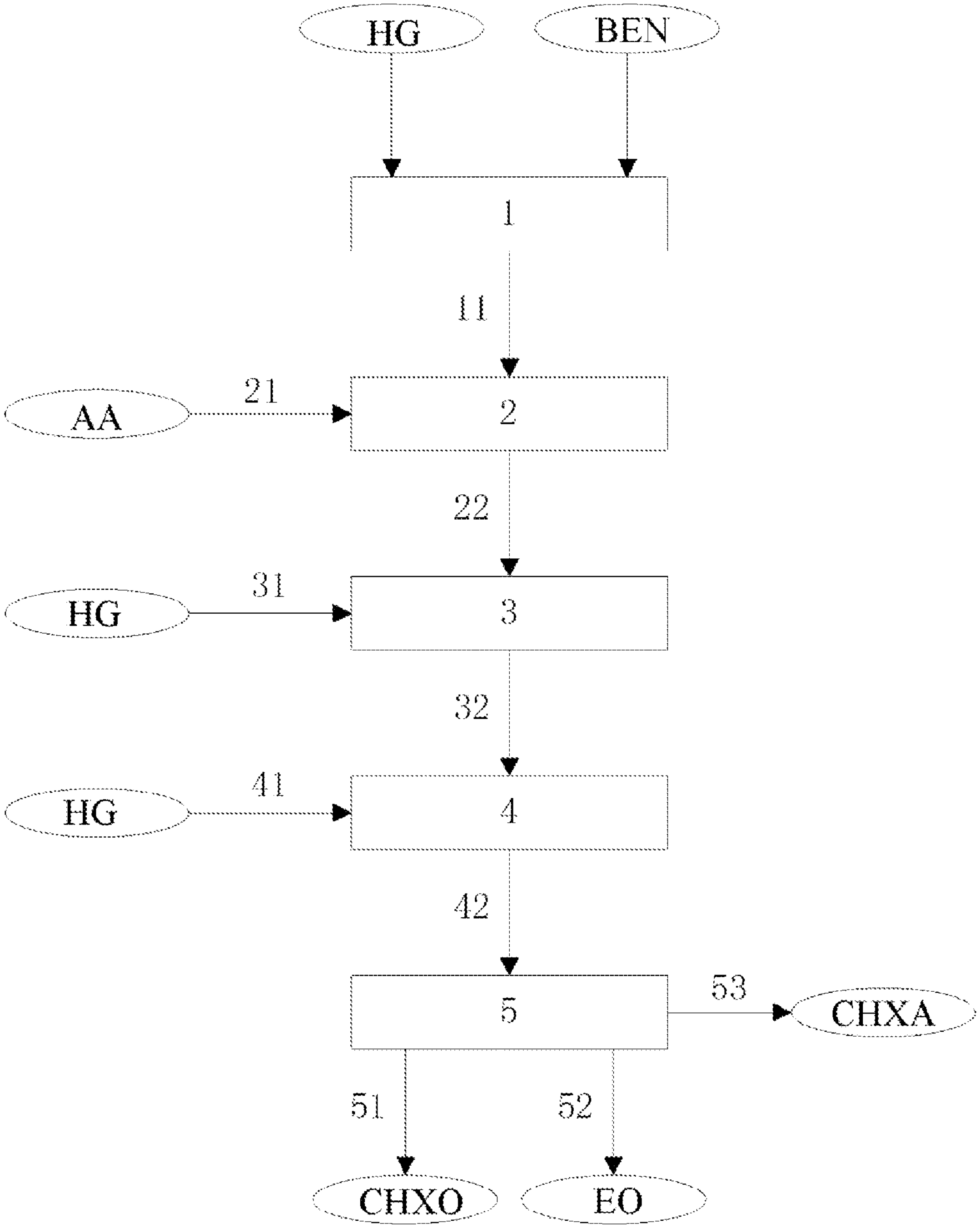

According to the embodiment of FIG. 5, benzene and hydrogen gas are introduced into the benzene hydrogenation reactor 1, in the presence of a benzene hydrogenation catalyst, to conduct a hydrogenation reaction, the benzene hydrogenation product stream via the line 11 is introduced into the addition esterification reactor 2, mixed with acetic acid introduced via the line 21, in the presence of a solid acid catalyst, to conduct an addition esterification reaction, the addition esterification product stream via the line 22 is introduced into the hydrogenation reactor 3, in the presence of a noble metal catalyst, contacts with hydrogen gas, to conduct the hydrogenation reaction of benzene and carboxylic acid at the same time, the hydrogenation product stream is introduced into the hydrogenation reactor 4, in the presence of an ester hydrogenation catalyst, contacts with hydrogen gas to conduct an ester hydrogenation reaction, the hydrogenation product stream is introduced into the product separation unit 5, upon separation to obtain the cyclohexanol stream 51, the ethanol stream 52, and the cyclohexane stream 53.

Figure 6:
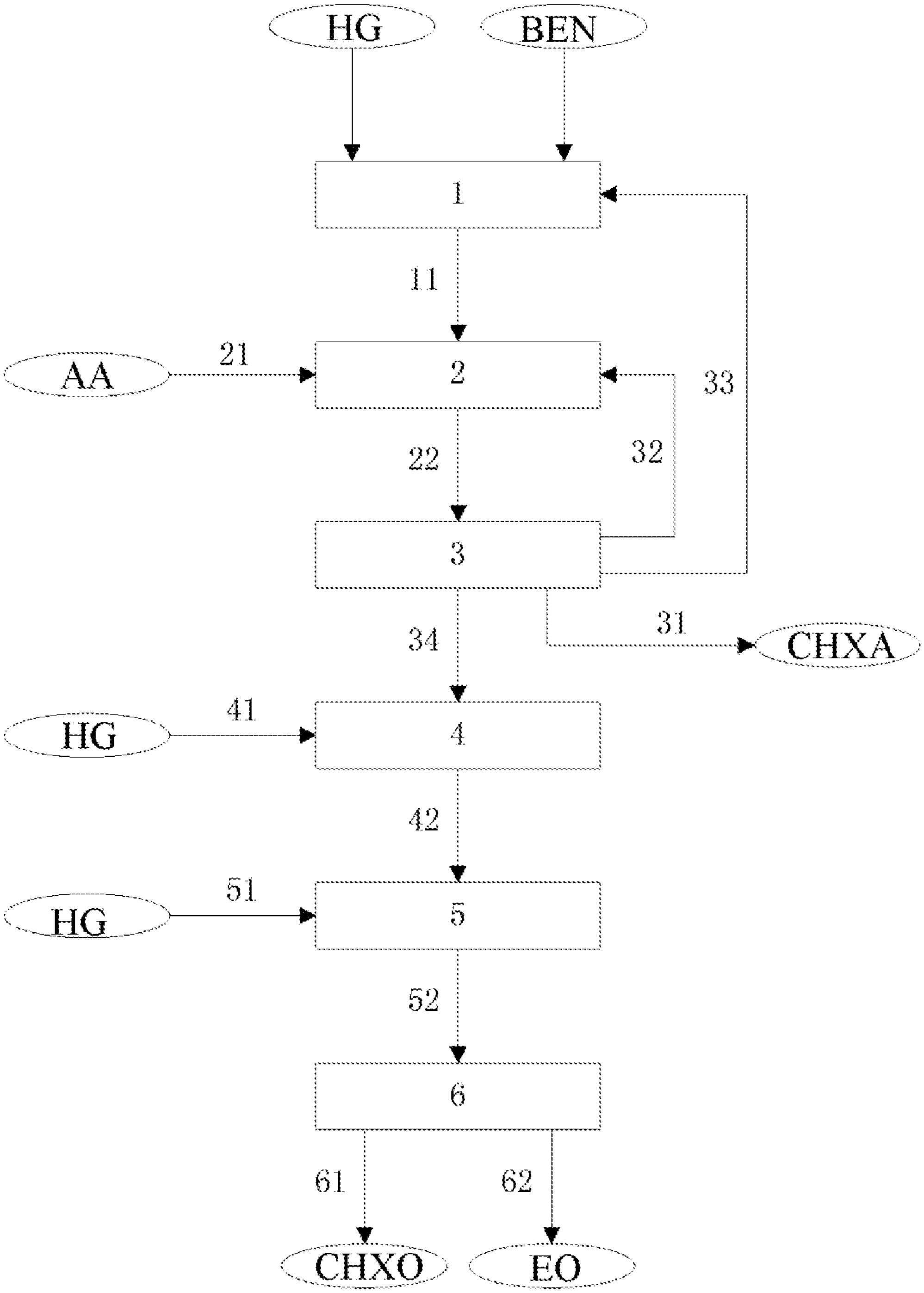

According to the embodiment of FIG. 6, benzene and hydrogen gas are introduced into the benzene hydrogenation reactor 1, in the presence of a benzene hydrogenation catalyst, to conduct a hydrogenation reaction, the benzene hydrogenation product stream via the line 11 is introduced into the addition esterification reactor 2, mixed with acetic acid introduced via the line 21, in the presence of a solid acid catalyst, to conduct an addition esterification reaction, the addition esterification product stream via the line 22 is introduced into the addition esterification product separation unit 3, upon separation to obtain the cyclohexane stream 31, the cyclohexene stream 32, the benzene stream 33, the acetic acid/acetic acid cyclohexyl ester stream 34, the benzene stream is recycled back to the benzene hydrogenation reactor 1, the cyclohexene stream is recycled back to the addition esterification reactor 2, the cyclohexane stream as the by-product is discharged from the apparatus, the acetic acid/acetic acid cyclohexyl ester stream is introduced into the carboxylic acid hydrogenation reactor 4, in the presence of a carboxylic acid hydrogenation catalyst, contacts with hydrogen gas to conduct a carboxylic acid hydrogenation reaction, the carboxylic acid hydrogenation product stream is introduced into the ester hydrogenation reactor 5, in the presence of an ester hydrogenation catalyst, contacts with hydrogen gas to conduct an ester hydrogenation reaction, the ester hydrogenation reaction product stream is introduced into the hydrogenation product separation unit 6, upon separation to obtain the cyclohexanol stream 61, the ethanol stream 62.

Figure 7:
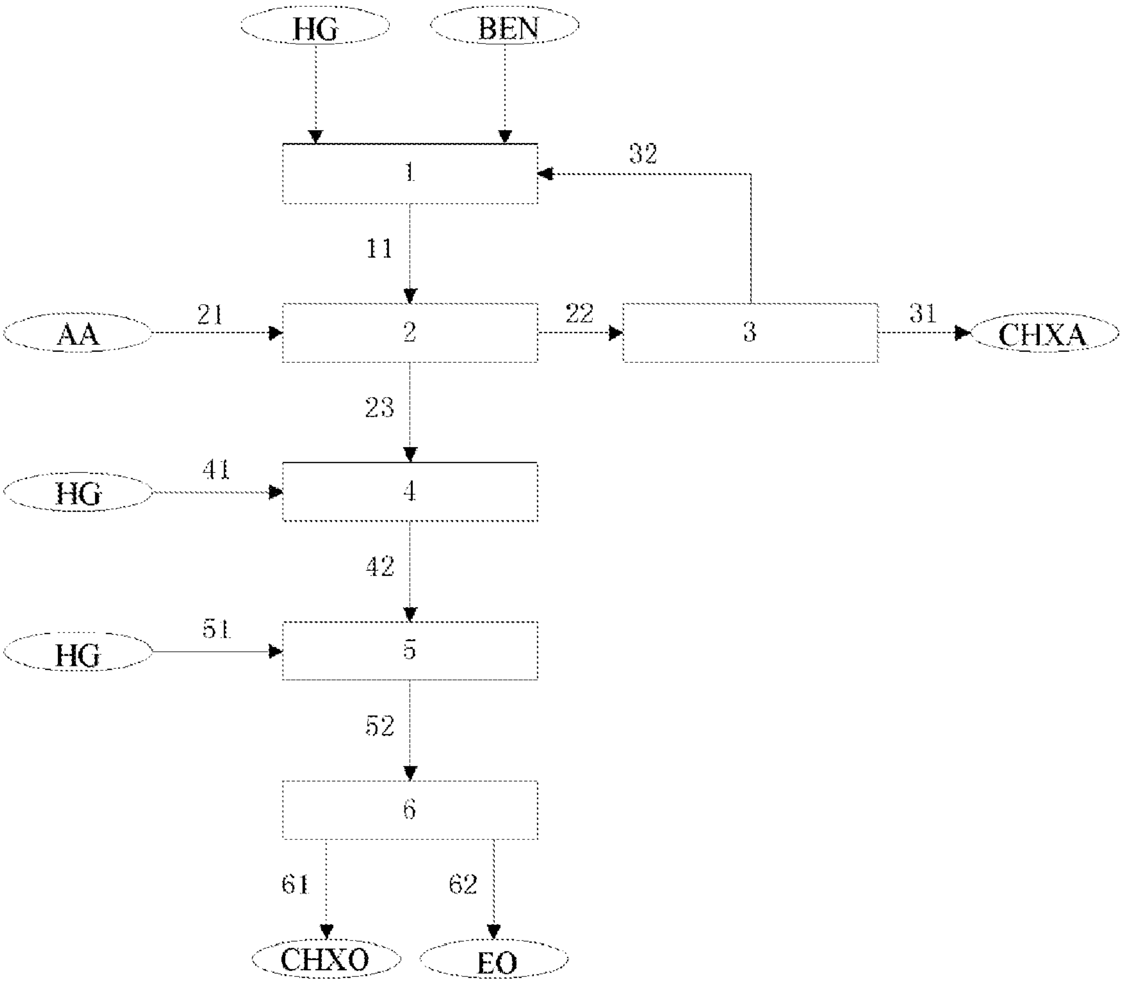

According to the embodiment of FIG. 7, benzene and hydrogen gas are introduced into the benzene hydrogenation reactor 1, in the presence of a benzene selective hydrogenation catalyst, to conduct a hydrogenation reaction, the benzene hydrogenation product stream via the line 11 is introduced into the reactive rectification tower 2, mixed with acetic acid introduced via the line 21, in the presence of a solid acid catalyst, to conduct an addition esterification reaction, and at the same time, to separate the esterification product, from the tower top of the reactive rectification tower 2 here is obtained the cyclohexane/benzene stream, from the tower bottom of the reactive rectification tower 2 here is obtained the acetic acid/acetic acid cyclohexyl ester stream; the cyclohexane/benzene stream via the line 22 is introduced into the addition esterification product separation unit 3, upon separation to obtain the cyclohexane stream and the benzene stream, the benzene stream is recycled back to the benzene hydrogenation reactor 1, the cyclohexane stream as the by-product is discharged from the apparatus, the acetic acid/acetic acid cyclohexyl ester stream is introduced into the carboxylic acid hydrogenation reactor 4, in the presence of a carboxylic acid hydrogenation catalyst, contacts with hydrogen gas to conduct a carboxylic acid hydrogenation reaction, the carboxylic acid hydrogenation product stream is introduced into the ester hydrogenation reactor 5, in the presence of an ester hydrogenation catalyst, contacts with hydrogen gas to conduct an ester hydrogenation reaction, the ester hydrogenation reaction product stream is introduced into the hydrogenation product separation unit 6, upon separation to obtain the cyclohexanol stream 61, the ethanol stream 62.

Figure 8:
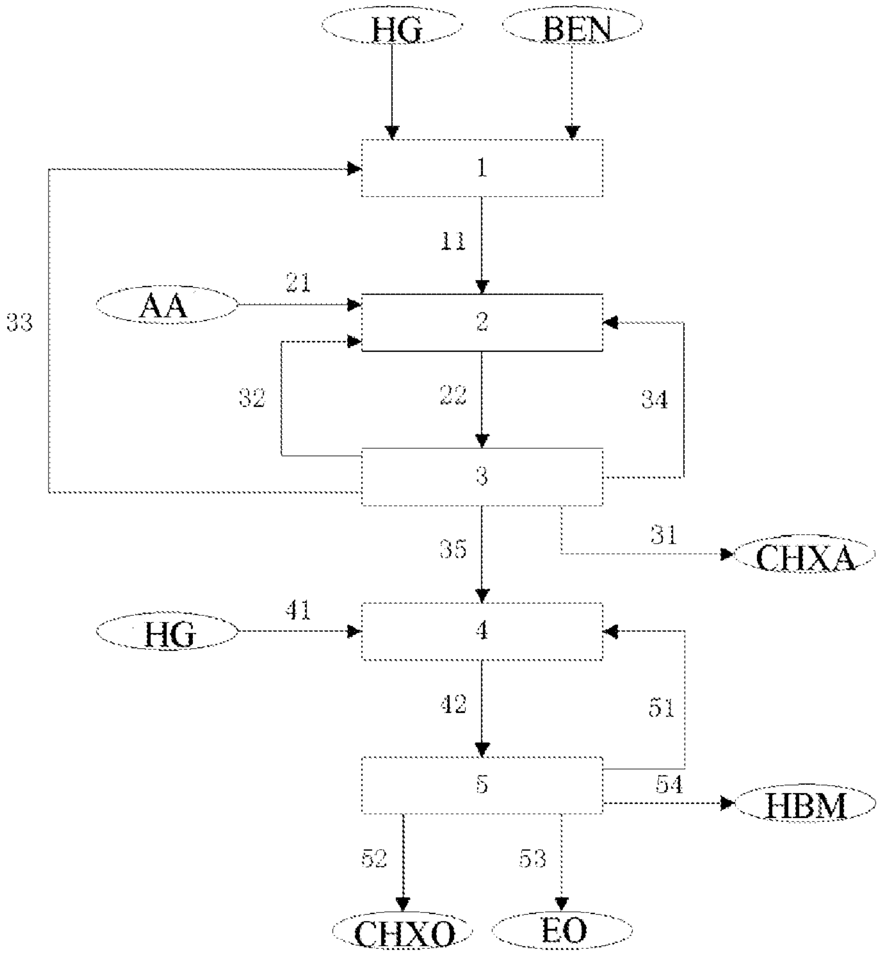

According to the embodiment of FIG. 8, benzene and hydrogen gas are introduced into the benzene hydrogenation reactor 1, in the presence of a benzene hydrogenation catalyst, to conduct a hydrogenation reaction, the benzene hydrogenation product stream via the line 11 is introduced into the addition esterification reactor 2, mixed with acetic acid introduced via the line 21, in the presence of a solid acid catalyst, to conduct an addition esterification reaction, the addition esterification product stream via the line 22 is introduced into the addition esterification product separation unit 3, upon separation to obtain the cyclohexane stream 31, the cyclohexene stream 32, the benzene stream 33, the acetic acid stream 34 and the acetic acid cyclohexyl ester stream 35, the benzene stream is recycled back to the benzene hydrogenation reactor 1, the cyclohexene stream and the acetic acid stream are recycled back to the addition esterification reactor 2, the acetic acid cyclohexyl ester stream is introduced into the ester hydrogenation reactor 4, in the presence of an ester hydrogenation catalyst, contacts with hydrogen gas to conduct an ester hydrogenation reaction, the ester hydrogenation product stream is introduced into the ester hydrogenation product separation unit 5, upon separation to obtain the cyclohexanol stream 52, the ethanol stream 53, the acetic acid cyclohexyl ester stream 51 and the high-boiling material stream 54, the cyclohexanol stream and the ethanol stream as the product are discharged from the apparatus, the high-boiling material stream as the by-product is discharged from the apparatus, the acetic acid cyclohexyl ester stream is recycled back to the ester hydrogenation reactor 4.

Figure 9:
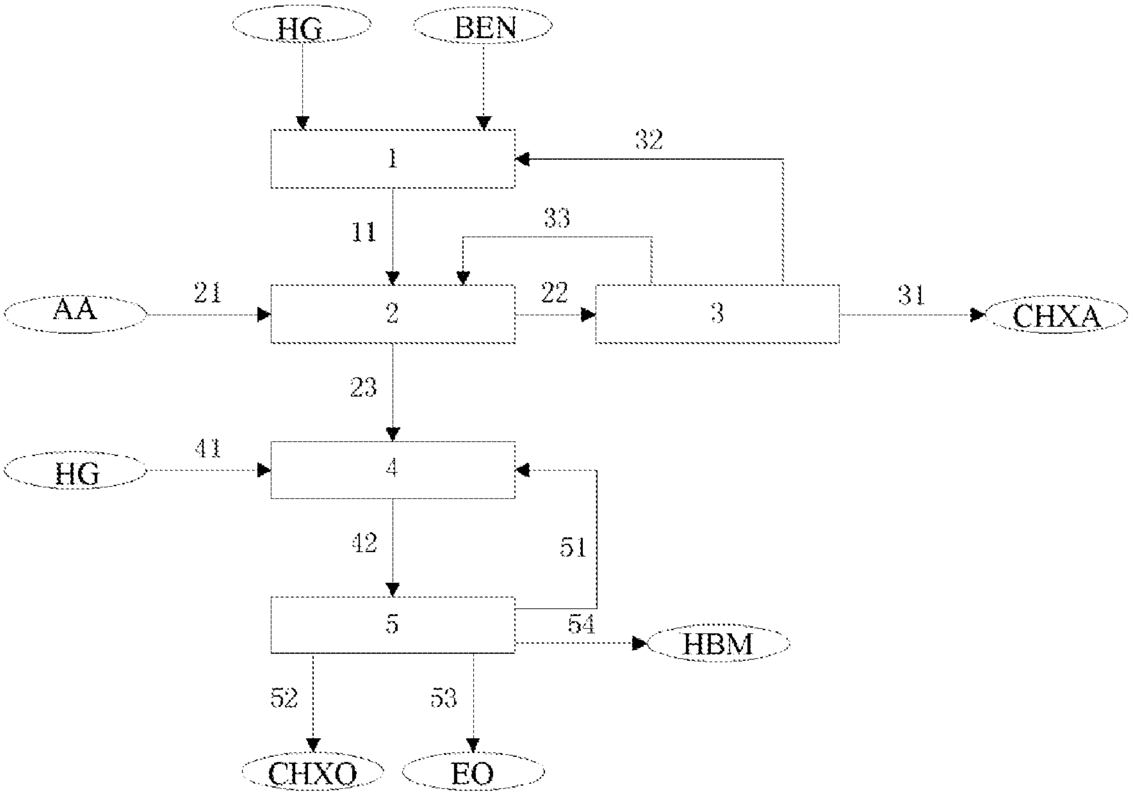

According to the embodiment of FIG. 9, benzene and hydrogen gas are introduced into the benzene hydrogenation reactor 1, in the presence of a benzene hydrogenation catalyst, to conduct a hydrogenation reaction, the benzene hydrogenation product stream via the line 11 is introduced into the reactive rectification tower 2, mixed with acetic acid introduced via the line 21, in the presence of a solid acid catalyst, to conduct an addition esterification reaction, and at the same time, to conduct a separation of the addition esterification product, from the tower top of the reactive rectification tower 2 here is obtained the cyclohexane/benzene/acetic acid stream, from the tower bottom of the reactive rectification tower 2 here is obtained the acetic acid cyclohexyl ester stream; the cyclohexane/benzene/acetic acid stream via the line 22 is introduced into the addition esterification product separation unit 3, upon separation to obtain the cyclohexane stream, the benzene stream and the acetic acid stream, the cyclohexane stream as the by-product is discharged from the apparatus, the benzene stream is recycled back to the benzene hydrogenation reactor 1, the acetic acid stream is recycled back to the addition esterification reactor 2, the acetic acid cyclohexyl ester stream is introduced into the ester hydrogenation reactor 4, in the presence of an ester hydrogenation catalyst, contacts with hydrogen gas to conduct an ester hydrogenation reaction, the ester hydrogenation product stream is introduced into the ester hydrogenation product separation unit 5, upon separation to obtain the cyclohexanol stream 52, the ethanol stream 53, the acetic acid cyclohexyl ester stream 51 and the high-boiling material stream 54, the cyclohexanol stream and the ethanol stream as the product are discharged from the apparatus, the high-boiling material stream as the by-product is discharged from the apparatus, the acetic acid cyclohexyl ester stream is recycled back to the ester hydrogenation reactor 4.

Figure 10:
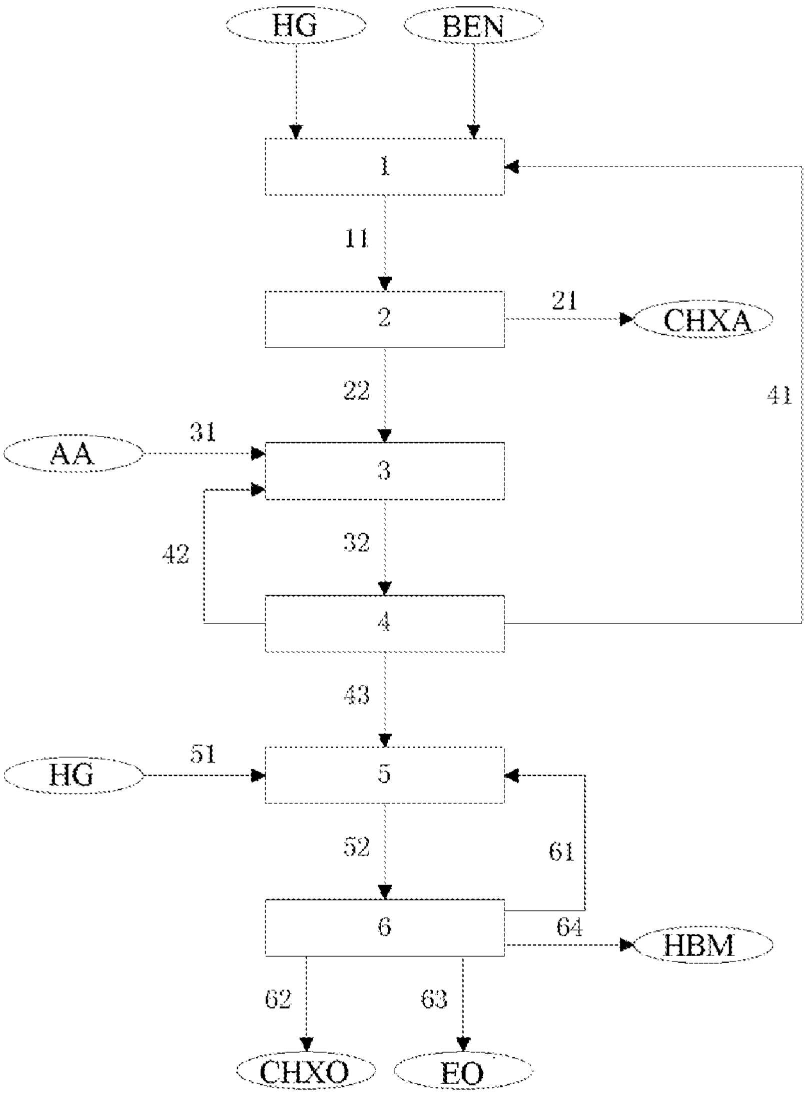

According to the embodiment of FIG. 10, benzene and hydrogen gas are introduced into the benzene hydrogenation reactor 1, in the presence of a benzene hydrogenation catalyst, to conduct a hydrogenation reaction, the benzene hydrogenation product stream via the line 11 is introduced into the benzene hydrogenation product separation unit 2, upon separation to obtain the cyclohexane stream 21 and the cyclohexene/benzene stream 22, the cyclohexane stream 21 as the by-product is discharged from the apparatus, the cyclohexene/benzene stream via the line 22 is introduced into the addition esterification reactor 3, mixed with acetic acid introduced via the line 31, in the presence of a solid acid catalyst, to conduct an addition esterification reaction, the addition esterification product stream via the line 32 is introduced into the addition esterification product separation unit 4, upon separation to obtain the cyclohexene/benzene stream 41, the acetic acid stream 42 and the acetic acid cyclohexyl ester stream 43, the cyclohexene/benzene stream 41 is recycled back to the benzene hydrogenation reactor 1 or further isolated into the cyclohexene stream and the benzene stream, the acetic acid stream 42 is recycled back to the addition esterification reactor 3, the acetic acid cyclohexyl ester stream 43 is introduced into the ester hydrogenation reactor 5, in the presence of an ester hydrogenation catalyst, contacts with hydrogen gas 51 to conduct an ester hydrogenation reaction, the ester hydrogenation product stream 52 is introduced into the ester hydrogenation product separation unit 6, upon separation to obtain the cyclohexanol stream 62, the ethanol stream 63, the acetic acid cyclohexyl ester stream 61 and the high-boiling material stream 64, the cyclohexanol stream 62 and the ethanol stream 63 as the product are discharged from the apparatus, the high-boiling material stream 64 as the by-product is discharged from the apparatus, the acetic acid cyclohexyl ester stream 61 is recycled back to the ester hydrogenation reactor 5.

Figure 11:
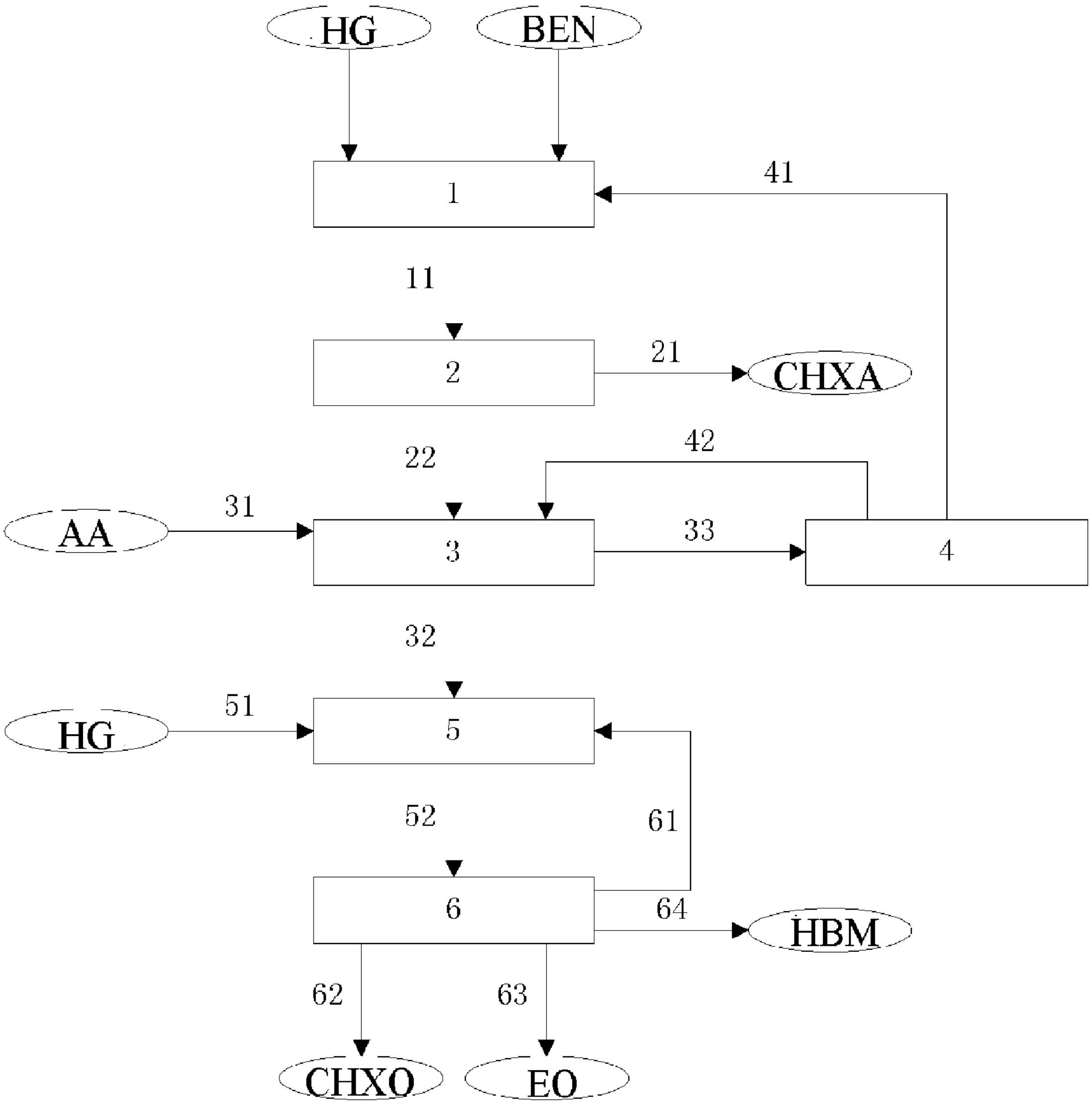

According to the embodiment of FIG. 11, benzene and hydrogen gas are introduced into the benzene hydrogenation reactor 1, in the presence of a benzene hydrogenation catalyst, to conduct a hydrogenation reaction, the benzene hydrogenation product stream via the line 11 is introduced into the benzene hydrogenation product separation unit 2, upon separation to obtain the cyclohexane stream 21 and the cyclohexene/benzene stream 22, the cyclohexane stream as the by-product is discharged from the apparatus, the cyclohexene/benzene stream via the line 22 is introduced into the reactive rectification tower 3, mixed with acetic acid introduced via the line 31, in the presence of a solid acid catalyst, to conduct an addition esterification reaction, and at the same time, to conduct a separation of the addition esterification product, from the tower top of the reactive rectification tower 3 here is obtained the acetic acid/benzene stream, from the tower bottom of the reactive rectification tower 3 here is obtained the acetic acid cyclohexyl ester stream, the acetic acid/benzene stream via the line 33 is introduced into the addition esterification product separation unit 4, upon separation to obtain the benzene stream 41 and the acetic acid stream 42, the benzene stream 41 is recycled back to the benzene hydrogenation reactor 1, the acetic acid stream 42 is recycled back to the addition esterification reactor 3, the acetic acid cyclohexyl ester stream 32 is introduced into the ester hydrogenation reactor 5, in the presence of an ester hydrogenation catalyst, contacts with hydrogen gas to conduct an ester hydrogenation reaction, the ester hydrogenation product stream 52 is introduced into the ester hydrogenation product separation unit 6, upon separation to obtain the cyclohexanol stream 62, the ethanol stream 63, the acetic acid cyclohexyl ester stream 61 and the high-boiling material stream 64, the cyclohexanol stream and the ethanol stream as the product are discharged from the apparatus, the high-boiling material stream as the by-product is discharged from the apparatus, the acetic acid cyclohexyl ester stream is recycled back to the ester hydrogenation reactor 5.

Figure 12:
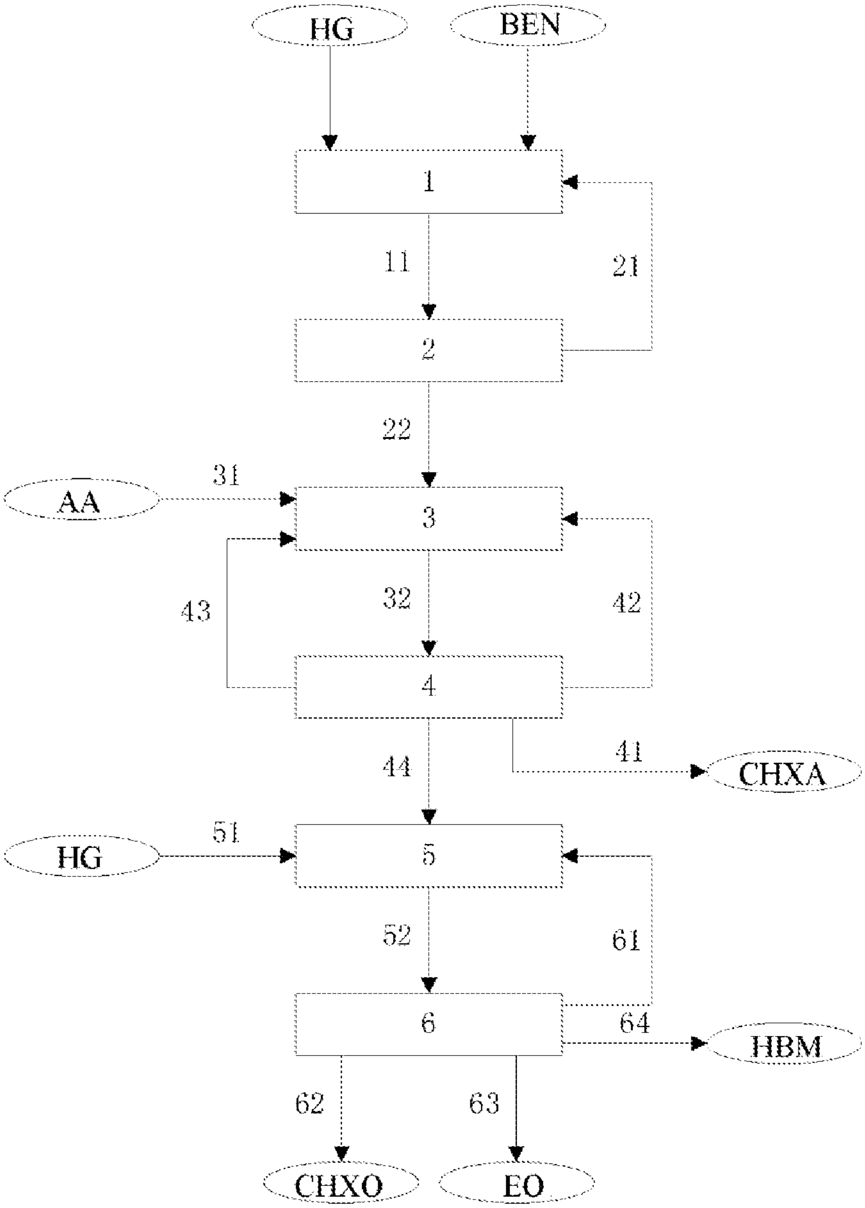

According to the embodiment of FIG. 12, benzene and hydrogen gas are introduced into the benzene hydrogenation reactor 1, in the presence of a benzene hydrogenation catalyst, to conduct a hydrogenation reaction, the benzene hydrogenation product stream via the line 11 is introduced into the benzene hydrogenation product separation unit 2, upon separation to obtain the cyclohexene/cyclohexane stream and the benzene stream, the benzene stream via the line 21 is recycled back to the benzene hydrogenation reactor 1, the cyclohexene/cyclohexane stream via the line 22 is introduced into the addition esterification reactor 3, mixed with acetic acid introduced via the line 31, in the presence of a solid acid catalyst, to conduct an addition esterification reaction, the addition esterification product stream via the line 32 is introduced into the addition esterification product separation unit 4, upon separation to obtain the cyclohexane stream 41, the cyclohexene stream 42, the acetic acid stream 43 and the acetic acid cyclohexyl ester stream 44, the cyclohexane stream 41 as the by-product is discharged from the apparatus, the acetic acid stream 43 and the cyclohexene stream 42 are recycled back to the addition esterification reactor 3, the acetic acid cyclohexyl ester stream 44 is introduced into the ester hydrogenation reactor 5, in the presence of an ester hydrogenation catalyst, contacts with hydrogen gas to conduct an ester hydrogenation reaction, the ester hydrogenation product stream 51 is introduced into the ester hydrogenation product separation unit 6, upon separation to obtain the cyclohexanol stream 62, the ethanol stream 63, the acetic acid cyclohexyl ester stream 61 and the high-boiling material stream 64, the cyclohexanol stream 62 and the ethanol stream 63 as the product are discharged from the apparatus, the high-boiling material stream 64 as the by-product is discharged from the apparatus, the acetic acid cyclohexyl ester stream 61 is recycled back to the ester hydrogenation reactor 5.

Figure 13:
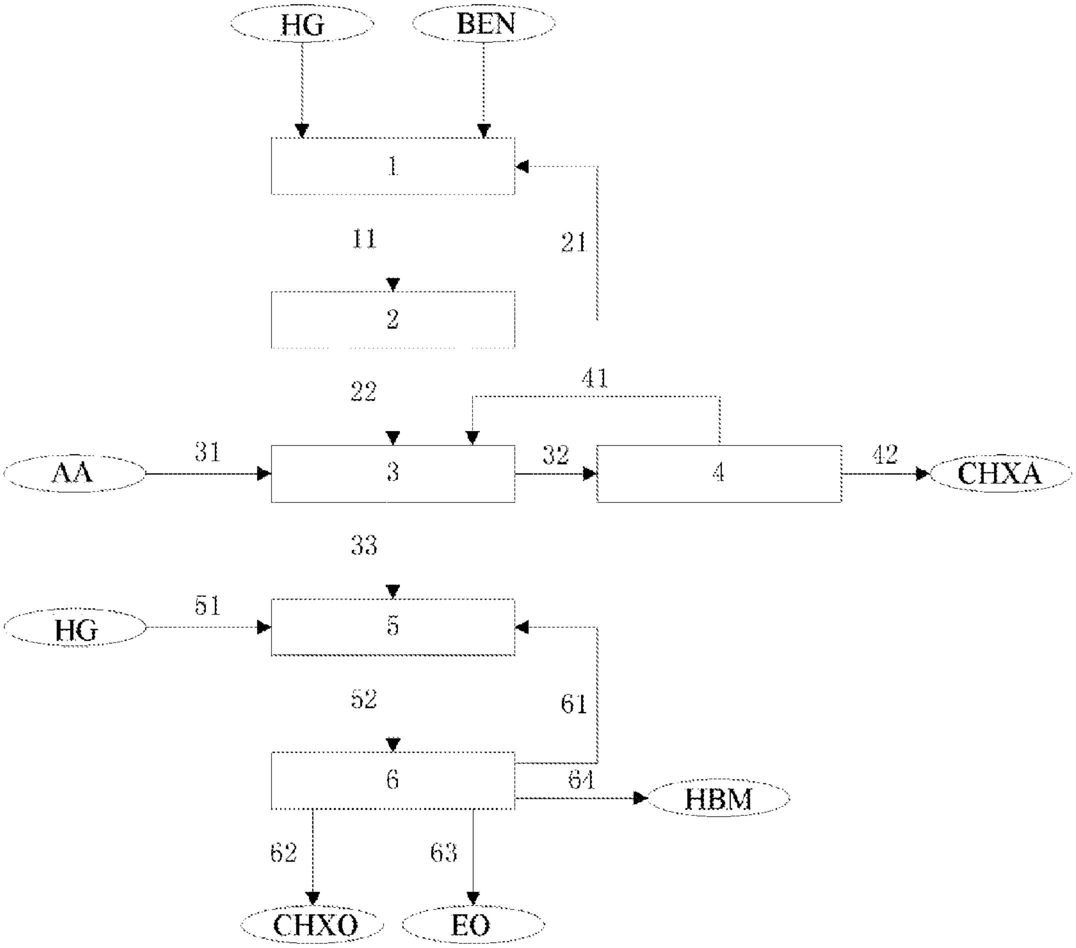

According to the embodiment of FIG. 13, benzene and hydrogen gas are introduced into the benzene hydrogenation reactor 1, in the presence of a benzene hydrogenation catalyst, to conduct a hydrogenation reaction, the benzene hydrogenation product stream via the line 11 is introduced into the benzene hydrogenation product separation unit 2, upon separation to obtain the cyclohexene/cyclohexane stream and the benzene stream, the benzene stream via the line 21 is recycled back to the benzene hydrogenation reactor 1, the cyclohexene/cyclohexane stream via the line 22 is introduced into the reactive rectification tower 3, mixed with acetic acid introduced via the line 31, in the presence of a solid acid catalyst, to conduct an addition esterification reaction, and at the same time, to conduct a separation of the addition esterification product, from the tower top of the reactive rectification tower 3 here is obtained the acetic acid/cyclohexane stream, from the tower bottom of the reactive rectification tower 3 here is obtained the acetic acid cyclohexyl ester stream, the acetic acid/cyclohexane stream via the line 32 is introduced into the addition esterification product separation unit 4, upon separation to obtain the cyclohexane stream 42 and the acetic acid stream 41, the cyclohexane stream 42 as the by-product is discharged from the apparatus, the acetic acid stream 41 is recycled back to the addition esterification reactor 3, the acetic acid cyclohexyl ester stream 33 is introduced into the ester hydrogenation reactor 5, in the presence of an ester hydrogenation catalyst, contacts with hydrogen gas to conduct an ester hydrogenation reaction, the ester hydrogenation product stream is introduced into the ester hydrogenation product separation unit 6, upon separation to obtain the cyclohexanol stream 62, the ethanol stream 63, the acetic acid cyclohexyl ester stream 61 and the high-boiling material stream 64, the cyclohexanol stream and the ethanol stream as the product are discharged from the apparatus, the high-boiling material stream as the by-product is discharged from the apparatus, the acetic acid cyclohexyl ester stream is recycled back to the ester hydrogenation reactor 5.

Figure 14:
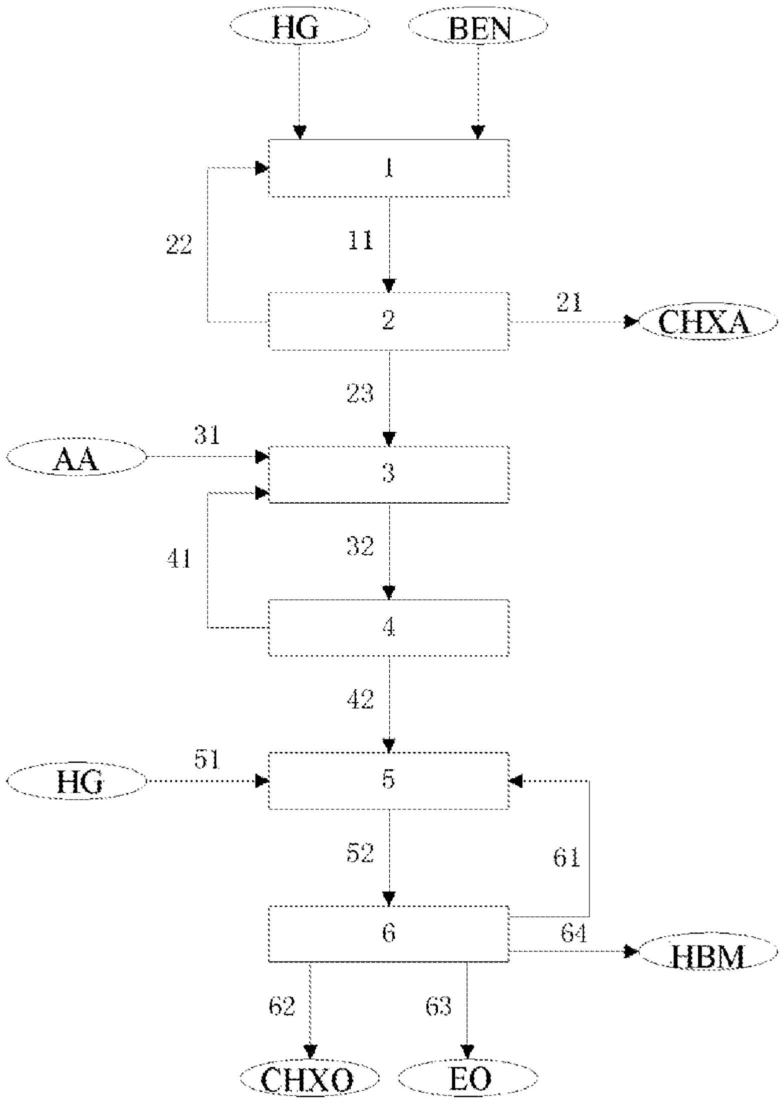

According to the embodiment of FIG. 14, benzene and hydrogen gas are introduced into the benzene hydrogenation reactor 1, in the presence of a benzene hydrogenation catalyst, to conduct a hydrogenation reaction, the benzene hydrogenation product stream via the line 11 is introduced into the benzene hydrogenation product separation unit 2, upon separation to obtain the cyclohexane stream and the cyclohexene stream and the benzene stream, the cyclohexane stream 21 as the by-product is discharged from the apparatus, the benzene stream via the line 22 is recycled back to the benzene hydrogenation reactor 1, the cyclohexene stream via the line 23 is introduced into the addition esterification reactor 3, mixed with acetic acid introduced via the line 31, in the presence of a solid acid catalyst, to conduct an addition esterification reaction, the addition esterification product stream via the line 32 is introduced into the addition esterification product separation unit 4, upon separation to obtain the cyclohexene/acetic acid stream 41 and the acetic acid cyclohexyl ester stream 42, the cyclohexene/acetic acid stream is recycled back to the addition esterification reactor 3, the acetic acid cyclohexyl ester stream is introduced into the ester hydrogenation reactor 5, in the presence of an ester hydrogenation catalyst, contacts with hydrogen gas to conduct an ester hydrogenation reaction, the ester hydrogenation product stream is introduced into the ester hydrogenation product separation unit 6, upon separation to obtain the ethanol stream 63, the cyclohexanol stream 62, the acetic acid cyclohexyl ester stream 61 and the high-boiling material stream 64, the cyclohexanol stream and the ethanol stream as the product are discharged from the apparatus, the high-boiling material stream as the by-product is discharged from the apparatus, the acetic acid cyclohexyl ester stream is recycled back to the ester hydrogenation reactor 5.

Figure 15:
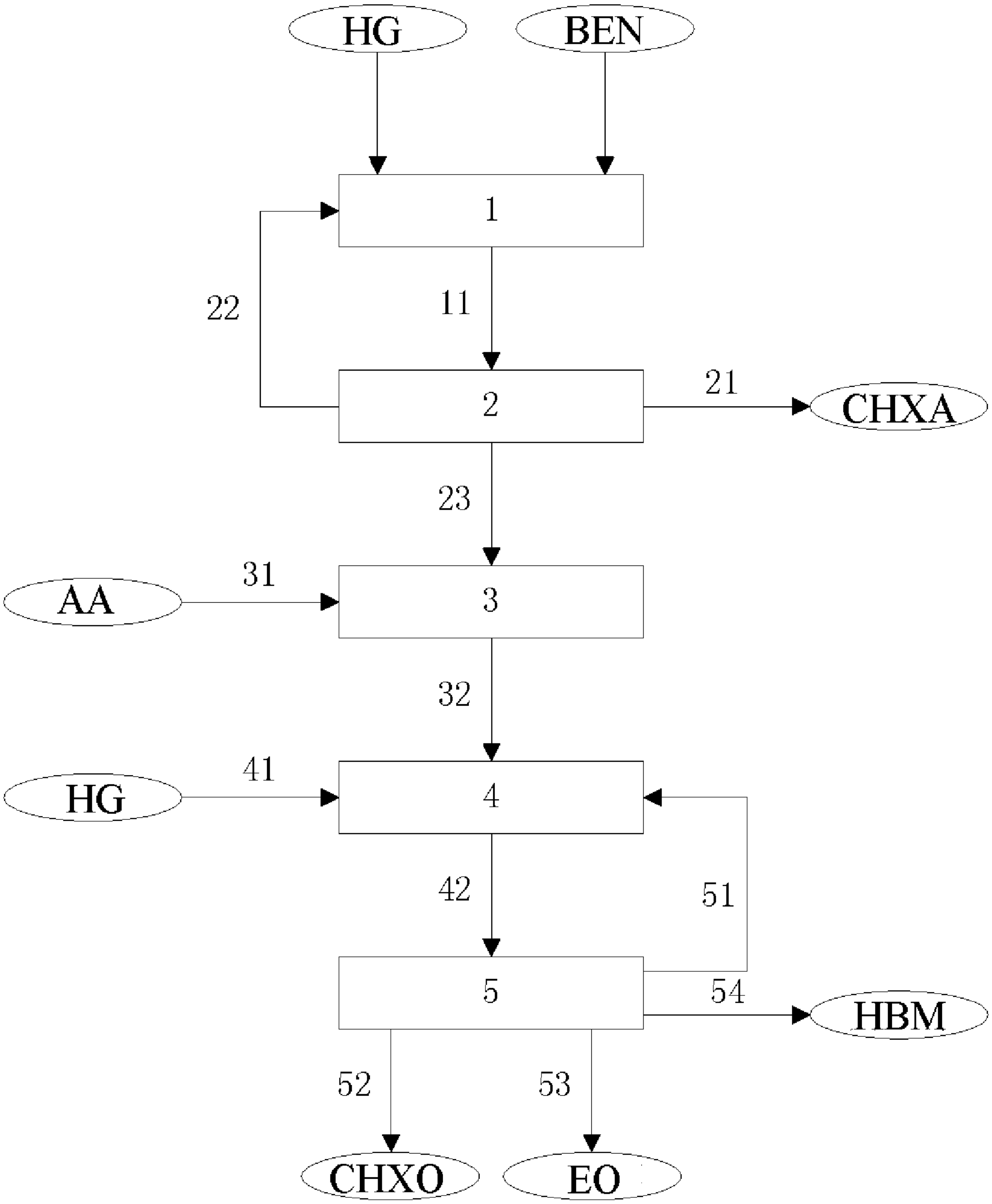

According to the embodiment of FIG. 15, benzene and hydrogen gas are introduced into the benzene hydrogenation reactor 1, in the presence of a benzene hydrogenation catalyst, to conduct a hydrogenation reaction, the benzene hydrogenation product stream via the line 11 is introduced into the benzene hydrogenation product separation unit 2, upon separation to obtain the cyclohexane stream, the cyclohexene stream and the benzene stream, the cyclohexane stream 21 as the by-product is discharged from the apparatus, the benzene stream 22 is recycled back to the benzene hydrogenation reactor 1, the cyclohexene stream via the line 23 is introduced into the reactive rectification tower 3, mixed with acetic acid introduced via the line 31, in the presence of a solid acid catalyst, to conduct an addition esterification reaction, and at the same time, to conduct a separation of the addition esterification product, from the tower top of the reactive rectification tower 3 here is discharged a small stream (to carry away lighter impurities in the feed), from the tower bottom of the reactive rectification tower 3 here is obtained the acetic acid cyclohexyl ester stream, the acetic acid cyclohexyl ester stream is introduced into the ester hydrogenation reactor 4, in the presence of an ester hydrogenation catalyst, contacts with hydrogen gas to conduct an ester hydrogenation reaction, the ester hydrogenation product stream is introduced into the ester hydrogenation product separation unit 5, upon separation to obtain the ethanol stream 53, the cyclohexanol stream 52, the acetic acid cyclohexyl ester stream 51 and the high-boiling material stream 54, the cyclohexanol stream and the ethanol stream as the product are discharged from the apparatus, the high-boiling material stream as the by-product is discharged from the apparatus, the acetic acid cyclohexyl ester stream is recycled back to the ester hydrogenation reactor 5.

Figure 16:
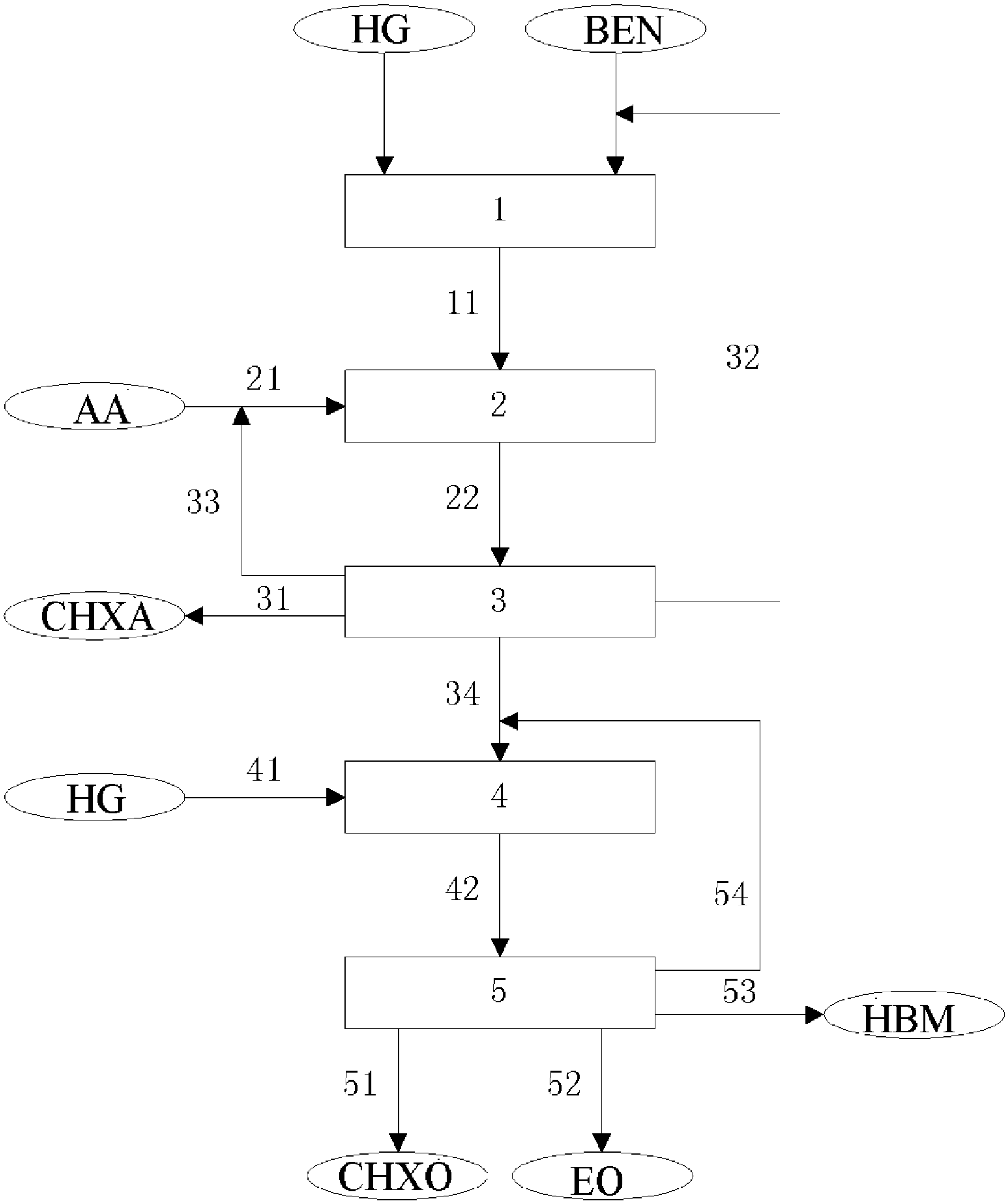

According to the embodiment of FIG. 16, benzene and hydrogen gas are introduced into the benzene hydrogenation reactor 1, in the presence of a benzene selective hydrogenation catalyst, to conduct a hydrogenation reaction, the benzene hydrogenation product stream via the line 11 is introduced into the addition esterification reactor 2, mixed with acetic acid introduced via the line 21, in the presence of a solid acid catalyst, to conduct an addition esterification reaction, the addition esterification product stream via the line 22 is introduced into the addition esterification product separation unit 3, upon separation to obtain the cyclohexane stream 31, the benzene stream 32, the acetic acid stream 33 and the acetic acid cyclohexyl ester stream 34, the benzene stream is recycled back to the benzene hydrogenation reactor 1, the acetic acid stream is recycled back to the addition esterification reactor 2, the acetic acid cyclohexyl ester stream is introduced into the ester hydrogenation reactor 4, in the presence of an ester hydrogenation catalyst, contacts with hydrogen gas to conduct an ester hydrogenation reaction, the ester hydrogenation product stream is introduced into the ester hydrogenation product separation unit 5, upon separation to obtain the cyclohexanol stream 51, the ethanol stream 52, the high-boiling material stream 53 and the acetic acid cyclohexyl ester stream 54, the cyclohexanol stream and the ethanol stream as the product are discharged from the apparatus, the high-boiling material stream as the by-product is discharged from the apparatus, the acetic acid cyclohexyl ester stream is recycled back to the ester hydrogenation reactor 4.

EXAMPLE

The following examples intend to illustrate this invention, rather than to limit same.

The First Embodiment

Examples 1 to 6

Catalyst Production

The catalysts of Examples 1 to 6 were produced in line with the following procedure: A predetermined amount of each soluble metal salts was weighted in line with the formulation of Table 1, placed into a 2000 mL three necked flask, there was added water so as to dissolve and produce same into a solution of about 1000 mL, onto the flask, there were equipped with a stirrer, a pH meter and a thermometer, and then the flask was placed into a thermostatic waterbath whose temperature was adjustable, starting stirring, adjusting the temperature of the thermostatic waterbath, a precipitating agent solution with a predetermined concentration was dropwise introduced into the flask, the introduction speed of the aqueous precipitating agent solution was controlled such that the temperature of the solution did not increase by more than 1 degrees Celsius. As the pH value of the solution increased, precipitation began to form in the solution, and gradually increased in terms of amount as the pH value increased, when the pH value of the solution reached a predetermined value, the introduction of the aqueous precipitating agent solution was terminated. Then, still under stirring, with the temperature retained at a predetermined value, the reaction system was aged for a predetermined duration. The stirring was stopped, and the reaction system was naturally cooled to RT, the precipitation was filtered on a high-speed centrifuge, and washed for 5 times with deionized water, and then the resultant precipitation was dried in an oven and then calcinated in a Muffle furnace, to obtain a mixed metal oxide. The mixed metal oxide was impregnated with an alkaline solution with a predetermined concentration at RT, filtered under vacuum, separated off the impregnation solution, and then the resultant mixture was dried in an oven and then calcinated in a Muffle furnace, to obtain the final mixed metal oxide. An ICP method was used to analyze the composition of the sample. The production conditions in details and the results were listed in Table 1.

Examples 7 to 15

Catalyst Evaluation in an Autoclave

Examples 7 to 15 related to an acetic acid cyclohexyl ester hydrogenation experiment in an autoclave by the catalyst obtained from each of Examples 1 to 6 respectively, whose procedure was as follows: a predetermined amount of the catalyst powder was placed into a 500 mL autoclave, then there was added 250 g acetic acid cyclohexyl ester, after closing the autoclave, the inside thereof was replaced with nitrogen gas for 3 times, then there was supplied hydrogen gas to a predetermined pressure, gradually heated, at about 80 degrees Celsius, the pressure in the autoclave began to drop, which indicated that the catalyst in the autoclave began to initiate an ester hydrogenation reaction by reduction, hydrogen gas was replenished as needed to retain the pressure inside the autoclave at a predetermined value, and at the end, heated to a predetermined temperature, and at this temperature, with the pressure retained, reacted for a predetermined duration, and then the reaction was terminated, cooled to the room temperature, and then the reaction product and the catalyst were discharged. The composition of the product was determined by vapor phase chromatography analysis, and based on the analytic results, the following calculation formula was used to obtain the single-pass conversion of acetic acid cyclohexyl ester and the single-pass selectivity to cyclohexanol.

The single-pass conversion of acetic acid cyclohexyl ester=[1−the mole number of unreacted acetic acid cyclohexyl ester/(the mole number of unreacted acetic acid cyclohexyl ester+the mole number of cyclohexane+the mole number of cyclohexanol+the mole number of ethyl cyclohexyl ether]×100%

The single-pass selectivity to cyclohexanol=[the mole number of cyclohexanol/(the mole number of cyclohexanol+the mole number of cyclohexane+the mole number of ethyl cyclohexyl ether)]×100%

Example 16

Ester Hydrogenation in a Fixed Bed

The catalyst powder obtained from Example 3 was tableted, and crashed and screened out particles of 40 to 60 mesh, 40 g of the catalyst particles was loaded into a Φ20×2.5×800 mm jacketed stainless steel tube reactor at the middle part thereof, below and above which there were packed a predetermined amount of quartz sand, supplied with hydrogen gas (500 mL/min) to conduct a reduction under the conditions of 280 degrees Celsius and 6 MPa for 24 h, and then lowered to the predetermined reaction temperature. Acetic acid cyclohexyl ester via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 3. The results revealed that, the single-pass conversion of the acetic acid cyclohexyl ester hydrogenation reaction was up to 99.5% or more, the single-pass selectivity to the ester product was greater than 99.0%, and after a run time of 1000 h, the single-pass conversion and the single-pass selectivity did not significantly drop.

Comparative Examples 1 to 2

The catalyst was produced in line with the formulation of Example 1, with the exception that no NaOH solution treatment was involved, and the second drying and calcination treatment was not conducted. The production conditions and the composition of the resultant catalyst were listed in Table 1 as Comparative Example 1.

The resultant catalyst was evaluated with the acetic acid cyclohexyl ester hydrogenation in an autoclave. The evaluation conditions and the results were listed in Table 2 as Comparative Example 2.

The results revealed that, the catalyst, if not treated by an alkaline, will result in more production of cyclohexane and ethyl cyclohexyl ether as the by-product, leading to relatively lowered hydrogenation reaction single-pass selectivity.

TABLE 1

Catalyst production results

| Example | Ingredients | precipitating agent | precipitation conditions | aging conditions | first heat treatment conditions | alkali solution treatment conditions | second heat treatment conditions | catalyst weight (before reduction) | catalyst composition (before reduction, percentage by weight) |
|---|---|---|---|---|---|---|---|---|---|
| Example 1 | copper nitrate trihydrate: 0.4 mol<br>zinc nitrate hexahydrate: 0.3 mol<br>aluminium nitrate nonahydrate: 0.3 mol | 5% NaOH | temperature: 40 degrees Celsius<br>end point pH: 8.0 | temperature: 40 degrees Celsius<br>duration: 2 h | drying temperature: 120 degrees Celsius<br>drying duration: 5 h<br>calcination temperature: 350 degrees Celsius<br>calcination duration: 6 h | 1% KOH impregnated for 1 h | drying temperature: 120 degrees Celsius<br>drying duration: 5 h<br>calcination temperature: 350 degrees Celsius<br>calcination duration: 5 h | 65.6 g | CuO: 44.22%<br>ZnO: 33.8%<br>$Al_2O_3$: 21.28%<br>KOH: 0.7% |
| Example 2 | copper nitrate trihydrate: 0.4 mol<br>zinc nitrate hexahydrate: 0.3 mol<br>lanthanum nitrate hexahydrate: 0.3 mol | 5% NaOH | temperature: RT<br>end point pH: 9.0 | temperature: 60 degrees Celsius<br>duration: 1 h | drying temperature: 120 degrees Celsius<br>drying duration: 6 h<br>calcination temperature: 400 degrees Celsius<br>calcination duration: 5 h | 1% KOH impregnated for 1 h | drying temperature: 120 degrees Celsius<br>drying duration: 5 h<br>calcination temperature: 300 degrees Celsius<br>calcination duration: 6 h | 93.5 g | CuO: 30.06%<br>ZnO: 22.97%<br>$La_2O_3$: 46.21%<br>KOH: 0.76% |

TABLE 1-continued

Catalyst production results

| Example | Ingredients | precipitating agent | precipitation conditions | aging conditions | first heat treatment conditions | alkali solution treatment conditions | second heat treatment conditions | catalyst weight (before reduction) | catalyst composition (before reduction, percentage by weight) |
|---|---|---|---|---|---|---|---|---|---|
| Example 3 | copper nitrate trihydrate: 0.4 mol zinc nitrate hexahydrate: 0.3 mol aluminium nitrate nonahydrate: 0.2 mol lanthanum nitrate hexahydrate: 0.1 mol | 5% NaOH | temperature: 60 degrees Celsius end point pH: 7.0 | temperature: 60 degrees Celsius duration: 1 h | drying temperature: 100 degrees Celsius drying duration: 8 h calcination temperature: 320 degrees Celsius calcination duration: 8 h | 1% KOH impregnated for 1 h | drying temperature: 120 degrees Celsius drying duration: 5 h calcination temperature: 300 degrees Celsius calcination duration: 6 h | 81.8 g | CuO: 36.01% ZnO: 27.52% $Al_2O_3$: 17.33% $La_2O_3$: 18.46% KOH: 0.68% |
| Example 4 | copper nitrate trihydrate: 0.5 mol zinc nitrate hexahydrate: 0.3 mol aluminium nitrate nonahydrate: 0.1 mol lanthanum nitrate hexahydrate: 0.1 mol | 5% NaOH | temperature: 60 degrees Celsius end point pH: 7.0 | temperature: 80 degrees Celsius duration: 1 h | drying temperature: 120 degrees Celsius drying duration: 6 h calcination temperature: 350 degrees Celsius calcination duration: 6 h | 1% $Ba(OH)_2$ impregnated for 1 h | drying temperature: 120 degrees Celsius drying duration: 5 h calcination temperature: 300 degrees Celsius calcination duration: 6 h | 80.3 g | CuO: 45.68% ZnO: 28.12% $Al_2O_3$: 6.0% $La_2O_3$: 18.86% $Ba(OH)_2$: 1.16% |
| Example 5 | copper nitrate trihydrate: 0.4 mol zinc nitrate hexahydrate: 0.3 mol zirconium nitrate pentahydrate: 0.2 mol stannous chloride dihydrate: 0.1 mol | 5% $Na_2CO_3$ | temperature: 60 degrees Celsius end point pH: 8.5 | temperature: 80 degrees Celsius duration: 1 h | drying temperature: 120 degrees Celsius drying duration: 6 h calcination temperature: 350 degrees Celsius calcination duration: 6 h | 2% NaOH impregnated for 1 h | drying temperature: 120 degrees Celsius drying duration: 5 h calcination temperature: 350 degrees Celsius calcination duration: 6 h | 88.2 g | CuO: 32.85% ZnO: 25.1% $ZrO_2$: 25.42% $SnO_2$: 15.6% NaOH: 1.03% |
| Example 6 | copper nitrate trihydrate: 0.4 mol zinc nitrate hexahydrate: 0.3 mol aluminium nitrate nonahydrate: 0.2 mol thorium nitrate tetrahydrate: 0.1 mol | 5% $Na_2CO_3$ | temperature: 60 degrees Celsius end point pH: 7.0 | temperature: 80 degrees Celsius duration: 1 h | drying temperature: 120 degrees Celsius drying duration: 6 h calcination temperature: 350 degrees Celsius calcination duration: 6 h | 2% NaOH impregnated for 1 h | drying temperature: 150 degrees Celsius drying duration: 4 h calcination temperature: 320 degrees Celsius calcination duration: 6 h | 84.5 g | CuO: 33.95% ZnO: 25.94% $Al_2O_3$: 10.8% $ThO_2$: 28.2% NaOH: 1.1% |
| Comparative Example 1 | copper nitrate trihydrate: 0.4 mol zinc nitrate hexahydrate: 0.3 mol aluminium nitrate nonahydrate: 0.3 mol | 5% NaOH | temperature: 40 degrees Celsius end point pH: 8.0 | temperature: 40 degrees Celsius duration: 2 h | drying temperature: 120 degrees Celsius drying duration: 5 h calcination temperature: 350 degrees Celsius calcination duration: 6 h | | | 65.0 g | CuO: 44.38% ZnO: 34.02% $Al_2O_3$: 21.6% |

TABLE 2

Catalyst evaluation in an autoclave results

| Example | feed ratio | reaction conditions | reaction results: ethanol m % | reaction results: acetic acid ethyl ester m % | reaction results: cyclohexane m % |
|---|---|---|---|---|---|
| Example 7 | catalyst from: Example 1 catalyst amount: 40 g acetic acid cyclohexyl ester amount: 250 g | temperature: 250 degrees Celsius pressure: 6.0 MPa reaction duration: 4 h | 30.21 | 1.09 | 0.34 |
| Example 8 | catalyst from: Example 2 catalyst amount: 40 g acetic acid cyclohexyl ester amount: 250 g | temperature: 250 degrees Celsius pressure: 6.0 MPa reaction duration: 4 h | 30.55 | 0.77 | 0.28 |
| Example 9 | catalyst from: Example 3 catalyst amount: 40 g acetic acid cyclohexyl ester amount: 250 g | temperature: 250 degrees Celsius pressure: 6.0 MPa reaction duration: 4 h | 30.82 | 0.56 | 0.29 |
| Example 10 | catalyst from: Example 3 catalyst amount: 30 g acetic acid cyclohexyl ester amount: 250 g | temperature: 250 degrees Celsius pressure: 10.0 MPa reaction duration: 4 h | 31.15 | 0.30 | 0.57 |
| Example 11 | catalyst from: Example 3 catalyst amount: 30 g acetic acid cyclohexyl ester amount: 250 g | temperature: 280 degrees Celsius pressure: 12.0 MPa reaction duration: 2 h | 31.49 | 0.00 | 1.15 |
| Example 12 | catalyst from: Example 3 catalyst amount: 30 g acetic acid cyclohexyl ester amount: 250 g | temperature: 200 degrees Celsius pressure: 4.0 MPa reaction duration: 6 h | 26.90 | 3.87 | 0.11 |
| Example 13 | catalyst from: Example 4 catalyst amount: 40 g acetic acid cyclohexyl ester amount: 250 g | temperature: 250 degrees Celsius pressure: 6.0 MPa reaction duration: 4 h | 30.70 | 0.57 | 0.34 |
| Example 14 | catalyst from: Example 5 catalyst amount: 40 g acetic acid cyclohexyl ester amount: 250 g | temperature: 250 degrees Celsius pressure: 6.0 MPa reaction duration: 4 h | 30.80 | 0.48 | 0.23 |
| Example 15 | catalyst from: Example 6 catalyst amount: 40 g acetic acid cyclohexyl ester amount: 250 g | temperature: 250 degrees Celsius pressure: 6.0 MPa reaction duration: 4 h | 31.09 | 0.27 | 0.29 |
| Comparative Example 2 | catalyst from: Comparative Example 1 catalyst amount: 40 g acetic acid cyclohexyl ester amount: 250 g | temperature: 250 degrees Celsius pressure: 6.0 MPa reaction duration: 4 h | 27.43 | 2.43 | 1.10 |

| Example | reaction results: ethyl cyclohexyl ether m % | reaction results: cyclohexanol m % | reaction results: acetic acid cyclohexyl ester m % | single-pass conversion of cyclohexyl ester % | single-pass selectivity to cyclohexanol % |
|---|---|---|---|---|---|
| Example 7 | 0.43 | 67.74 | 0.19 | 99.80 | 98.92 |
| Example 8 | 0.35 | 67.83 | 0.22 | 99.78 | 99.11 |
| Example 9 | 0.35 | 67.92 | 0.08 | 99.92 | 99.11 |
| Example 10 | 0.26 | 67.72 | 0.00 | 100.00 | 98.71 |
| Example 11 | 0.26 | 67.09 | 0.00 | 100.00 | 97.70 |
| Example 12 | 0.40 | 67.15 | 1.56 | 98.40 | 99.35 |
| Example 13 | 0.70 | 67.64 | 0.05 | 99.95 | 98.61 |

TABLE 2-continued

| Catalyst evaluation in an autoclave results | | | | | |
|---|---|---|---|---|---|
| Example 14 | 0.52 | 67.78 | 0.19 | 99.80 | 99.01 |
| Example 15 | 0.44 | 67.87 | 0.05 | 99.95 | 99.00 |
| Comparative Example 2 | 4.20 | 63.85 | 0.98 | 99.00 | 93.28 |

TABLE 3

Acetic acid cyclohexyl ester hydrogenation data on a fixed bed of Example 16

| | reaction conditions | | | | | | reaction results | | | | | | single- | |
|---|---|---|---|---|---|---|---|---|---|---|---|---|---|---|
| run time h | temperature degrees Celsius | pressure MPa | ester feed g/h | hydrogen gas feed mL/min | space velocity h−1 | hydrogen/ester ratio by molar | ethanol m % | acetic acid ethyl ester m % | cyclohexane m % | ethyl cyclohexyl ether m % | cyclohexanol m % | acetic acid cyclohexyl ester m % | pass conversion of cyclohexyl ester % | single-pass selectivity to cyclohexanol % |
| 24 | 200 | 6 | 20 | 400 | 0.5 | 7.62 | 24.54 | 5.51 | 0.10 | 0.31 | 65.74 | 3.81 | 96.10 | 99.46 |
| 48 | 200 | 6 | 20 | 400 | 0.5 | 7.62 | 24.54 | 5.51 | 0.10 | 0.31 | 65.74 | 3.81 | 96.10 | 99.46 |
| 72 | 200 | 6 | 20 | 400 | 0.5 | 7.62 | 24.70 | 5.38 | 0.10 | 0.31 | 65.79 | 3.72 | 96.19 | 99.46 |
| 96 | 220 | 6 | 20 | 400 | 0.5 | 7.62 | 27.30 | 3.53 | 0.16 | 0.41 | 67.18 | 1.42 | 98.54 | 99.25 |
| 120 | 220 | 6 | 20 | 400 | 0.5 | 7.62 | 27.24 | 3.58 | 0.16 | 0.41 | 67.17 | 1.44 | 98.52 | 99.25 |
| 144 | 220 | 6 | 20 | 400 | 0.5 | 7.62 | 27.19 | 3.63 | 0.16 | 0.41 | 67.16 | 1.46 | 98.50 | 99.25 |
| 168 | 235 | 6 | 20 | 400 | 0.5 | 7.62 | 29.55 | 1.68 | 0.17 | 0.43 | 67.87 | 0.30 | 99.69 | 99.22 |
| 192 | 235 | 6 | 20 | 400 | 0.5 | 7.62 | 29.31 | 1.90 | 0.17 | 0.42 | 67.85 | 0.34 | 99.65 | 99.23 |
| 216 | 235 | 6 | 20 | 400 | 0.5 | 7.62 | 29.20 | 2.01 | 0.17 | 0.42 | 67.84 | 0.36 | 99.63 | 99.23 |
| 240 | 250 | 6 | 20 | 400 | 0.5 | 7.62 | 31.09 | 0.27 | 0.23 | 0.44 | 67.93 | 0.05 | 99.95 | 99.10 |
| 264 | 250 | 6 | 20 | 400 | 0.5 | 7.62 | 31.03 | 0.33 | 0.23 | 0.44 | 67.92 | 0.06 | 99.94 | 99.10 |
| 288 | 250 | 6 | 20 | 400 | 0.5 | 7.62 | 31.03 | 0.33 | 0.23 | 0.44 | 67.92 | 0.06 | 99.94 | 99.10 |
| 312 | 265 | 6 | 20 | 400 | 0.5 | 7.62 | 31.18 | 0.17 | 0.34 | 0.53 | 67.76 | 0.01 | 99.99 | 98.80 |
| 336 | 265 | 6 | 20 | 400 | 0.5 | 7.62 | 30.94 | 0.41 | 0.34 | 0.52 | 67.76 | 0.03 | 99.97 | 98.81 |
| 360 | 265 | 6 | 20 | 400 | 0.5 | 7.62 | 31.06 | 0.29 | 0.34 | 0.52 | 67.76 | 0.02 | 99.98 | 98.81 |
| 384 | 300 | 6 | 20 | 400 | 0.5 | 7.62 | 31.24 | 0.06 | 1.15 | 0.88 | 66.67 | 0.00 | 100.00 | 97.00 |
| 408 | 300 | 6 | 20 | 400 | 0.5 | 7.62 | 31.18 | 0.12 | 1.15 | 0.88 | 66.67 | 0.00 | 100.00 | 97.01 |
| 432 | 300 | 6 | 20 | 400 | 0.5 | 7.62 | 31.18 | 0.12 | 1.15 | 0.88 | 66.67 | 0.00 | 100.00 | 97.01 |
| 456 | 250 | 3 | 20 | 400 | 0.5 | 7.62 | 28.02 | 3.10 | 0.22 | 0.41 | 67.69 | 0.56 | 99.43 | 99.15 |
| 480 | 250 | 3 | 20 | 400 | 0.5 | 7.62 | 28.14 | 2.99 | 0.22 | 0.42 | 67.70 | 0.54 | 99.45 | 99.14 |
| 504 | 250 | 3 | 20 | 400 | 0.5 | 7.62 | 26.95 | 4.08 | 0.21 | 0.41 | 67.61 | 0.73 | 99.25 | 99.16 |
| 528 | 250 | 12 | 20 | 400 | 0.5 | 7.62 | 31.32 | 0.05 | 0.23 | 0.44 | 67.94 | 0.01 | 99.99 | 99.10 |
| 552 | 250 | 12 | 20 | 400 | 0.5 | 7.62 | 31.32 | 0.05 | 0.23 | 0.44 | 67.94 | 0.01 | 99.99 | 99.10 |
| 576 | 250 | 12 | 20 | 400 | 0.5 | 7.62 | 31.26 | 0.11 | 0.23 | 0.44 | 67.94 | 0.02 | 99.98 | 99.10 |
| 600 | 250 | 6 | 10 | 400 | 0.25 | 15.24 | 31.32 | 0.05 | 0.23 | 0.44 | 67.94 | 0.01 | 99.99 | 99.10 |
| 624 | 250 | 6 | 10 | 400 | 0.25 | 15.24 | 31.32 | 0.05 | 0.23 | 0.44 | 67.94 | 0.01 | 99.99 | 99.10 |
| 648 | 250 | 6 | 10 | 400 | 0.25 | 15.24 | 31.32 | 0.05 | 0.23 | 0.44 | 67.94 | 0.01 | 99.99 | 99.10 |
| 672 | 250 | 6 | 40 | 400 | 1 | 3.81 | 21.03 | 9.54 | 0.19 | 0.36 | 67.17 | 1.71 | 98.25 | 99.24 |
| 696 | 250 | 6 | 40 | 400 | 1 | 3.81 | 21.96 | 8.68 | 0.19 | 0.37 | 67.24 | 1.56 | 98.41 | 99.23 |
| 720 | 250 | 6 | 40 | 400 | 1 | 3.81 | 21.82 | 8.81 | 0.19 | 0.37 | 67.23 | 1.58 | 98.38 | 99.23 |
| 744 | 250 | 6 | 20 | 2000 | 0.5 | 38.09 | 31.15 | 0.22 | 0.23 | 0.44 | 67.93 | 0.04 | 99.96 | 99.10 |
| 768 | 250 | 6 | 20 | 2000 | 0.5 | 38.09 | 31.21 | 0.16 | 0.23 | 0.44 | 67.94 | 0.03 | 99.97 | 99.10 |
| 792 | 250 | 6 | 20 | 2000 | 0.5 | 38.09 | 31.26 | 0.11 | 0.23 | 0.44 | 67.94 | 0.02 | 99.98 | 99.10 |
| 816 | 250 | 6 | 20 | 400 | 0.5 | 7.62 | 30.67 | 0.65 | 0.23 | 0.43 | 67.89 | 0.12 | 99.88 | 99.11 |
| 840 | 250 | 6 | 20 | 400 | 0.5 | 7.62 | 30.62 | 0.71 | 0.23 | 0.43 | 67.89 | 0.13 | 99.87 | 99.11 |
| 864 | 250 | 6 | 20 | 400 | 0.5 | 7.62 | 30.67 | 0.65 | 0.23 | 0.43 | 67.89 | 0.12 | 99.88 | 99.11 |
| 888 | 250 | 6 | 20 | 400 | 0.5 | 7.62 | 31.09 | 0.27 | 0.23 | 0.44 | 67.93 | 0.05 | 99.95 | 99.10 |
| 912 | 250 | 6 | 20 | 400 | 0.5 | 7.62 | 31.15 | 0.22 | 0.23 | 0.44 | 67.93 | 0.04 | 99.96 | 99.10 |
| 936 | 250 | 6 | 20 | 400 | 0.5 | 7.62 | 30.62 | 0.71 | 0.23 | 0.43 | 67.89 | 0.13 | 99.87 | 99.11 |
| 960 | 250 | 6 | 20 | 400 | 0.5 | 7.62 | 30.50 | 0.81 | 0.23 | 0.43 | 67.88 | 0.15 | 99.85 | 99.11 |
| 984 | 250 | 6 | 20 | 400 | 0.5 | 7.62 | 30.73 | 0.60 | 0.23 | 0.43 | 67.90 | 0.11 | 99.89 | 99.11 |
| 1008 | 250 | 6 | 20 | 400 | 0.5 | 7.62 | 30.44 | 0.87 | 0.23 | 0.43 | 67.88 | 0.16 | 99.84 | 99.11 |

The Second Embodiment

Example 1

This example illustrates a process for producing acetic acid cyclohexyl ester in a fixed bed reactor with cyclohexene and acetic acid as the feed.

The fixed bed reactor was a Φ48×4×1200 mm 316L stainless steel tube, whose outer was equipped with hot water jacket, into which jacket there may be supplied hot water so as to control the reaction temperature. 500 mL of a macroporous hydrogenous strong-acid ion exchange resin (synthesized at lab according to a classical literature method, wherein a styrene solution containing 15% divinylbenzene was subject to a suspension copolymerization and produced into base spherical particles, and then sulfonated by concentrated sulfuric acid, with a measured exchange capacity of 5.2 mmol $H^{+}$/g on dry basis) was loaded into the fixed bed reactor at the middle part thereof, below and above which there were packed a predetermined amount of quartz sand. Cyclohexene and acetic acid via a dosing pump were pumped respectively into the fixed bed reactor to conduct the reaction, the temperature of hot water in the fixed bed reactor jacket was adjusted to control the reaction temperature, the ready-state reaction conditions and reaction results were listed in Table 1.

TABLE 1

Experimental data observed with the fixed bed catalyzed by the macroporous hydrogenous strong-acid ion exchange resin

| reactor operation conditions | | |
|---|---|---|
| operation pressure | the normal pressure | |
| jacket hot water temperature | 90 degrees Celsius | |
| catalyst bed temperature | 90 to 95 degrees Celsius | |
| mass | reactor feed | reactor outlet |
| flow rate g/h | 2612 | 2612 |
| temperature degrees Celsius | 25 | 95 |
| composition (ratio by mass) | | |
| cyclohexene | 47.7% | 5.15% |
| benzene | | |
| cyclohexane | | |
| acetic acid | 52.3% | 21.1% |
| acetic acid cyclohexyl ester | | 73.4% |
| polymers | | 0.35% |

Example 2

This example illustrates the results of a hydrogenation of a mixed stream of acetic acid and acetic acid cyclohexyl ester.

The reaction system comprised of one single fixed bed reactor, which was a jacketed titanium steel tube, with a size of Φ20×2.5×800 mm. The catalyst was loaded as two layers into the reactor. As the upper layer there was loaded 20 g silica supported platinum-palladium-tin based acetic acid hydrogenation catalyst (synthesized at lab, with a composition of Pt (10%)-Pd (5%)-Sn (5%)/$SiO_2$, by a method wherein a macroporous silica carrier of 20 to 40 mesh (with a BET specific surface area of 400 $m^2/g$, a pore volume of 0.35 mL/g) was impregnated with a mixed solution of chloroplatinic acid, palladium chloride and stannous chloride, and then dried at 120 degrees Celsius, calcinated at a temperature of 500 degrees Celsius); As the lower layer there was loaded 20 g copper-zinc-aluminium based ester hydrogenation catalyst (synthesized at lab, with a composition of CuO 40%, ZnO 29.6%, $Al_2O_3$ 30.4%, by a method wherein to a copper, zinc, chromium nitrate solution, there was added a NaOH solution till pH=9.0, and then centrifugal separated, washed, dried, tableted, calcinated). The catalysts were loaded into the reactor at the middle part (the constant temperature section) thereof, the two catalyst layers were separated apart by glass-fiber fabric, to both ends of the reactor there were packed a predetermined amount of quartz sand, functioning as a section for evaporating the feed stock by heating or as a packing. To the reactor jacket, there may be supplied heat conducting oil to control the reaction temperature. Upon completion of the catalyst loading into the reactor, the reaction system was connected, after passing the air tightness test, there was supplied hydrogen gas (500 mL/min) to conduct a reduction reaction under the conditions of 300 degrees Celsius and 6 MPa for 24 h, and then lowered to a predetermined temperature and pressure of the hydrogenation reaction. A mixture of acetic acid and acetic acid cyclohexyl ester (the reactor outlet stream from Example 1) via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 2.

TABLE 2

Experimental data observed with the hydrogenation of a mixed stream of acetic acid and acetic acid cyclohexyl ester

| | reaction conditions | | | | | | reaction results | | |
|---|---|---|---|---|---|---|---|---|---|
| run time | temperature degrees Celsius | pressure MPa | feed g/h | hydrogen gas feed mL/min | space velocity $h^{-1}$ | hydrogen/ester ratio 50 | ethanol m % | acetic acid ethyl ester m % | cycyclohexane m % |
| 60 | 240 | 6 | 20 | 4000 | 0.5 | 50 | 40.05 | 0.66 | 4.52 |
| 120 | 250 | 6 | 20 | 4000 | 0.5 | 50 | 40.66 | 0.24 | 4.52 |
| 180 | 250 | 6 | 20 | 4000 | 0.5 | 25 | 39.33 | 1.09 | 4.62 |
| 240 | 250 | 6 | 20 | 4000 | 0.5 | 12.5 | 38.60 | 1.07 | 4.63 |
| 300 | 250 | 6 | 20 | 4000 | 0.5 | 50 | 39.96 | 0.49 | 4.63 |
| 360 | 260 | 6 | 20 | 4000 | 0.5 | 50 | 40.3 | 0.1 | 4.63 |

| | reaction results | | | | | | |
|---|---|---|---|---|---|---|---|
| run time | cycyclohexanol m % | ethyl cyclohexyl ether m % | acetic acid cyclohexyl ester m % | acetic acid m % | heavier components | single-pass conversion of cyclohexyl ester % | single-pass selectivity to cyclohexanol % |
| 60 | 53.05 | 0.34 | 0.76 | 0.19 | 0.49 | 99.05 | 98.1 |
| 120 | 53.26 | 0.34 | 0.38 | 0.11 | 0.49 | 99.5 | 99.0 |
| 180 | 52.78 | 0.27 | 1.15 | 0.39 | 0.38 | 99.0 | 99.8 |
| 240 | 51.33 | 1.32 | 2.14 | 0.52 | 0.39 | 97.1 | 98.04 |

TABLE 2-continued

| Experimental data observed with the hydrogenation of a mixed stream of acetic acid and acetic acid cyclohexyl ester | | | | | | | |
|---|---|---|---|---|---|---|---|
| 300 | 52.29 | 1.36 | 0.75 | 0.19 | 0.39 | 99.05 | 97.1 |
| 360 | 52.0 | 2.41 | 0.1 | 0.06 | 0.39 | 99.8 | 96.2 |

The Third Embodiment

Example 1

This example illustrates a process for producing acetic acid cyclohexyl ester in a reactive rectification tower with cyclohexene and acetic acid as the feed.

The experiment was performed on a reactive rectification model experiment apparatus with these specifications: the main part of the model apparatus was a stainless steel tower having a diameter (inner diameter) of 50 mm, a height of 3 m, the lower part of which communicated with a bottom having a volume of 5 L, inside the bottom there was installed a 10 KW electrical heating rod, which was used to via an intelligent controller through silicon controlled rectifier (SCR) control the heating at the bottom. The tower top communicated with a condenser having a heat exchange area of 0.5 $m^2$, vapor from the tower top was condensed by this condenser into liquid and then introduced into a reflux tank having a volume of 2 L. Liquid in the reflux tank was partially refluxed by a reflux pump back to the reaction tower, partially withdrawn as lighter components. The operation parameters of the tower were controlled by and displayed on an intelligent type automatic control instrument. The tower reflux rate was controlled by a reflux control valve, the top withdrawal was controlled by a level controller at the reflux tank. The bottom withdrawal was controlled by a bottom blow-off valve which was controlled by a bottom level controller.

A high temperature resistant sulfonic acid type ion exchange resin (with a trade name of Amberlyst 45, produced by the Rhom&Hass company) was by a multi-stage high speed grinder ground into powder having a particle size of less than 200 mesh (0.074 mm), there was added a porogenic agent, a lubricant, an antioxidant and a binder, mixed homogeneously with a high-speed mixer, and then with an internal mixer at 180 degrees Celsius mixed for 10 min, to completely plasticize the mass, and then injected into a mould and formed into a raschig ring type resin catalyst packing having a diameter of 5 mm, a height of 5 mm and a wall thickness of 1 mm. 1950 mL of the packing was loaded into the middle part of a model reaction tower (with a height of 1 m, corresponding to a theoretical plate number of 8), above and below which there was each loaded 1950 mL of a glass spring packing having a diameter of 3 mm and a length of 6 mm (with a loading height of 1 m, corresponding to a theoretical plate number of 10). Cyclohexene and acetic acid via a dosing pump were pumped respectively into a preheater and preheated and then introduced into the reaction tower, adjusting the heating at the bottom and the reflux rate at the tower top to continuously conduct the reaction, the steady-state reaction conditions and reaction results were listed in Table 1.

TABLE 1

Experimental data observed with the reactive rectification catalyzed by the high temperature resistant sulfonic acid type ion exchange resin catalyst

| operation conditions | |
|---|---|
| operation pressure | 0.3 MPa |
| top temperature | 130 degrees Celsius |
| catalyst section temperature | 125 to 140 degrees Celsius |
| bottom temperature | 190 degrees Celsius |
| reflux ratio | 300 |

| mass | reactive rectification tower feed | top with-drawal | bottom with-drawal |
|---|---|---|---|
| flow rate g/h | 1012 | 8 | 1004 |
| temperature degrees Celsius | 40 | 40 | 190 |
| composition (wt %) | | | |
| acetic acid | 59.4% | 11.4% | 30.5% |
| benzene | | | |
| cyclohexene | 40.6% | 88.6% | |
| cyclohexane | | | |
| acetic acid cyclohexyl ester | | | 69.4% |
| polymers | | | 0.1% |

Example 2

This example illustrates the hydrogenation results of a mixed stream of acetic acid and acetic acid cyclohexyl ester.

The reaction system comprised of one single fixed bed reactor, which was a jacketed titanium steel tube, with a size of Φ20×2.5×800 mm. The catalyst was loaded as two layers into the reactor. As the upper layer there was loaded 20 g silica supported platinum-palladium-tin based acetic acid hydrogenation catalyst (synthesized at lab, with a composition of Pt (10 m %)-Pd (5 m %)-Sn (5 m %)/$SiO_2$, by a method wherein a macroporous silica carrier of 20 to 40 mesh (with a BET specific surface area of 400 $m^2$/g, a pore volume of 0.35 mL/g) was impregnated with a mixed solution of chloroplatinic acid, palladium chloride and stannous chloride, and then dried at 120 degrees Celsius, calcinated at a temperature of 500 degrees Celsius); As the lower layer there was loaded 20 g copper-zinc-aluminium based ester hydrogenation catalyst (synthesized at lab, with a composition of CuO 40 m %, ZnO 29.6 m %, $Al_2O_3$ 30.4 m %, by a method wherein to a copper, zinc, chromium nitrate solution, there was added a NaOH solution till pH=9.0, and then centrifugal separated, washed, dried, tableted, calcinated). The catalysts were loaded into the reactor at the middle part (the constant temperature section) thereof, the two catalyst layers were separated apart by glass-fiber fabric, to both ends of the reactor there were packed a predetermined amount of quartz sand, functioning as a section for evaporating the feed stock by heating or as a packing. To the reactor jacket, there may be supplied heat conducting oil to control the reaction temperature. Upon completion of the catalyst loading into the reactor, the reaction system was connected, after passing the air tightness test, there was supplied hydrogen gas (500 mL/min) to conduct a reduction reaction under the conditions of 300 degrees Celsius and 6 MPa for 24 h, and then lowered to a predetermined temperature and pressure of the hydrogenation reaction. A mixture of acetic acid and acetic acid cyclohexyl ester (the tower bottom stream from Example 1) via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 2.

TABLE 2

Experimental data observed with the hydrogenation of a mixed stream of acetic acid and acetic acid cyclohexyl ester

| | reaction conditions | | | | | | reaction results | | |
|---|---|---|---|---|---|---|---|---|---|
| run time h | temperature degrees Celsius | pressure MPa | feed g/h | hydrogen gas feed mL/min | space velocity $h^{-1}$ | hydrogen/ester ratio 50 | ethanol m % | acetic acid ethyl ester m % | cyclohexane m % |
| 60 | 240 | 6 | 20 | 4000 | 0.5 | 50 | 47.29 | 0.28 | 0 |
| 120 | 250 | 6 | 20 | 4000 | 0.5 | 50 | 47.82 | 0.12 | 0 |
| 180 | 250 | 6 | 20 | 2000 | 0.5 | 25 | 47.33 | 0.24 | 0 |
| 240 | 250 | 5 | 20 | 1000 | 0.5 | 12.5 | 45.68 | 0.95 | 0 |
| 300 | 250 | 4 | 20 | 4000 | 0.5 | 50 | 47.03 | 0.47 | 0 |
| 360 | 260 | 6 | 20 | 4000 | 0.5 | 50 | 47.56 | 0.07 | 0 |

| | reaction results | | | | | | |
|---|---|---|---|---|---|---|---|
| run time h | cyclohexanol m % | ethyl cyclohexyl ether m % | acetic acid cyclohexyl ester m % | acetic acid m % | heavier components m % | single-pass conversion of cyclohexyl ester % | single-pass selectivity to cyclohexanol % |
| 60 | 50.28 | 0.65 | 1.10 | 0.29 | 0.11 | 98.5 | 99.00 |
| 120 | 50.69 | 0.82 | 0.37 | 0.08 | 0.11 | 99.5 | 98.75 |
| 180 | 49.99 | 1.44 | 0.73 | 0.16 | 0.11 | 99 | 97.80 |
| 240 | 48.82 | 1.60 | 2.20 | 0.64 | 0.11 | 97 | 97.50 |
| 300 | 50.16 | 1.18 | 0.73 | 0.32 | 0.11 | 99 | 98.20 |
| 360 | 49.86 | 2.25 | 0.11 | 0.05 | 0.11 | 99.85 | 96.60 |

The Fourth Embodiment

Examples 1 to 4 illustrates a process for producing acetic acid cyclohexyl ester by a reactive rectification.

Examples 1 to 4 were all performed on a reactive rectification model experiment apparatus with these specifications: the main part of the model apparatus was a stainless steel tower having a diameter (inner diameter) of 50 mm, a height of 3 m, the lower part of which communicated with a bottom having a volume of 5 L, inside the bottom there was installed a 10 KW electrical heating rod, which was used to via an intelligent controller through silicon controlled rectifier (SCR) control the heating at the bottom. The tower top communicated with a condenser having a heat exchange area of 0.5 $m^2$, vapor from the tower top was condensed by this condenser into liquid and then introduced into a reflux tank having a volume of 2 L. Liquid in the reflux tank was partially refluxed by a reflux pump back to the reaction tower, partially withdrawn as lighter components. The operation parameters of the tower were controlled by and displayed on an intelligent type automatic control instrument. The tower reflux rate was controlled by a reflux control valve, the top withdrawal was controlled by a level controller at the reflux tank. The bottom withdrawal was controlled by a bottom blow-off valve which was controlled by a bottom level controller. Acetic acid and cyclohexene as the feed were respectively supplied into a 30 L storage tank, and through a dosing pump were pumped respectively into the corresponding preheater and preheated to a predetermined temperature and then introduced into the reaction tower, the feeding rate was controlled by the dosing pump and accurately metered by an electronic balance.

Example 1

A high temperature resistant sulfonic acid type ion exchange resin (with a trade name of Amberlyst 45, produced by the Rhom&Hass company) was by a multi-stage high speed grinder ground into powder having a particle size of less than 200 mesh (0.074 mm), there was added a porogenic agent, a lubricant, an antioxidant and a binder, mixed homogeneously with a high-speed mixer, and then with an internal mixer at 180 degrees Celsius mixed for 10 min, to completely plasticize the mass, and then injected into a mould and formed into a raschig ring type resin catalyst packing having a diameter of 5 mm, a height of 5 mm and a wall thickness of 1 mm. 1950 mL of the packing was loaded into the middle part of a model reaction tower (with a height of 1 m, corresponding to a theoretical plate number of 8), above and below which there was each loaded 1950 mL of a glass spring packing having a diameter of 3 mm and a length of 6 mm (with a loading height of 1 m, corresponding to a theoretical plate number of 10). Cyclohexene and acetic acid via a dosing pump were pumped respectively into a preheater and preheated and then introduced into the reaction tower, adjusting the heating at the bottom and the reflux rate at the tower top to continuously conduct the reaction, the steady-state reaction conditions and reaction results were listed in Table 1.

Example 2

The reaction tower and the catalyst arrangement were the same as Example 1, with the exception that a mixture of cyclohexene, cyclohexane and benzene was used in place of cyclohexene to conduct the experiment, and the reaction tower was operated at 0.3 MPa. The heating at the bottom and the reflux rate at the tower top were controlled so as to continuously conduct the reaction, the steady-state reaction conditions and reaction results were listed in Table 2.

Example 3

A Φ3 to 4 spherical $H_{0.5}Cs_{2.5}PW_{12}O_{40}/SiO_2$ catalyst (obtained by: $H_{0.5}Cs_{2.5}PW_{12}O_{40}$ powder and wide hole silica gel powder having a particle size of less than 200 mesh were on a mixer thoroughly mixed, and then, ball-formed on a coating machine by using silica sol as the binder, and then dried, calcinated) was sandwiched between titanium wire mesh corrugated plates, and produced into a cylindrical structured packing having a diameter of 50 mm and a height of 50 mm. The packing type catalyst L was loaded into the middle part of a model reaction tower (with a height of 1 m, corresponding to a theoretical plate number of 12), above and below which there was each loaded 1950 mL of a glass spring packing having a diameter of 4 mm and a height of 4 mm (with a loading height of 1 m, corresponding to a theoretical plate number of 15). Cyclohexene and benzene via a dosing pump were pumped respectively into a pre-heater and preheated and then introduced into the reaction tower, adjusting the heating at the bottom and the reflux rate at the tower top to continuously conduct the reaction, the steady-state reaction conditions and reaction results were listed in Table 3.

Example 4

The reaction tower and the catalyst arrangement were the same as Example 3, with the exception that a mixture of cyclohexene, cyclohexane and benzene was used in place of cyclohexene to conduct the experiment, and the reaction tower was operated at 0.2 MPa. The heating at the bottom and the reflux rate at the tower top was controlled so as to continuously conduct the reaction, the steady-state reaction conditions and reaction results were listed in Table 4.

Examples 5 to 8 illustrate a process for producing acetic acid cyclohexyl ester by pre-esterification and reactive rectification.

Examples 5 to 8 were all conducted on an acetic acid cyclohexyl ester model experiment apparatus. The model apparatus comprised of a fixed bed pre-esterification reactor and a reactive rectification esterification tower. The pre-esterification reactor was a Φ48×4×1200 mm 316L stainless steel tube, whose outer was equipped with hot water jacket, to which jacket there may be supplied hot water so as to control the reaction temperature. The reactive rectification esterification tower was a titanium steel (TA2) tower having a diameter (inner diameter) of 50 mm and a height of 3 m. The lower part of the tower communicated with a bottom having a volume of 5 L, inside the bottom there was installed a 10 KW electrical heating rod, which was used to via an intelligent controller through a silicon controlled rectifier (SCR) control the heating at the bottom. The tower top communicated with a condenser having a heat exchange area of 0.5 $m^2$ and a reflux tank having a volume of 2 L. Acetic acid and cyclohexene as the feed were respectively supplied into a 30 L storage tank, and through a dosing pump were pumped respectively into the pre-esterification reactor to conduct a reaction, the pre-esterification product was introduced into the reactive rectification tower for a further reaction. By adjusting the heating power to the bottom, the heating to the reaction tower was adjusted. A reflux ratio regulator at the tower top was used to adjust the tower reflux ratio. Lighter components were withdrawn from the top. The acetic acid cyclohexyl ester product was withdrawn from the tower bottom.

Example 5

500 mL of a macroporous hydrogenous strong-acid ion exchange resin (synthesized at lab according to a classical literature method, wherein a styrene solution containing 15% divinylbenzene was subject to a suspension copolymerization and produced into base spherical particles, and then sulfonated by concentrated sulfuric acid, with a measured exchange capacity of 5.2 mmol $H^{+}$/g on dry basis) was loaded into a pre-reactor at the middle part thereof, below and above which there were packed a predetermined amount of quartz sand. Further, a high temperature resistant sulfonic acid type ion exchange resin (with a trade name of Amberlyst 45, produced by the Rhom&Hass company) was by a multi-stage high speed grinder ground into powder having a particle size of less than 200 mesh (0.074 mm), there was added a porogenic agent, a lubricant, an antioxidant and a binder, mixed homogeneously with a high-speed mixer, and then with an internal mixer at 180 degrees Celsius mixed for 10 min, to completely plasticize the mass, and then injected into a mould and formed into a raschig ring type resin catalyst packing having a diameter of 5 mm, a height of 5 mm and a wall thickness of 1 mm. 1950 mL of the packing was loaded into the middle part of a model reaction tower (with a height of 1 m, corresponding to a theoretical plate number of 8), above and below which there was each loaded 1950 mL of a glass spring packing having a diameter of 3 mm and a length of 6 mm (with a loading height of 1 m, corresponding to a theoretical plate number of 10). Cyclohexene and acetic acid via a dosing pump were pumped respectively into the pre-reactor to conduct the reaction, then the pre-reaction product was introduced into the reaction tower for a further reaction. The temperature of hot water in the pre-reactor jacket was controlled so as to control the pre-reaction temperature. The heating at the bottom and the reflux rate at the tower top were controlled so as to continuously conduct the reaction, the ready-state reaction conditions and reaction results were listed in Table 5.

Example 6

The reaction tower and the catalyst arrangement were the same as Example 5, with the exception that a mixture of cyclohexene, cyclohexane and benzene was used in place of cyclohexene to conduct the experiment, and the pre-reactor pressure was 2.0 MPa, the reaction tower was operated at the normal pressure. The heating at the bottom and the reflux rate at the tower top was controlled so as to continuously conduct the reaction, the ready-state reaction conditions and reaction results were listed in Table 6.

Example 7

500 mL of a Φ3 to 4 spherical $H_{0.5}Cs_{2.5}PW_{12}O_{40}/SiO_2$ catalyst was loaded into a pre-reactor at the middle part thereof, below and above which there were packed a predetermined amount of quartz sand. Further, a Φ3 to 4 spherical $H_{0.5}Cs_{2.5}PW_{12}O_{40}/SiO_2$ catalyst (obtained by: $H_{0.5}Cs_{2.5}PW_{12}O_{40}$ powder and wide hole silica gel powder having a particle size of less than 200 mesh were on a mixer thoroughly mixed, and then, ball-formed on a coating machine by using silica sol as the binder, and then dried, calcinated) was sandwiched between titanium wire mesh corrugated plates, and produced into a cylindrical structured packing having a diameter of 50 mm and a height of 50 mm. The packing type catalyst L was loaded into the middle part of a model reaction tower (with a height of 1 m, corresponding to a theoretical plate number of 12), above and below which there was each loaded 1950 mL of a glass spring packing having a diameter of 4 mm and a height of 4 mm (with a loading height of 1 m, corresponding to a theoretical plate number of 15). Cyclohexene and acetic acid via a dosing pump were pumped respectively into the pre-reactor to conduct the reaction, then the pre-reaction product was introduced into the reaction tower for a further reaction. The temperature of hot water in the pre-reactor jacket was controlled so as to control the pre-reaction temperature. The heating at the bottom and the reflux rate at the tower top were controlled so as to continuously conduct the reaction, the ready-state reaction conditions and reaction results were listed in Table 7.

Example 8

The reaction tower and the catalyst arrangement were the same as Example 7, with the exception that a mixture of cyclohexene, cyclohexane and benzene was used in place of cyclohexene to conduct the experiment, the pre-reaction pressure was 2.0 MPa, and the reaction tower was operated at 0.2 MPa. The heating at the bottom and the reflux rate at the tower top were controlled so as to continuously conduct the reaction, the ready-state reaction conditions and reaction results were listed in Table 8.

Examples 9 to 10 illustrate a process for hydrogenating acetic acid cyclohexyl ester.

Example 9

The hydrogenation feed stock was acetic acid cyclohexyl ester having a purity of 99.6%. 40 g copper-zinc-aluminium based ester hydrogenation catalyst (synthesized at lab, with a composition of CuO 40.5%, ZnO 29.6%, $Al_2O_3$ 30.4%, by a method wherein to a copper, zinc, chromium nitrate solution, there was added a NaOH solution till pH=9.0, and then centrifugal separated, washed, dried, tableted, calcinated) was loaded into a Φ20×2.5×800 mm jacketed stainless steel tube reactor at the middle part thereof, below and above which there were packed a predetermined amount of quartz sand, supplied with hydrogen gas (500 mL/min) to conduct a reduction under the conditions of 280 degrees Celsius and 6 MPa for 24 h, and then lowered to a predetermined temperature and pressure of the hydrogenation reaction. Acetic acid cyclohexyl ester via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 9. Table 9 revealed that, when a copper-zinc-aluminium based catalyst was used, the single-pass conversion of the acetic acid cyclohexyl ester hydrogenation reaction was up to 99.0% or more, the single-pass selectivity to cyclohexanol was greater than 99.9%, and after a run time of 1000 h, the single-pass conversion and the single-pass selectivity did not drop.

Example 10

The hydrogenation feed stock was acetic acid cyclohexyl ester having a purity of 99.6%.

40 g copper-chromium based ester hydrogenation catalyst (commercially available from Taiyuan Xinjida Chemical Ltd., with a trade name of C1-XH-1, with a CuO content of 55%, as tablet having a diameter of 5 mm, crashed into particles of 10 to 20 mesh) was loaded into a Φ20×2.5×800 mm jacketed stainless steel tube reactor at the middle part thereof, below and above which there were packed a predetermined amount of quartz sand, supplied with hydrogen gas (500 mL/min) to conduct a reduction under the conditions of 280 degrees Celsius and 6 MPa for 24 h, and then the system was lowered to a predetermined temperature and pressure of the reaction. Acetic acid cyclohexyl ester via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 10. Table 10 revealed that, when a copper-zinc-aluminium based catalyst was used, the single-pass conversion of the acetic acid cyclohexyl ester hydrogenation reaction was up to 98.0% or more, the single-pass selectivity to cyclohexanol was greater than 99.9%, and after a run time of 500 h, the single-pass conversion and selectivity did not drop.

Example 11

4000 g of each reaction product from Examples 9 to 10 was collected, to conduct a separation by rectification experiment. The rectification was performed on a glass tower of 2 m height, the tower column was loaded with Φ3 mm stainless steel Dixon high-efficient rectification packing, and the bottom was a 5 L glass flask, heated by an electric jacket, with a voltage regulator to adjust the heating at the bottom. The tower reflux was controlled by a reflux ratio regulator. The separation by rectification results were listed in Table 11.

TABLE 1

| operation conditions | |
|---|---|
| operation pressure | the normal pressure |
| top temperature | 117 degrees Celsius |
| catalyst section temperature | 120 to 145 degrees Celsius |
| bottom temperature | 184 degrees Celsius |
| reflux ratio | 2 |

TABLE 1-continued

| mass | cyclohexene feed stock | acetic acid feed | top with-drawal | bottom with-drawal |
|---|---|---|---|---|
| position | catalyst bed at lower part | catalyst bed at upper part | tower top at reflux pump outlet | tower bottom at discharge outlet |
| flow rate g/h | 411 | 601 | 303 | 709 |
| temperature degrees Celsius | 75 | 75 | 40 | 184 |
| composition (ratio by mass) | | | | |
| cyclohexene | 100% | | 1.3% | |
| benzene | | | | |
| cyclohexane | | | | |
| acetic acid | | 100% | 98.7% | 0.42% |
| acetic acid cyclohexyl ester | | | | 99.30% |
| polymers | | | | 0.28% |

Calculation from the experimental data revealed a single-pass conversion of cyclohexene of 99%, a single-pass selectivity to acetic acid cyclohexyl ester of 99.72%.

TABLE 2

| operation conditions | |
|---|---|
| operation pressure | 0.3 MPa |
| top temperature | 118 degrees Celsius |
| catalyst section temperature | 140 to 146 degrees Celsius |
| bottom temperature | 200 degrees Celsius |
| reflux ratio | 5 |

| mass | cyclohexene feed stock | acetic acid feed | top with-drawal | bottom with-drawal |
|---|---|---|---|---|
| position | catalyst bed at lower part | catalyst bed at upper part | tower top at reflux pump outlet | tower bottom at discharge outlet |
| flow rate g/h | 1027 | 601 | 921 | 707 |
| temperature degrees Celsius | | | 40 | 225 |
| composition (ratio by mass) | | | | |
| cyclohexene | 40.0% | | 0.55% | |
| benzene | 19.0% | | 21.17% | |
| cyclohexane | 41.0% | | 45.71% | |
| acetic acid | | | 32.57% | 0.84% |
| acetic acid cyclohexyl ester | | | | 98.6% |
| polymers | | | | 0.56% |

Calculation from the experimental data revealed a single-pass conversion of cyclohexene of 98.8%, a single-pass selectivity to acetic acid cyclohexyl ester of 98.0%.

TABLE 3

| operation conditions | |
|---|---|
| operation pressure | 0.2 MPa |
| top temperature | 140 degrees Celsius |
| reaction section temperature | 140 to 170 degrees Celsius |
| bottom temperature | 208 degrees Celsius |
| reflux ratio | 2 |

TABLE 3-continued

| mass | cyclohexene feed stock | acetic acid feed | top with-drawal | bottom with-drawal |
|---|---|---|---|---|
| position | catalyst bed at lower part | catalyst bed at upper part | tower top at reflux pump outlet | tower bottom at discharge outlet |
| flow rate g/h | 616 | 601 | 158 | 1058 |
| temperature degrees Celsius | | | 40 | 208 |
| composition (ratio by mass) | | | | |
| cyclohexene | 100% | | 5.06% | |
| benzene | | | | |
| cyclohexane | | | | |
| acetic acid | | 100% | 94.94% | |
| acetic acid cyclohexyl ester | | | | 99.43% |
| polymers | | | | 0.57% |

Calculation from the experimental data revealed a single-pass conversion of cyclohexene of 98.7%, a single-pass selectivity to acetic acid cyclohexyl ester of 99.43%.

TABLE 4

| operation conditions | |
|---|---|
| operation pressure | 3 MPa |
| top temperature | 102 degrees Celsius |
| reaction section temperature | 145 to 180 degrees Celsius |
| bottom temperature | 209 degrees Celsius |
| reflux ratio | 5 |

| mass | cyclohexene feed stock | acetic acid feed | top with-drawal | bottom with-drawal |
|---|---|---|---|---|
| position | catalyst bed at lower part | catalyst bed at upper part | tower top at reflux pump outlet | tower bottom at discharge outlet |
| flow rate g/h | 1540 | 601 | 1084 | 1056 |
| temperature degrees Celsius | | | 40 | 209 |
| composition (ratio by mass) | | | | |
| cyclohexene | 40.0% | | 0.36% | |
| benzene | 19.0% | | 27.03% | |
| cyclohexane | 41.0% | | 58.21% | |
| acetic acid | | 100% | 14.39% | |
| acetic acid cyclohexyl ester | | | | 99.62% |
| polymers | | | | 0.38% |

Calculation from the experimental data revealed a single-pass conversion of cyclohexene of 99.35%, a single-pass selectivity to acetic acid cyclohexyl ester of 99.6%.

TABLE 5

| pre-reactor operation conditions | |
|---|---|
| operation pressure | the normal pressure |
| jacket hot water temperature | 90 degrees Celsius |
| catalyst bed temperature | 90 to 95 degrees Celsius |
| reaction tower operation conditions | |
| operation pressure | the normal pressure |
| top temperature | 117 degrees Celsius |
| catalyst section temperature | 130 to 165 degrees Celsius |
| bottom temperature | 184 degrees Celsius |
| reflux ratio | 1.5 |

TABLE 5-continued

| mass | pre-reactor feed | pre-reactor outlet (reaction tower inlet) | top with-drawal | bottom with-drawal |
|---|---|---|---|---|
| flow rate g/h | 2433 | 2433 | 308 | 2125 |
| temperature degrees Celsius | 25 | 95 | | |
| composition (ratio by mass) | | | | |
| cyclohexene | 50.6% | 5.75% | 0.97% | |
| benzene | | | | |
| cyclohexane | | | | |
| acetic acid | 49.4% | 12.78% | 99.03% | 0.28% |
| acetic acid cyclohexyl ester | | 77.15% | | 99.15% |
| polymers | | 0.32% | | 0.56% |

Calculation from the experimental data revealed a single-pass conversion of cyclohexene of 99.76%, a single-pass selectivity to acetic acid cyclohexyl ester of 99.03%.

TABLE 6

| pre-reactor operation conditions | |
|---|---|
| operation pressure | the normal pressure |
| jacket hot water temperature | 120 degrees Celsius |
| catalyst bed temperature | 120 to 125 degrees Celsius |
| reaction tower operation conditions | |
| operation pressure | 0.1 MPa |
| top temperature | 78 degrees Celsius |
| catalyst section temperature | 145 to 165 degrees Celsius |
| bottom temperature | 183 degrees Celsius |
| reflux ratio | 2 |

| mass | pre-reactor feed | pre-reactor outlet (reaction tower inlet) | top with-drawal | bottom with-drawal |
|---|---|---|---|---|
| flow rate g/h | 4282 | 4282 | 2168 | 2114 |
| temperature degrees Celsius | 25 | | | |
| composition (ratio by mass) | | | | |
| cyclohexene | 28.6% | 7.01% | 0.92% | |
| benzene | 13.7% | 13.7% | 27.03% | |
| cyclohexane | 29.5% | 29.5% | 58.21% | |
| acetic acid | 28.1% | 12.3% | 13.84% | 1.09% |
| acetic acid cyclohexyl ester | | 37.4% | | 98.39% |
| polymers | | 0.19% | | 0.52% |

Calculation from the experimental data revealed a single-pass conversion of cyclohexene of 98.38%, a single-pass selectivity to acetic acid cyclohexyl ester of 99.11%.

TABLE 7

| pre-reactor operation conditions | |
|---|---|
| operation pressure | 1.0 MPa |
| jacket hot water temperature | 140 degrees Celsius |
| catalyst bed temperature | 140 to 145 degrees Celsius |
| reaction tower operation conditions | |
| operation pressure | 0.2 MPa |
| top temperature | 142 degrees Celsius |
| catalyst section temperature | 120 to 145 degrees Celsius |
| bottom temperature | 209 degrees Celsius |
| reflux ratio | 4 |

TABLE 7-continued

| mass | pre-reactor feed | pre-reactor outlet (reaction tower inlet) | top with-drawal | bottom with-drawal |
|---|---|---|---|---|
| flow rate g/h | 3034 | 3034 | 902 | 2132 |
| temperature degrees Celsius | 25 | | | |
| composition (ratio by mass) | | | | |
| cyclohexene | 40.6% | 4.12% | 0.1% | |
| benzene | | | | |
| cyclohexane | | | | |
| acetic acid | 59.4% | 32.66% | 99.9% | 0.28% |
| acetic acid cyclohexyl ester | | 63.28% | | 99.34% |
| polymers | | 0.89% | | 0.38% |

Calculation from the experimental data revealed a single-pass conversion of cyclohexene of 99.9%, a single-pass selectivity to acetic acid cyclohexyl ester of 99.35%.

TABLE 8

| pre-reactor operation conditions | |
|---|---|
| operation pressure | the normal pressure |
| jacket hot water temperature | 160 degrees Celsius |
| catalyst bed temperature | 160 to 165 degrees Celsius |
| reaction tower operation conditions | 184 degrees Celsius |
| operation pressure | 0.3 MPa |
| top temperature | 118 degrees Celsius |
| catalyst section temperature | 140 to 165 degrees Celsius |
| bottom temperature | 225 degrees Celsius |
| reflux ratio | 2 |

| mass | pre-reactor feed | pre-reactor outlet (reaction tower inlet) | top with-drawal | bottom with-drawal |
|---|---|---|---|---|
| flow rate g/h | 4882 | 4882 | 2761 | 2121 |
| temperature degrees Celsius | 25 | | | |
| composition (ratio by mass) | | | | |
| cyclohexene | 25.2% | 5.43% | 0.43% | |
| benzene | 12.0% | 12.0% | 21.22% | |
| cyclohexane | 25.9% | 25.85% | 45.71% | |
| acetic acid | 36.9% | 22.51% | 32.63% | 0.75% |
| acetic acid cyclohexyl ester | | 34.08% | | 98.77% |
| polymers | | 0.12% | | 0.47% |

Calculation from the experimental data revealed a single-pass conversion of cyclohexene of 99.02%, a single-pass selectivity to acetic acid cyclohexyl ester of 99.19%.

TABLE 9

Experimental data observed with the cyclohexyl ester hydrogenation by the copper-zinc-aluminium based catalyst

| | reaction conditions | | | | | | reaction results | | | | | | | |
|---|---|---|---|---|---|---|---|---|---|---|---|---|---|---|
| run time h | temperature degrees Celsius | pressure MPa | ester feed g/h | hydrogen gas feed mL/min | space velocity $h^{-1}$ | hydrogen/ester ratio | ethanol m % | acetic acid ethyl ester m % | cyclohexane m % | cyclohexanol m % | ethyl cyclohexyl ether m % | acetic acid cyclohexyl ester m % | single-pass conversion of cyclohexyl ester % | single-pass selectivity to cyclohexanol % |
| 24 | 200 | 6 | 20 | 400 | 0.5 | 7.62 | 23.17 | 1.21 | 0.04 | 51.06 | 1.99 | 22.53 | 77.00 | 99.93 |
| 48 | 200 | 6 | 20 | 400 | 0.5 | 7.62 | 23.14 | 1.27 | 0.10 | 50.99 | 2.06 | 22.43 | 77.10 | 99.81 |
| 72 | 200 | 6 | 20 | 400 | 0.5 | 7.62 | 23.27 | 1.21 | 0.15 | 51.19 | 1.95 | 22.23 | 77.30 | 99.73 |
| 96 | 220 | 6 | 20 | 400 | 0.5 | 7.62 | 25.74 | 1.94 | 0.14 | 57.47 | 2.69 | 12.02 | 87.70 | 99.76 |
| 120 | 220 | 6 | 20 | 400 | 0.5 | 7.62 | 25.96 | 2.00 | 0.10 | 58.14 | 2.66 | 11.14 | 88.60 | 99.83 |
| 144 | 220 | 6 | 20 | 400 | 0.5 | 7.62 | 26.17 | 2.06 | 0.13 | 58.68 | 2.70 | 10.26 | 89.50 | 99.79 |
| 168 | 235 | 6 | 20 | 400 | 0.5 | 7.62 | 27.59 | 2.30 | 0.15 | 62.04 | 2.95 | 4.97 | 94.90 | 99.77 |
| 192 | 235 | 6 | 20 | 400 | 0.5 | 7.62 | 27.77 | 2.27 | 0.30 | 62.14 | 3.00 | 4.54 | 95.35 | 99.54 |
| 216 | 235 | 6 | 20 | 400 | 0.5 | 7.62 | 27.59 | 2.42 | 0.21 | 62.17 | 3.02 | 4.58 | 95.30 | 99.68 |
| 240 | 250 | 6 | 20 | 400 | 0.5 | 7.62 | 28.98 | 1.93 | 0.09 | 64.91 | 2.33 | 1.75 | 98.20 | 99.87 |
| 264 | 250 | 6 | 20 | 400 | 0.5 | 7.62 | 28.98 | 1.99 | 0.20 | 65.12 | 2.15 | 1.56 | 98.40 | 99.70 |
| 288 | 250 | 6 | 20 | 400 | 0.5 | 7.62 | 29.04 | 1.93 | 0.18 | 64.98 | 2.31 | 1.56 | 98.40 | 99.74 |
| 312 | 265 | 6 | 20 | 400 | 0.5 | 7.62 | 29.20 | 1.87 | 0.15 | 65.11 | 2.40 | 1.27 | 98.70 | 99.77 |
| 336 | 265 | 6 | 20 | 400 | 0.5 | 7.62 | 29.14 | 1.81 | 0.13 | 64.98 | 2.29 | 1.66 | 98.30 | 99.81 |
| 360 | 265 | 6 | 20 | 400 | 0.5 | 7.62 | 29.14 | 1.87 | 0.21 | 65.18 | 2.14 | 1.46 | 98.50 | 99.68 |
| 384 | 300 | 6 | 20 | 400 | 0.5 | 7.62 | 28.83 | 1.69 | 0.23 | 64.24 | 1.99 | 3.02 | 96.90 | 99.66 |
| 408 | 300 | 6 | 20 | 400 | 0.5 | 7.62 | 28.70 | 1.78 | 0.25 | 64.14 | 2.00 | 3.12 | 96.80 | 99.62 |
| 432 | 300 | 6 | 20 | 400 | 0.5 | 7.62 | 28.75 | 1.72 | 0.24 | 64.07 | 2.05 | 3.17 | 96.75 | 99.64 |
| 456 | 250 | 3 | 20 | 400 | 0.5 | 7.62 | 24.97 | 3.42 | 0.64 | 55.96 | 5.35 | 9.66 | 90.12 | 98.97 |
| 480 | 250 | 3 | 20 | 400 | 0.5 | 7.62 | 25.04 | 3.27 | 0.65 | 55.68 | 5.41 | 9.95 | 89.82 | 98.95 |
| 504 | 250 | 3 | 20 | 400 | 0.5 | 7.62 | 24.84 | 3.29 | 0.12 | 55.74 | 5.50 | 10.51 | 89.25 | 99.81 |
| 528 | 250 | 15 | 20 | 400 | 0.5 | 7.62 | 30.44 | 0.72 | 0.13 | 65.82 | 1.82 | 1.07 | 98.90 | 99.81 |
| 552 | 250 | 15 | 20 | 400 | 0.5 | 7.62 | 30.41 | 0.78 | 0.16 | 65.95 | 1.72 | 0.97 | 99.00 | 99.76 |
| 576 | 250 | 15 | 20 | 400 | 0.5 | 7.62 | 30.50 | 0.72 | 0.15 | 65.95 | 1.80 | 0.88 | 99.10 | 99.78 |
| 600 | 250 | 6 | 10 | 400 | 0.25 | 15.24 | 29.88 | 1.33 | 0.18 | 66.24 | 1.50 | 0.88 | 99.10 | 99.74 |
| 624 | 250 | 6 | 10 | 400 | 0.25 | 15.24 | 29.86 | 1.36 | 0.17 | 66.21 | 1.58 | 0.83 | 99.15 | 99.75 |
| 648 | 250 | 6 | 10 | 400 | 0.25 | 15.24 | 29.78 | 1.42 | 0.16 | 66.21 | 1.55 | 0.88 | 99.10 | 99.76 |
| 672 | 250 | 6 | 40 | 400 | 1 | 3.81 | 22.17 | 0.83 | 0.18 | 48.52 | 1.34 | 26.95 | 72.51 | 99.64 |
| 696 | 250 | 6 | 40 | 400 | 1 | 3.81 | 22.51 | 0.97 | 0.18 | 49.57 | 1.36 | 25.41 | 74.08 | 99.64 |
| 720 | 250 | 6 | 40 | 400 | 1 | 3.81 | 22.48 | 0.94 | 0.19 | 49.39 | 1.37 | 25.64 | 73.84 | 99.64 |
| 744 | 250 | 6 | 20 | 2000 | 0.5 | 38.09 | 30.90 | 0.48 | 0.21 | 67.43 | 0.60 | 0.39 | 99.60 | 99.70 |
| 768 | 250 | 6 | 20 | 2000 | 0.5 | 38.09 | 30.86 | 0.54 | 0.37 | 67.43 | 0.50 | 0.29 | 99.70 | 99.45 |
| 792 | 250 | 6 | 20 | 2000 | 0.5 | 38.09 | 30.93 | 0.51 | 0.36 | 67.46 | 0.55 | 0.19 | 99.80 | 99.48 |
| 816 | 250 | 6 | 20 | 400 | 0.5 | 7.62 | 28.92 | 1.87 | 0.35 | 64.92 | 1.80 | 2.14 | 97.80 | 99.48 |
| 840 | 250 | 6 | 20 | 400 | 0.5 | 7.62 | 28.83 | 1.93 | 0.28 | 64.92 | 1.80 | 2.24 | 97.70 | 99.58 |
| 864 | 250 | 6 | 20 | 400 | 0.5 | 7.62 | 28.86 | 1.93 | 0.30 | 64.98 | 1.78 | 2.14 | 97.80 | 99.55 |
| 888 | 250 | 6 | 20 | 400 | 0.5 | 7.62 | 28.98 | 1.87 | 0.35 | 64.98 | 1.87 | 1.95 | 98.00 | 99.48 |
| 912 | 250 | 6 | 20 | 400 | 0.5 | 7.62 | 28.98 | 1.75 | 0.34 | 64.71 | 1.88 | 2.34 | 97.60 | 99.49 |
| 936 | 250 | 6 | 20 | 400 | 0.5 | 7.62 | 28.86 | 1.69 | 0.21 | 64.38 | 1.94 | 2.92 | 97.00 | 99.68 |
| 960 | 250 | 6 | 20 | 400 | 0.5 | 7.62 | 29.08 | 1.63 | 0.18 | 64.78 | 1.90 | 2.44 | 97.50 | 99.72 |
| 984 | 250 | 6 | 20 | 400 | 0.5 | 7.62 | 28.83 | 1.69 | 0.20 | 64.38 | 1.88 | 3.02 | 96.90 | 99.69 |
| 1008 | 250 | 6 | 20 | 400 | 0.5 | 7.62 | 28.92 | 1.75 | 0.25 | 64.64 | 1.90 | 2.53 | 97.40 | 99.62 |

TABLE 10

Experimental data observed with the cyclohexyl ester hydrogenation by the copper-chromium based catalyst

| | reaction conditions | | | | | | reaction results | | | | | | | |
|---|---|---|---|---|---|---|---|---|---|---|---|---|---|---|
| run time h | temperature degrees Celsius | pressure MPa | ester feed g/h | hydrogen gas feed mL/min | space velocity $h^{-1}$ | hydrogen/ester ratio | ethanol m % | acetic acid ethyl ester m % | heavy boiling materials m % | cyclohexanol m % | ethyl cyclohexyl ether m % | acetic acid cyclohexyl ester m % | single-pass conversion of cyclohexyl ester % | single-pass selectivity to cyclohexanol % |
| 24 | 230 | 6 | 20 | 400 | 0.5 | 7.62 | 26.37 | 0.97 | 0.47 | 57.52 | 1.49 | 13.19 | 86.50 | 99.22 |
| 48 | 230 | 6 | 20 | 400 | 0.5 | 7.62 | 26.24 | 1.03 | 0.69 | 57.32 | 1.33 | 13.38 | 86.30 | 98.83 |
| 72 | 250 | 6 | 20 | 400 | 0.5 | 7.62 | 27.91 | 1.33 | 0.77 | 61.42 | 1.45 | 7.12 | 92.70 | 98.79 |
| 96 | 250 | 6 | 20 | 400 | 0.5 | 7.62 | 28.15 | 1.45 | 0.46 | 62.29 | 1.69 | 5.95 | 93.90 | 99.28 |
| 120 | 320 | 20 | 20 | 400 | 0.5 | 7.62 | 28.43 | 1.39 | 0.63 | 62.83 | 1.46 | 5.26 | 94.60 | 99.04 |
| 144 | 320 | 20 | 20 | 400 | 0.5 | 7.62 | 28.64 | 2.05 | 0.78 | 64.72 | 1.37 | 2.44 | 97.50 | 98.83 |
| 168 | 260 | 6 | 20 | 400 | 0.5 | 7.62 | 28.20 | 2.29 | 0.50 | 64.73 | 1.25 | 3.02 | 96.90 | 99.25 |

TABLE 10-continued

Experimental data observed with the cyclohexyl ester hydrogenation by the copper-chromium based catalyst

| | reaction conditions | | | | | | reaction results | | | | | | single-pass | single- |
|---|---|---|---|---|---|---|---|---|---|---|---|---|---|---|
| run time h | temperature degrees Celsius | pressure MPa | ester feed g/h | hydrogen gas feed mL/min | space velocity $h^{-1}$ | hydrogen/ester ratio | ethanol m % | acetic acid ethyl ester m % | heavy boiling materials m % | cyclohexanol m % | ethyl cyclohexyl ether m % | acetic acid cyclohexyl ester m % | conversion of cyclohexyl ester % | pass selectivity to cyclohexanol % |
| 192 | 260 | 6 | 20 | 400 | 0.5 | 7.62 | 28.37 | 2.26 | 0.62 | 64.83 | 1.33 | 2.58 | 97.35 | 99.07 |
| 216 | 260 | 10 | 20 | 400 | 0.5 | 7.62 | 29.15 | 1.18 | 0.19 | 64.81 | 1.02 | 3.64 | 96.26 | 99.71 |
| 240 | 260 | 10 | 20 | 400 | 0.5 | 7.62 | 28.79 | 1.69 | 0.10 | 65.33 | 0.98 | 3.12 | 96.80 | 99.86 |
| 264 | 260 | 6 | 10 | 400 | 0.25 | 15.24 | 28.98 | 1.99 | 0.70 | 65.12 | 1.65 | 1.56 | 98.40 | 98.96 |
| 288 | 260 | 6 | 10 | 400 | 0.25 | 15.24 | 29.04 | 1.93 | 0.62 | 64.98 | 1.87 | 1.56 | 98.40 | 99.08 |
| 312 | 260 | 4 | 20 | 400 | 0.5 | 7.62 | 28.58 | 1.87 | 0.66 | 63.77 | 1.90 | 3.22 | 96.70 | 99.01 |
| 336 | 260 | 4 | 20 | 400 | 0.5 | 7.62 | 28.52 | 1.81 | 0.33 | 63.64 | 2.09 | 3.61 | 96.30 | 99.50 |
| 360 | 260 | 6 | 20 | 800 | 0.5 | 15.24 | 28.61 | 1.27 | 0.23 | 64.04 | 0.78 | 5.07 | 94.80 | 99.65 |
| 384 | 260 | 6 | 20 | 800 | 0.5 | 15.24 | 28.58 | 1.45 | 0.18 | 64.52 | 0.69 | 4.58 | 95.30 | 99.72 |
| 408 | 260 | 6 | 20 | 600 | 0.5 | 11.43 | 28.33 | 1.42 | 0.23 | 63.88 | 0.68 | 5.46 | 94.40 | 99.65 |
| 432 | 260 | 6 | 20 | 600 | 0.5 | 11.43 | 28.37 | 1.44 | 0.24 | 63.97 | 0.70 | 5.28 | 94.58 | 99.63 |
| 456 | 260 | 6 | 20 | 600 | 0.5 | 11.43 | 28.28 | 1.48 | 0.26 | 63.88 | 0.66 | 5.44 | 94.42 | 99.60 |
| 480 | 260 | 6 | 20 | 600 | 0.5 | 11.43 | 28.26 | 1.42 | 0.26 | 63.71 | 0.67 | 5.67 | 94.18 | 99.60 |
| 504 | 260 | 6 | 20 | 600 | 0.5 | 11.43 | 28.24 | 1.47 | 0.24 | 63.80 | 0.65 | 5.60 | 94.25 | 99.63 |

TABLE 11

Experimental results observed with the acetic acid cyclohexyl ester hydrogenation product separation by rectification

| | reaction conditions | | | analytic results | | | | | |
|---|---|---|---|---|---|---|---|---|---|
| | temperature | | fraction | | acetic acid ethyl | | | ethyl cyclohexyl | acetic acid cyclohexyl |
| fraction No. | degrees Celsius | degrees Celsius | weight g | ethanol m % | ester m % | cyclohexane m % | cyclohexanol m % | ether m % | ester m % |
| 0 (distillation feed) | | | 4000 | 29.30 | 0.66 | | 63.30 | 2.50 | 2.98 |
| 1 (ethanol product) | 79 | 81 | 1139.9 | 95.93 | | | | | |
| 2 (transitional fraction) | 81 | 155 | 50.5 | 76.24 | | | 18.81 | 0.99 | |
| 3 (alcohol ketone product) | 155 | 162 | 2549.6 | | | | 96.15 | 3.85 | |
| 4 (bottom residue) | >162 | | 200.2 | | 13.18 | | 27.07 | 0.2 | 59.55 |
| loss | | | 59.8 | | | | | | |
| total | | | 4000 | | | | | | |

Example 12

This example illustrates the experimental results obtained with a catalytic dehydrogenation of cyclohexane to produce benzene.

The feed to the catalytic dehydrogenation was a C6 hydrocarbon mixture obtained by distillation of the tower top stream from Example 4, the mixture was washed by water to remove minor acetic acid and then analyzed by vapor phase chromatography, to contain 67.5 m % cyclohexane, 32.3 m % benzene and 0.2 m % cyclohexene.

The reactor was a tubular fixed bed reactor, which was a jacketed titanium steel tube, with a size of Φ20×2.5×800 mm. The catalyst was a supported platinum-rhodium based catalyst (with a Pt content of 0.3 m %, a Rh content of 0.1 m %). The reaction conditions included: a temperature of 480 degrees Celsius, a pressure of 0.7 MPa, a weight hourly space velocity of 5 h−1. On-line chromatography revealed that, cyclohexane in the reaction feed stock was quantitatively converted into benzene.

The Fifth Embodiment

Example 1

100 mL of a macroporous hydrogenous strong-acid ion exchange resin (synthesized at lab according to a classical literature method, wherein a styrene solution containing 15% divinylbenzene was subject to a suspension copolymerization and produced into base spherical particles, and then sulfonated by concentrated sulfuric acid, with a measured exchange capacity of 5.2 mmol $H^{+}$/g on dry basis) was loaded into a Φ32×4×1000 mm jacketed stainless steel tube reactor at the middle part thereof, below and above which there were packed a predetermined amount of quartz sand. Acetic acid and cyclohexene were pumped via a dosing pump at a predetermined flow rate respectively into the reactor to conduct a reaction, to the outer jacket of the reaction tube there was supplied hot water to control the reaction temperature, with a counterbalance valve at the reactor outlet to control the reactor pressure. The reactor outlet product was sampled by an on-line sampling valve for on-line chromatography analysis. The reaction conditions and results were listed in Table 1.

As can be seen from Table 1, when a strong-acid ion exchange resin catalyst was used for the reaction of cyclohexene and acetic acid, there were obtained a single-pass conversion of cyclohexene of greater than 90%, a single-pass selectivity to ester product of greater than 99%, and after a run time of 600 hours, the catalyst activity and the single-pass selectivity remained steady.

Example 2

The experiment apparatus and the process procedure of Example 1 were used to conduct the esterification experiment of acetic acid and cyclohexene, with the exception that $Cs_{2.5}H_{0.5}PW_{12}O_{40}/SiO_2$ was used as the catalyst (hereinafter referred to as $PW/SiO_2$). The reaction conditions and results were listed in Table 2. As can be seen from Table 2, the reaction of cyclohexene and acetic acid resulted in a single-pass conversion of up to 95%, a single-pass selectivity to ester product of greater than 99%, and after a run time of 480 hours, the catalyst activity and the single-pass selectivity remained steady.

Example 3

The experiment apparatus and the process procedure were the same as Example 1, with the exception that the catalyst was a phosphorus modified H-beta molecular sieve catalyst (obtained by a method wherein a H-beta molecular sieve having a silica alumina ratio of 50 was modified by 85% phosphoric acid, and then kneaded with alumina and then extruded, dried at a temperature of 120 degrees Celsius, calcinated at a temperature of 500 degrees Celsius, with a phosphorus content of 2%). The reaction conditions and results were listed in Table 3. As can be seen from Table 3, the reaction of cyclohexene and acetic acid resulted in a single-pass conversion of 90%, a single-pass selectivity to ester product of greater than 99%, and after a run time of 480 hours, the catalyst activity and the single-pass selectivity remained steady.

Example 4

The addition esterification product obtained from each of Examples 1 to 3 was collected to conduct a separation by rectification experiment. The rectification was performed on a glass tower type rectification apparatus having a height of 2 m and a diameter of 40 mm, wherein the tower column was loaded with Φ3 mm stainless steel Dixon high-efficient rectification packing, the bottom was a 5 L glass flask, with a loading capacity of 4 L, and heated by an electric jacket, with a voltage regulator to adjust the heating at the bottom. The tower reflux was controlled by a reflux ratio regulator. The separation by rectification results were listed in Table 4.

Example 5

The experiment apparatus, the catalyst and the process procedure were the same as Example 1, with the exception that the cyclohexene feed stock comprised of benzene 53.3%, cyclohexene 35.4%, cyclohexane 11.3%. The reaction conditions and results were listed in Table 5. As can be seen from Table 5, when a strong-acid ion exchange resin catalyst was used for catalyzing the reaction between the cyclohexene feed stock and acetic acid, there were obtained a single-pass conversion of cyclohexene of greater than 80%, a single-pass selectivity to ester product of greater than 99%, and after a run time of 600 hours, the catalyst activity and the single-pass selectivity remained steady.

Example 6

The hydrogenation feed stock was acetic acid cyclohexyl ester having a purity of 99.6%. 40 g copper-zinc-aluminium based ester hydrogenation catalyst (synthesized at lab, with a composition of CuO 40.5%, ZnO 29.6%, $Al_2O_3$ 30.4%, by a method wherein to a copper, zinc, aluminium nitrate solution, there was added a NaOH solution till pH=9.0, and then centrifugal separated, washed, dried, tableted, calcinated) was loaded into a Φ20×2.5×800 mm jacketed stainless steel tube reactor at the middle part thereof, below and above which there were packed a predetermined amount of quartz sand, supplied with hydrogen gas (500 mL/min) to conduct a reduction under the conditions of 280 degrees Celsius and 6 MPa for 24 h, and then lowered to a predetermined temperature and pressure of the hydrogenation reaction. Acetic acid cyclohexyl ester via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 6. Table 6 revealed that, when a copper-zinc-aluminium based catalyst was used, the single-pass conversion of the acetic acid cyclohexyl ester hydrogenation reaction was up to 99% or more, the single-pass selectivity to cyclohexanol was greater than 99.9%, and after a run time of 1000 h, the single-pass conversion and the single-pass selectivity did not drop.

Example 7

The hydrogenation feed stock was acetic acid cyclohexyl ester having a purity of 99.6%. 40 g copper-chromium based ester hydrogenation catalyst (commercially available from Taiyuan Xinjida Chemical Ltd., with a trade name of C1-XH-1, with a CuO content of 55%, as tablet having a diameter of 5 mm, crashed into particles of 10 to 20 mesh) was loaded into a Φ20×2.5×800 mm jacketed stainless steel tube reactor at the middle part thereof, below and above which there were packed a predetermined amount of quartz sand, supplied with hydrogen gas (500 mL/min) to conduct a reduction under the conditions of 280 degrees Celsius and 6 MPa for 24 h, and then the system was lowered to a predetermined temperature and pressure of the reaction. Acetic acid cyclohexyl ester via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 7. Table 7 revealed that, when a copper-zinc-aluminium based catalyst was used, the single-pass conversion of the acetic acid cyclohexyl ester hydrogenation reaction was up to 98% or more, the single-pass selectivity to cyclohexanol was greater than 99.9%, and after a run time of 500 h, the single-pass conversion and selectivity did not drop.

Example 8

4000 g of each reaction product of Examples 6 to 7 was collected to conduct a separation by rectification experiment. The rectification was performed on a glass tower of 2 m height, and the tower column was loaded with Φ3 mm stainless steel Dixon high-efficient rectification packing, the bottom was a 5 L glass flask, heated by an electric jacket, with a voltage regulator to adjust the heating at the bottom. The tower reflux was controlled by a reflux ratio regulator. The separation by rectification results were listed in Table 8.

TABLE 1

Experimental data observed with the esterification of acetic acid and cyclohexene catalyzed by the strong-acid ion exchange resin

| | reaction conditions | | | | on-line analytic results | | | | | |
|---|---|---|---|---|---|---|---|---|---|---|
| run time h | temperature degrees Celsius | pressure MPa | acetic acid feeding rate mL/h | cyclohexene feed stock feeding rate mL/h | cyclohexene m % | acetic acid m % | acetic acid cyclohexyl ester m % | heavier polymers m % | single-pass conversion of cyclohexene % | selectivity to ester % |
| 24 | 70 | the normal pressure | 120 | 106 | 5.84 | 34.28 | 59.60 | 0.28 | 85.6 | 99.2 |
| 48 | 70 | the normal pressure | 120 | 106 | 5.68 | 34.14 | 59.94 | 0.24 | 86 | 99.3 |
| 72 | 70 | 1 | 120 | 106 | 5.60 | 34.13 | 59.96 | 0.31 | 86.2 | 99.1 |
| 96 | 80 | 1 | 120 | 106 | 3.85 | 32.79 | 63.14 | 0.22 | 90.5 | 99.4 |
| 120 | 80 | 1 | 120 | 106 | 3.97 | 32.90 | 62.87 | 0.26 | 90.2 | 99.3 |
| 144 | 80 | 2 | 120 | 106 | 3.81 | 32.73 | 63.27 | 0.18 | 90.6 | 99.5 |
| 168 | 90 | 2 | 120 | 106 | 2.60 | 31.90 | 65.24 | 0.27 | 93.6 | 99.3 |
| 192 | 90 | 3 | 120 | 106 | 2.51 | 31.87 | 65.31 | 0.30 | 93.8 | 99.2 |
| 216 | 90 | 5 | 120 | 106 | 2.64 | 31.96 | 65.10 | 0.30 | 93.5 | 99.2 |
| 240 | 90 | 5 | 180 | 106 | 1.53 | 47.10 | 51.25 | 0.12 | 95.1 | 99.6 |
| 264 | 90 | 5 | 180 | 106 | 1.63 | 47.21 | 50.99 | 0.18 | 94.8 | 99.4 |
| 288 | 100 | 10 | 180 | 106 | 1.59 | 47.17 | 51.09 | 0.15 | 94.9 | 99.5 |
| 312 | 100 | 10 | 360 | 212 | 4.25 | 49.08 | 46.56 | 0.11 | 86.4 | 99.6 |
| 336 | 100 | 15 | 360 | 212 | 4.22 | 49.12 | 46.48 | 0.19 | 86.5 | 99.3 |
| 360 | 150 | 20 | 360 | 212 | 6.03 | 50.52 | 43.14 | 0.30 | 80.7 | 98.8 |
| 384 | 150 | 20 | 360 | 212 | 6.10 | 50.55 | 43.08 | 0.28 | 80.5 | 98.9 |
| 408 | 90 | 10 | 180 | 106 | 1.56 | 47.12 | 51.20 | 0.12 | 95.0 | 99.6 |
| 432 | 90 | 0.5 | 150 | 106 | 2.65 | 40.99 | 56.13 | 0.23 | 92.5 | 99.3 |
| 456 | 90 | 0.5 | 150 | 106 | 2.58 | 40.97 | 56.19 | 0.26 | 92.7 | 99.2 |
| 480 | 90 | 0.5 | 150 | 106 | 2.61 | 40.94 | 56.25 | 0.20 | 92.6 | 99.4 |
| 504 | 90 | 0.5 | 150 | 106 | 2.79 | 41.05 | 56.00 | 0.16 | 92.1 | 99.5 |
| 528 | 90 | 0.5 | 150 | 106 | 2.75 | 41.05 | 56.00 | 0.20 | 92.2 | 99.4 |
| 552 | 90 | 0.5 | 150 | 106 | 2.82 | 41.03 | 56.05 | 0.10 | 92.0 | 99.7 |
| 576 | 90 | 0.5 | 150 | 106 | 2.86 | 41.17 | 55.71 | 0.26 | 91.9 | 99.2 |
| 600 | 90 | 0.5 | 150 | 106 | 2.79 | 41.10 | 55.89 | 0.23 | 92.1 | 99.3 |

TABLE 2

Experimental data observed with the esterification of acetic acid and cyclohexene catalyzed by $Cs_{2.5}H_{0.5}PW_{12}O_{40}/SiO_2$

| | reaction conditions | | | | on-line analytic results | | | | | |
|---|---|---|---|---|---|---|---|---|---|---|
| run time h | temperature degrees Celsius | pressure MPa | acetic acid feeding rate mL/h | cyclohexene feed stock feeding rate mL/h | cyclohexene m % | acetic acid m % | acetic acid cyclohexyl ester m % | heavier polymers m % | single-pass conversion of cyclohexene % | selectivity to ester % |
| 24 | 60 | the normal pressure | 120 | 106 | 7.99 | 35.74 | 56.14 | 0.13 | 80.3 | 99.6 |
| 48 | 60 | the normal pressure | 120 | 106 | 7.50 | 35.39 | 56.98 | 0.13 | 81.5 | 99.6 |
| 72 | 60 | the normal pressure | 120 | 106 | 7.46 | 35.36 | 57.05 | 0.13 | 81.6 | 99.6 |
| 96 | 70 | 2 | 120 | 106 | 4.66 | 33.35 | 61.81 | 0.18 | 88.5 | 99.5 |
| 120 | 70 | 2 | 120 | 106 | 4.62 | 33.35 | 61.82 | 0.22 | 88.6 | 99.4 |
| 144 | 70 | 5 | 120 | 106 | 4.54 | 33.26 | 62.02 | 0.18 | 88.8 | 99.5 |
| 168 | 80 | 5 | 120 | 106 | 3.93 | 32.87 | 62.94 | 0.26 | 90.3 | 99.3 |
| 192 | 80 | 5 | 120 | 106 | 3.73 | 32.75 | 63.22 | 0.29 | 90.8 | 99.2 |
| 216 | 80 | 5 | 120 | 106 | 3.85 | 32.84 | 63.01 | 0.29 | 90.5 | 99.2 |
| 240 | 90 | 5 | 120 | 106 | 3.20 | 32.37 | 64.13 | 0.30 | 92.1 | 99.2 |
| 264 | 90 | 5 | 120 | 106 | 2.92 | 32.16 | 64.62 | 0.30 | 92.8 | 99.2 |
| 288 | 90 | 5 | 120 | 106 | 3.00 | 32.25 | 64.41 | 0.34 | 92.6 | 99.1 |

TABLE 2-continued

Experimental data observed with the esterification of acetic acid and cyclohexene catalyzed by $Cs_{2.5}H_{0.5}PW_{12}O_{40}/SiO_2$

| | reaction conditions | | | | on-line analytic results | | | | | |
|---|---|---|---|---|---|---|---|---|---|---|
| run time h | temperature degrees Celsius | pressure MPa | acetic acid feeding rate mL/h | cyclohexene feed stock feeding rate mL/h | cyclohexene m % | acetic acid m % | acetic acid cyclohexyl ester m % | heavier polymers m % | single-pass conversion of cyclohexene % | selectivity to ester % |
| 312 | 150 | 10 | 120 | 106 | 6.73 | 35.08 | 57.72 | 0.47 | 83.4 | 98.6 |
| 336 | 150 | 10 | 120 | 106 | 6.57 | 35.03 | 57.82 | 0.58 | 83.8 | 98.3 |
| 360 | 150 | 10 | 120 | 106 | 2.55 | 31.98 | 65.05 | 0.42 | 93.7 | 98.9 |
| 384 | 150 | 10 | 150 | 106 | 1.73 | 40.45 | 57.42 | 0.40 | 95.1 | 98.8 |
| 408 | 200 | 20 | 150 | 106 | 1.84 | 40.53 | 57.24 | 0.40 | 94.8 | 98.8 |
| 432 | 200 | 20 | 150 | 106 | 1.87 | 40.55 | 57.18 | 0.40 | 94.7 | 98.8 |
| 456 | 200 | 20 | 150 | 106 | 1.87 | 40.55 | 57.18 | 0.40 | 94.7 | 98.8 |
| 480 | 200 | 20 | 150 | 106 | 1.91 | 40.58 | 57.11 | 0.40 | 94.6 | 98.8 |

TABLE 3

Experimental data observed with the esterification of acetic acid and cyclohexene by the H-beta catalyst

| | reaction conditions | | | | on-line analytic results | | | | | |
|---|---|---|---|---|---|---|---|---|---|---|
| run time h | temperature degrees Celsius | pressure MPa | acetic acid feeding rate mL/h | cyclohexene feed stock feeding rate mL/h | cyclohexene m % | acetic acid m % | acetic acid cyclohexyl ester m % | heavier polymers m % | single-pass conversion of cyclohexene % | selectivity to ester % |
| 24 | 70 | the normal pressure | 150 | 106 | 8.61 | 45.32 | 45.87 | 0.19 | 75.6 | 99.3 |
| 48 | 70 | the normal pressure | 150 | 106 | 8.30 | 45.07 | 46.47 | 0.16 | 76.5 | 99.4 |
| 72 | 70 | the normal pressure | 150 | 106 | 8.68 | 45.32 | 45.89 | 0.11 | 75.4 | 99.6 |
| 96 | 70 | the normal pressure | 150 | 106 | 8.65 | 45.35 | 45.81 | 0.19 | 75.5 | 99.3 |
| 120 | 70 | the normal pressure | 150 | 106 | 8.72 | 45.42 | 45.65 | 0.21 | 75.3 | 99.2 |
| 144 | 80 | 2 | 150 | 106 | 6.64 | 43.93 | 49.17 | 0.26 | 81.2 | 99.1 |
| 168 | 80 | 2 | 150 | 106 | 6.74 | 43.97 | 49.09 | 0.20 | 80.9 | 99.3 |
| 192 | 80 | 2 | 150 | 106 | 6.78 | 43.99 | 49.03 | 0.20 | 80.8 | 99.3 |
| 216 | 80 | 2 | 150 | 106 | 6.88 | 44.05 | 48.90 | 0.17 | 80.5 | 99.4 |
| 240 | 80 | 2 | 150 | 106 | 6.67 | 43.89 | 49.26 | 0.17 | 81.1 | 99.4 |
| 264 | 90 | 5 | 150 | 106 | 4.70 | 42.53 | 52.50 | 0.28 | 86.7 | 99.1 |
| 288 | 90 | 5 | 150 | 106 | 4.73 | 42.55 | 52.44 | 0.28 | 86.6 | 99.1 |
| 312 | 120 | 5 | 150 | 106 | 4.80 | 42.58 | 52.38 | 0.24 | 86.4 | 99.2 |
| 336 | 120 | 10 | 150 | 106 | 4.52 | 42.35 | 52.91 | 0.22 | 87.2 | 99.3 |
| 360 | 120 | 10 | 150 | 106 | 4.66 | 42.50 | 52.56 | 0.28 | 86.8 | 99.1 |
| 384 | 150 | 10 | 150 | 106 | 3.46 | 41.93 | 53.91 | 0.70 | 90.2 | 97.8 |
| 408 | 150 | 10 | 150 | 106 | 3.39 | 41.95 | 53.86 | 0.80 | 90.4 | 97.5 |
| 432 | 150 | 10 | 150 | 106 | 3.28 | 41.78 | 54.26 | 0.67 | 90.7 | 97.9 |
| 456 | 150 | 10 | 150 | 106 | 3.35 | 41.86 | 54.09 | 0.70 | 90.5 | 97.8 |
| 480 | 150 | 10 | 150 | 106 | 3.32 | 41.90 | 53.98 | 0.80 | 90.6 | 97.5 |

TABLE 4

Experiment results observed with the addition esterification product separation by rectification

| | | | analytic results (%) | | | |
|---|---|---|---|---|---|---|
| sample No. | temperature sections, degrees Celsius | weight g | cyclohexene | acetic acid | acetic acid cyclohexyl ester | high-boiling materials |
| 0 | esterification product | 3800 | 4.5 | 48.5 | 46.8 | 0.2 |
| 1 | 78 to 118 (unreacted feed stock) | 1850 | 8.68 | 91.32 | 0 | 0 |
| 2 | 118 to 173 (transitional section) | 68 | 0 | 63.24 | 36.76 | 0 |
| 3 | 173 to 175 (ester product section) | 1656 | 0 | 0 | 99.64 | 0.36 |
| 4 | >176 residues | 163 | 0 | 0 | 59.54 | 40.46 |
| 1 to 4 in total | | 3740 | | | | |

TABLE 5

Experimental data observed with the esterification of acetic acid and cyclohexane/cyclohexene/benzene catalyzed by the strong-acid ion exchange resin

| | reaction conditions | | | | single-pass | |
|---|---|---|---|---|---|---|
| run time h | temperature degrees Celsius | pressure MPa | acetic acid feeding rate mL/h | Cyclohexene feed stock feeding rate mL/h | conversion of cyclohexene % | single-pass selectivity to ester % |
| 24 | 70 | the normal pressure | 60 | 135 | 74.8 | 99.5 |
| 48 | 70 | the normal pressure | 60 | 135 | 74.6 | 99.5 |
| 72 | 70 | 1 | 60 | 135 | 74.7 | 99.3 |
| 96 | 80 | 1 | 60 | 135 | 77.0 | 99.2 |
| 120 | 80 | 1 | 60 | 135 | 77.2 | 99.1 |
| 144 | 80 | 2 | 60 | 135 | 77.5 | 99.2 |
| 168 | 90 | 2 | 60 | 120 | 77.5 | 99.3 |
| 192 | 90 | 3 | 60 | 135 | 78.8 | 99.1 |
| 216 | 90 | 5 | 60 | 135 | 79.1 | 99.3 |
| 240 | 90 | 5 | 90 | 135 | 79.0 | 99.3 |
| 264 | 90 | 5 | 90 | 135 | 79.6 | 99.1 |
| 288 | 100 | 10 | 90 | 135 | 82.8 | 98.9 |
| 312 | 100 | 10 | 180 | 270 | 82.9 | 99.0 |
| 336 | 100 | 15 | 180 | 270 | 82.7 | 98.4 |
| 360 | 150 | 20 | 180 | 270 | 77.7 | 96.3 |
| 384 | 150 | 20 | 180 | 270 | 77.8 | 96.4 |
| 408 | 90 | 10 | 90 | 135 | 78.3 | 99.2 |
| 432 | 90 | 0.5 | 90 | 135 | 80.2 | 99.2 |
| 456 | 90 | 0.5 | 90 | 135 | 80.5 | 99.1 |
| 480 | 90 | 0.5 | 90 | 135 | 80.6 | 99.3 |
| 504 | 90 | 0.5 | 90 | 135 | 80.4 | 99.2 |
| 528 | 90 | 0.5 | 90 | 135 | 80.1 | 99.1 |
| 552 | 90 | 0.5 | 90 | 135 | 80.5 | 99.3 |
| 576 | 90 | 0.5 | 90 | 135 | 80.8 | 99.2 |
| 600 | 90 | 0.5 | 90 | 135 | 80.8 | 99.5 |

TABLE 6

Experimental data observed with the acetic acid cyclohexyl ester hydrogenation catalyzed by the copper-zinc-aluminium based catalyst

| | reaction conditions | | | | | | reaction results | |
|---|---|---|---|---|---|---|---|---|
| | | | | hydrogen | | | | |
| run time h | temperature degrees Celsius | pressure MPa | ester feed g/h | gas feed mL/min | space velocity $h^{-1}$ | hydrogen/ester ratio | ethanol m % | acetic acid ethyl ester m % |
| 24 | 200 | 6 | 20 | 400 | 0.5 | 7.62 | 23.17 | 1.21 |
| 48 | 200 | 6 | 20 | 400 | 0.5 | 7.62 | 23.14 | 1.27 |
| 72 | 200 | 6 | 20 | 400 | 0.5 | 7.62 | 23.27 | 1.21 |
| 96 | 220 | 6 | 20 | 400 | 0.5 | 7.62 | 25.74 | 1.94 |
| 120 | 220 | 6 | 20 | 400 | 0.5 | 7.62 | 25.96 | 2.00 |
| 144 | 220 | 6 | 20 | 400 | 0.5 | 7.62 | 26.17 | 2.06 |
| 168 | 235 | 6 | 20 | 400 | 0.5 | 7.62 | 27.59 | 2.30 |
| 192 | 235 | 6 | 20 | 400 | 0.5 | 7.62 | 27.77 | 2.27 |
| 216 | 235 | 6 | 20 | 400 | 0.5 | 7.62 | 27.59 | 2.42 |
| 240 | 250 | 6 | 20 | 400 | 0.5 | 7.62 | 28.98 | 1.93 |
| 264 | 250 | 6 | 20 | 400 | 0.5 | 7.62 | 28.98 | 1.99 |
| 288 | 250 | 6 | 20 | 400 | 0.5 | 7.62 | 29.04 | 1.93 |
| 312 | 265 | 6 | 20 | 400 | 0.5 | 7.62 | 29.20 | 1.87 |
| 336 | 265 | 6 | 20 | 400 | 0.5 | 7.62 | 29.14 | 1.81 |
| 360 | 265 | 6 | 20 | 400 | 0.5 | 7.62 | 29.14 | 1.87 |
| 384 | 300 | 6 | 20 | 400 | 0.5 | 7.62 | 28.83 | 1.69 |
| 408 | 300 | 6 | 20 | 400 | 0.5 | 7.62 | 28.70 | 1.78 |
| 432 | 300 | 6 | 20 | 400 | 0.5 | 7.62 | 28.75 | 1.72 |
| 456 | 250 | 3 | 20 | 400 | 0.5 | 7.62 | 24.97 | 3.42 |
| 480 | 250 | 3 | 20 | 400 | 0.5 | 7.62 | 25.04 | 3.27 |
| 504 | 250 | 3 | 20 | 400 | 0.5 | 7.62 | 24.84 | 3.29 |
| 528 | 250 | 15 | 20 | 400 | 0.5 | 7.62 | 30.44 | 0.72 |
| 552 | 250 | 15 | 20 | 400 | 0.5 | 7.62 | 30.41 | 0.78 |
| 576 | 250 | 15 | 20 | 400 | 0.5 | 7.62 | 30.50 | 0.72 |
| 600 | 250 | 6 | 10 | 400 | 0.25 | 15.24 | 29.88 | 1.33 |
| 624 | 250 | 6 | 10 | 400 | 0.25 | 15.24 | 29.86 | 1.36 |
| 648 | 250 | 6 | 10 | 400 | 0.25 | 15.24 | 29.78 | 1.42 |

TABLE 6-continued

Experimental data observed with the acetic acid cyclohexyl ester hydrogenation catalyzed by the copper-zinc-aluminium based catalyst

| | | | | | | | | |
|---|---|---|---|---|---|---|---|---|
| 672 | 250 | 6 | 40 | 400 | 1 | 3.81 | 22.17 | 0.83 |
| 696 | 250 | 6 | 40 | 400 | 1 | 3.81 | 22.51 | 0.97 |
| 720 | 250 | 6 | 40 | 400 | 1 | 3.81 | 22.48 | 0.94 |
| 744 | 250 | 6 | 20 | 2000 | 0.5 | 38.09 | 30.90 | 0.48 |
| 768 | 250 | 6 | 20 | 2000 | 0.5 | 38.09 | 30.86 | 0.54 |
| 792 | 250 | 6 | 20 | 2000 | 0.5 | 38.09 | 30.93 | 0.51 |
| 816 | 250 | 6 | 20 | 400 | 0.5 | 7.62 | 28.92 | 1.87 |
| 840 | 250 | 6 | 20 | 400 | 0.5 | 7.62 | 28.83 | 1.93 |
| 864 | 250 | 6 | 20 | 400 | 0.5 | 7.62 | 28.86 | 1.93 |
| 888 | 250 | 6 | 20 | 400 | 0.5 | 7.62 | 28.98 | 1.87 |
| 912 | 250 | 6 | 20 | 400 | 0.5 | 7.62 | 28.98 | 1.75 |
| 936 | 250 | 6 | 20 | 400 | 0.5 | 7.62 | 28.86 | 1.69 |
| 960 | 250 | 6 | 20 | 400 | 0.5 | 7.62 | 29.08 | 1.63 |
| 984 | 250 | 6 | 20 | 400 | 0.5 | 7.62 | 28.83 | 1.69 |
| 1008 | 250 | 6 | 20 | 400 | 0.5 | 7.62 | 28.92 | 1.75 |

| | reaction results | | | | | |
|---|---|---|---|---|---|---|
| run time h | cyclohexane m % | cyclohexanol m % | ethyl cyclohexyl ether m % | acetic acid cyclohexyl ester m % | single-pass conversion of cyclohexyl ester % | single-pass selectivity to cyclohexanol % |
| 24 | 0.04 | 51.06 | 1.99 | 22.53 | 77.00 | 99.93 |
| 48 | 0.10 | 50.99 | 2.06 | 22.43 | 77.10 | 99.81 |
| 72 | 0.15 | 51.19 | 1.95 | 22.23 | 77.30 | 99.73 |
| 96 | 0.14 | 57.47 | 2.69 | 12.02 | 87.70 | 99.76 |
| 120 | 0.10 | 58.14 | 2.66 | 11.14 | 88.60 | 99.83 |
| 144 | 0.13 | 58.68 | 2.70 | 10.26 | 89.50 | 99.79 |
| 168 | 0.15 | 62.04 | 2.95 | 4.97 | 94.90 | 99.77 |
| 192 | 0.30 | 62.14 | 3.00 | 4.54 | 95.35 | 99.54 |
| 216 | 0.21 | 62.17 | 3.02 | 4.58 | 95.30 | 99.68 |
| 240 | 0.09 | 64.91 | 2.33 | 1.75 | 98.20 | 99.87 |
| 264 | 0.20 | 65.12 | 2.15 | 1.56 | 98.40 | 99.70 |
| 288 | 0.18 | 64.98 | 2.31 | 1.56 | 98.40 | 99.74 |
| 312 | 0.15 | 65.11 | 2.40 | 1.27 | 98.70 | 99.77 |
| 336 | 0.13 | 64.98 | 2.29 | 1.66 | 98.30 | 99.81 |
| 360 | 0.21 | 65.18 | 2.14 | 1.46 | 98.50 | 99.68 |
| 384 | 0.23 | 64.24 | 1.99 | 3.02 | 96.90 | 99.66 |
| 408 | 0.25 | 64.14 | 2.00 | 3.12 | 96.80 | 99.62 |
| 432 | 0.24 | 64.07 | 2.05 | 3.17 | 96.75 | 99.64 |
| 456 | 0.64 | 55.96 | 5.35 | 9.66 | 90.12 | 98.97 |
| 480 | 0.65 | 55.68 | 5.41 | 9.95 | 89.82 | 98.95 |
| 504 | 0.12 | 55.74 | 5.50 | 10.51 | 89.25 | 99.81 |
| 528 | 0.13 | 65.82 | 1.82 | 1.07 | 98.90 | 99.81 |
| 552 | 0.16 | 65.95 | 1.72 | 0.97 | 99.00 | 99.76 |
| 576 | 0.15 | 65.95 | 1.80 | 0.88 | 99.10 | 99.78 |
| 600 | 0.18 | 66.24 | 1.50 | 0.88 | 99.10 | 99.74 |
| 624 | 0.17 | 66.21 | 1.58 | 0.83 | 99.15 | 99.75 |
| 648 | 0.16 | 66.21 | 1.55 | 0.88 | 99.10 | 99.76 |
| 672 | 0.18 | 48.52 | 1.34 | 26.95 | 72.51 | 99.64 |
| 696 | 0.18 | 49.57 | 1.36 | 25.41 | 74.08 | 99.64 |
| 720 | 0.19 | 49.39 | 1.37 | 25.64 | 73.84 | 99.64 |
| 744 | 0.21 | 67.43 | 0.60 | 0.39 | 99.60 | 99.70 |
| 768 | 0.37 | 67.43 | 0.50 | 0.29 | 99.70 | 99.45 |
| 792 | 0.36 | 67.46 | 0.55 | 0.19 | 99.80 | 99.48 |
| 816 | 0.35 | 64.92 | 1.80 | 2.14 | 97.80 | 99.48 |
| 840 | 0.28 | 64.92 | 1.80 | 2.24 | 97.70 | 99.58 |
| 864 | 0.30 | 64.98 | 1.78 | 2.14 | 97.80 | 99.55 |
| 888 | 0.35 | 64.98 | 1.87 | 1.95 | 98.00 | 99.48 |
| 912 | 0.34 | 64.71 | 1.88 | 2.34 | 97.60 | 99.49 |
| 936 | 0.21 | 64.38 | 1.94 | 2.92 | 97.00 | 99.68 |
| 960 | 0.18 | 64.78 | 1.90 | 2.44 | 97.50 | 99.72 |
| 984 | 0.20 | 64.38 | 1.88 | 3.02 | 96.90 | 99.69 |
| 1008 | 0.25 | 64.64 | 1.90 | 2.53 | 97.40 | 99.62 |

TABLE 7

Experimental data observed with the acetic acid cyclohexyl ester hydrogenation catalyzed by the copper-chromium based catalyst

| | reaction conditions | | | | | | reaction results | | |
|---|---|---|---|---|---|---|---|---|---|
| run time h | temperature degrees Celsius | pressure MPa | ester feed g/h | hydrogen gas feed mL/min | space velocity $h^{-1}$ | hydrogen/ ester ratio | ethanol m % | acetic acid ethyl ester m % | high boiling materials m % |
| 24 | 230 | 6 | 20 | 400 | 0.5 | 7.62 | 26.37 | 0.97 | 0.47 |
| 48 | 230 | 6 | 20 | 400 | 0.5 | 7.62 | 26.24 | 1.03 | 0.69 |
| 72 | 250 | 6 | 20 | 400 | 0.5 | 7.62 | 27.91 | 1.33 | 0.77 |
| 96 | 250 | 6 | 20 | 400 | 0.5 | 7.62 | 28.15 | 1.45 | 0.46 |
| 120 | 320 | 20 | 20 | 400 | 0.5 | 7.62 | 28.43 | 1.39 | 0.63 |
| 144 | 320 | 20 | 20 | 400 | 0.5 | 7.62 | 28.64 | 2.05 | 0.78 |
| 168 | 260 | 6 | 20 | 400 | 0.5 | 7.62 | 28.20 | 2.29 | 0.50 |
| 192 | 260 | 6 | 20 | 400 | 0.5 | 7.62 | 28.37 | 2.26 | 0.62 |
| 216 | 260 | 10 | 20 | 400 | 0.5 | 7.62 | 29.15 | 1.18 | 0.19 |
| 240 | 260 | 10 | 20 | 400 | 0.5 | 7.62 | 28.79 | 1.69 | 0.10 |
| 264 | 260 | 6 | 10 | 400 | 0.25 | 15.24 | 28.98 | 1.99 | 0.70 |
| 288 | 260 | 6 | 10 | 400 | 0.25 | 15.24 | 29.04 | 1.93 | 0.62 |
| 312 | 260 | 4 | 20 | 400 | 0.5 | 7.62 | 28.58 | 1.87 | 0.66 |
| 336 | 260 | 4 | 20 | 400 | 0.5 | 7.62 | 28.52 | 1.81 | 0.33 |
| 360 | 260 | 6 | 20 | 800 | 0.5 | 15.24 | 28.61 | 1.27 | 0.23 |
| 384 | 260 | 6 | 20 | 800 | 0.5 | 15.24 | 28.58 | 1.45 | 0.18 |
| 408 | 260 | 6 | 20 | 600 | 0.5 | 11.43 | 28.33 | 1.42 | 0.23 |
| 432 | 260 | 6 | 20 | 600 | 0.5 | 11.43 | 28.37 | 1.44 | 0.24 |
| 456 | 260 | 6 | 20 | 600 | 0.5 | 11.43 | 28.28 | 1.48 | 0.26 |
| 480 | 260 | 6 | 20 | 600 | 0.5 | 11.43 | 28.26 | 1.42 | 0.26 |
| 504 | 260 | 6 | 20 | 600 | 0.5 | 11.43 | 28.24 | 1.47 | 0.24 |

| | reaction results | | | | |
|---|---|---|---|---|---|
| run time h | cyclohexanol m % | ethyl cyclohexyl ether m % | acetic acid cyclohexyl ester m % | single-pass conversion of cyclohexyl ester % | single-pass selectivity to cyclohexanol % |
| 24 | 57.52 | 1.49 | 13.19 | 86.50 | 99.22 |
| 48 | 57.32 | 1.33 | 13.38 | 86.30 | 98.83 |
| 72 | 61.42 | 1.45 | 7.12 | 92.70 | 98.79 |
| 96 | 62.29 | 1.69 | 5.95 | 93.90 | 99.28 |
| 120 | 62.83 | 1.46 | 5.26 | 94.60 | 99.04 |
| 144 | 64.72 | 1.37 | 2.44 | 97.50 | 98.83 |
| 168 | 64.73 | 1.25 | 3.02 | 96.90 | 99.25 |
| 192 | 64.83 | 1.33 | 2.58 | 97.35 | 99.07 |
| 216 | 64.81 | 1.02 | 3.64 | 96.26 | 99.71 |
| 240 | 65.33 | 0.98 | 3.12 | 96.80 | 99.86 |
| 264 | 65.12 | 1.65 | 1.56 | 98.40 | 98.96 |
| 288 | 64.98 | 1.87 | 1.56 | 98.40 | 99.08 |
| 312 | 63.77 | 1.90 | 3.22 | 96.70 | 99.01 |
| 336 | 63.64 | 2.09 | 3.61 | 96.30 | 99.50 |
| 360 | 64.04 | 0.78 | 5.07 | 94.80 | 99.65 |
| 384 | 64.52 | 0.69 | 4.58 | 95.30 | 99.72 |
| 408 | 63.88 | 0.68 | 5.46 | 94.40 | 99.65 |
| 432 | 63.97 | 0.70 | 5.28 | 94.58 | 99.63 |
| 456 | 63.88 | 0.66 | 5.44 | 94.42 | 99.60 |
| 480 | 63.71 | 0.67 | 5.67 | 94.18 | 99.60 |
| 504 | 63.80 | 0.65 | 5.60 | 94.25 | 99.63 |

TABLE 8

Experiment results observed with the acetic acid cyclohexyl ester hydrogenation product separation by rectification

| fraction No. | reaction conditions: temperature degrees Celsius | degrees Celsius | fraction weight g | ethanol m % | analytic results: acetic ethyl ester m % | cyclohexane | cyclohexanol m % | ethyl cyclohexyl ether | acetic acid cyclohexyl ester |
|---|---|---|---|---|---|---|---|---|---|
| 0 | distillation feed | | 4000 | 29.3 | 0.66 | | 63.30 | 2.50 | 2.98 |
| 1 (ethanol product) | 79 | 81 | 1139.9 | 95.93 | | | | | |
| 2 (transitional fraction) | 81 | 155 | 50.5 | 76.24 | | | 18.81 | 0.99 | |
| 3 (alcohol ketone product) | 155 | 162 | 2549.6 | | | | 96.15 | 3.85 | |
| 4 (bottom residue) | >162 | | 200.2 | | 13.18 | | 27.07 | 0.2 | 59.55 |
| loss | | | 59.8 | | | | | | |
| total | | | 4000 | | | | | | |

The Sixth Embodiment

Example 1

This example illustrates a process for producing cyclohexene by a benzene selective hydrogenation.

Benzene and hydrogen gas at a ratio by molar of 1:3 were supplied into a hydrogenation reactor loaded with ruthenium based catalyst particles, under the conditions wherein the reaction temperature was 135 degrees Celsius, the reaction pressure was 4.5 MPa, the residence time was 15 min, to conduct a benzene hydrogenation reaction, after separating hydrogen gas from the reaction product, the liquid product was collected. The reaction ran continuously for 1000 h. Upon completion of the experiment, the collected liquid product was subject to vapor phase chromatography analysis, showing a composition of: benzene 53.3%, cyclohexene 35.4%, cyclohexane 11.3%.

Example 2

100 mL of a macroporous hydrogenous strong-acid ion exchange resin (synthesized at lab according to a classical literature method, wherein a styrene solution containing 15% divinylbenzene was subject to a suspension copolymerization and produced into base spherical particles, and then sulfonated by concentrated sulfuric acid, with a measured exchange capacity of 5.2 mmol $H^{+}$/g on dry basis) was loaded into a Φ32×4×1000 mm jacketed stainless steel tube reactor at the middle part thereof, below and above which there were packed a predetermined amount of quartz sand. Acetic acid and a cyclohexene feed stock (comprising benzene 53.3%, cyclohexene 35.4%, cyclohexane 11.3%) were pumped via a dosing pump at a predetermined flow rate respectively into the reactor to conduct a reaction, to the outer jacket of the reaction tube there was supplied hot water to control the reaction temperature, with a counterbalance valve at the reactor outlet to control the reactor pressure. The reactor outlet product was sampled by an on-line sampling valve for on-line chromatography analysis, on the basis of the product composition, there was calculated the single-pass conversion of cyclohexene and the single-pass selectivity to acetic acid cyclohexyl ester. The reaction conditions and results were listed in Table 1.

As can be seen from Table 1, when a strong-acid ion exchange resin catalyst was used for catalyzing the reaction between the cyclohexene feed stock and acetic acid, there were obtained a single-pass conversion of cyclohexene of greater than 80%, a single-pass selectivity to the ester product of greater than 99%, and after a run time of 600 hours, the catalyst activity and the single-pass selectivity remained steady.

TABLE 1

Experimental data observed with the esterification of acetic acid and cyclohexane/cyclohexene/benzene catalyzed by the strong-acid ion exchange resin

| run time h | reaction conditions: temperature degrees Celsius | pressure MPa | acetic acid feeding rate mL/h | cyclohexene feed stock feeding rate mL/h | single-pass conversion of cyclohexene % | single-pass selectivity to acetic acid cyclohexyl ester % |
|---|---|---|---|---|---|---|
| 24 | 70 | the normal pressure | 60 | 135 | 74.8 | 99.5 |
| 48 | 70 | the normal pressure | 60 | 135 | 74.6 | 99.5 |
| 72 | 70 | 1 | 60 | 135 | 74.7 | 99.3 |
| 96 | 80 | 1 | 60 | 135 | 77.0 | 99.2 |
| 120 | 80 | 1 | 60 | 135 | 77.2 | 99.1 |
| 144 | 80 | 2 | 60 | 135 | 77.5 | 99.2 |
| 168 | 90 | 2 | 60 | 120 | 77.5 | 99.3 |
| 192 | 90 | 3 | 60 | 135 | 78.8 | 99.1 |

TABLE 1-continued

Experimental data observed with the esterification of acetic acid and cyclohexane/cyclohexene/benzene catalyzed by the strong-acid ion exchange resin

| | reaction conditions | | | | single-pass | |
|---|---|---|---|---|---|---|
| run time h | temperature degrees Celsius | pressure MPa | acetic acid feeding rate mL/h | cyclohexene feed stock feeding rate mL/h | conversion of cyclohexene % | single-pass selectivity to acetic acid cyclohexyl ester % |
| 216 | 90 | 5 | 60 | 135 | 79.1 | 99.3 |
| 240 | 90 | 5 | 90 | 135 | 79.0 | 99.3 |
| 264 | 90 | 5 | 90 | 135 | 79.6 | 99.1 |
| 288 | 100 | 10 | 90 | 135 | 82.8 | 98.9 |
| 312 | 100 | 10 | 180 | 270 | 82.9 | 99.0 |
| 336 | 100 | 15 | 180 | 270 | 82.7 | 98.4 |
| 360 | 150 | 20 | 180 | 270 | 77.7 | 96.3 |
| 384 | 150 | 20 | 180 | 270 | 77.8 | 96.4 |
| 408 | 90 | 10 | 90 | 135 | 78.3 | 99.2 |
| 432 | 90 | 0.5 | 90 | 135 | 80.2 | 99.2 |
| 456 | 90 | 0.5 | 90 | 135 | 80.5 | 99.1 |
| 480 | 90 | 0.5 | 90 | 135 | 80.6 | 99.3 |
| 504 | 90 | 0.5 | 90 | 135 | 80.4 | 99.2 |
| 528 | 90 | 0.5 | 90 | 135 | 80.1 | 99.1 |
| 552 | 90 | 0.5 | 90 | 135 | 80.5 | 99.3 |
| 576 | 90 | 0.5 | 90 | 135 | 80.8 | 99.2 |
| 600 | 90 | 0.5 | 90 | 135 | 80.8 | 99.5 |

Example 3

The experiment apparatus, the process procedure and the feed stock were the same as Example 2, with the exception that the catalyst was a phosphorus modified H-beta molecular sieve catalyst (obtained by a method wherein a H-beta molecular sieve having a silica alumina ratio of 50 was modified by 85% phosphoric acid, and then kneaded with alumina and then extruded, dried at a temperature of 120 degrees Celsius, calcinated at a temperature of 500 degrees Celsius, with a phosphorus content of 2%). The reaction conditions and results were listed in Table 2. As can be seen from Table 2, the reaction of cyclohexene and acetic acid resulted in a single-pass conversion of greater than 80%, a single-pass selectivity to the ester product of greater than 99%, and after a run time of 480 hours, the catalyst activity and the single-pass selectivity remained steady.

TABLE 2

Experimental data observed with the esterification of acetic acid and cyclohexane/cyclohexene/benzene catalyzed by the H-beta molecular sieve catalyst

| | reaction conditions | | | | single-pass | single-pass selectivity to acetic |
|---|---|---|---|---|---|---|
| run time h | temperature degrees Celsius | pressure MPa | acetic acid feeding rate mL/h | cyclohexene feed stock feeding rate mL/h | conversion of cyclohexene % | acid cyclohexyl ester % |
| 24 | 70 | the normal pressure | 90 | 135 | 69.8 | 99.2 |
| 48 | 70 | the normal pressure | 90 | 135 | 70.3 | 99.2 |
| 72 | 70 | the normal pressure | 90 | 135 | 70.4 | 99.3 |
| 96 | 70 | the normal pressure | 90 | 135 | 70.3 | 99.1 |
| 120 | 70 | the normal pressure | 90 | 135 | 72.3 | 99.2 |
| 144 | 80 | 2 | 90 | 135 | 74.5 | 99.1 |
| 168 | 80 | 2 | 90 | 135 | 74.7 | 99.3 |
| 192 | 80 | 2 | 90 | 135 | 75.8 | 99.2 |
| 216 | 80 | 2 | 90 | 135 | 75.9 | 99.1 |
| 240 | 80 | 2 | 90 | 135 | 76.3 | 99.1 |
| 264 | 90 | 5 | 90 | 135 | 79.4 | 99.2 |
| 288 | 90 | 5 | 90 | 135 | 78.9 | 99.3 |
| 312 | 120 | 5 | 90 | 135 | 80.4 | 99.0 |
| 336 | 120 | 10 | 90 | 135 | 80.3 | 99.1 |
| 360 | 120 | 10 | 90 | 135 | 80.2 | 99.2 |
| 384 | 150 | 10 | 90 | 135 | 82.8 | 96.5 |
| 408 | 150 | 10 | 90 | 135 | 82.9 | 96.8 |

TABLE 2-continued

Experimental data observed with the esterification of acetic acid and cyclohexane/cyclohexene/benzene catalyzed by the H-beta molecular sieve catalyst

| | reaction conditions | | | | single-pass | single-pass selectivity to acetic |
|---|---|---|---|---|---|---|
| run time h | temperature degrees Celsius | pressure MPa | acetic acid feeding rate mL/h | cyclohexene feed stock feeding rate mL/h | conversion of cyclohexene % | acid cyclohexyl ester % |
| 432 | 150 | 10 | 90 | 135 | 83.6 | 96.7 |
| 456 | 150 | 10 | 90 | 135 | 84.2 | 96.6 |
| 480 | 150 | 10 | 90 | 135 | 84.5 | 96.7 |

Example 4

This example illustrates a process for hydrogenating an esterification reaction mixture.

The hydrogenation feed stock was a cyclohexene/acetic acid esterification reaction mixture containing benzene and cyclohexane (comprising cyclohexane 7.4%, benzene 35.4%, cyclohexene 4.6%, acetic acid 20.5%, acetic acid cyclohexyl ester 32.2%, polymers 0.2%).

The reaction system comprised of two fixed bed reactors in series. The two reactors were each a jacketed titanium steel tube, with a size of Φ20×2.5×800 mm. The preceding reactor was an acetic acid, benzene and cyclohexene hydrogenation reactor, inside which there was loaded 40 g silica supported platinum-palladium-tin based acetic acid hydrogenation catalyst (synthesized at lab, with a composition of Pt (10 m %)-Pd (5 m %)-Sn (5 m %)/$SiO_2$, by a method wherein a macroporous silica carrier of 20 to 40 mesh (with a BET specific surface area of 400 $m^2/g$, a pore volume of 0.35 mL/g) was impregnated with a mixed solution of chloroplatinic acid, palladium chloride and stannous chloride, and then dried at 120 degrees Celsius, calcinated at a temperature of 500 degrees Celsius). The succeeding reactor was an ester hydrogenation reactor, inside which there was loaded 40 g copper-zinc-aluminium based ester hydrogenation catalyst (synthesized at lab, with a composition of CuO 40%, ZnO 29.6%, $Al_2O_3$ 30.4%, by a method wherein to a copper, zinc, chromium nitrate solution, there was added a NaOH solution till pH=9.0, and then centrifugal separated, washed, dried, tableted, calcinated). The catalyst was loaded into the reactor at the middle part thereof, below and above which there were packed a predetermined amount of quartz sand, functioning as a section for evaporating the feed stock by heating or as a packing. To the reactor jacket, there may be supplied heat conducting oil to control the reaction temperature. Upon completion of the catalyst loading into the reactor, the reaction system was connected, after passing the air tightness test, there was supplied hydrogen gas (1000 mL/min) to conduct a reduction reaction under the conditions of 300 degrees Celsius and 6 MPa for 24 h, and then lowered to a predetermined temperature and pressure of the hydrogenation reaction. The mixture of acetic acid and acetic acid cyclohexyl ester via a dosing pump were pumped respectively into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 3.

TABLE 3

Experimental data observed with the hydrogenation

| | reaction conditions | | | | preceding reactor | | | |
|---|---|---|---|---|---|---|---|---|
| | | | | | | | single-pass | |
| run time h | feed stock g/h | hydrogen gas feed mL/min | total feed space velocity $h^{-1}$ | hydrogen/ feed mol/mol | reaction temperature degrees Celsius | reaction pressure MPa | conversion of acetic acid % | single-pass selectivity to ethanol % |
| 24 | 40 | 2000 | 0.5 | 11.6 | 210 | 6 | 85.5 | 99.4 |
| 48 | 40 | 2000 | 0.5 | 11.6 | 210 | 6 | 85.7 | 99.3 |
| 72 | 40 | 2000 | 0.5 | 11.6 | 210 | 6 | 85.6 | 99.6 |
| 96 | 40 | 2000 | 0.5 | 11.6 | 230 | 6 | 94.5 | 99.3 |
| 120 | 40 | 2000 | 0.5 | 11.6 | 230 | 6 | 94.7 | 99.3 |
| 144 | 40 | 2000 | 0.5 | 11.6 | 230 | 6 | 94.3 | 99.2 |
| 168 | 40 | 2000 | 0.5 | 11.6 | 250 | 6 | 99.3 | 99.1 |
| 192 | 40 | 2000 | 0.5 | 11.6 | 250 | 6 | 99.4 | 99.2 |
| 216 | 40 | 2000 | 0.5 | 11.6 | 250 | 6 | 99.5 | 99.3 |
| 240 | 40 | 2000 | 0.5 | 11.6 | 265 | 6 | 99.5 | 99.2 |
| 264 | 40 | 2000 | 0.5 | 11.6 | 265 | 6 | 99.6 | 98.9 |
| 288 | 40 | 2000 | 0.5 | 11.6 | 265 | 6 | 99.5 | 98.6 |
| 312 | 40 | 2000 | 0.5 | 11.6 | 280 | 6 | 99.6 | 96.8 |
| 336 | 40 | 2000 | 0.5 | 11.6 | 280 | 6 | 99.7 | 96.9 |
| 360 | 40 | 2000 | 0.5 | 11.6 | 280 | 6 | 99.8 | 96.9 |
| 384 | 40 | 2000 | 0.5 | 11.6 | 250 | 4 | 97.1 | 98.8 |
| 408 | 40 | 2000 | 0.5 | 11.6 | 250 | 4 | 94.9 | 99.1 |

TABLE 3-continued

Experimental data observed with the hydrogenation

| | | | | | | | | |
|---|---|---|---|---|---|---|---|---|
| 432 | 40 | 2000 | 0.5 | 11.6 | 250 | 4 | 94.6 | 99.2 |
| 456 | 40 | 2000 | 0.5 | 11.6 | 250 | 15 | 99.2 | 99.1 |
| 480 | 40 | 2000 | 0.5 | 11.6 | 250 | 15 | 99.1 | 99.2 |
| 504 | 40 | 2000 | 0.5 | 11.6 | 250 | 15 | 99.3 | 99.1 |
| 528 | 20 | 2000 | 0.25 | 23.2 | 250 | 6 | 99.4 | 99.2 |
| 552 | 20 | 2000 | 0.25 | 23.2 | 250 | 6 | 99.5 | 99.3 |
| 576 | 20 | 2000 | 0.25 | 23.2 | 250 | 6 | 99.3 | 99.5 |
| 600 | 60 | 2000 | 1 | 5.8 | 250 | 6 | 80.3 | 93.6 |
| 624 | 60 | 2000 | 1 | 5.8 | 250 | 6 | 80.4 | 93.7 |
| 648 | 60 | 2000 | 1 | 5.8 | 250 | 6 | 80.4 | 93.6 |
| 672 | 20 | 3000 | 0.5 | 34.8 | 250 | 6 | 99.2 | 99.3 |
| 696 | 20 | 3000 | 0.5 | 34.8 | 250 | 6 | 99.5 | 99.4 |
| 720 | 20 | 3000 | 0.5 | 34.8 | 250 | 6 | 99.3 | 99.3 |
| 744 | 40 | 2000 | 0.5 | 11.6 | 250 | 6 | 99.5 | 99.2 |
| 768 | 40 | 2000 | 0.5 | 11.6 | 250 | 6 | 99.4 | 99.2 |
| 792 | 40 | 2000 | 0.5 | 11.6 | 250 | 6 | 99.3 | 99.3 |
| 816 | 40 | 2000 | 0.5 | 11.6 | 250 | 6 | 99.0 | 99.2 |
| 840 | 40 | 2000 | 0.5 | 11.6 | 250 | 6 | 98.9 | 99.1 |
| 864 | 40 | 2000 | 0.5 | 11.6 | 250 | 6 | 98.7 | 99.2 |
| 888 | 40 | 2000 | 0.5 | 11.6 | 250 | 6 | 98.8 | 99.1 |

| | preceding reactor | | succeeding reactor | | | | total |
|---|---|---|---|---|---|---|---|
| run time h | conversion of benzene % | single-pass conversion of cyclohexene % | reaction temperature degrees Celsius | reaction pressure MPa | single-pass conversion of acetic acid cyclohexyl ester % | single-pass selevtivity to cyclohexanol % | single-pass selectivity to ethanol % |
| 24 | 100 | 100 | 200 | 5.5 | 75.6 | 99.3 | 97.1 |
| 48 | 100 | 100 | 200 | 5.5 | 75.3 | 99.1 | 97.2 |
| 72 | 100 | 100 | 200 | 5.5 | 75.1 | 99.2 | 97.1 |
| 96 | 100 | 100 | 230 | 5.5 | 89.5 | 99.1 | 96.2 |
| 120 | 100 | 100 | 230 | 5.5 | 90.1 | 99.2 | 95.4 |
| 144 | 100 | 100 | 230 | 5.5 | 89.6 | 99.2 | 95.7 |
| 168 | 100 | 100 | 250 | 5.5 | 96.7 | 99.1 | 94.8 |
| 192 | 100 | 100 | 250 | 5.5 | 96.5 | 99.0 | 94.5 |
| 216 | 100 | 100 | 250 | 5.5 | 97.3 | 99.0 | 94.7 |
| 240 | 100 | 100 | 265 | 5.5 | 97.4 | 98.9 | 94.5 |
| 264 | 100 | 100 | 265 | 5.5 | 97.2 | 98.7 | 93.8 |
| 288 | 100 | 100 | 265 | 5.5 | 97.0 | 98.6 | 93.9 |
| 312 | 100 | 100 | 280 | 5.5 | 96.8 | 94.9 | 93.2 |
| 336 | 100 | 100 | 280 | 5.5 | 96.5 | 94.7 | 93.6 |
| 360 | 100 | 100 | 280 | 5.5 | 96.4 | 94.5 | 93.3 |
| 384 | 100 | 100 | 250 | 3 | 94.1 | 99.0 | 95.9 |
| 408 | 100 | 100 | 250 | 3 | 94.2 | 99.1 | 95.8 |
| 432 | 100 | 100 | 250 | 3 | 93.8 | 99.1 | 95.9 |
| 456 | 100 | 100 | 250 | 12 | 99.1 | 99.3 | 97.8 |
| 480 | 100 | 100 | 250 | 12 | 99.3 | 99.2 | 97.6 |
| 504 | 100 | 100 | 250 | 12 | 99.1 | 99.3 | 97.4 |
| 528 | 100 | 100 | 250 | 5.5 | 99.5 | 99.3 | 97.3 |
| 552 | 100 | 100 | 250 | 5.5 | 99.6 | 99.5 | 97.1 |
| 576 | 100 | 100 | 250 | 5.5 | 99.5 | 99.6 | 97.4 |
| 600 | 100 | 100 | 250 | 5.5 | 92.8 | 94.7 | 91.9 |
| 624 | 100 | 100 | 250 | 5.5 | 92.3 | 94.3 | 91.2 |
| 648 | 100 | 100 | 250 | 5.5 | 92.7 | 94.9 | 91.4 |
| 672 | 100 | 100 | 250 | 5.5 | 99.5 | 99.3 | 99.1 |
| 696 | 100 | 100 | 250 | 5.5 | 99.4 | 99.2 | 98.9 |
| 720 | 100 | 100 | 250 | 5.5 | 99.5 | 99.4 | 98.7 |
| 744 | 100 | 100 | 250 | 5.5 | 96.8 | 99.1 | 96.4 |
| 768 | 100 | 100 | 250 | 5.5 | 96.7 | 99.1 | 95.7 |
| 792 | 100 | 100 | 250 | 5.5 | 96.5 | 99.2 | 96.1 |
| 816 | 100 | 100 | 250 | 5.5 | 96.3 | 99.1 | 96.0 |
| 840 | 100 | 100 | 250 | 5.5 | 96.4 | 99.0 | 96.3 |
| 864 | 100 | 100 | 250 | 5.5 | 96.6 | 99.2 | 96.2 |
| 888 | 100 | 100 | 250 | 5.5 | 96.3 | 99.0 | 96.1 |

Example 5

This example illustrates a process for hydrogenating an esterification reaction mixture.

The hydrogenation feed stock was a cyclohexene/acetic acid esterification reaction mixture containing benzene and cyclohexane, with a composition of cyclohexane 7.4%, benzene 35.4%, cyclohexene 4.6%, acetic acid 20.5%, acetic acid cyclohexyl ester 32.2%, polymers 0.2%.

The reaction system comprised of one single fixed bed reactor, which was a jacketed titanium steel tube, with a size of Φ20×2.5×800 mm. The catalyst was loaded as two layers into the reactor. As the upper layer there was loaded 20 g silica supported platinum-palladium-tin based acetic acid hydrogenation catalyst (synthesized at lab, with a composition of Pt (10%)-Pd (5%)-Sn (5%)/$SiO_2$, by a method wherein a macroporous silica carrier of 20 to 40 mesh (with a BET specific surface area of 400 $m^2$/g, a pore volume of 0.35 mL/g) was impregnated with a mixed solution of chloroplatinic acid, palladium chloride and stannous chloride, and then dried at 120 degrees Celsius, calcinated at a temperature of 500 degrees Celsius); As the lower layer there was loaded 20 g copper-zinc-aluminium based ester hydrogenation catalyst (synthesized at lab, with a composition of CuO 40.5%, ZnO 29.6%, $Al_2O_3$ 30.4%, by a method wherein to a copper, zinc, chromium nitrate solution, there was added a NaOH solution till pH=9.0, and then centrifugal separated, washed, dried, tableted, calcinated). The catalysts were loaded into the reactor at the middle part (the constant temperature section) thereof, and the two catalyst layers were separated apart by glass-fiber fabric, to both ends of the reactor there were packed a predetermined amount of quartz sand, functioning as a section for evaporating the feed stock by heating or as a packing. To the reactor jacket, there may be supplied heat conducting oil to control the reaction temperature. Upon completion of the catalyst loading into the reactor, the reaction system was connected, after passing the air tightness test, there was supplied hydrogen gas (500 mL/min) to conduct a reduction reaction under the conditions of 300 degrees Celsius and 6 MPa for 24 h, and then lowered to a predetermined temperature and pressure of the hydrogenation reaction. The mixture of acetic acid and acetic acid cyclohexyl ester via a dosing pump were pumped respectively into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 4.

TABLE 4

Experimental data observed with the hydrogenation

| | reaction conditions | | | | | | reaction results |
|---|---|---|---|---|---|---|---|
| run time h | feed stock g/h | hydrogen gas feed mL/min | total feed space velocity $h^{-1}$ | hydrogen/feed mol/mol | reaction temperature degrees Celsius | reaction pressure MPa | single-pass conversion of acetic acid % |
| 24 | 20 | 1000 | 0.5 | 11.6 | 240 | 6 | 97.6 |
| 48 | 20 | 1000 | 0.5 | 11.6 | 240 | 6 | 97.7 |
| 72 | 20 | 1000 | 0.5 | 11.6 | 240 | 6 | 97.5 |
| 96 | 20 | 1000 | 0.5 | 11.6 | 240 | 6 | 97.3 |
| 120 | 20 | 1000 | 0.5 | 11.6 | 240 | 6 | 97.1 |
| 144 | 20 | 1000 | 0.5 | 11.6 | 240 | 6 | 97.2 |
| 168 | 20 | 1000 | 0.5 | 11.6 | 240 | 6 | 97.1 |
| 192 | 20 | 1000 | 0.5 | 11.6 | 240 | 6 | 97.0 |
| 216 | 20 | 1000 | 0.5 | 11.6 | 240 | 6 | 96.8 |
| 240 | 20 | 1000 | 0.5 | 11.6 | 250 | 6 | 98.7 |
| 264 | 20 | 1000 | 0.5 | 11.6 | 250 | 6 | 99.0 |
| 288 | 20 | 1000 | 0.5 | 11.6 | 250 | 6 | 98.9 |
| 312 | 20 | 1000 | 0.5 | 11.6 | 250 | 6 | 99.0 |
| 336 | 20 | 1000 | 0.5 | 11.6 | 250 | 6 | 98.8 |
| 360 | 20 | 1000 | 0.5 | 11.6 | 250 | 6 | 98.6 |
| 384 | 20 | 1000 | 0.5 | 11.6 | 250 | 6 | 98.5 |
| 408 | 20 | 1000 | 0.5 | 11.6 | 250 | 6 | 98.7 |
| 432 | 20 | 1000 | 0.5 | 11.6 | 250 | 6 | 98.4 |
| 456 | 20 | 1000 | 0.5 | 11.6 | 250 | 6 | 98.2 |
| 480 | 20 | 1000 | 0.5 | 11.6 | 250 | 6 | 98.1 |
| 504 | 20 | 1000 | 0.5 | 11.6 | 250 | 6 | 98.0 |
| 528 | 20 | 1000 | 0.5 | 11.6 | 260 | 6 | 98.1 |
| 552 | 20 | 1000 | 0.5 | 11.6 | 260 | 6 | 98.0 |
| 576 | 20 | 1000 | 0.5 | 11.6 | 250 | 6 | 97.8 |
| 600 | 20 | 1000 | 0.5 | 11.6 | 260 | 6 | 97.6 |
| 624 | 20 | 1000 | 0.5 | 11.6 | 260 | 6 | 97.5 |
| 648 | 20 | 1000 | 0.5 | 11.6 | 260 | 6 | 97.3 |
| 672 | 20 | 1000 | 0.5 | 11.6 | 260 | 6 | 97.0 |

TABLE 4-continued

Experimental data observed with the hydrogenation reaction results

| run time h | single-pass conversion of acetic acid cyclohexyl ester % | conversion of benzene % | single-pass conversion of cyclohexene % | single-pass selectivity to cyclohexanol % | total single-pass selectivity to ethanol % |
|---|---|---|---|---|---|
| 24 | 96.8 | 100 | 100 | 99.2 | 96.3 |
| 48 | 97.0 | 100 | 100 | 99.0 | 96.4 |
| 72 | 97.2 | 100 | 100 | 99.1 | 96.3 |
| 96 | 97.1 | 100 | 100 | 99.1 | 96.2 |
| 120 | 97.2 | 100 | 100 | 99.2 | 96.4 |
| 144 | 97.1 | 100 | 100 | 99.1 | 96.5 |
| 168 | 96.9 | 100 | 100 | 99.2 | 96.6 |
| 192 | 97.2 | 100 | 100 | 99.1 | 96.5 |
| 216 | 97.0 | 100 | 100 | 99.0 | 96.4 |
| 240 | 97.3 | 100 | 100 | 99.2 | 95.7 |
| 264 | 96.7 | 100 | 100 | 99.0 | 96.5 |
| 288 | 96.8 | 100 | 100 | 98.9 | 96.4 |
| 312 | 96.9 | 100 | 100 | 99.0 | 96.5 |
| 336 | 96.8 | 100 | 100 | 99.1 | 96.3 |
| 360 | 96.8 | 100 | 100 | 99.2 | 96.5 |
| 384 | 96.9 | 100 | 100 | 99.1 | 96.4 |
| 408 | 96.8 | 100 | 100 | 99.2 | 96.5 |
| 432 | 96.9 | 100 | 100 | 99.1 | 96.5 |
| 456 | 96.3 | 100 | 100 | 99.2 | 96.6 |
| 480 | 96.1 | 100 | 100 | 99.1 | 96.6 |
| 504 | 97.0 | 100 | 100 | 99.0 | 96.4 |
| 528 | 97.1 | 100 | 100 | 99.0 | 96.5 |
| 552 | 97.3 | 100 | 100 | 99.0 | 96.6 |
| 576 | 97.1 | 100 | 100 | 99.0 | 96.7 |
| 600 | 97.2 | 100 | 100 | 99.1 | 96.4 |
| 624 | 97.3 | 100 | 100 | 99.1 | 96.5 |
| 648 | 97.2 | 100 | 100 | 99.0 | 96.6 |
| 672 | 97.3 | 100 | 100 | 99.1 | 96.7 |

Example 6

4000 g of each reaction product (having a vapor phase chromatography analysis composition of: ethanol 27.4 m %, acetic acid ethyl ester 0.2 m %, cyclohexane 40.2 m %, water 6.4 m %, acetic acid 0.2 m %, cyclohexanol 25.0 m %, acetic acid cyclohexyl ester 0.3 m %, others 0.3 m %) of Examples 5 to 6 was collected, to conduct a separation by rectification experiment. The rectification was performed on a glass tower of 2 m height, and the tower column was loaded with Φ3 mm stainless steel Dixon high-efficient rectification packing, the bottom was a 5 L glass flask, heated by an electric jacket, with a voltage regulator to adjust the heating at the bottom. The tower reflux was controlled by a reflux ratio regulator. Upon separation, 845 g cyclohexanol as the product was obtained, with a vapor phase chromatography purity of 99.4%.

The Seventh Embodiment

Example 1

This example illustrates a process for producing cyclohexene by a benzene selective hydrogenation.

Benzene and hydrogen gas at a ratio by molar of 1:3 were supplied into a hydrogenation reactor loaded with ruthenium based catalyst particles, under the conditions wherein the reaction temperature was 135 degrees Celsius, the reaction pressure was 4.5 MPa, the residence time was 15 min, to conduct a benzene hydrogenation reaction, after separating hydrogen gas from the reaction product, the liquid product was collected. The reaction ran continuously for 1000 h. Upon completion of the experiment, the collected liquid product was subject to vapor phase chromatography analysis, showing a composition of: benzene 53.3%, cyclohexene 35.4%, cyclohexane 11.3%.

Example 2

100 mL of a macroporous hydrogenous strong-acid ion exchange resin (synthesized at lab according to a classical literature method, wherein a styrene solution containing 15% divinylbenzene was subject to a suspension copolymerization and produced into base spherical particles, and then sulfonated by concentrated sulfuric acid, with a measured exchange capacity of 5.2 mmol $H^+$/g on dry basis) was loaded into a Φ32×4×1000 mm jacketed stainless steel tube reactor at the middle part thereof, below and above which there were packed a predetermined amount of quartz sand. Acetic acid and a cyclohexene feed stock (comprising benzene 53.3%, cyclohexene 35.4%, cyclohexane 11.3%) were pumped via a dosing pump at a predetermined flow rate respectively into the reactor to conduct a reaction, to the outer jacket of the reaction tube there was supplied hot water to control the reaction temperature, with a counterbalance valve at the reactor outlet to control the reactor pressure. The reactor outlet product was sampled by an on-line sampling valve for on-line chromatography analysis, on the basis of the product composition, there was calculated the single-pass conversion of cyclohexene and the single-pass selectivity to acetic acid cyclohexyl ester. The reaction conditions and results were listed in Table 1.

As can be seen from Table 1, when a strong-acid ion exchange resin catalyst was used for catalyzing the reaction between the cyclohexene feed stock and acetic acid, there were obtained a single-pass conversion of cyclohexene of greater than 80%, a single-pass selectivity to the ester product of greater than 99%, and after a run time of 600 hours, the catalyst activity and the single-pass selectivity remained steady.

TABLE 1

Experimental data observed with the esterification of acetic acid and cyclohexane/cyclohexene/benzene catalyzed by the strong-acid ion exchange resin

| run time h | reaction conditions temperature degrees Celsius | pressure MPa | acetic acid feeding rate mL/h | cyclohexene feed stock feeding rate mL/h | single-pass conversion of cyclohexene % | single-pass selectivity to acetic acid cyclohexyl ester % |
|---|---|---|---|---|---|---|
| 24 | 70 | the normal pressure | 60 | 135 | 74.8 | 99.5 |
| 48 | 70 | the normal pressure | 60 | 135 | 74.6 | 99.5 |
| 72 | 70 | 1 | 60 | 135 | 74.7 | 99.3 |
| 96 | 80 | 1 | 60 | 135 | 77.0 | 99.2 |
| 120 | 80 | 1 | 60 | 135 | 77.2 | 99.1 |
| 144 | 80 | 2 | 60 | 135 | 77.5 | 99.2 |
| 168 | 90 | 2 | 60 | 120 | 77.5 | 99.3 |
| 192 | 90 | 3 | 60 | 135 | 78.8 | 99.1 |
| 216 | 90 | 5 | 60 | 135 | 79.1 | 99.3 |
| 240 | 90 | 5 | 90 | 135 | 79.0 | 99.3 |
| 264 | 90 | 5 | 90 | 135 | 79.6 | 99.1 |
| 288 | 100 | 10 | 90 | 135 | 82.8 | 98.9 |
| 312 | 100 | 10 | 180 | 270 | 82.9 | 99.0 |
| 336 | 100 | 15 | 180 | 270 | 82.7 | 98.4 |
| 360 | 150 | 20 | 180 | 270 | 77.7 | 96.3 |
| 384 | 150 | 20 | 180 | 270 | 77.8 | 96.4 |
| 408 | 90 | 10 | 90 | 135 | 78.3 | 99.2 |
| 432 | 90 | 0.5 | 90 | 135 | 80.2 | 99.2 |
| 456 | 90 | 0.5 | 90 | 135 | 80.5 | 99.1 |
| 480 | 90 | 0.5 | 90 | 135 | 80.6 | 99.3 |
| 504 | 90 | 0.5 | 90 | 135 | 80.4 | 99.2 |
| 528 | 90 | 0.5 | 90 | 135 | 80.1 | 99.1 |
| 552 | 90 | 0.5 | 90 | 135 | 80.5 | 99.3 |
| 576 | 90 | 0.5 | 90 | 135 | 80.8 | 99.2 |
| 600 | 90 | 0.5 | 90 | 135 | 80.8 | 99.5 |

Example 3

The experiment apparatus, the process procedure and the feed stock were the same as Example 2, with the exception that the catalyst was a phosphorus modified H-beta molecular sieve catalyst (obtained by a method wherein a H-beta molecular sieve having a silica alumina ratio of 50 was modified by 85% phosphoric acid, and then kneaded with alumina and then extruded, dried at a temperature of 120 degrees Celsius, calcinated at a temperature of 500 degrees Celsius, with a phosphorus content of 2 m %). The reaction conditions and results were listed in Table 2. As can be seen from Table 2, the reaction of cyclohexene and acetic acid resulted in a single-pass conversion of greater than 80%, a single-pass selectivity to the ester product of greater than 99%, and after a run time of 480 hours, the catalyst activity and the single-pass selectivity remained steady.

TABLE 2

Experimental data observed with the esterification of acetic acid and cyclohexane/cyclohexene/benzene catalyzed by the H-beta molecular sieve catalyst

| run time h | reaction conditions temperature degrees Celsius | pressure MPa | acetic acid feeding rate mL/h | cyclohexene feed stock feeding rate mL/h | single-pass conversion of cyclohexene % | single-pass selectivity to acetic acid cyclohexyl ester % |
|---|---|---|---|---|---|---|
| 24 | 70 | the normal pressure | 90 | 135 | 69.8 | 99.2 |
| 48 | 70 | the normal pressure | 90 | 135 | 70.3 | 99.2 |
| 72 | 70 | the normal pressure | 90 | 135 | 70.4 | 99.3 |
| 96 | 70 | the normal pressure | 90 | 135 | 70.3 | 99.1 |
| 120 | 70 | the normal pressure | 90 | 135 | 72.3 | 99.2 |
| 144 | 80 | 2 | 90 | 135 | 74.5 | 99.1 |

TABLE 2-continued

Experimental data observed with the esterification of acetic acid and cyclohexane/cyclohexene/benzene catalyzed by the H-beta molecular sieve catalyst

| | reaction conditions | | | | single-pass | single-pass selectivity |
|---|---|---|---|---|---|---|
| run time h | temperature degrees Celsius | pressure MPa | acetic acid feeding rate mL/h | cyclohexene feed stock feeding rate mL/h | conversion of cyclohexene % | to acetic acid cyclohexyl ester % |
| 168 | 80 | 2 | 90 | 135 | 74.7 | 99.3 |
| 192 | 80 | 2 | 90 | 135 | 75.8 | 99.2 |
| 216 | 80 | 2 | 90 | 135 | 75.9 | 99.1 |
| 240 | 80 | 2 | 90 | 135 | 76.3 | 99.1 |
| 264 | 90 | 5 | 90 | 135 | 79.4 | 99.2 |
| 288 | 90 | 5 | 90 | 135 | 78.9 | 99.3 |
| 312 | 120 | 5 | 90 | 135 | 80.4 | 99.0 |
| 336 | 120 | 10 | 90 | 135 | 80.3 | 99.1 |
| 360 | 120 | 10 | 90 | 135 | 80.2 | 99.2 |
| 384 | 150 | 10 | 90 | 135 | 82.8 | 96.5 |
| 408 | 150 | 10 | 90 | 135 | 82.9 | 96.8 |
| 432 | 150 | 10 | 90 | 135 | 83.6 | 96.7 |
| 456 | 150 | 10 | 90 | 135 | 84.2 | 96.6 |
| 480 | 150 | 10 | 90 | 135 | 84.5 | 96.7 |

Example 4

The addition esterification product obtained from each of Examples 2 and 3 was collected, to conduct a separation by rectification experiment. The rectification was performed on a glass tower type rectification apparatus having a height of 2 m and a diameter of 40 mm, and the tower column was loaded with Φ3 mm stainless steel Dixon high-efficient rectification packing, the bottom was a 5 L glass flask, with a loading capacity of 4 L, and heated by an electric jacket, with a voltage regulator to adjust the heating at the bottom. The tower reflux was controlled by a reflux ratio regulator. The separation by rectification results were listed in Table 3.

TABLE 3

Experiment results observed with the addition esterification product separation by rectification

| | | | analytic results/m % | | | | | |
|---|---|---|---|---|---|---|---|---|
| sample No. | temperature sections, degrees Celsius | weight/g | cyclohexane | cyclohexene | benzene | acetic acid | acetic acid cyclohexyl ester | high-boiling materials |
| 0 | esterification product | 3795 | 7.4 | 4.4 | 35.1 | 20.5 | 32.3 | 0.3 |
| 1 | 78 to 80 (unreacted feed stock) | 1816 | 15.5 | 9.2 | 73.3 | 2.0 | | |
| 2 | 80 to 175 (acid and ester product) | 1880 | | | | 39.5 | 60.5 | |
| 3 | >176 (residues) | 99 | | | | | 88.6 | 11.4 |

Example 5 to 6 illustrate a process for producing acetic acid cyclohexyl ester by a reactive rectification.

The experiments of Examples 5 to 6 were all performed on a reactive rectification model experiment apparatus with these specifications: the main part of the model apparatus was a stainless steel tower having a diameter (inner diameter) of 50 mm, a height of 3 m, the lower part of which communicated with a bottom having a volume of 5 L, inside the bottom there was installed a 10 KW electrical heating rod, which was used to via an intelligent controller through a silicon controlled rectifier (SCR) control the heating at the bottom. The tower top communicated with a condenser having a heat exchange area of 0.5 $m^2$, vapor from the tower top was condensed by this condenser into liquid and then introduced into a reflux tank having a volume of 2 L. Liquid in the reflux tank was partially refluxed by a reflux pump back to the reaction tower, partially withdrawn as lighter components. The operation parameters of the tower were controlled by and displayed on an intelligent type automatic control instrument. The tower reflux rate was controlled by a reflux control valve, the top withdrawal was controlled by a level controller at the reflux tank. The bottom withdrawal was controlled by a bottom blow-off valve which was controlled by a bottom level controller. Acetic acid and a cyclohexene feed stock were respectively supplied into a 30 L storage tank, and through a dosing pump were pumped respectively into the corresponding preheater and preheated to a predetermined temperature and then introduced into the reaction tower, the feeding rate was controlled by the dosing pump and accurately metered by an electronic balance.

Example 5

A high temperature resistant sulfonic acid type ion exchange resin (with a trade name of Amberlyst 45, produced by the Rhom&Hass company) was by a multi-stage high speed grinder ground into powder having a particle size of less than 200 mesh (0.074 mm), there was added a porogenic agent, a lubricant, an antioxidant and a binder, mixed homogeneously with a high-speed mixer, and then with an internal mixer at 180 degrees Celsius mixed for 10 min, to completely plasticize the mass, and then injected into a mould and formed into a raschig ring type resin catalyst packing having a diameter of 5 mm, a height of 5 mm and a wall thickness of 1 mm. 1950 mL of the packing was loaded into the middle part of a model reaction tower (with a height of 1 m, corresponding to a theoretical plate number of 8), above and below which there was each loaded 1950 mL of a glass spring packing having a diameter of 3 mm and a length of 6 mm (with a loading height of 1 m, corresponding to a theoretical plate number of 10). A cyclohexene feed stock and acetic acid via a dosing pump were pumped respectively into a preheater and preheated and then introduced into the reaction tower, adjusting the heating at the bottom and the reflux rate at the tower top to continuously conduct the reaction, the steady-state reaction conditions and reaction results were listed in Table 4.

TABLE 4

Experimental data observed with the reactive rectification by the high temperature resistant sulfonic acid type ion exchange resin catalyst

| operation conditions | |
|---|---|
| operation pressure | 0.3 MPa |
| top temperature | 118 degrees Celsius |
| catalyst section temperature | 125 to 140 degrees Celsius |
| bottom temperature | 194 degrees Celsius |
| reflux ratio | 5 |

| mass | cyclohexene feed stock | acetic acid feed | top with-drawal | bottom with-drawal |
|---|---|---|---|---|
| position | catalyst bed at lower part | catalyst bed at upper part | tower top at reflux pump outlet | tower bottom at discharge outlet |
| flow rate g/h | 1160 | 601 | 826.3 | 934.2 |
| temperature degrees Celsius | 40 | 40 | 118 | 194 |
| composition (ratio by mass) | | | | |
| acetic acid | | 100% | 8.8% | 25.0% |
| benzene | 53.3% | | 74.8% | |
| cyclohexene | 35.4% | | 0.5% | |
| cyclohexane | 11.3% | | 15.9% | |
| acetic acid cyclohexyl ester | | | | 74.6% |
| polymers | | | | 0.4% |

Calculation from the experimental data revealed a single-pass conversion of cyclohexene of 99%, a single-pass selectivity to acetic acid cyclohexyl ester of 99.2%.

Example 6

A Φ3 to 4 spherical $H_{0.5}$ $Cs_{2.5}PW_{12}O_{40}/SiO_2$ catalyst (obtained by: $H_{0.5}Cs_{2.5}PW_{12}O_{40}$ powder and wide hole silica gel powder having a particle size of less than 200 mesh were on a mixer thoroughly mixed, and then, ball-formed on a coating machine by using silica sol as the binder, and then dried, calcinated) was sandwiched between titanium wire mesh corrugated plates, and produced into a cylindrical structured packing having a diameter of 50 mm and a height of 50 mm. The packing type catalyst L was loaded into the middle part of a model reaction tower (with a height of 1 m, corresponding to a theoretical plate number of 12), above and below which there was each loaded 1950 mL of a glass spring packing having a diameter of 4 mm and a height of 4 mm (with a loading height of 1 m, corresponding to a theoretical plate number of 15). A cyclohexene feed stock and acetic acid via a dosing pump were pumped respectively into a preheater and preheated and then introduced into the reaction tower, adjusting the heating at the bottom and the reflux rate at the tower top to continuously conduct the reaction, the steady-state reaction conditions and reaction results were listed in Table 5.

TABLE 5

Experimental data observed with the reactive rectification by the $H_{0.5}Cs_{2.5}PW_{12}O_{40}/SiO_2$ catalyst

| operation conditions | |
|---|---|
| operation pressure | 0.2 MPa |
| top temperature | 103 degrees Celsius |
| reaction section temperature | 110 to 140 degrees Celsius |
| bottom temperature | 186 degrees Celsius |
| reflux ratio | 4 |

| mass | cyclohexene feed stock | acetic acid feed | top with-drawal | bottom with-drawal |
|---|---|---|---|---|
| position | catalyst bed at lower part | catalyst bed at upper part | tower top at reflux pump outlet | tower bottom at discharge outlet |
| flow rate g/h | 1392 | 600.5 | 963.5 | 1029 |
| temperature degrees Celsius | | | 40 | 186 |
| composition (ratio by mass) | | | | |
| acetic acid | | 100% | 6.3% | 18.1% |
| benzene | 53.3% | | 77.0% | |
| cyclohexene | 35.4% | | 0.4% | |
| cyclohexane | 11.3% | | 16.3% | |
| acetic acid cyclohexyl ester | | | | 81.5% |
| polymers | | | | 0.4% |

Calculation from the experimental data revealed a single-pass conversion of cyclohexene of 98.3%, a single-pass selectivity to acetic acid cyclohexyl ester of 99.5%.

Example 7

This example illustrates a process for hydrogenating a mixture of acetic acid and acetic acid cyclohexyl ester.

The hydrogenation feed stock was a mixture of acetic acid and acetic acid cyclohexyl ester (comprising acetic acid 39.5%, acetic acid cyclohexyl ester 60.5%).

The reaction system comprised of two fixed bed reactors in series. The two reactors were each a jacketed titanium steel tube, with a size of Φ20×2.5×800 mm. The preceding reactor was an acetic acid hydrogenation reactor, inside which there was loaded 40 g silica supported platinum-palladium-tin based acetic acid hydrogenation catalyst (synthesized at lab, with a composition of Pt (10 m %)-Pd (5 m %)-Sn (5 m %)/$SiO_2$, by a method wherein a macroporous silica carrier of 20 to 40 mesh (with a BET specific surface area of 400 $m^2/g$, a pore volume of 0.35 mL/g) was impregnated with a mixed solution of chloroplatinic acid, palladium chloride and stannous chloride, and then dried at 120 degrees Celsius, calcinated at a temperature of 500 degrees Celsius). The succeeding reactor was an ester hydrogenation reactor, inside which there was loaded 40 g copper-zinc-aluminium based ester hydrogenation catalyst (synthesized at lab, with a composition of CuO 40%, ZnO 29.6%, $Al_2O_3$ 30.4%, by a method wherein to a copper, zinc, chromium nitrate solution, there was added a NaOH solution till pH=9.0, and then centrifugal separated, washed, dried, tableted, calcinated). The catalyst was loaded into the reactor at the middle part thereof, below and above which there were packed a predetermined amount of quartz sand, functioning as a section for evaporating the feed stock by heating or as a packing. To the reactor jacket, there may be supplied heat conducting oil to control the reaction temperature. Upon completion of the catalyst loading into the reactor, the reaction system was connected, after passing the air tightness test, there was supplied hydrogen gas (1000 mL/min) to conduct a reduction reaction under the conditions of 300 degrees Celsius and 6 MPa for 24 h, and then lowered to a predetermined temperature and pressure of the hydrogenation reaction. The mixture of acetic acid and acetic acid cyclohexyl ester via a dosing pump were pumped respectively into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 6.

Example 8

This example illustrates a process for hydrogenating a mixture of acetic acid and acetic acid cyclohexyl ester.

The hydrogenation feed stock was a mixture of acetic acid and acetic acid cyclohexyl ester (comprising acetic acid 39.5%, acetic acid cyclohexyl ester 60.5%).

The reaction system comprised of one single fixed bed reactor, which was a jacketed titanium steel tube, with a size of Φ20×2.5×800 mm. The catalyst was loaded as two layers into the reactor. As the upper layer there was loaded 20 g silica supported platinum-palladium-tin based acetic acid hydrogenation catalyst (synthesized at lab, with a composition of Pt (10%)-Pd (5%)-Sn (5%)/$SiO_2$, by a method wherein a macroporous silica carrier of 20 to 40 mesh (with a BET specific surface area of 400 $m^2$/g, a pore volume of 0.35 mL/g) was impregnated with a mixed solution of chloroplatinic acid, palladium chloride and stannous chloride, and then dried at 120 degrees Celsius, calcinated at a temperature of 500 degrees Celsius); As the lower layer there was loaded 20 g copper-zinc-aluminium based ester

TABLE 6

Experimental data observed with the acetic acid/acetic acid cyclohexyl ester hydrogenation

| | reaction conditions | | | | preceding reactor | | | | succeeding reactor | | | | |
|---|---|---|---|---|---|---|---|---|---|---|---|---|---|
| run time h | feed g/h | hydrogen gas feed mL/min | total feed space velocity $h^{-1}$ | hydrogen/feed mol/mol | reaction temperature degrees Celsius | reaction pressure MPa | single-pass conversion of acetic acid % | single-pass selectivity to ethanol % | reaction temperature degrees Celsius | reaction pressure MPa | single-pass conversion of acetic acid cyclohexyl ester % | single-pass selectivity to cyclohexanol % | total single-pass selectivity to ethanol % |
| 24 | 40 | 2000 | 0.5 | 12.4 | 210 | 6 | 86.2 | 99.5 | 200 | 5.5 | 76.4 | 99.6 | 97.3 |
| 48 | 40 | 2000 | 0.5 | 12.4 | 210 | 6 | 87.1 | 99.4 | 200 | 5.5 | 76.3 | 99.4 | 97.3 |
| 72 | 40 | 2000 | 0.5 | 12.4 | 210 | 6 | 86.5 | 99.6 | 200 | 5.5 | 76.1 | 99.5 | 97.2 |
| 96 | 40 | 2000 | 0.5 | 12.4 | 230 | 6 | 95.3 | 99.2 | 230 | 5.5 | 90.2 | 99.4 | 96.5 |
| 120 | 40 | 2000 | 0.5 | 12.4 | 230 | 6 | 95.5 | 99.2 | 230 | 5.5 | 90.4 | 99.5 | 96.4 |
| 144 | 40 | 2000 | 0.5 | 12.4 | 230 | 6 | 95.3 | 99.3 | 230 | 5.5 | 89.9 | 99.6 | 96.5 |
| 168 | 40 | 2000 | 0.5 | 12.4 | 250 | 6 | 99.5 | 99.2 | 250 | 5.5 | 97.5 | 99.3 | 95.8 |
| 192 | 40 | 2000 | 0.5 | 12.4 | 250 | 6 | 99.6 | 99.1 | 250 | 5.5 | 97.3 | 99.2 | 95.7 |
| 216 | 40 | 2000 | 0.5 | 12.4 | 250 | 6 | 99.6 | 99.1 | 250 | 5.5 | 98.5 | 99.0 | 95.6 |
| 240 | 40 | 2000 | 0.5 | 12.4 | 265 | 6 | 99.6 | 99.0 | 265 | 5.5 | 98.4 | 98.1 | 94.8 |
| 264 | 40 | 2000 | 0.5 | 12.4 | 265 | 6 | 99.8 | 98.8 | 265 | 5.5 | 98.2 | 98.9 | 94.9 |
| 288 | 40 | 2000 | 0.5 | 12.4 | 265 | 6 | 99.7 | 98.5 | 265 | 5.5 | 98.0 | 98.6 | 94.9 |
| 312 | 40 | 2000 | 0.5 | 12.4 | 280 | 6 | 99.8 | 96.3 | 280 | 5.5 | 97.3 | 95.5 | 93.5 |
| 336 | 40 | 2000 | 0.5 | 12.4 | 280 | 6 | 99.8 | 96.7 | 280 | 5.5 | 97.3 | 95.6 | 93.5 |
| 360 | 40 | 2000 | 0.5 | 12.4 | 280 | 6 | 99.7 | 96.9 | 280 | 5.5 | 97.4 | 95.5 | 93.5 |
| 384 | 40 | 2000 | 0.5 | 12.4 | 250 | 4 | 96.7 | 98.6 | 250 | 3 | 96.10 | 99.2 | 96.5 |
| 408 | 40 | 2000 | 0.5 | 12.4 | 250 | 4 | 96.5 | 99.0 | 250 | 3 | 95.2 | 99.2 | 96.7 |
| 432 | 40 | 2000 | 0.5 | 12.4 | 250 | 4 | 96.6 | 99.1 | 250 | 3 | 94.8 | 99.1 | 96.8 |
| 456 | 40 | 2000 | 0.5 | 12.4 | 250 | 15 | 99.6 | 99.2 | 250 | 12 | 99.5 | 99.6 | 98.2 |
| 480 | 40 | 2000 | 0.5 | 12.4 | 250 | 15 | 99.7 | 99.3 | 250 | 12 | 99.6 | 99.7 | 98.2 |
| 504 | 40 | 2000 | 0.5 | 12.4 | 250 | 15 | 99.6 | 99.3 | 250 | 12 | 99.4 | 99.7 | 98.2 |
| 528 | 20 | 2000 | 0.25 | 24.8 | 250 | 6 | 99.5 | 99.5 | 250 | 5.5 | 99.6 | 99.6 | 97.6 |
| 552 | 20 | 2000 | 0.25 | 24.8 | 250 | 6 | 99.7 | 99.6 | 250 | 5.5 | 99.7 | 99.7 | 97.7 |
| 576 | 20 | 2000 | 0.25 | 24.8 | 250 | 6 | 99.6 | 99.6 | 250 | 5.5 | 99.6 | 99.73 | 97.5 |
| 600 | 80 | 2000 | 1 | 6.2 | 250 | 6 | 82.3 | 92.5 | 250 | 5.5 | 92.2 | 94.5 | 91.4 |
| 624 | 80 | 2000 | 1 | 6.2 | 250 | 6 | 82.5 | 92.7 | 250 | 5.5 | 93.21 | 94.7 | 91.6 |
| 648 | 80 | 2000 | 1 | 6.2 | 250 | 6 | 82.4 | 92.6 | 250 | 5.5 | 93.5 | 94.6 | 91.8 |
| 672 | 20 | 3000 | 0.5 | 37.2 | 250 | 6 | 99.6 | 99.5 | 250 | 5.5 | 99.8 | 99.4 | 99.0 |
| 696 | 20 | 3000 | 0.5 | 37.2 | 250 | 6 | 99.7 | 99.5 | 250 | 5.5 | 99.7 | 99.3 | 98.9 |
| 720 | 20 | 3000 | 0.5 | 37.2 | 250 | 6 | 99.7 | 99.6 | 250 | 5.5 | 99.7 | 99.3 | 98.9 |
| 744 | 40 | 2000 | 0.5 | 12.4 | 250 | 6 | 99.3 | 99.3 | 250 | 5.5 | 97.2 | 99.2 | 96.7 |
| 768 | 40 | 2000 | 0.5 | 12.4 | 250 | 6 | 99.2 | 99.1 | 250 | 5.5 | 97.3 | 99.2 | 96.5 |
| 792 | 40 | 2000 | 0.5 | 12.4 | 250 | 6 | 99.2 | 99.2 | 250 | 5.5 | 97.5 | 99.3 | 96.6 |
| 816 | 40 | 2000 | 0.5 | 12.4 | 250 | 6 | 99.2 | 99.1 | 250 | 5.5 | 97.3 | 99.2 | 96.4 |
| 840 | 40 | 2000 | 0.5 | 12.4 | 250 | 6 | 99.2 | 99.1 | 250 | 5.5 | 97.3 | 99.2 | 96.6 |
| 864 | 40 | 2000 | 0.5 | 12.4 | 250 | 6 | 99.2 | 99.2 | 250 | 5.5 | 97.5 | 99.3 | 96.7 |
| 888 | 40 | 2000 | 0.5 | 12.4 | 250 | 6 | 99.0 | 99.2 | 250 | 5.5 | 97.3 | 99.2 | 96.6 |

hydrogenation catalyst (synthesized at lab, with a composition of CuO 40%, ZnO 29.6%, $Al_2O_3$ 30.4%, by a method wherein to a copper, zinc, chromium nitrate solution, there was added a NaOH solution till pH=9.0, and then centrifugal separated, washed, dried, tableted, calcinated). The catalyst was loaded into the reactor at the middle part (the constant temperature section) thereof, the two catalyst layers were separated apart by glass-fiber fabric, to both ends of the reactor there were packed a predetermined amount of quartz sand, functioning as a section for evaporating the feed stock by heating or as a packing. To the reactor jacket, there may be supplied heat conducting oil to control the reaction temperature. Upon completion of the catalyst loading into the reactor, the reaction system was connected, after passing the air tightness test, there was supplied hydrogen gas (500 mL/min) to conduct a reduction reaction under the conditions of 300 degrees Celsius and 6 MPa for 24 h, and then lowered to a predetermined temperature and pressure of the hydrogenation reaction. The mixture of acetic acid and acetic acid cyclohexyl ester via a dosing pump were pumped respectively into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 7.

TABLE 7

Experimental data observed with the acetic acid/acetic acid cyclohexyl ester hydrogenation

| reaction conditions | | | | | | | reaction results | | | |
|---|---|---|---|---|---|---|---|---|---|---|
| run time h | feed g/h | hydrogen gas feed mL/min | total feed space velocity $h^{-1}$ | hydrogen/ feed mol/mol | reaction temperature degrees Celsius | reaction pressure MPa | single-pass conversion of acetic acid % | single-pass conversion of acetic acid cyclohexyl ester % | single-pass selectivity to cyclohexanol % | total single-pass selectivity to ethanol % |
| 24 | 20 | 1000 | 0.5 | 12.4 | 240 | 6 | 98.8 | 97.2 | 99.0 | 96.5 |
| 48 | 20 | 1000 | 0.5 | 12.4 | 240 | 6 | 98.6 | 97.1 | 99.1 | 96.7 |
| 72 | 20 | 1000 | 0.5 | 12.4 | 240 | 6 | 98.5 | 97.0 | 99.0 | 96.6 |
| 96 | 20 | 1000 | 0.5 | 12.4 | 240 | 6 | 98.4 | 97.5 | 99.3 | 96.8 |
| 120 | 20 | 1000 | 0.5 | 12.4 | 240 | 6 | 98.3 | 97.3 | 99.1 | 96.7 |
| 144 | 20 | 1000 | 0.5 | 12.4 | 240 | 6 | 98.2 | 97.5 | 99.0 | 96.6 |
| 168 | 20 | 1000 | 0.5 | 12.4 | 240 | 6 | 98.1 | 97.2 | 99.1 | 96.8 |
| 192 | 20 | 1000 | 0.5 | 12.4 | 240 | 6 | 98.0 | 97.3 | 99.2 | 96.7 |
| 216 | 20 | 1000 | 0.5 | 12.4 | 240 | 6 | 98.0 | 97.1 | 99.0 | 96.6 |
| 240 | 20 | 1000 | 0.5 | 12.4 | 250 | 6 | 99.3 | 98.5 | 99.1 | 95.8 |
| 264 | 20 | 1000 | 0.5 | 12.4 | 250 | 6 | 99.2 | 97.2 | 98.9 | 96.9 |
| 288 | 20 | 1000 | 0.5 | 12.4 | 250 | 6 | 99.1 | 97.0 | 98.8 | 96.7 |
| 312 | 20 | 1000 | 0.5 | 12.4 | 250 | 6 | 99.1 | 97.1 | 99.0 | 96.5 |
| 336 | 20 | 1000 | 0.5 | 12.4 | 250 | 6 | 99.0 | 96.9 | 99.2 | 96.7 |
| 360 | 20 | 1000 | 0.5 | 12.4 | 250 | 6 | 98.8 | 96.7 | 99.1 | 96.8 |
| 384 | 20 | 1000 | 0.5 | 12.4 | 250 | 6 | 98.9 | 96.8 | 99.1 | 96.9 |
| 408 | 20 | 1000 | 0.5 | 12.4 | 250 | 6 | 98.5 | 96.7 | 99.1 | 96.7 |
| 432 | 20 | 1000 | 0.5 | 12.4 | 250 | 6 | 98.6 | 96.8 | 99.2 | 96.8 |
| 456 | 20 | 1000 | 0.5 | 12.4 | 250 | 6 | 98.6 | 96.5 | 99.1 | 96.9 |
| 480 | 20 | 1000 | 0.5 | 12.4 | 250 | 6 | 98.7 | 96.4 | 99.0 | 96.7 |
| 504 | 20 | 1000 | 0.5 | 12.4 | 250 | 6 | 98.6 | 96.6 | 99.1 | 96.3 |
| 528 | 20 | 1000 | 0.5 | 12.4 | 260 | 6 | 98.3 | 96.2 | 99.2 | 96.7 |
| 552 | 20 | 1000 | 0.5 | 12.4 | 260 | 6 | 98.5 | 96.3 | 99.1 | 96.5 |
| 576 | 20 | 1000 | 0.5 | 12.4 | 250 | 6 | 98.2 | 96.5 | 99.0 | 96.8 |
| 600 | 20 | 1000 | 0.5 | 12.4 | 260 | 6 | 98.1 | 96.3 | 99.2 | 96.5 |
| 624 | 20 | 1000 | 0.5 | 12.4 | 260 | 6 | 98.2 | 96.3 | 99.1 | 96.6 |
| 648 | 20 | 1000 | 0.5 | 12.4 | 260 | 6 | 98.0 | 96.5 | 99.2 | 96.8 |
| 672 | 20 | 1000 | 0.5 | 12.4 | 260 | 6 | 98.0 | 96.3 | 99.2 | 96.6 |

Example 10

4000 g of the hydrogenation reaction product from each of Examples 8 to 9 was collected, to conduct a separation by rectification experiment. The rectification was performed on a glass tower of 2 m height, and the tower column was loaded with Φ3 mm stainless steel Dixon high-efficient rectification packing, the bottom was a 5 L glass flask, heated by an electric jacket, with a voltage regulator to adjust the heating at the bottom. The tower reflux was controlled by a reflux ratio regulator. The separation by rectification results were listed in Table 8.

TABLE 8

Experimental data observed with the hydrogenation product separation by rectification

| fraction No. | distillation conditions: temperature degrees Celsius | temperature degrees Celsius | fraction weight g | composition (GC): ethanol m % | acetic acid ethyl ester m % | water m % | acetic acid m % | cyclohexanol (one) m % | acetic acid cyclohexyl ester m % | others m % |
|---|---|---|---|---|---|---|---|---|---|---|
| 0/distillation feed stock | | | 4000 | 41.1 | 0.5 | 10.0 | 0.2 | 46.5 | 0.7 | 0.9 |
| 1/ethanol product | 75 | 78 | 1700 | 93.9 | 1.1 | 5.0 | | | | |
| 2/transitional fraction | 78 | 160 | 550 | 10.5 | | 57.5 | 1.5 | 20.5 | 10.0 | |
| 3/cyclohexanol product | 160 | 162 | 1500 | | | | | 99.5 | 0.5 | |
| 4/bottom residue | | | 260 | | | | | | 86.2 | 13.8 |

The Eighth Embodiment

Example 1

This example illustrates a process for producing cyclohexene by a benzene selective hydrogenation.

Benzene and hydrogen gas at a ratio by molar of 1:3 were supplied into a hydrogenation reactor loaded with ruthenium based catalyst particles, under the conditions wherein the reaction temperature was 135 degrees Celsius, the reaction pressure was 4.5 MPa, the residence time was 15 min, to conduct a benzene hydrogenation reaction, after separating hydrogen gas from the reaction product, the liquid product was collected. The reaction ran continuously for 1000 h. Upon completion of the experiment, the collected liquid product was subject to vapor phase chromatography analysis, showing a composition of: benzene 53.3%, cyclohexene 35.4%, cyclohexane 11.3%.

Example 2

100 mL of a macroporous hydrogenous strong-acid ion exchange resin (synthesized at lab according to a classical literature method, wherein a styrene solution containing 15% divinylbenzene was subject to a suspension copolymerization and produced into base spherical particles, and then sulfonated by concentrated sulfuric acid, with a measured exchange capacity of 5.2 mmol $H^{+}$/g on dry basis) was loaded into a Φ32×4×1000 mm jacketed stainless steel tube reactor at the middle part thereof, below and above which there were packed a predetermined amount of quartz sand. Acetic acid and a cyclohexene feed stock (comprising benzene 53.3%, cyclohexene 35.4%, cyclohexane 11.3%) were pumped via a dosing pump at a predetermined flow rate respectively into the reactor to conduct a reaction, to the outer jacket of the reaction tube there was supplied hot water to control the reaction temperature, with a counterbalance valve at the reactor outlet to control the reactor pressure. The reactor outlet product was sampled by an on-line sampling valve for on-line chromatography analysis, on the basis of the product composition, there was calculated the single-pass conversion of cyclohexene and the single-pass selectivity to acetic acid cyclohexyl ester. The reaction conditions and results were listed in Table 1.

As can be seen from Table 1, when a strong-acid ion exchange resin catalyst was used for catalyzing the reaction between the cyclohexene feed stock and acetic acid, there were obtained a single-pass conversion of cyclohexene of greater than 80%, a single-pass selectivity to the ester product of greater than 99%, and after a run time of 600 hours, the catalyst activity and the single-pass selectivity remained steady.

TABLE 1

Experimental data observed with the esterification of acetic acid and cyclohexane/cyclohexene/benzene catalyzed by the strong-acid ion exchange resin

| run time h | reaction conditions: temperature degrees Celsius | pressure MPa | acetic acid feeding rate mL/h | cyclohexene feed stock feeding rate mL/h | single-pass conversion of cyclohexene % | single-pass selectivity to ester % |
|---|---|---|---|---|---|---|
| 24 | 70 | the normal pressure | 60 | 135 | 74.8 | 99.5 |
| 48 | 70 | the normal pressure | 60 | 135 | 74.6 | 99.5 |
| 72 | 70 | 1 | 60 | 135 | 74.7 | 99.3 |
| 96 | 80 | 1 | 60 | 135 | 77.0 | 99.2 |
| 120 | 80 | 1 | 60 | 135 | 77.2 | 99.1 |
| 144 | 80 | 2 | 60 | 135 | 77.5 | 99.2 |
| 168 | 90 | 2 | 60 | 120 | 77.5 | 99.3 |
| 192 | 90 | 3 | 60 | 135 | 78.8 | 99.1 |
| 216 | 90 | 5 | 60 | 135 | 79.1 | 99.3 |
| 240 | 90 | 5 | 90 | 135 | 79.0 | 99.3 |
| 264 | 90 | 5 | 90 | 135 | 79.6 | 99.1 |
| 288 | 100 | 10 | 90 | 135 | 82.8 | 98.9 |

TABLE 1-continued

Experimental data observed with the esterification of acetic acid and cyclohexane/cyclohexene/benzene catalyzed by the strong-acid ion exchange resin

| | reaction conditions | | | | | |
|---|---|---|---|---|---|---|
| run time h | temperature degrees Celsius | pressure MPa | acetic acid feeding rate mL/h | cyclohexene feed stock feeding rate mL/h | single-pass conversion of cyclohexene % | single-pass selectivity to ester % |
| 312 | 100 | 10 | 180 | 270 | 82.9 | 99.0 |
| 336 | 100 | 15 | 180 | 270 | 82.7 | 98.4 |
| 360 | 150 | 20 | 180 | 270 | 77.7 | 96.3 |
| 384 | 150 | 20 | 180 | 270 | 77.8 | 96.4 |
| 408 | 90 | 10 | 90 | 135 | 78.3 | 99.2 |
| 432 | 90 | 0.5 | 90 | 135 | 80.2 | 99.2 |
| 456 | 90 | 0.5 | 90 | 135 | 80.5 | 99.1 |
| 480 | 90 | 0.5 | 90 | 135 | 80.6 | 99.3 |
| 504 | 90 | 0.5 | 90 | 135 | 80.4 | 99.2 |
| 528 | 90 | 0.5 | 90 | 135 | 80.1 | 99.1 |
| 552 | 90 | 0.5 | 90 | 135 | 80.5 | 99.3 |
| 576 | 90 | 0.5 | 90 | 135 | 80.8 | 99.2 |
| 600 | 90 | 0.5 | 90 | 135 | 80.8 | 99.5 |

Example 3

The experiment apparatus, the process procedure and the feed stock were the same as Example 2, with the exception that the catalyst was a phosphorus modified H-beta molecular sieve catalyst (obtained by a method wherein a H-beta molecular sieve having a silica alumina ratio of 50 was modified by 85% phosphoric acid, and then kneaded with alumina and then extruded, dried at a temperature of 120 degrees Celsius, calcinated at a temperature of 500 degrees Celsius, with a phosphorus content of 2%). The reaction conditions and results were listed in Table 2. As can be seen from Table 2, the single-pass conversion of the reaction of cyclohexene and acetic acid was greater than 80%, the single-pass selectivity to the ester product was greater than 99%, and after a run time of 480 hours, the catalyst activity and the single-pass selectivity remained steady.

Example 4

The addition esterification product obtained from each of Examples 2 and 3 was collected, to conduct a separation by rectification experiment. The rectification was performed on a glass tower type rectification apparatus having a height of 2 m and a diameter of 40 mm, and the tower column was loaded with Φ3 mm stainless steel Dixon high-efficient rectification packing, the bottom was a 5 L glass flask, with a loading capacity of 4 L, and heated by an electric jacket, with a voltage regulator to adjust the heating at the bottom. The tower reflux was controlled by a reflux ratio regulator. The separation by rectification results were listed in Table 3.

TABLE 2

Experimental data observed with the esterification of acetic acid and cyclohexane/cyclohexene/benzene catalyzed by the H-beta molecular sieve catalyst

| | reaction conditions | | | | | |
|---|---|---|---|---|---|---|
| run time h | temperature degrees Celsius | pressure MPa | acetic acid feeding rate mL/h | cyclohexene feed stock feeding rate mL/h | single-pass conversion of cyclohexene % | single-pass selectivity to ester % |
| 24 | 70 | the normal pressure | 90 | 135 | 69.8 | 99.2 |
| 48 | 70 | the normal pressure | 90 | 135 | 70.3 | 99.2 |
| 72 | 70 | the normal pressure | 90 | 135 | 70.4 | 99.3 |
| 96 | 70 | the normal pressure | 90 | 135 | 70.3 | 99.1 |
| 120 | 70 | the normal pressure | 90 | 135 | 72.3 | 99.2 |
| 144 | 80 | 2 | 90 | 135 | 74.5 | 99.1 |
| 168 | 80 | 2 | 90 | 135 | 74.7 | 99.3 |
| 192 | 80 | 2 | 90 | 135 | 75.8 | 99.2 |
| 216 | 80 | 2 | 90 | 135 | 75.9 | 99.1 |
| 240 | 80 | 2 | 90 | 135 | 76.3 | 99.1 |
| 264 | 90 | 5 | 90 | 135 | 79.4 | 99.2 |
| 288 | 90 | 5 | 90 | 135 | 78.9 | 99.3 |
| 312 | 120 | 5 | 90 | 135 | 80.4 | 99.0 |
| 336 | 120 | 10 | 90 | 135 | 80.3 | 99.1 |
| 360 | 120 | 10 | 90 | 135 | 80.2 | 99.2 |
| 384 | 150 | 10 | 90 | 135 | 82.8 | 96.5 |
| 408 | 150 | 10 | 90 | 135 | 82.9 | 96.8 |
| 432 | 150 | 10 | 90 | 135 | 83.6 | 96.7 |
| 456 | 150 | 10 | 90 | 135 | 84.2 | 96.6 |
| 480 | 150 | 10 | 90 | 135 | 84.5 | 96.7 |

TABLE 3

| Experiment results observed with the addition esterification product separation by rectification | | | | | | | | |
|---|---|---|---|---|---|---|---|---|
| | | | analytic results/m % | | | | | |
| sample No. | temperature sections, degrees Celsius | weight/g | cyclohexane | cyclohexene | benzene | acetic acid | acetic acid cyclohexyl ester | high boiling materials |
| 0 | esterification product | 3795 | 7.4 | 4.4 | 35.1 | 20.5 | 32.3 | 0.3 |
| 1 | 78 to 118 (unreacted feed stock) | 2535 | 11.2 | 6.6 | 52.6 | 29.6 | | |
| 2 | 118 to 173 (transitional section) | 65 | | | | 42.3 | 57.7 | |
| 3 | 173 to 175 (ester product section) | 1155 | | | | | 99.6 | 0.4 |
| 4 | >176 residues | 41 | | | | | 92.6 | 7.4 |
| 1 to 4 in total | | | | | | | | |

Example 5 to 6 illustrate a process for producing acetic acid cyclohexyl ester by a reactive rectification.

The experiments of Examples 5 to 6 were all performed on a reactive rectification model experiment apparatus with these specifications: the main part of the model apparatus was a stainless steel tower having a diameter (inner diameter) of 50 mm, a height of 3 m, the lower part of which communicated with a bottom having a volume of 5 L, inside the bottom there was installed a 10 KW electrical heating rod, which was used to via an intelligent controller through a silicon controlled rectifier (SCR) control the heating at the bottom. The tower top communicated with a condenser having a heat exchange area of 0.5 $m^2$, vapor from the tower top was condensed by this condenser into liquid and then introduced into a reflux tank having a volume of 2 L. Liquid in the reflux tank was partially refluxed by a reflux pump back to the reaction tower, partially withdrawn as lighter components. The operation parameters of the tower were controlled by and displayed on an intelligent type automatic control instrument. The tower reflux rate was controlled by a reflux control valve, the top withdrawal was controlled by a level controller at the reflux tank. The bottom withdrawal was controlled by a bottom blow-off valve which was controlled by a bottom level controller. Acetic acid and a cyclohexene feed stock were respectively supplied into a 30 L storage tank, and through a dosing pump were pumped respectively into the corresponding preheater and preheated to a predetermined temperature and then introduced into the reaction tower, the feeding rate was controlled by the dosing pump and accurately metered by an electronic balance.

Example 5

A high temperature resistant sulfonic acid type ion exchange resin (with a trade name of Amberlyst 45, produced by the Rhom&Hass company) was by a multi-stage high speed grinder ground into powder having a particle size of less than 200 mesh (0.074 mm), there was added a porogenic agent, a lubricant, an antioxidant and a binder, mixed homogeneously with a high-speed mixer, and then with an internal mixer at 180 degrees Celsius mixed for 10 min, to completely plasticize the mass, and then injected into a mould and formed into a raschig ring type resin catalyst packing having a diameter of 5 mm, a height of 5 mm and a wall thickness of 1 mm. 1950 mL of the packing was loaded into the middle part of a model reaction tower (with a height of 1 m, corresponding to a theoretical plate number of 8), above and below which there was each loaded 1950 mL of a glass spring packing having a diameter of 3 mm and a length of 6 mm (with a loading height of 1 m, corresponding to a theoretical plate number of 10). A cyclohexene feed stock and acetic acid via a dosing pump were pumped respectively into a preheater and preheated and then introduced into the reaction tower, adjusting the heating at the bottom and the reflux rate at the tower top to continuously conduct the reaction, the steady-state reaction conditions and reaction results were listed in Table 4.

TABLE 4

| Experimental data observed with the reactive rectification by the high temperature resistant sulfonic acid type ion exchange resin catalyst | | | | |
|---|---|---|---|---|
| operation conditions | | | | |
| operation pressure | 0.3 MPa | | | |
| top temperature | 118 degrees Celsius | | | |
| catalyst section temperature | 140 to 146 degrees Celsius | | | |
| bottom temperature | 200 degrees Celsius | | | |
| reflux ratio | 5 | | | |
| mass | cyclohexene feed stock | acetic acid feed | top with-drawal | bottom with-drawal |
| position | catalyst bed at lower part | catalyst bed at upper part | tower top at reflux pump outlet | tower bottom at discharge outlet |
| flow rate g/h | 1027 | 601 | 921 | 707 |
| temperature degrees Celsius | | | 40 | 225 |
| composition (ratio by mass) | | | | |
| cyclohexene | 40.0% | | 0.55% | |
| benzene | 19.0% | | 21.17% | |
| cyclohexane | 41.0% | | 45.71% | |
| acetic acid | | | 32.57% | 0.84% |
| acetic acid cyclohexyl ester | | | | 98.6% |
| polymers | | | | 0.56% |

Calculation from the experimental data revealed a single-pass conversion of cyclohexene of 98.8%, a single-pass selectivity to acetic acid cyclohexyl ester of 98.0%.

Example 6

A Φ3 to 4 spherical $H_{0.5}Cs_{2.5}PW_{12}O_{40}/SiO_2$ catalyst (obtained by: $H_{0.5}Cs_{2.5}PW_{12}O_{40}$ powder and wide hole silica gel powder having a particle size of less than 200 mesh were on a mixer thoroughly mixed, and then, ball-formed on a coating machine by using silica sol as the binder, and then dried, calcinated) was sandwiched between titanium wire mesh corrugated plates, and produced into a cylindrical structured packing having a diameter of 50 mm and a height of 50 mm. The packing type catalyst L was loaded into the middle part of a model reaction tower (with a height of 1 m, corresponding to a theoretical plate number of 12), above and below which there was each loaded 1950 mL of a glass spring packing having a diameter of 4 mm and a height of 4 mm (with a loading height of 1 m, corresponding to a theoretical plate number of 15). A cyclohexene feed stock and acetic acid via a dosing pump were pumped respectively into a preheater and preheated and then introduced into the reaction tower, adjusting the heating at the bottom and the reflux rate at the tower top to continuously conduct the reaction, the steady-state reaction conditions and reaction results were listed in Table 5.

TABLE 5

Experimental data observed with the reactive rectification by the $H_{0.5}Cs_{2.5}PW_{12}O_{40}/SiO_2$ catalyst

| operation conditions | |
|---|---|
| operation pressure | 0.3 MPa |
| top temperature | 102 degrees Celsius |
| reaction section temperature | 145 to 180 degrees Celsius |
| bottom temperature | 209 degrees Celsius |
| reflux ratio | 5 |

| mass | cyclohexene feed stock | acetic acid feed | top withdrawal | bottom withdrawal |
|---|---|---|---|---|
| position | catalyst bed at lower part | catalyst bed at upper part | tower top at reflux pump outlet | tower bottom at discharge outlet |
| flow rate g/h | 1540 | 601 | 1084 | 1056 |
| temperature degrees Celsius | | | 40 | 209 |
| composition (ratio by mass) | | | | |
| cyclohexene | 40.0% | | 0.36% | |
| benzene | 19.0% | | 27.03% | |
| cyclohexane | 41.0% | | 58.21% | |
| acetic acid | | 100% | 14.39% | |

TABLE 5-continued

Experimental data observed with the reactive rectification by the $H_{0.5}Cs_{2.5}PW_{12}O_{40}/SiO_2$ catalyst

| | | | | |
|---|---|---|---|---|
| acetic acid cyclohexyl ester | | | | 99.62% |
| polymers | | | | 0.38% |

Calculation from the experimental data revealed a single-pass conversion of cyclohexene of 99.35%, a single-pass selectivity to acetic acid cyclohexyl ester of 99.6%.

Example 7 to 8 illustrate a process for hydrogenating acetic acid cyclohexyl ester.

Example 7

The hydrogenation feed stock was acetic acid cyclohexyl ester having a purity of 99.6%. 40 g copper-zinc-aluminium based ester hydrogenation catalyst (synthesized at lab, with a composition of CuO 40.5%, ZnO 29.6%, $Al_2O_3$ 30.4%. obtained by a method wherein to a copper, zinc, chromium nitrate solution, there was added a NaOH solution till pH=9.0, and then centrifugal separated, washed, dried, tableted, calcinated) was loaded into a Φ20×2.5×800 mm jacketed stainless steel tube reactor at the middle part thereof, below and above which there were packed a predetermined amount of quartz sand, supplied with hydrogen gas (500 mL/min) to conduct a reduction under the conditions of 280 degrees Celsius and 6 MPa for 24 h, and then lowered to a predetermined temperature and pressure of the hydrogenation reaction. Acetic acid cyclohexyl ester via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 6. Table 6 revealed that, when a copper-zinc-aluminium based catalyst was used, the single-pass conversion of the acetic acid cyclohexyl ester hydrogenation reaction was up to 99.0% or more, the single-pass selectivity to cyclohexanol was greater than 99.9%, and after a run time of 1000 h, the single-pass conversion and the single-pass selectivity did not drop.

TABLE 6

Experimental data observed with the acetic acid cyclohexyl ester hydrogenation by the copper-zinc-aluminium based ester hydrogenation catalyst

| | reaction conditions | | | | | | reaction results | | | | | | |
|---|---|---|---|---|---|---|---|---|---|---|---|---|---|
| run time h | temperature degrees Celsius | pressure MPa | ester feed g/h | hydrogen gas feed mL/min | space velocity $h^{-1}$ | hydrogen/ester ratio | ethanol m % | cyclohexanol m % | acetic acid cyclohexyl ester m % | lighter impurities m % | heavier impurities m % | single-pass conversion of cyclohexyl ester % | single-pass selectivity to cyclohexanol % |
| 24 | 200 | 6 | 20 | 400 | 0.5 | 7.62 | 23.23 | 51.12 | 22.47 | 1.29 | 1.89 | 76.79 | 99.81 |
| 48 | 200 | 6 | 20 | 400 | 0.5 | 7.62 | 23.12 | 50.95 | 22.45 | 1.36 | 2.12 | 76.93 | 99.79 |
| 72 | 200 | 6 | 20 | 400 | 0.5 | 7.62 | 23.25 | 51.15 | 22.26 | 1.36 | 1.98 | 77.06 | 99.68 |

TABLE 6-continued

Experimental data observed with the acetic acid cyclohexyl ester hydrogenation by the copper-zinc-aluminium based ester hydrogenation catalyst

| | reaction conditions | | | | | | reaction results | | | | | | |
|---|---|---|---|---|---|---|---|---|---|---|---|---|---|
| run time h | temperature degrees Celsius | pressure MPa | ester feed g/h | hydrogen gas feed mL/min | space velocity $h^{-1}$ | hydrogen/ester ratio | ethanol m % | cyclohexanol m % | acetic acid cyclohexyl ester m % | lighter impurities m % | heavier impurities m % | single-pass conversion of cyclohexyl ester % | single-pass selectivity to cyclohexanol % |
| 96 | 220 | 6 | 20 | 400 | 0.5 | 7.62 | 25.62 | 57.26 | 12.27 | 2.13 | 2.72 | 87.81 | 99.65 |
| 120 | 220 | 6 | 20 | 400 | 0.5 | 7.62 | 25.88 | 58.06 | 11.13 | 2.22 | 2.71 | 89.07 | 99.75 |
| 144 | 220 | 6 | 20 | 400 | 0.5 | 7.62 | 26.2 | 58.71 | 10.28 | 2.13 | 2.68 | 89.82 | 99.76 |
| 168 | 235 | 6 | 20 | 400 | 0.5 | 7.62 | 27.51 | 62.1 | 4.99 | 2.54 | 2.86 | 95.50 | 99.73 |
| 192 | 235 | 6 | 20 | 400 | 0.5 | 7.62 | 27.61 | 63.1 | 3.77 | 2.62 | 2.9 | 97.11 | 99.40 |
| 216 | 235 | 6 | 20 | 400 | 0.5 | 7.62 | 27.5 | 62.5 | 4.28 | 2.6 | 3.12 | 96.46 | 99.55 |
| 240 | 250 | 6 | 20 | 400 | 0.5 | 7.62 | 28.89 | 65.05 | 1.68 | 2.07 | 2.31 | 98.31 | 99.78 |
| 264 | 250 | 6 | 20 | 400 | 0.5 | 7.62 | 28.9 | 65.22 | 1.82 | 2.05 | 2.01 | 98.18 | 99.71 |
| 288 | 250 | 6 | 20 | 400 | 0.5 | 7.62 | 29.12 | 65.05 | 1.61 | 2.05 | 2.17 | 98.12 | 99.73 |
| 312 | 265 | 6 | 20 | 400 | 0.5 | 7.62 | 29.2 | 65.11 | 1.27 | 2.02 | 2.4 | 98.41 | 99.73 |
| 336 | 265 | 6 | 20 | 400 | 0.5 | 7.62 | 29.12 | 64.82 | 1.02 | 2.92 | 2.12 | 99.21 | 97.99 |
| 360 | 265 | 6 | 20 | 400 | 0.5 | 7.62 | 29.21 | 64.9 | 1.55 | 2.04 | 2.3 | 98.04 | 99.60 |
| 384 | 300 | 6 | 20 | 400 | 0.5 | 7.62 | 28.91 | 64.21 | 3.12 | 1.87 | 1.89 | 96.33 | 99.59 |
| 408 | 300 | 6 | 20 | 400 | 0.5 | 7.62 | 28.8 | 64.02 | 3.23 | 1.93 | 2.02 | 96.30 | 99.56 |
| 432 | 300 | 6 | 20 | 400 | 0.5 | 7.62 | 28.6 | 63.95 | 3.32 | 2.01 | 2.12 | 96.44 | 99.54 |
| 456 | 250 | 3 | 20 | 400 | 0.5 | 7.62 | 24.86 | 55.85 | 9.75 | 4.12 | 5.42 | 92.10 | 98.70 |
| 480 | 250 | 3 | 20 | 400 | 0.5 | 7.62 | 24.92 | 55.46 | 11.05 | 2.96 | 5.61 | 89.89 | 98.62 |
| 504 | 250 | 3 | 20 | 400 | 0.5 | 7.62 | 24.84 | 55.74 | 10.51 | 3.41 | 5.5 | 90.85 | 99.74 |
| 528 | 250 | 15 | 20 | 400 | 0.5 | 7.62 | 30.2 | 65.63 | 1.42 | 0.83 | 1.92 | 96.69 | 99.73 |
| 552 | 250 | 15 | 20 | 400 | 0.5 | 7.62 | 30.27 | 65.86 | 1.04 | 0.98 | 1.85 | 97.18 | 99.69 |
| 576 | 250 | 15 | 20 | 400 | 0.5 | 7.62 | 30.25 | 65.86 | 1.13 | 0.86 | 1.9 | 97.04 | 99.71 |
| 600 | 250 | 6 | 10 | 400 | 0.25 | 15.24 | 29.78 | 66.15 | 1.03 | 1.52 | 1.52 | 98.09 | 99.70 |
| 624 | 250 | 6 | 10 | 400 | 0.25 | 15.24 | 29.85 | 66.25 | 0.82 | 1.51 | 1.57 | 98.28 | 99.71 |
| 648 | 250 | 6 | 10 | 400 | 0.25 | 15.24 | 29.81 | 66.15 | 0.95 | 1.6 | 1.49 | 98.19 | 99.73 |
| 672 | 250 | 6 | 40 | 400 | 1 | 3.81 | 22.21 | 48.49 | 26.93 | 1.02 | 1.35 | 72.02 | 99.58 |
| 696 | 250 | 6 | 40 | 400 | 1 | 3.81 | 22.47 | 49.52 | 25.42 | 1.17 | 1.42 | 73.81 | 99.57 |
| 720 | 250 | 6 | 40 | 400 | 1 | 3.81 | 22.51 | 49.42 | 25.53 | 1.14 | 1.4 | 73.59 | 99.57 |
| 744 | 250 | 6 | 20 | 2000 | 0.5 | 38.09 | 30.98 | 67.39 | 0.32 | 0.69 | 0.62 | 97.50 | 99.65 |
| 768 | 250 | 6 | 20 | 2000 | 0.5 | 38.09 | 30.79 | 67.38 | 0.34 | 0.97 | 0.52 | 97.84 | 99.26 |
| 792 | 250 | 6 | 20 | 2000 | 0.5 | 38.09 | 30.89 | 67.32 | 0.31 | 0.94 | 0.54 | 97.73 | 99.32 |
| 816 | 250 | 6 | 20 | 400 | 0.5 | 7.62 | 28.88 | 64.82 | 2.23 | 2.25 | 1.82 | 97.74 | 99.34 |
| 840 | 250 | 6 | 20 | 400 | 0.5 | 7.62 | 28.81 | 64.82 | 2.36 | 2.25 | 1.76 | 97.66 | 99.47 |
| 864 | 250 | 6 | 20 | 400 | 0.5 | 7.62 | 28.91 | 65.01 | 2.13 | 2.19 | 1.76 | 97.84 | 99.47 |
| 888 | 250 | 6 | 20 | 400 | 0.5 | 7.62 | 28.96 | 64.95 | 2.01 | 2.27 | 1.81 | 97.94 | 99.34 |
| 912 | 250 | 6 | 20 | 400 | 0.5 | 7.62 | 28.91 | 64.67 | 2.4 | 2.11 | 1.91 | 97.40 | 99.36 |
| 936 | 250 | 6 | 20 | 400 | 0.5 | 7.62 | 28.85 | 64.35 | 2.92 | 1.93 | 1.95 | 96.69 | 99.59 |
| 960 | 250 | 6 | 20 | 400 | 0.5 | 7.62 | 29.12 | 64.76 | 2.36 | 1.84 | 1.92 | 97.09 | 99.65 |
| 984 | 250 | 6 | 20 | 400 | 0.5 | 7.62 | 28.77 | 64.21 | 3.07 | 1.97 | 1.98 | 96.59 | 99.54 |
| 1008 | 250 | 6 | 20 | 400 | 0.5 | 7.62 | 28.91 | 64.61 | 2.58 | 2.01 | 1.89 | 97.12 | 99.52 |

Example 8

The hydrogenation feed stock was acetic acid cyclohexyl ester having a purity of 99.6%. 40 g copper-chromium based ester hydrogenation catalyst (commercially available from Taiyuan Xinjida Chemical Ltd., with a trade name of C1-XH-1, with a CuO content of 55%, as tablet having a diameter of 5 mm, crashed into particles of 10 to 20 mesh) was loaded into a Φ20×2.5×800 mm jacketed stainless steel tube reactor at the middle part thereof, below and above which there were packed a predetermined amount of quartz sand, supplied with hydrogen gas (500 mL/min) to conduct a reduction under the conditions of 280 degrees Celsius and 6 MPa for 24 h, and then the system was lowered to a predetermined temperature and pressure of the reaction. Acetic acid cyclohexyl ester via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 7. Table 7 revealed that, when a copper-zinc-aluminium based catalyst was used, the single-pass conversion of the acetic acid cyclohexyl ester hydrogenation reaction was up to 98.0% or more, the single-pass selectivity to cyclohexanol was greater than 99.9%, and after a run time of 500 h, the single-pass conversion and selectivity did not drop.

TABLE 7

Experimental data observed with the acetic acid cyclohexyl ester hydrogenation by the copper-chromium based ester hydrogenation catalyst

| | reaction conditions | | | | | | reaction results | | | | | | |
|---|---|---|---|---|---|---|---|---|---|---|---|---|---|
| run time h | temperature degrees Celsius | pressure MPa | ester feed stock g/h | hydrogen gas feed mL/min | space velocity $h^{-1}$ | hydrogen/ester ratio | ethanol m % | cyclohexanol m % | acetic acid cyclohexyl ester m % | lighter impurities m % | heavier impurities m % | single-pass conversion of cyclohexyl ester % | single-pass selectivity to cyclohexanol % |
| 24 | 230 | 6 | 20 | 400 | 0.5 | 7.62 | 26.28 | 57.45 | 13.27 | 0.98 | 2.02 | 85.51 | 99.22 |
| 48 | 230 | 6 | 20 | 400 | 0.5 | 7.62 | 26.2 | 57.25 | 13.37 | 1.08 | 2.1 | 85.52 | 98.91 |
| 72 | 250 | 6 | 20 | 400 | 0.5 | 7.62 | 27.85 | 61.35 | 7.12 | 1.36 | 2.32 | 92.06 | 98.79 |
| 96 | 250 | 6 | 20 | 400 | 0.5 | 7.62 | 28.11 | 61.25 | 7.01 | 1.46 | 2.17 | 91.85 | 99.32 |
| 120 | 320 | 20 | 20 | 400 | 0.5 | 7.62 | 28.39 | 62.75 | 5.42 | 1.41 | 2.03 | 93.75 | 99.24 |
| 144 | 320 | 20 | 20 | 400 | 0.5 | 7.62 | 28.61 | 64.65 | 2.41 | 2.15 | 2.18 | 97.86 | 98.88 |
| 168 | 260 | 6 | 20 | 400 | 0.5 | 7.62 | 28.15 | 64.71 | 3.04 | 2.32 | 1.78 | 97.72 | 99.27 |
| 192 | 260 | 6 | 20 | 400 | 0.5 | 7.62 | 28.26 | 64.75 | 2.67 | 2.29 | 2.03 | 98.03 | 99.08 |
| 216 | 260 | 10 | 20 | 400 | 0.5 | 7.62 | 29.11 | 64.79 | 3.52 | 1.25 | 1.33 | 95.54 | 99.70 |
| 240 | 260 | 10 | 20 | 400 | 0.5 | 7.62 | 28.65 | 65.25 | 3.2 | 1.73 | 1.17 | 96.77 | 99.83 |
| 264 | 260 | 6 | 10 | 400 | 0.25 | 15.24 | 28.92 | 65.06 | 1.55 | 2.01 | 2.46 | 98.53 | 98.94 |
| 288 | 260 | 6 | 10 | 400 | 0.25 | 15.24 | 29.02 | 64.92 | 1.5 | 1.99 | 2.57 | 98.40 | 99.08 |
| 312 | 260 | 4 | 20 | 400 | 0.5 | 7.62 | 28.49 | 63.71 | 3.24 | 1.89 | 2.67 | 96.64 | 99.02 |
| 336 | 260 | 4 | 20 | 400 | 0.5 | 7.62 | 28.41 | 63.58 | 3.59 | 1.88 | 2.54 | 96.23 | 99.49 |
| 360 | 260 | 6 | 20 | 800 | 0.5 | 15.24 | 28.59 | 64.01 | 4.94 | 1.32 | 1.14 | 94.34 | 99.62 |
| 384 | 260 | 6 | 20 | 800 | 0.5 | 15.24 | 28.55 | 64.44 | 4.55 | 1.47 | 0.99 | 95.02 | 99.68 |
| 408 | 260 | 6 | 20 | 600 | 0.5 | 11.43 | 28.29 | 63.75 | 5.57 | 1.45 | 0.94 | 93.95 | 99.64 |
| 432 | 260 | 6 | 20 | 600 | 0.5 | 11.43 | 28.33 | 63.88 | 5.3 | 1.48 | 1.01 | 94.27 | 99.62 |
| 456 | 260 | 6 | 20 | 600 | 0.5 | 11.43 | 28.21 | 63.81 | 5.5 | 1.52 | 0.96 | 94.18 | 99.61 |
| 480 | 260 | 6 | 20 | 600 | 0.5 | 11.43 | 28.19 | 63.66 | 5.68 | 1.46 | 1.01 | 93.93 | 99.58 |
| 504 | 260 | 6 | 20 | 600 | 0.5 | 11.43 | 28.18 | 63.75 | 5.65 | 1.49 | 0.93 | 94.01 | 99.64 |

Example 9

4000 g of each reaction product of Examples 7 to 8 was collected, to conduct a separation by rectification experiment. The rectification was performed on a glass tower of 2 m height, and the tower column was loaded with Φ3 mm stainless steel Dixon high-efficient rectification packing, the bottom was a 5 L glass flask, heated by an electric jacket, with a voltage regulator to adjust the heating at the bottom. The tower reflux was controlled by a reflux ratio regulator. The separation by rectification results were listed in Table 8.

TABLE 8

Experimental data observed with the acetic acid cyclohexyl ester hydrogenation product separation by rectification

| | reaction conditions | | | analytic results | | | | |
|---|---|---|---|---|---|---|---|---|
| | temperature | | fraction | | | acetic acid cyclohexyl | lighter | heavier |
| fraction No. | degrees Celsius | degrees Celsius | weight g | ethanol m % | cyclohexanol m % | ester m % | impurities m % | impurities m % |
| 0 (distillation feed stock) | | | 4000 | 27.96 | 62.39 | 5.89 | 1.77 | 1.99 |
| 1 (ethanol product) | 79 | 81 | 1143.7 | 96.27 | 1.88 | | 1.85 | |
| 2 (transitional fraction) | 81 | 155 | 52.2 | 76.24 | 22.2 | | 1.56 | |
| 3 (alcohol ketone product) | 155 | 162 | 2476.8 | | 95.92 | 1.21 | 1.96 | 0.91 |
| 4 (bottom residue) | >162 | | 298 | | | 75.6 | | 24.4 |
| loss | | | 29.3 | | | | | |
| total | | | 4000 | | | | | |

The Ninth Embodiment

Example 1

This example illustrates a process for producing cyclohexene by a benzene selective hydrogenation.

Benzene and hydrogen gas at a ratio by molar of 1:3 were supplied into a hydrogenation reactor loaded with ruthenium based catalyst particles, under the conditions wherein the reaction temperature was 135 degrees Celsius, the reaction pressure was 4.5 MPa, the residence time was 15 min, to conduct a benzene hydrogenation reaction, after separating hydrogen gas from the reaction product, the liquid product was collected. The reaction ran continuously for 1000 h. Upon completion of the experiment, the collected liquid product was subject to vapor phase chromatography analysis, showing a composition of: benzene 53.3 m %, cyclohexene 35.4 m %, cyclohexane 11.3 m %. Using N,N-dimethyl acetamide as the extractant, the liquid product was subject to an extractive separation to obtain a mixture of cyclohexene and benzene.

Example 2

100 mL of a macroporous hydrogenous strong-acid ion exchange resin (synthesized at lab according to a classical literature method, wherein a styrene solution containing 15% divinylbenzene was subject to a suspension copolymerization and produced into base spherical particles, and then sulfonated by concentrated sulfuric acid, with a measured exchange capacity of 5.2 mmol $H^{+}$/g on dry basis) was loaded into a Φ32×4×1000 mm jacketed stainless steel tube reactor at the middle part thereof, below and above which there were packed a predetermined amount of quartz sand. Acetic acid and a cyclohexene feed stock (obtained from the process of Example 1, with a composition of: benzene 60 m %, cyclohexene 40 m %) were pumped via a dosing pump at a predetermined flow rate respectively into the reactor to conduct a reaction, to the outer jacket of the reaction tube there was supplied hot water to control the reaction temperature, with a counterbalance valve at the reactor outlet to control the reactor pressure. The reactor outlet product was sampled by an on-line sampling valve for on-line chromatography analysis, on the basis of the product composition, there was calculated the single-pass conversion of cyclohexene and the single-pass selectivity to acetic acid cyclohexyl ester. The reaction conditions and results were listed in Table 1.

As can be seen from Table 1, when a strong-acid ion exchange resin catalyst was used for the reaction of cyclohexene and acetic acid, there were obtained a single-pass conversion of cyclohexene of greater than 80%, a single-pass selectivity to the ester product of greater than 99%, and after a run time of 600 hours, the catalyst activity and the single-pass selectivity remained steady.

Example 3

The experiment apparatus, the process procedure and the feed stock were the same as Example 2, with the exception that the catalyst was a phosphorus modified H-beta molecular sieve catalyst (obtained by a method wherein a H-beta molecular sieve having a silica alumina ratio of 50 was modified by 85% phosphoric acid, and then kneaded with alumina and then extruded, dried at a temperature of 120 degrees Celsius, calcinated at a temperature of 500 degrees Celsius, with a phosphorus content of 2%). The reaction conditions and results were listed in Table 2. As can be seen from Table 2, the single-pass conversion of cyclohexene was 80%, the single-pass selectivity to the ester product was greater than 99%, and after a run time of 480 hours, the catalyst activity and the single-pass selectivity remained steady.

Example 4

The addition esterification product obtained from each of Examples 2 and 3 was collected, to conduct a separation by rectification experiment. The rectification was performed on a glass tower type rectification apparatus having a height of 2 m and a diameter of 40 mm, and the tower column was loaded with Φ3 mm stainless steel Dixon high-efficient rectification packing, the bottom was a 5 L glass flask, with a loading capacity of 4 L, and heated by an electric jacket, with a voltage regulator to adjust the heating at the bottom. The tower reflux was controlled by a reflux ratio regulator. The separation by rectification results were listed in Table 3.

Example 5 to 6 illustrate a reactive rectification process for producing acetic acid cyclohexyl ester.

The experiments of Example 5 to 6 were all performed on a reactive rectification model experiment apparatus with these specifications: the main part of the model apparatus was a stainless steel tower having a diameter (inner diameter) of 50 mm, a height of 3 m, the lower part of which communicated with a bottom having a volume of 5 L, inside the bottom there was installed a 10 KW electrical heating rod, which was used to via an intelligent controller through a silicon controlled rectifier (SCR) control the heating at the bottom. The tower top communicated with a condenser having a heat exchange area of 0.5 $m^2$, vapor from the tower top was condensed by this condenser into liquid and then introduced into a reflux tank having a volume of 2 L. Liquid in the reflux tank was partially refluxed by a reflux pump back to the reaction tower, partially withdrawn as lighter components. The operation parameters of the tower were controlled by and displayed on an intelligent type automatic control instrument. The tower reflux rate was controlled by a reflux control valve, the top withdrawal was controlled by a level controller at the reflux tank. The bottom withdrawal was controlled by a bottom blow-off valve which was controlled by a bottom level controller. Acetic acid and a cyclohexene feed stock (the same as Example 2) were respectively supplied into a 30 L storage tank, and through a dosing pump were pumped respectively into the corresponding preheater and preheated to a predetermined temperature and then introduced into the reaction tower, the feeding rate was controlled by the dosing pump and accurately metered by an electronic balance.

Example 5

A high temperature resistant sulfonic acid type ion exchange resin (with a trade name of Amberlyst 45, produced by the Rhom&Hass company) was by a multi-stage high speed grinder ground into powder having a particle size of less than 200 mesh (0.074 mm), there was added a porogenic agent, a lubricant, an antioxidant and a binder, mixed homogeneously with a high-speed mixer, and then with an internal mixer at 180 degrees Celsius mixed for 10 min, to completely plasticize the mass, and then injected into a mould and formed into a raschig ring type resin catalyst packing having a diameter of 5 mm, a height of 5 mm and a wall thickness of 1 mm. 1950 mL of the packing was loaded into the middle part of a model reaction tower (with a height of 1 m, corresponding to a theoretical plate number of 8), above and below which there was each loaded 1950 mL of a glass spring packing having a diameter of 3 mm and a length of 6 mm (with a loading height of 1 m, corresponding to a theoretical plate number of 10). A cyclohexene feed stock and acetic acid via a dosing pump were pumped respectively into a preheater and preheated and then introduced into the reaction tower, adjusting the heating at the bottom and the reflux rate at the tower top to continuously conduct the reaction, the steady-state reaction conditions and reaction results were listed in Table 4.

Example 6

A Φ3 to 4 spherical $H_{0.5}Cs_{2.5}PW_{12}O_{40}/SiO_2$ catalyst (obtained by: $H_{0.5}Cs_{2.5}PW_{12}O_{40}$ powder and wide hole silica gel powder having a particle size of less than 200 mesh were on a mixer thoroughly mixed, and then, ball-formed on a coating machine by using silica sol as the binder, and then dried, calcinated) was sandwiched between titanium wire mesh corrugated plates, and produced into a cylindrical structured packing having a diameter of 50 mm and a height of 50 mm. The packing type catalyst L was loaded into the middle part of a model reaction tower (with a height of 1 m, corresponding to a theoretical plate number of 12), above and below which there was each loaded 1950 mL of a glass spring packing having a diameter of 4 mm and a height of 4 mm (with a loading height of 1 m, corresponding to a theoretical plate number of 15). A cyclohexene feed stock and acetic acid via a dosing pump were pumped respectively into a preheater and preheated and then introduced into the reaction tower, adjusting the heating at the bottom and the reflux rate at the tower top to continuously conduct the reaction, the steady-state reaction conditions and reaction results were listed in Table 5.

Examples 7 to 8 illustrate the hydrogenation of acetic acid cyclohexyl ester.

Example 7

Acetic acid cyclohexyl ester having a purity of 99.6% was used as the hydrogenation feed stock.

40 g copper-zinc-aluminium based ester hydrogenation catalyst (synthesized at lab, with a composition of CuO 40.5%, ZnO 29.6%, $Al_2O_3$ 30.4%, by a method wherein to a copper, zinc, chromium nitrate solution, there was added a NaOH solution till pH=9.0, and then centrifugal separated, washed, dried, tableted, calcinated) was loaded into a Φ20×2.5×800 mm jacketed stainless steel tube reactor at the middle part thereof, below and above which there were packed a predetermined amount of quartz sand, supplied with hydrogen gas (500 mL/min) to conduct a reduction under the conditions of 280 degrees Celsius and 6 MPa for 24 h, and then lowered to a predetermined temperature and pressure of the hydrogenation reaction. Acetic acid cyclohexyl ester via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 6. Table 6 revealed that, when a copper-zinc-aluminium based ester hydrogenation catalyst was used, the single-pass conversion of the acetic acid cyclohexyl ester hydrogenation reaction was up to 99%, the single-pass selectivity to cyclohexanol was greater than 99%, and after a run time of 1000 h, the single-pass conversion and the single-pass selectivity did not drop.

Example 8

Acetic acid cyclohexyl ester having a purity of 99.6% was used as the hydrogenation feed stock.

40 g copper-chromium based ester hydrogenation catalyst (commercially available from Taiyuan Xinjida Chemical Ltd., with a trade name of C1-XH-1, with a CuO content of 55%, as tablet having a diameter of 5 mm, crashed into particles of 10 to 20 mesh) was loaded into a Φ20×2.5×800 mm jacketed stainless steel tube reactor at the middle part thereof, below and above which there were packed a predetermined amount of quartz sand, supplied with hydrogen gas (500 mL/min) to conduct a reduction under the conditions of 280 degrees Celsius and 6 MPa for 24 h, and then the system was lowered to a predetermined temperature and pressure of the reaction. Acetic acid cyclohexyl ester via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 7. Table 7 revealed that, when a copper-zinc-aluminium based ester hydrogenation catalyst was used, the single-pass conversion of the acetic acid cyclohexyl ester hydrogenation reaction was up to 98% or more, the single-pass selectivity to cyclohexanol was greater than 99%, and after a run time of 500 h, the single-pass conversion and the single-pass selectivity did not drop.

Example 9

4000 g of each reaction product of Examples 7 to 8 was collected, to conduct a separation by rectification experiment. The rectification was performed on a glass tower of 2 m height, and the tower column was loaded with Φ3 mm stainless steel Dixon high-efficient rectification packing, the bottom was a 5 L glass flask, heated by an electric jacket, with a voltage regulator to adjust the heating at the bottom. The tower reflux was controlled by a reflux ratio regulator. The separation by rectification results were listed in Table 8.

TABLE 1

Experimental data observed with the esterification reaction of acetic acid and cyclohexene/benzene catalyzed by the strong-acid ion exchange resin

| run time h | reaction conditions: temperature degrees Celsius | pressure MPa | acetic acid feeding rate mL/h | cyclohexene/benzene feeding rate mL/h | single-pass conversion of cyclohexene % | single-pass selectivity to ester % |
|---|---|---|---|---|---|---|
| 24 | 70 | the normal pressure | 60 | 120 | 76.5 | 99.1 |
| 48 | 70 | the normal pressure | 60 | 120 | 76.6 | 99.2 |
| 72 | 70 | 1 | 60 | 120 | 76.2 | 99.1 |
| 96 | 80 | 1 | 60 | 120 | 78.5 | 99.0 |
| 120 | 80 | 1 | 60 | 120 | 79.2 | 99.2 |
| 144 | 80 | 2 | 60 | 120 | 79.6 | 99.3 |
| 168 | 90 | 2 | 60 | 120 | 78.5 | 99.2 |
| 192 | 90 | 3 | 60 | 120 | 80.8 | 99.1 |
| 216 | 90 | 5 | 60 | 120 | 81.0 | 99.2 |
| 240 | 90 | 5 | 90 | 120 | 81.1 | 99.2 |
| 264 | 90 | 5 | 90 | 120 | 81.8 | 99.3 |
| 288 | 100 | 10 | 90 | 120 | 84.9 | 99.0 |
| 312 | 100 | 10 | 180 | 240 | 84.4 | 98.8 |
| 336 | 100 | 15 | 180 | 240 | 84.5 | 98.3 |
| 360 | 150 | 20 | 180 | 240 | 79.9 | 96.5 |
| 384 | 150 | 20 | 180 | 240 | 80.2 | 96.2 |
| 408 | 90 | 10 | 90 | 120 | 81.0 | 99.3 |
| 432 | 90 | 0.5 | 90 | 120 | 82.5 | 99.1 |
| 456 | 90 | 0.5 | 90 | 120 | 82.2 | 99.2 |
| 480 | 90 | 0.5 | 90 | 120 | 82.4 | 99.2 |
| 504 | 90 | 0.5 | 90 | 120 | 82.1 | 99.3 |
| 528 | 90 | 0.5 | 90 | 120 | 82.2 | 99.4 |
| 552 | 90 | 0.5 | 90 | 120 | 82.6 | 99.5 |
| 576 | 90 | 0.5 | 90 | 120 | 82.9 | 99.3 |
| 600 | 90 | 0.5 | 90 | 120 | 82.7 | 99.4 |

TABLE 2

Experimental data observed with the esterification reaction of acetic acid and cyclohexene/benzene catalyzed by the H-beta molecular sieve catalyst

| run time h | reaction conditions: temperature degrees Celsius | pressure MPa | acetic acid feeding rate mL/h | cyclohexene/benzene feeding rate mL/h | single-pass conversion of cyclohexene % | single-pass selectivity to ester % |
|---|---|---|---|---|---|---|
| 24 | 70 | the normal pressure | 90 | 120 | 72.3 | 99.5 |
| 48 | 70 | the normal pressure | 90 | 120 | 72.2 | 99.3 |
| 72 | 70 | the normal pressure | 90 | 120 | 72.5 | 99.1 |
| 96 | 70 | the normal pressure | 90 | 120 | 72.4 | 99.4 |
| 120 | 70 | the normal pressure | 90 | 120 | 72.3 | 99.3 |
| 144 | 80 | 2 | 90 | 120 | 76.2 | 99.2 |
| 168 | 80 | 2 | 90 | 120 | 77.4 | 99.1 |
| 192 | 80 | 2 | 90 | 120 | 77.6 | 99.1 |
| 216 | 80 | 2 | 90 | 120 | 78.0 | 99.2 |
| 240 | 80 | 2 | 90 | 120 | 78.1 | 99.2 |
| 264 | 90 | 5 | 90 | 120 | 81.2 | 99.3 |
| 288 | 90 | 5 | 90 | 120 | 81.6 | 99.2 |
| 312 | 120 | 5 | 90 | 120 | 82.4 | 98.9 |
| 336 | 120 | 10 | 90 | 120 | 82.2 | 99.0 |
| 360 | 120 | 10 | 90 | 120 | 82.6 | 99.1 |
| 384 | 150 | 10 | 90 | 120 | 85.2 | 96.8 |
| 408 | 150 | 10 | 90 | 120 | 85.6 | 96.7 |
| 432 | 150 | 10 | 90 | 120 | 85.9 | 96.9 |
| 456 | 150 | 10 | 90 | 120 | 86.3 | 96.8 |
| 480 | 150 | 10 | 90 | 120 | 86.6 | 96.5 |

TABLE 3

| Experiment results observed with the addition esterification product separation by rectification | | | | | | | |
|---|---|---|---|---|---|---|---|
| | | | analytic results (%) | | | | |
| sample No. | temperature sections, degrees Celsius | weight g | benzene | cyclohexene | acetic acid | acetic acid cyclohexyl ester | high-boiling materials |
| 0 | esterification product | 4000 | 34.5 | 3.3 | 28 | 33.7 | 0.5 |
| 1 | 78 to 118 (unreacted feed stock) | 2520 | 54.8 | 5.2 | 40 | | |
| 2 | 118 to 173 (transitional section) | 205 | | | 54.6 | 45.4 | |
| 3 | 173 to 175 (ester product section) | 1225 | | | | 99.6 | 0.4 |
| 4 | >176 residues | 50 | | | | 70 | 30 |

TABLE 4

Experimental data observed with the reactive rectification by the high temperature resistant sulfonic acid type ion exchange resin catalyst

| operation conditions | |
|---|---|
| operation pressure | 0.3 MPa |
| top temperature | 120 degrees Celsius |
| reaction section temperature | 125 to 150 degrees Celsius |
| bottom temperature | 225 degrees Celsius |
| reflux ratio | 5 |

| mass | cyclohexene/ benzene feed | acetic acid feed | top with-drawal | bottom with-drawal |
|---|---|---|---|---|
| position | catalyst bed at lower part | catalyst bed at upper part | tower top at reflux pump outlet | tower bottom at discharge outlet |
| flow rate g/h | 1027 | 300 | 622 | 705 |
| temperature degrees Celsius | | | 40 | 225 |
| composition (ratio by mass) | | | | |
| cyclohexene | 40% | | 0.5 | |
| benzene | 60% | | 98.7 | 0.4 |
| acetic acid | | 100% | 0.8 | 0.3 |
| acetic acid cyclohexyl ester | | | | 98.9 |
| polymers | | | | 0.7 |

Calculation from the experimental data revealed a single-pass conversion of cyclohexene of 99.5%, a single-pass selectivity to acetic acid cyclohexyl ester of 99.3%.

TABLE 5

Experimental data observed with the reactive rectification by the $H_{0.5}Cs_{2.5}PW_{12}O_{40}/SiO_2$ catalyst

| operation conditions | |
|---|---|
| operation pressure | 0.2 MPa |
| top temperature | 104 degrees Celsius |
| reaction section temperature | 115 to 150 degrees Celsius |
| bottom temperature | 208 degrees Celsius |
| reflux ratio | 4 |

| mass | cyclohexene/ benzene feed | acetic acid feed | top with-drawal | bottom with-drawal |
|---|---|---|---|---|
| position | catalyst bed at lower part | catalyst bed at upper part | tower top at reflux pump outlet | tower bottom at discharge outlet |
| flow rate g/h | 1642 | 601 | 1113 | 1130 |
| temperature degrees Celsius | | | 40 | 208 |
| composition (ratio by mass) | | | | |
| cyclohexene | 40.0% | | 0.4% | |
| benzene | 60.0% | | 88.5% | |
| acetic acid | | 100% | 11.1% | 0.3% |
| acetic acid cyclohexyl ester | | | | 99.4% |
| polymers | | | | 0.3% |

Calculation from the experimental data revealed a single-pass conversion of cyclohexene of 99.4%, a single-pass selectivity to acetic acid cyclohexyl ester of 99.6%.

TABLE 6

Experimental data observed with the acetic acid cyclohexyl ester hydrogenation catalyzed by the copper-zinc-aluminium based catalyst

| | reaction conditions | | | | | | reaction results | | | | | single-pass conversion | single-pass |
|---|---|---|---|---|---|---|---|---|---|---|---|---|---|
| run time h | temper-ature degrees Celsius | pres-sure MPa | ester feed g/h | hydrogen gas feed mL/min | space velocity $h^{-1}$ | hydrogen/ ester ratio | ethanol m % | cyclohexanol m % | acetic acid cyclohexyl ester m % | lighter impurities m % | heavier impurities m % | of cyclohexyl ester % | selectivity to cyclohexanol % |
| 24 | 200 | 6 | 20 | 400 | 0.5 | 7.62 | 23.52 | 51.28 | 22.1 | 1.29 | 1.89 | 76.79 | 99.81 |
| 48 | 200 | 6 | 20 | 400 | 0.5 | 7.62 | 23.35 | 51.02 | 22.25 | 1.36 | 2.12 | 76.93 | 99.79 |
| 72 | 200 | 6 | 20 | 400 | 0.5 | 7.62 | 23.22 | 51.35 | 22.19 | 1.36 | 1.98 | 77.06 | 99.68 |
| 96 | 220 | 6 | 20 | 400 | 0.5 | 7.62 | 25.52 | 57.35 | 12.4 | 2.13 | 2.72 | 87.81 | 99.65 |
| 120 | 220 | 6 | 20 | 400 | 0.5 | 7.62 | 25.92 | 57.95 | 11.39 | 2.22 | 2.71 | 89.07 | 99.75 |
| 144 | 220 | 6 | 20 | 400 | 0.5 | 7.62 | 26.15 | 58.61 | 10.25 | 2.13 | 2.68 | 89.82 | 99.76 |
| 168 | 235 | 6 | 20 | 400 | 0.5 | 7.62 | 27.42 | 61.8 | 5.49 | 2.54 | 2.86 | 95.50 | 99.73 |
| 192 | 235 | 6 | 20 | 400 | 0.5 | 7.62 | 27.58 | 62.85 | 4.42 | 2.62 | 2.9 | 97.11 | 99.40 |
| 216 | 235 | 6 | 20 | 400 | 0.5 | 7.62 | 26.95 | 62.36 | 4.78 | 2.6 | 3.12 | 96.46 | 99.55 |
| 240 | 250 | 6 | 20 | 400 | 0.5 | 7.62 | 28.92 | 65.12 | 1.48 | 2.07 | 2.31 | 98.31 | 99.78 |
| 264 | 250 | 6 | 20 | 400 | 0.5 | 7.62 | 28.6 | 64.92 | 2.37 | 2.05 | 2.01 | 98.18 | 99.71 |
| 288 | 250 | 6 | 20 | 400 | 0.5 | 7.62 | 28.85 | 64.95 | 1.82 | 2.05 | 2.17 | 98.12 | 99.73 |

TABLE 6-continued

Experimental data observed with the acetic acid cyclohexyl ester hydrogenation catalyzed by the copper-zinc-aluminium based catalyst

| | reaction conditions | | | | | | reaction results | | | | | single-pass conversion | single-pass |
|---|---|---|---|---|---|---|---|---|---|---|---|---|---|
| run time h | temperature degrees Celsius | pressure MPa | ester feed g/h | hydrogen gas feed mL/min | space velocity $h^{-1}$ | hydrogen/ester ratio | ethanol m % | cyclohexanol m % | acetic acid cyclohexyl ester m % | lighter impurities m % | heavier impurities m % | of cyclohexyl ester % | selectivity to cyclohexanol % |
| 312 | 265 | 6 | 20 | 400 | 0.5 | 7.62 | 28.95 | 65.08 | 1.57 | 2.02 | 2.4 | 98.41 | 99.73 |
| 336 | 265 | 6 | 20 | 400 | 0.5 | 7.62 | 29.03 | 64.75 | 1.08 | 2.92 | 2.12 | 99.21 | 97.99 |
| 360 | 265 | 6 | 20 | 400 | 0.5 | 7.62 | 29.18 | 64.01 | 2.23 | 2.04 | 2.3 | 98.04 | 99.60 |
| 384 | 300 | 6 | 20 | 400 | 0.5 | 7.62 | 28.85 | 64.12 | 3.4 | 1.87 | 1.89 | 96.33 | 99.59 |
| 408 | 300 | 6 | 20 | 400 | 0.5 | 7.62 | 28.75 | 63.95 | 3.2 | 1.93 | 2.02 | 96.30 | 99.56 |
| 432 | 300 | 6 | 20 | 400 | 0.5 | 7.62 | 28.62 | 63.88 | 3.36 | 2.01 | 2.12 | 96.44 | 99.54 |
| 456 | 250 | 3 | 20 | 400 | 0.5 | 7.62 | 24.79 | 55.79 | 9.8 | 4.12 | 5.42 | 92.10 | 98.70 |
| 480 | 250 | 3 | 20 | 400 | 0.5 | 7.62 | 24.89 | 55.52 | 11.03 | 2.96 | 5.61 | 89.89 | 98.62 |
| 504 | 250 | 3 | 20 | 400 | 0.5 | 7.62 | 24.76 | 55.68 | 10.47 | 3.41 | 5.5 | 90.85 | 99.74 |
| 528 | 250 | 15 | 20 | 400 | 0.5 | 7.62 | 30.03 | 65.72 | 1.46 | 0.83 | 1.92 | 96.69 | 99.73 |
| 552 | 250 | 15 | 20 | 400 | 0.5 | 7.62 | 30.31 | 65.93 | 1.01 | 0.98 | 1.85 | 97.18 | 99.69 |
| 576 | 250 | 15 | 20 | 400 | 0.5 | 7.62 | 30.26 | 65.88 | 0.95 | 0.86 | 1.9 | 97.04 | 99.71 |
| 600 | 250 | 6 | 10 | 400 | 0.25 | 15.24 | 29.69 | 66.25 | 1.1 | 1.52 | 1.52 | 98.09 | 99.70 |
| 624 | 250 | 6 | 10 | 400 | 0.25 | 15.24 | 29.77 | 66.31 | 0.79 | 1.51 | 1.57 | 98.28 | 99.71 |
| 648 | 250 | 6 | 10 | 400 | 0.25 | 15.24 | 29.88 | 66.02 | 0.97 | 1.6 | 1.49 | 98.19 | 99.73 |
| 672 | 250 | 6 | 40 | 400 | 1 | 3.81 | 22.32 | 68.33 | 6.86 | 1.02 | 1.35 | 72.02 | 99.58 |
| 696 | 250 | 6 | 40 | 400 | 1 | 3.81 | 22.39 | 69.44 | 5.6 | 1.17 | 1.42 | 73.81 | 99.57 |
| 720 | 250 | 6 | 40 | 400 | 1 | 3.81 | 22.56 | 69.38 | 5.37 | 1.14 | 1.4 | 73.59 | 99.57 |
| 744 | 250 | 6 | 20 | 2000 | 0.5 | 38.09 | 30.92 | 67.26 | 0.23 | 0.69 | 0.62 | 97.50 | 99.65 |
| 768 | 250 | 6 | 20 | 2000 | 0.5 | 38.09 | 30.88 | 67.33 | 0.16 | 0.97 | 0.52 | 97.84 | 99.26 |
| 792 | 250 | 6 | 20 | 2000 | 0.5 | 38.09 | 30.79 | 67.28 | 0.38 | 0.94 | 0.54 | 97.73 | 99.32 |
| 816 | 250 | 6 | 20 | 400 | 0.5 | 7.62 | 28.91 | 64.85 | 2.25 | 2.25 | 1.82 | 97.74 | 99.34 |
| 840 | 250 | 6 | 20 | 400 | 0.5 | 7.62 | 28.86 | 64.79 | 2.3 | 2.25 | 1.76 | 97.66 | 99.47 |
| 864 | 250 | 6 | 20 | 400 | 0.5 | 7.62 | 28.85 | 65.11 | 1.95 | 2.19 | 1.76 | 97.84 | 99.47 |
| 888 | 250 | 6 | 20 | 400 | 0.5 | 7.62 | 29.01 | 65.13 | 1.74 | 2.27 | 1.81 | 97.94 | 99.34 |
| 912 | 250 | 6 | 20 | 400 | 0.5 | 7.62 | 29.05 | 64.62 | 2.24 | 2.11 | 1.91 | 97.40 | 99.36 |
| 936 | 250 | 6 | 20 | 400 | 0.5 | 7.62 | 28.85 | 64.33 | 2.8 | 1.93 | 1.95 | 96.69 | 99.59 |
| 960 | 250 | 6 | 20 | 400 | 0.5 | 7.62 | 29.15 | 64.81 | 2.27 | 1.84 | 1.92 | 97.09 | 99.65 |
| 984 | 250 | 6 | 20 | 400 | 0.5 | 7.62 | 28.69 | 64.19 | 3.07 | 1.97 | 1.98 | 96.59 | 99.54 |
| 1008 | 250 | 6 | 20 | 400 | 0.5 | 7.62 | 28.89 | 64.52 | 2.7 | 2.01 | 1.89 | 97.12 | 99.52 |

TABLE 7 the Experimental data observed with the acetic acid cyclohexyl ester hydrogenation catalyzed by the copper-chromium based catalyst

| | reaction conditions | | | | | | reaction results | | | | | single-pass conversion | single-pass |
|---|---|---|---|---|---|---|---|---|---|---|---|---|---|
| run time h | temperature degrees Celsius | pressure MPa | ester feed g/h | hydrogen gas feed mL/min | space velocity $h^{-1}$ | hydrogen/ester ratio | ethanol m % | cyclohexanol m % | acetic acid cyclohexyl ester m % | lighter impurities m % | heavier impurities m % | of cyclohexyl ester % | selectivity to cyclohexanol % |
| 24 | 230 | 6 | 20 | 400 | 0.5 | 7.5 | 26.19 | 57.39 | 13.4 | 0.97 | 2.05 | 85.45 | 99.17 |
| 48 | 230 | 6 | 20 | 400 | 0.5 | 7.5 | 26.25 | 57.18 | 13.49 | 1.02 | 2.06 | 85.27 | 98.97 |
| 72 | 250 | 6 | 20 | 400 | 0.5 | 7.5 | 27.92 | 61.41 | 6.99 | 1.29 | 2.39 | 92.13 | 98.69 |
| 96 | 250 | 6 | 20 | 400 | 0.5 | 7.5 | 28.01 | 61.33 | 7.04 | 1.38 | 2.24 | 91.92 | 99.22 |
| 120 | 320 | 20 | 20 | 400 | 0.5 | 7.5 | 28.42 | 62.76 | 5.35 | 1.37 | 2.1 | 93.79 | 99.14 |
| 144 | 320 | 20 | 20 | 400 | 0.5 | 7.5 | 28.59 | 64.72 | 2.27 | 2.22 | 2.2 | 98.10 | 98.85 |
| 168 | 260 | 6 | 20 | 400 | 0.5 | 7.5 | 28.22 | 64.65 | 2.86 | 2.37 | 1.9 | 97.87 | 99.10 |
| 192 | 260 | 6 | 20 | 400 | 0.5 | 7.5 | 28.31 | 64.66 | 2.69 | 2.29 | 2.05 | 97.93 | 99.05 |
| 216 | 260 | 10 | 20 | 400 | 0.5 | 7.5 | 29.01 | 64.71 | 3.53 | 1.32 | 1.43 | 95.67 | 99.56 |
| 240 | 260 | 10 | 20 | 400 | 0.5 | 7.5 | 28.75 | 64.26 | 3.97 | 1.75 | 1.27 | 95.53 | 99.68 |
| 264 | 260 | 6 | 10 | 400 | 0.25 | 15.0 | 28.88 | 65.02 | 1.47 | 2.13 | 2.5 | 98.72 | 98.89 |
| 288 | 260 | 6 | 10 | 400 | 0.25 | 15.0 | 28.97 | 64.91 | 1.47 | 2.01 | 2.64 | 98.51 | 98.98 |
| 312 | 260 | 4 | 20 | 400 | 0.5 | 7.5 | 28.52 | 63.81 | 3.12 | 1.87 | 2.68 | 96.76 | 99.01 |
| 336 | 260 | 4 | 20 | 400 | 0.5 | 7.5 | 28.46 | 63.62 | 3.39 | 1.92 | 2.61 | 96.44 | 99.39 |
| 360 | 260 | 6 | 20 | 800 | 0.5 | 15.0 | 28.47 | 64.12 | 4.83 | 1.37 | 1.21 | 94.67 | 99.52 |
| 384 | 260 | 6 | 20 | 800 | 0.5 | 15.0 | 28.51 | 64.38 | 4.58 | 1.45 | 1.08 | 95.02 | 99.56 |
| 408 | 260 | 6 | 20 | 600 | 0.5 | 11.25 | 28.32 | 63.69 | 5.52 | 1.49 | 0.98 | 93.99 | 99.58 |
| 432 | 260 | 6 | 20 | 600 | 0.5 | 11.25 | 28.41 | 63.89 | 5.12 | 1.52 | 1.06 | 94.41 | 99.55 |
| 456 | 260 | 6 | 20 | 600 | 0.5 | 11.25 | 28.33 | 63.88 | 5.25 | 1.57 | 0.97 | 94.37 | 99.60 |
| 480 | 260 | 6 | 20 | 600 | 0.5 | 11.25 | 28.17 | 63.59 | 5.75 | 1.45 | 1.04 | 93.85 | 99.54 |
| 504 | 260 | 6 | 20 | 600 | 0.5 | 11.25 | 28.21 | 63.71 | 5.58 | 1.53 | 0.97 | 94.07 | 99.58 |

TABLE 8

Experimental data observed with the acetic acid cyclohexyl ester hydrogenation product separation by rectification

| | reaction conditions | | | analytic results | | | | |
|---|---|---|---|---|---|---|---|---|
| | temperature | | fraction | | | acetic acid | lighter | heavier |
| fraction No. | degrees Celsius | degrees Celsius | weight g | ethanol m % | cyclohexanol m % | cyclohexyl ester m % | impurities m % | impurities m % |
| 0 (distillation feed stock) | | | 4000 | 28.06 | 62.71 | 5.62 | 1.63 | 1.98 |
| 1 (ethanol product) | 79 | 81 | 1152.3 | 97.37 | 1.46 | | 1.17 | |
| 2 (transitional fraction) | 81 | 155 | 55.2 | 75.42 | 22.2 | | 2.38 | |
| 3 (alcohol ketone product) | 155 | 162 | 2488.3 | | 96.2 | 1.21 | 1.86 | 0.73 |
| 4 (bottom residue) | >162 | | 292 | | | 76.6 | | 23.4 |
| loss | | | 12.2 | | | | | |
| total | | | 4000 | | | | | |

The Tenth Embodiment

Example 1

This example illustrates a process for producing cyclohexene by a benzene selective hydrogenation.

Benzene and hydrogen gas at a ratio by molar of 1:3 were supplied into a hydrogenation reactor loaded with ruthenium based catalyst particles, under the conditions wherein the reaction temperature was 135 degrees Celsius, the reaction pressure was 4.5 MPa, the residence time was 15 min, to conduct a benzene hydrogenation reaction, after separating hydrogen gas from the reaction product, the liquid product was collected. The reaction ran continuously for 1000 h. Upon completion of the experiment, the collected liquid product was subject to vapor phase chromatography analysis, showing a composition of: benzene 53.3 m %, cyclohexene 35.4 m %, cyclohexane 11.3 m %. Using N,N-dimethyl acetamide as the extractant, the liquid product was subject to an extractive separation to obtain a mixture of cyclohexane and cyclohexene.

Example 2

100 mL of a macroporous hydrogenous strong-acid ion exchange resin (synthesized at lab according to a classical literature method, wherein a styrene solution containing 15% divinylbenzene was subject to a suspension copolymerization and produced into base spherical particles, and then sulfonated by concentrated sulfuric acid, with a measured exchange capacity of 5.2 mmol $H^{+}$/g on dry basis) was loaded into a Φ32×4×1000 mm jacketed stainless steel tube reactor at the middle part thereof, below and above which there were packed a predetermined amount of quartz sand. Acetic acid and a cyclohexene feed stock (obtained from the process of Example 1, with a composition of: cyclohexene 75 m %, cyclohexane 25 m %) were pumped via a dosing pump at a predetermined flow rate respectively into the reactor to conduct a reaction, to the outer jacket of the reaction tube there was supplied hot water to control the reaction temperature, with a counterbalance valve at the reactor outlet to control the reactor pressure. The reactor outlet product was sampled by an on-line sampling valve for on-line chromatography analysis, on the basis of the product composition, there was calculated the single-pass conversion of cyclohexene and the single-pass selectivity to acetic acid cyclohexyl ester. The reaction conditions and results were listed in Table 1.

As can be seen from Table 1, when a strong-acid ion exchange resin catalyst was used for the reaction of cyclohexene and acetic acid, there were obtained a single-pass conversion of cyclohexene of greater than 90%, a single-pass selectivity to the ester product of greater than 99%, and after a run time of 600 hours, the catalyst activity and the single-pass selectivity remained steady.

Example 3

The experiment apparatus, the process procedure and the feed stock were the same as Example 2, with the exception that the catalyst was a phosphorus modified H-beta molecular sieve catalyst (obtained by a method wherein a H-beta molecular sieve having a silica alumina ratio of 50 was modified by 85% phosphoric acid, and then kneaded with alumina and then extruded, dried at a temperature of 120 degrees Celsius, calcinated at a temperature of 500 degrees Celsius, with a phosphorus content of 2%). The reaction conditions and results were listed in Table 2. As can be seen from Table 2, the single-pass conversion of cyclohexene was 90%, the single-pass selectivity to the ester product was greater than 99%, and after a run time of 480 hours, the catalyst activity and the single-pass selectivity remained steady.

Example 4

The addition esterification product obtained from each of Examples 2 and 3 was collected, to conduct a separation by rectification experiment. The rectification was performed on a glass tower type rectification apparatus having a height of 2 m and a diameter of 40 mm, and the tower column was loaded with Φ3 mm stainless steel Dixon high-efficient rectification packing, the bottom was a 5 L glass flask, with a loading capacity of 4 L, and heated by an electric jacket, with a voltage regulator to adjust the heating at the bottom. The tower reflux was controlled by a reflux ratio regulator. The separation by rectification results were listed in Table 3.

Examples 5 to 6 illustrate a process for producing acetic acid cyclohexyl ester by a reactive rectification.

The experiments of Examples 5 to 6 were all performed on a reactive rectification model experiment apparatus with these specifications: the main part of the model apparatus was a stainless steel tower having a diameter (inner diameter) of 50 mm, a height of 3 m, the lower part of which communicated with a bottom having a volume of 5 L, inside the bottom there was installed a 10 KW electrical heating rod, which was used to via an intelligent controller through a silicon controlled rectifier (SCR) control the heating at the bottom. The tower top communicated with a condenser having a heat exchange area of 0.5 $m^2$, vapor from the tower top was condensed by this condenser into liquid and then introduced into a reflux tank having a volume of 2 L. Liquid in the reflux tank was partially refluxed by a reflux pump back to the reaction tower, partially withdrawn as lighter components. The operation parameters of the tower were controlled by and displayed on an intelligent type automatic control instrument. The tower reflux rate was controlled by a reflux control valve, the top withdrawal was controlled by a level controller at the reflux tank. The bottom withdrawal was controlled by a bottom blow-off valve which was controlled by a bottom level controller. Acetic acid and a cyclohexene feed stock (the same as Example 2) were respectively supplied into a 30 L storage tank, and through a dosing pump were pumped respectively into the corresponding preheater and preheated to a predetermined temperature and then introduced into the reaction tower, the feeding rate was controlled by the dosing pump and accurately metered by an electronic balance.

Example 5

A high temperature resistant sulfonic acid type ion exchange resin (with a trade name of Amberlyst 45, produced by the Rhom&Hass company) was by a multi-stage high speed grinder ground into powder having a particle size of less than 200 mesh (0.074 mm), there was added a porogenic agent, a lubricant, an antioxidant and a binder, mixed homogeneously with a high-speed mixer, and then with an internal mixer at 180 degrees Celsius mixed for 10 min, to completely plasticize the mass, and then injected into a mould and formed into a raschig ring type resin catalyst packing having a diameter of 5 mm, a height of 5 mm and a wall thickness of 1 mm. 1950 mL of the packing was loaded into the middle part of a model reaction tower (with a height of 1 m, corresponding to a theoretical plate number of 8), above and below which there was each loaded 1950 mL of a glass spring packing having a diameter of 3 mm and a length of 6 mm (with a loading height of 1 m, corresponding to a theoretical plate number of 10). A cyclohexene feed stock and acetic acid via a dosing pump were pumped respectively into a preheater and preheated and then introduced into the reaction tower, adjusting the heating at the bottom and the reflux rate at the tower top to continuously conduct the reaction, the steady-state reaction conditions and reaction results were listed in Table 4.

Example 6

A Φ3 to 4 spherical $H_{0.5}Cs_{2.5}PW_{12}O_{40}/SiO_2$ catalyst (obtained by: $H_{0.5}Cs_{2.5}PW_{12}O_{40}$ powder and wide hole silica gel powder having a particle size of less than 200 mesh were on a mixer thoroughly mixed, and then, ball-formed on a coating machine by using silica sol as the binder, and then dried, calcinated) was sandwiched between titanium wire mesh corrugated plates, and produced into a cylindrical structured packing having a diameter of 50 mm and a height of 50 mm. The packing type catalyst L was loaded into the middle part of a model reaction tower (with a height of 1 m, corresponding to a theoretical plate number of 12), above and below which there was each loaded 1950 mL of a glass spring packing having a diameter of 4 mm and a height of 4 mm (with a loading height of 1 m, corresponding to a theoretical plate number of 15). A cyclohexene feed stock and acetic acid via a dosing pump were pumped respectively into a preheater and preheated and then introduced into the reaction tower, adjusting the heating at the bottom and the reflux rate at the tower top to continuously conduct the reaction, the steady-state reaction conditions and reaction results were listed in Table 5.

Example 7s to 8 illustrate a process for hydrogenating acetic acid cyclohexyl ester.

Example 7

Acetic acid cyclohexyl ester having a purity of 99.6% was used as the hydrogenation feed stock.

40 g copper-zinc-aluminium based ester hydrogenation catalyst (synthesized at lab, with a composition of CuO 40.5%, ZnO 29.6%, $Al_2O_3$ 30.4%, by a method wherein to a copper, zinc, chromium nitrate solution, there was added a NaOH solution till pH=9.0, and then centrifugal separated, washed, dried, tableted, calcinated) was loaded into a Φ20×2.5×800 mm jacketed stainless steel tube reactor at the middle part thereof, below and above which there were packed a predetermined amount of quartz sand, supplied with hydrogen gas (500 mL/min) to conduct a reduction under the conditions of 280 degrees Celsius and 6 MPa for 24 h, and then lowered to a predetermined temperature and pressure of the hydrogenation reaction. Acetic acid cyclohexyl ester via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 6. Table 6 revealed that, when a copper-zinc-aluminium based ester hydrogenation catalyst was used, the single-pass conversion of the acetic acid cyclohexyl ester hydrogenation reaction was up to 99% or more, the single-pass selectivity to cyclohexanol was greater than 99%, and after a run time of 1000 h, the single-pass conversion and the single-pass selectivity did not drop.

Example 8

Acetic acid cyclohexyl ester having a purity of 99.6% was used as the hydrogenation feed stock.

40 g copper-chromium based ester hydrogenation catalyst (commercially available from Taiyuan Xinjida Chemical Ltd., with a trade name of C1-XH-1, with a CuO content of 55%, as tablet having a diameter of 5 mm, crashed into particles of 10 to 20 mesh) was loaded into a Φ20×2.5×800 mm jacketed stainless steel tube reactor at the middle part thereof, below and above which there were packed a predetermined amount of quartz sand, supplied with hydrogen gas (500 mL/min) to conduct a reduction under the conditions of 280 degrees Celsius and 6 MPa for 24 h, and then the system was lowered to a predetermined temperature and pressure of the reaction. Acetic acid cyclohexyl ester via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counter-balance valve at the reactor outlet to control the reactor pressure. The reaction product was sampled via an on-line sampling valve at the back of the reactor for on-line chromatography analysis. The reaction conditions and results were listed in Table 7. Table 7 revealed that, when a copper-zinc-aluminium based ester hydrogenation catalyst was used, the single-pass conversion of the acetic acid cyclohexyl ester hydrogenation reaction was up to 98% or more, the single-pass selectivity to cyclohexanol was greater than 99%, and after a run time of 500 h, the single-pass conversion and the single-pass selectivity did not drop.

Example 9

4000 g of each reaction product of Examples 7 to 8 was collected, to conduct a separation by rectification experiment. The rectification was performed on a glass tower of 2 m height, and the tower column was loaded with Φ3 mm stainless steel Dixon high-efficient rectification packing, the bottom was a 5 L glass flask, heated by an electric jacket, with a voltage regulator to adjust the heating at the bottom. The tower reflux was controlled by a reflux ratio regulator. The separation by rectification results were listed in Table 8.

TABLE 1

Experimental data observed with the esterification of acetic acid and cyclohexane/cyclohexene catalyzed by the strong-acid ion exchange resin

| | reaction conditions | | | | single- | |
|---|---|---|---|---|---|---|
| run time h | temper-ature degrees Celsius | pressure MPa | acetic acid feeding rate mL/h | cyclohexane/ cyclohexene feeding rate mL/h | pass conversion of cyclo-hexene % | single-pass selectivity to ester % |
| 24 | 70 | the normal pressure | 120 | 140 | 83.2 | 99.3 |
| 48 | 70 | the normal pressure | 120 | 140 | 83.5 | 99.2 |
| 72 | 70 | 1 | 120 | 140 | 83.5 | 99.0 |
| 96 | 80 | 1 | 120 | 140 | 88.1 | 99.3 |
| 120 | 80 | 1 | 120 | 140 | 87.2 | 99.2 |
| 144 | 80 | 2 | 120 | 140 | 88.3 | 99.4 |
| 168 | 90 | 2 | 120 | 140 | 91.3 | 99.4 |
| 192 | 90 | 3 | 120 | 140 | 91.7 | 99.3 |
| 216 | 90 | 5 | 120 | 140 | 91.4 | 99.1 |
| 240 | 90 | 5 | 180 | 140 | 92.9 | 99.3 |
| 264 | 90 | 5 | 180 | 140 | 92.7 | 99.3 |
| 288 | 100 | 10 | 180 | 140 | 92.0 | 99.4 |
| 312 | 100 | 10 | 360 | 280 | 82.9 | 99.5 |
| 336 | 100 | 15 | 360 | 280 | 82.7 | 99.5 |
| 360 | 150 | 20 | 360 | 280 | 77.9 | 98.5 |
| 384 | 150 | 20 | 360 | 280 | 78.0 | 98.7 |
| 408 | 90 | 10 | 180 | 140 | 92.5 | 99.5 |
| 432 | 90 | 0.5 | 150 | 140 | 90.6 | 99.4 |

TABLE 1-continued

Experimental data observed with the esterification of acetic acid and cyclohexane/cyclohexene catalyzed by the strong-acid ion exchange resin

| | reaction conditions | | | | single- | |
|---|---|---|---|---|---|---|
| run time h | temper-ature degrees Celsius | pressure MPa | acetic acid feeding rate mL/h | cyclohexane/ cyclohexene feeding rate mL/h | pass conversion of cyclo-hexene % | single-pass selectivity to ester % |
| 456 | 90 | 0.5 | 150 | 140 | 90.1 | 99.3 |
| 480 | 90 | 0.5 | 150 | 140 | 90.3 | 99.2 |
| 504 | 90 | 0.5 | 150 | 140 | 90.1 | 99.3 |
| 528 | 90 | 0.5 | 150 | 140 | 90.3 | 99.5 |
| 552 | 90 | 0.5 | 150 | 140 | 89.9 | 99.5 |
| 576 | 90 | 0.5 | 150 | 140 | 89.8 | 99.3 |
| 600 | 90 | 0.5 | 150 | 140 | 90.1 | 99.4 |

TABLE 2

Experimental data observed with the esterification of acetic acid and cyclohexene catalyzed by the H-beta molecular sieve catalyst

| | reaction conditions | | | | single- | |
|---|---|---|---|---|---|---|
| run time h | temper-ature degrees Celsius | pressure MPa | acetic acid feeding rate mL/h | cyclohexane/ cyclohexene feeding rate mL/h | pass conversion of cyclo-hexene % | single-pass selectivity to ester % |
| 24 | 70 | the normal pressure | 150 | 140 | 71.4 | 99.2 |
| 48 | 70 | the normal pressure | 150 | 140 | 72.5 | 99.2 |
| 72 | 70 | the normal pressure | 150 | 140 | 73.4 | 99.4 |
| 96 | 70 | the normal pressure | 150 | 140 | 73.1 | 99.4 |
| 120 | 70 | the normal pressure | 150 | 140 | 72.4 | 99.3 |
| 144 | 80 | 2 | 150 | 140 | 77.3 | 99.0 |
| 168 | 80 | 2 | 150 | 140 | 78.9 | 99.2 |
| 192 | 80 | 2 | 150 | 140 | 78.7 | 99.2 |
| 216 | 80 | 2 | 150 | 140 | 77.5 | 99.2 |
| 240 | 80 | 2 | 150 | 140 | 78.3 | 99.1 |
| 264 | 90 | 5 | 150 | 140 | 82.5 | 99.0 |
| 288 | 90 | 5 | 150 | 140 | 84.7 | 99.0 |
| 312 | 120 | 5 | 150 | 140 | 84.0 | 99.2 |
| 336 | 120 | 10 | 150 | 140 | 85.1 | 99.2 |
| 360 | 120 | 10 | 150 | 140 | 83.9 | 99.2 |
| 384 | 150 | 10 | 150 | 140 | 88.7 | 97.5 |
| 408 | 150 | 10 | 150 | 140 | 88.6 | 97.6 |
| 432 | 150 | 10 | 150 | 140 | 87.7 | 97.8 |
| 456 | 150 | 10 | 150 | 140 | 88.9 | 97.7 |
| 480 | 150 | 10 | 150 | 140 | 88.7 | 97.6 |

TABLE 3

Experimental data observed with the addition esterification product separation by rectification

| | | | analytic results (%) | | | | |
|---|---|---|---|---|---|---|---|
| sample No. | temperature sections, degrees Celsius | weight g | cyclohexane | cyclohexene | acetic acid | acetic acid cyclohexyl ester | high-boiling materials |
| 0 | esterification product | 3450 | 8.9 | 7.2 | 37 | 46.6 | 0.3 |
| 1 | 78 to 118 (unreacted feed stock) | 1755 | 17.5 | 14.1 | 68.4 | 0 | 0 |

TABLE 3-continued

| Experimental data observed with the addition esterification product separation by rectification | | | | | | | | |
|---|---|---|---|---|---|---|---|---|
| | | | analytic results (%) | | | | | |
| sample No. | temperature sections, degrees Celsius | weight g | cyclohexane | cyclohexene | acetic acid | acetic acid cyclohexyl ester | high-boiling materials |
| 2 | 118 to 173 (transitional section) | 117 | | 0 | 65.4 | 34.6 | 0 |
| 3 | 173 to 175 (ester product section) | 1450 | | 0 | 0 | 99.6 | 0.4 |
| 4 | >176 residues | 128 | | 0 | 0 | 96.4 | 3.6 |

TABLE 4

Experimental data observed with the reactive rectification by the high temperature resistant sulfonic acid type ion exchange resin catalyst

| operation conditions | |
|---|---|
| operation pressure | 0.3 MPa |
| top temperature | 125 degrees Celsius |
| reaction section temperature | 145 to 180 degrees Celsius |
| bottom temperature | 225 degrees Celsius |
| reflux ratio | 5 |

| mass | cyclohexane/ cyclohexene feed | acetic acid feed | top with-drawal | bottom with-drawal |
|---|---|---|---|---|
| position | catalyst bed at lower part | catalyst bed at upper part | tower top at reflux pump outlet | tower bottom at discharge outlet |
| flow rate g/h | 547 | 601 | 444 | 704 |
| temperature degrees Celsius | 25 | 25 | 40 | 225 |
| composition (ratio by mass) | | | | |
| cyclohexene | 75% | | 0.9% | |
| cyclohexane | 25% | | 30.86% | |
| acetic acid | | 100% | 68.24% | 0.43% |
| acetic acid cyclohexyl ester | | | | 99.01% |
| polymers | | | | 0.56% |

Calculation from the experimental data revealed a single-pass conversion of cyclohexene of 99.9%, a single-pass selectivity to acetic acid cyclohexyl ester of 99.2%.

TABLE 5

Experimental data observed with the reactive rectification by the $H_{0.5}Cs_{2.5}PW_{12}O_{40}/SiO_2$ catalyst

| operation conditions | |
|---|---|
| operation pressure | 0.2 |
| top temperature | 105 |
| reaction section temperature | 120 to 150 |
| bottom temperature | 209 |
| reflux ratio | 4 |

| mass | cyclohexane/ cyclohexene feed | acetic acid feed | top with-drawal | bottom with-drawal |
|---|---|---|---|---|
| position | catalyst bed at lower part | catalyst bed at upper part | tower top at reflux pump outlet | tower bottom at discharge outlet |
| flow rate | 1095 | 601 | 300 | 1396 |
| temperature | 25 | 25 | 40 | 209 |
| composition (ratio by mass) | | | | |
| cyclohexene | 75% | | 3.67% | |
| cyclohexane | 25% | | 91.33% | |
| acetic acid | | 100% | 5.0% | |
| acetic acid cyclohexyl ester | | | | 99.28% |
| polymers | | | | 0.62% |

Calculation from the experimental data revealed a single-pass conversion of cyclohexene of 98.66%, a single-pass selectivity to acetic acid cyclohexyl ester of 99.3%.

TABLE 6

Experimental data observed with the acetic acid cyclohexyl ester hydrogenation by the copper-zinc-aluminium based ester hydrogenation catalyst

| | reaction conditions | | | | | | reaction results | | | | | | |
|---|---|---|---|---|---|---|---|---|---|---|---|---|---|
| run time h | temperature degrees Celsius | pressure MPa | ester feed g/h | hydrogen gas feed mL/min | space velocity $h^{-1}$ | hydrogen/ ester ratio | ethanol m % | cyclohexanol m % | acetic acid cyclohexyl ester m % | lighter impurities m % | heavier impurities m % | single-pass conversion of cyclohexyl ester % | single-pass selectivity to cyclohexanol % |
| 24 | 200 | 6 | 20 | 400 | 0.5 | 7.62 | 23.23 | 51.12 | 22.47 | 1.29 | 1.89 | 76.79 | 99.81 |
| 48 | 200 | 6 | 20 | 400 | 0.5 | 7.62 | 23.12 | 50.95 | 22.45 | 1.36 | 2.12 | 76.93 | 99.79 |
| 72 | 200 | 6 | 20 | 400 | 0.5 | 7.62 | 23.25 | 51.15 | 22.26 | 1.36 | 1.98 | 77.06 | 99.68 |
| 96 | 220 | 6 | 20 | 400 | 0.5 | 7.62 | 25.62 | 57.26 | 12.27 | 2.13 | 2.72 | 87.81 | 99.65 |
| 120 | 220 | 6 | 20 | 400 | 0.5 | 7.62 | 25.88 | 58.06 | 11.13 | 2.22 | 2.71 | 89.07 | 99.75 |
| 144 | 220 | 6 | 20 | 400 | 0.5 | 7.62 | 26.2 | 58.71 | 10.28 | 2.13 | 2.68 | 89.82 | 99.76 |
| 168 | 235 | 6 | 20 | 400 | 0.5 | 7.62 | 27.51 | 62.1 | 4.99 | 2.54 | 2.86 | 95.50 | 99.73 |
| 192 | 235 | 6 | 20 | 400 | 0.5 | 7.62 | 27.61 | 63.1 | 3.77 | 2.62 | 2.9 | 97.11 | 99.40 |
| 216 | 235 | 6 | 20 | 400 | 0.5 | 7.62 | 27.5 | 62.5 | 4.28 | 2.6 | 3.12 | 96.46 | 99.55 |
| 240 | 250 | 6 | 20 | 400 | 0.5 | 7.62 | 28.89 | 65.05 | 1.68 | 2.07 | 2.31 | 98.31 | 99.78 |
| 264 | 250 | 6 | 20 | 400 | 0.5 | 7.62 | 28.9 | 65.22 | 1.82 | 2.05 | 2.01 | 98.18 | 99.71 |

TABLE 6-continued

Experimental data observed with the acetic acid cyclohexyl ester hydrogenation by the copper-zinc-aluminium based ester hydrogenation catalyst

| | reaction conditions | | | | | | reaction results | | | | | | |
|---|---|---|---|---|---|---|---|---|---|---|---|---|---|
| run time h | temperature degrees Celsius | pressure MPa | ester feed g/h | hydrogen gas feed mL/min | space velocity $h^{-1}$ | hydrogen/ester ratio | ethanol m % | cyclohexanol m % | acetic acid cyclohexyl ester m % | lighter impurities m % | heavier impurities m % | single-pass conversion of cyclohexyl ester % | single-pass selectivity to cyclohexanol % |
| 288 | 250 | 6 | 20 | 400 | 0.5 | 7.62 | 29.12 | 65.05 | 1.61 | 2.05 | 2.17 | 98.12 | 99.73 |
| 312 | 265 | 6 | 20 | 400 | 0.5 | 7.62 | 29.2 | 65.11 | 1.27 | 2.02 | 2.4 | 98.41 | 99.73 |
| 336 | 265 | 6 | 20 | 400 | 0.5 | 7.62 | 29.12 | 64.82 | 1.02 | 2.92 | 2.12 | 99.21 | 97.99 |
| 360 | 265 | 6 | 20 | 400 | 0.5 | 7.62 | 29.21 | 64.9 | 1.55 | 2.04 | 2.3 | 98.04 | 99.60 |
| 384 | 300 | 6 | 20 | 400 | 0.5 | 7.62 | 28.91 | 64.21 | 3.12 | 1.87 | 1.89 | 96.33 | 99.59 |
| 408 | 300 | 6 | 20 | 400 | 0.5 | 7.62 | 28.8 | 64.02 | 3.23 | 1.93 | 2.02 | 96.30 | 99.56 |
| 432 | 300 | 6 | 20 | 400 | 0.5 | 7.62 | 28.6 | 63.95 | 3.32 | 2.01 | 2.12 | 96.44 | 99.54 |
| 456 | 250 | 3 | 20 | 400 | 0.5 | 7.62 | 24.86 | 55.85 | 9.75 | 4.12 | 5.42 | 92.10 | 98.70 |
| 480 | 250 | 3 | 20 | 400 | 0.5 | 7.62 | 24.92 | 55.46 | 11.05 | 2.96 | 5.61 | 89.89 | 98.62 |
| 504 | 250 | 3 | 20 | 400 | 0.5 | 7.62 | 24.84 | 55.74 | 10.51 | 3.41 | 5.5 | 90.85 | 99.74 |
| 528 | 250 | 15 | 20 | 400 | 0.5 | 7.62 | 30.2 | 65.63 | 1.42 | 0.83 | 1.92 | 96.69 | 99.73 |
| 552 | 250 | 15 | 20 | 400 | 0.5 | 7.62 | 30.27 | 65.86 | 1.04 | 0.98 | 1.85 | 97.18 | 99.69 |
| 576 | 250 | 15 | 20 | 400 | 0.5 | 7.62 | 30.25 | 65.86 | 1.13 | 0.86 | 1.9 | 97.04 | 99.71 |
| 600 | 250 | 6 | 10 | 400 | 0.25 | 15.24 | 29.78 | 66.15 | 1.03 | 1.52 | 1.52 | 98.09 | 99.70 |
| 624 | 250 | 6 | 10 | 400 | 0.25 | 15.24 | 29.85 | 66.25 | 0.82 | 1.51 | 1.57 | 98.28 | 99.71 |
| 648 | 250 | 6 | 10 | 400 | 0.25 | 15.24 | 29.81 | 66.15 | 0.95 | 1.6 | 1.49 | 98.19 | 99.73 |
| 672 | 250 | 6 | 40 | 400 | 1 | 3.81 | 22.21 | 48.49 | 26.93 | 1.02 | 1.35 | 72.02 | 99.58 |
| 696 | 250 | 6 | 40 | 400 | 1 | 3.81 | 22.47 | 49.52 | 25.42 | 1.17 | 1.42 | 73.81 | 99.57 |
| 720 | 250 | 6 | 40 | 400 | 1 | 3.81 | 22.51 | 49.42 | 25.53 | 1.14 | 1.4 | 73.59 | 99.57 |
| 744 | 250 | 6 | 20 | 2000 | 0.5 | 38.09 | 30.98 | 67.39 | 0.32 | 0.69 | 0.62 | 97.50 | 99.65 |
| 768 | 250 | 6 | 20 | 2000 | 0.5 | 38.09 | 30.79 | 67.38 | 0.34 | 0.97 | 0.52 | 97.84 | 99.26 |
| 792 | 250 | 6 | 20 | 2000 | 0.5 | 38.09 | 30.89 | 67.32 | 0.31 | 0.94 | 0.54 | 97.73 | 99.32 |
| 816 | 250 | 6 | 20 | 400 | 0.5 | 7.62 | 28.88 | 64.82 | 2.23 | 2.25 | 1.82 | 97.74 | 99.34 |
| 840 | 250 | 6 | 20 | 400 | 0.5 | 7.62 | 28.81 | 64.82 | 2.36 | 2.25 | 1.76 | 97.66 | 99.47 |
| 864 | 250 | 6 | 20 | 400 | 0.5 | 7.62 | 28.91 | 65.01 | 2.13 | 2.19 | 1.76 | 97.84 | 99.47 |
| 888 | 250 | 6 | 20 | 400 | 0.5 | 7.62 | 28.96 | 64.95 | 2.01 | 2.27 | 1.81 | 97.94 | 99.34 |
| 912 | 250 | 6 | 20 | 400 | 0.5 | 7.62 | 28.91 | 64.67 | 2.4 | 2.11 | 1.91 | 97.40 | 99.36 |
| 936 | 250 | 6 | 20 | 400 | 0.5 | 7.62 | 28.85 | 64.35 | 2.92 | 1.93 | 1.95 | 96.69 | 99.59 |
| 960 | 250 | 6 | 20 | 400 | 0.5 | 7.62 | 29.12 | 64.76 | 2.36 | 1.84 | 1.92 | 97.09 | 99.65 |
| 984 | 250 | 6 | 20 | 400 | 0.5 | 7.62 | 28.77 | 64.21 | 3.07 | 1.97 | 1.98 | 96.59 | 99.54 |
| 1008 | 250 | 6 | 20 | 400 | 0.5 | 7.62 | 28.91 | 64.61 | 2.58 | 2.01 | 1.89 | 97.12 | 99.52 |

TABLE 7

Experimental data observed with the acetic acid cyclohexyl ester hydrogenation by the copper-chromium based ester hydrogenation catalyst

| | reaction conditions | | | | | | reaction results | | | | | | |
|---|---|---|---|---|---|---|---|---|---|---|---|---|---|
| run time h | temperature degrees Celsius | pressure MPa | ester feed stock g/h | hydrogen gas feed mL/min | space velocity $h^{-1}$ | hydrogen/ester ratio | ethanol m % | cyclohexanol m % | acetic acid cyclohexyl ester m % | lighter impurities m % | heavier impurities m % | single-pass conversion of cyclohexyl ester % | single-pass selectivity to cyclohexanol % |
| 24 | 230 | 6 | 20 | 400 | 0.5 | 7.62 | 26.28 | 57.45 | 13.27 | 0.98 | 2.02 | 85.51 | 99.22 |
| 48 | 230 | 6 | 20 | 400 | 0.5 | 7.62 | 26.2 | 57.25 | 13.37 | 1.08 | 2.1 | 85.52 | 98.91 |
| 72 | 250 | 6 | 20 | 400 | 0.5 | 7.62 | 27.85 | 61.35 | 7.12 | 1.36 | 2.32 | 92.06 | 98.79 |
| 96 | 250 | 6 | 20 | 400 | 0.5 | 7.62 | 28.11 | 61.25 | 7.01 | 1.46 | 2.17 | 91.85 | 99.32 |
| 120 | 320 | 20 | 20 | 400 | 0.5 | 7.62 | 28.39 | 62.75 | 5.42 | 1.41 | 2.03 | 93.75 | 99.24 |
| 144 | 320 | 20 | 20 | 400 | 0.5 | 7.62 | 28.61 | 64.65 | 2.41 | 2.15 | 2.18 | 97.86 | 98.88 |
| 168 | 260 | 6 | 20 | 400 | 0.5 | 7.62 | 28.15 | 64.71 | 3.04 | 2.32 | 1.78 | 97.72 | 99.27 |
| 192 | 260 | 6 | 20 | 400 | 0.5 | 7.62 | 28.26 | 64.75 | 2.67 | 2.29 | 2.03 | 98.03 | 99.08 |
| 216 | 260 | 10 | 20 | 400 | 0.5 | 7.62 | 29.11 | 64.79 | 3.52 | 1.25 | 1.33 | 95.54 | 99.70 |
| 240 | 260 | 10 | 20 | 400 | 0.5 | 7.62 | 28.65 | 65.25 | 3.2 | 1.73 | 1.17 | 96.77 | 99.83 |
| 264 | 260 | 6 | 10 | 400 | 0.25 | 15.24 | 28.92 | 65.06 | 1.55 | 2.01 | 2.46 | 98.53 | 98.94 |
| 288 | 260 | 6 | 10 | 400 | 0.25 | 15.24 | 29.02 | 64.92 | 1.5 | 1.99 | 2.57 | 98.40 | 99.08 |
| 312 | 260 | 4 | 20 | 400 | 0.5 | 7.62 | 28.49 | 63.71 | 3.24 | 1.89 | 2.67 | 96.64 | 99.02 |
| 336 | 260 | 4 | 20 | 400 | 0.5 | 7.62 | 28.41 | 63.58 | 3.59 | 1.88 | 2.54 | 96.23 | 99.49 |
| 360 | 260 | 6 | 20 | 800 | 0.5 | 15.24 | 28.59 | 64.01 | 4.94 | 1.32 | 1.14 | 94.34 | 99.62 |

TABLE 7-continued

Experimental data observed with the acetic acid cyclohexyl ester hydrogenation by the copper-chromium based ester hydrogenation catalyst

| | reaction conditions | | | | | | reaction results | | | | | | |
|---|---|---|---|---|---|---|---|---|---|---|---|---|---|
| run time h | temperature degrees Celsius | pressure MPa | ester feed stock g/h | hydrogen gas feed mL/min | space velocity $h^{-1}$ | hydrogen/ester ratio | ethanol m % | cyclohexanol m % | acetic acid cyclohexyl ester m % | lighter impurities m % | heavier impurities m % | single-pass conversion of cyclohexyl ester % | single-pass selectivity to cyclohexanol % |
| 384 | 260 | 6 | 20 | 800 | 0.5 | 15.24 | 28.55 | 64.44 | 4.55 | 1.47 | 0.99 | 95.02 | 99.68 |
| 408 | 260 | 6 | 20 | 600 | 0.5 | 11.43 | 28.29 | 63.75 | 5.57 | 1.45 | 0.94 | 93.95 | 99.64 |
| 432 | 260 | 6 | 20 | 600 | 0.5 | 11.43 | 28.33 | 63.88 | 5.3 | 1.48 | 1.01 | 94.27 | 99.62 |
| 456 | 260 | 6 | 20 | 600 | 0.5 | 11.43 | 28.21 | 63.81 | 5.5 | 1.52 | 0.96 | 94.18 | 99.61 |
| 480 | 260 | 6 | 20 | 600 | 0.5 | 11.43 | 28.19 | 63.66 | 5.68 | 1.46 | 1.01 | 93.93 | 99.58 |
| 504 | 260 | 6 | 20 | 600 | 0.5 | 11.43 | 28.18 | 63.75 | 5.65 | 1.49 | 0.93 | 94.01 | 99.64 |

TABLE 8

Experimental data observed with the separation by rectification of the acetic acid cyclohexyl ester hydrogenation product

| | reaction conditions | | | analytic results | | | | |
|---|---|---|---|---|---|---|---|---|
| | temperature | | fraction | | | acetic acid cyclohexyl | lighter | heavier |
| fraction No. | degrees Celsius | degrees Celsius | weight g | ethanol m % | cyclohexanol m % | ester m % | impurities m % | impurities m % |
| 0 (distillation feed stock) | | | 4000 | 27.96 | 62.39 | 5.89 | 1.77 | 1.99 |
| 1 (ethanol product) | 79 | 81 | 1143.7 | 96.27 | 1.88 | | 1.85 | |
| 2 (transitional fraction) | 81 | 155 | 52.2 | 76.24 | 22.2 | | 1.56 | |
| 3 (alcohol ketone product) | 155 | 162 | 2476.8 | | 95.92 | 1.21 | 1.96 | 0.91 |
| 4 (bottom residue) | >162 | | 298 | | | 75.6 | | 24.4 |
| loss | | | 29.3 | | | | | |
| total | | | 4000 | | | | | |

The Eleventh Embodiment

Example 1

This example illustrates a process by a benzene selective hydrogenation to produce cyclohexene.

Benzene and hydrogen gas at a ratio by molar of 1:3 were supplied into a hydrogenation reactor loaded with ruthenium based catalyst particles, under the conditions wherein the reaction temperature was 135 degrees Celsius, the reaction pressure was 4.5 MPa, the residence time was 15 min, to conduct a benzene hydrogenation reaction, after separating hydrogen gas from the reaction product, the liquid product was collected. The reaction ran continuously for 1000 h. Upon completion of the experiment, the collected liquid product was subject to vapor phase chromatography analysis, showing a composition of: benzene 53.3%, cyclohexene 35.4%, cyclohexane 11.3%. Using N,N-dimethyl acetamide as the extractant, the liquid product was subject to an extractive separation to obtain cyclohexene.

Example 2

100 mL of a macroporous hydrogenous strong-acid ion exchange resin (synthesized at lab according to a classical literature method, wherein a styrene solution containing 15% divinylbenzene was subject to a suspension copolymerization and produced into base spherical particles, and then sulfonated by concentrated sulfuric acid, with a measured exchange capacity of 5.2 mmol $H^{+}$/g on dry basis) was loaded into a Φ32×4×1000 mm jacketed stainless steel tube reactor at the middle part thereof, below and above which there were packed a predetermined amount of quartz sand. Acetic acid and cyclohexene (obtained from the process of Example 1) were pumped via a dosing pump at a predetermined flow rate respectively into the reactor to conduct a reaction, to the outer jacket of the reaction tube there was supplied hot water to control the reaction temperature, with a counterbalance valve at the reactor outlet to control the reactor pressure. The reactor outlet product was sampled by an on-line sampling valve for on-line chromatography analysis, on the basis of the product composition, there was calculated the single-pass conversion of cyclohexene and the single-pass selectivity to acetic acid cyclohexyl ester. The reaction conditions and results were listed in Table 1.

As can be seen from Table 1, when a strong-acid ion exchange resin catalyst was used for catalyzing the reaction between the cyclohexene feed stock and acetic acid, there were obtained a single-pass conversion of cyclohexene of greater than 90%, a single-pass selectivity to the ester product of greater than 99%, and after a run time of 600 hours, the catalyst activity and the single-pass selectivity remained steady.

TABLE 1

Experimental data observed with the esterification of acetic acid and cyclohexene catalyzed by the strong-acid ion exchange resin

| | reaction conditions | | | | on-line analytic results | | | | | |
|---|---|---|---|---|---|---|---|---|---|---|
| run time h | temperature degrees Celsius | pressure MPa | acetic acid feeding rate mL/h | cyclohexene feed stock feeding rate mL/h | cyclohexene m % | acetic acid m % | acetic acid cyclohexyl ester m % | heavier polymers m % | conversion of cyclohexene % | selectivity to ester % |
| 24 | 70 | the normal pressure | 120 | 106 | 5.84 | 34.28 | 59.60 | 0.28 | 85.6 | 99.2 |
| 48 | 70 | the normal pressure | 120 | 106 | 5.68 | 34.14 | 59.94 | 0.24 | 86 | 99.3 |
| 72 | 70 | 1 | 120 | 106 | 5.60 | 34.13 | 59.96 | 0.31 | 86.2 | 99.1 |
| 96 | 80 | 1 | 120 | 106 | 3.85 | 32.79 | 63.14 | 0.22 | 90.5 | 99.4 |
| 120 | 80 | 1 | 120 | 106 | 3.97 | 32.90 | 62.87 | 0.26 | 90.2 | 99.3 |
| 144 | 80 | 2 | 120 | 106 | 3.81 | 32.73 | 63.27 | 0.18 | 90.6 | 99.5 |
| 168 | 90 | 2 | 120 | 106 | 2.60 | 31.90 | 65.24 | 0.27 | 93.6 | 99.3 |
| 192 | 90 | 3 | 120 | 106 | 2.51 | 31.87 | 65.31 | 0.30 | 93.8 | 99.2 |
| 216 | 90 | 5 | 120 | 106 | 2.64 | 31.96 | 65.10 | 0.30 | 93.5 | 99.2 |
| 240 | 90 | 5 | 180 | 106 | 1.53 | 47.10 | 51.25 | 0.12 | 95.1 | 99.6 |
| 264 | 90 | 5 | 180 | 106 | 1.63 | 47.21 | 50.99 | 0.18 | 94.8 | 99.4 |
| 288 | 100 | 10 | 180 | 106 | 1.59 | 47.17 | 51.09 | 0.15 | 94.9 | 99.5 |
| 312 | 100 | 10 | 360 | 212 | 4.25 | 49.08 | 46.56 | 0.11 | 86.4 | 99.6 |
| 336 | 100 | 15 | 360 | 212 | 4.22 | 49.12 | 46.48 | 0.19 | 86.5 | 99.3 |
| 360 | 150 | 20 | 360 | 212 | 6.03 | 50.52 | 43.14 | 0.30 | 80.7 | 98.8 |
| 384 | 150 | 20 | 360 | 212 | 6.10 | 50.55 | 43.08 | 0.28 | 80.5 | 98.9 |
| 408 | 90 | 10 | 180 | 106 | 1.56 | 47.12 | 51.20 | 0.12 | 95.0 | 99.6 |
| 432 | 90 | 0.5 | 150 | 106 | 2.65 | 40.99 | 56.13 | 0.23 | 92.5 | 99.3 |
| 456 | 90 | 0.5 | 150 | 106 | 2.58 | 40.97 | 56.19 | 0.26 | 92.7 | 99.2 |
| 480 | 90 | 0.5 | 150 | 106 | 2.61 | 40.94 | 56.25 | 0.20 | 92.6 | 99.4 |
| 504 | 90 | 0.5 | 150 | 106 | 2.79 | 41.05 | 56.00 | 0.16 | 92.1 | 99.5 |
| 528 | 90 | 0.5 | 150 | 106 | 2.75 | 41.05 | 56.00 | 0.20 | 92.2 | 99.4 |
| 552 | 90 | 0.5 | 150 | 106 | 2.82 | 41.03 | 56.05 | 0.10 | 92.0 | 99.7 |
| 576 | 90 | 0.5 | 150 | 106 | 2.86 | 41.17 | 55.71 | 0.26 | 91.9 | 99.2 |
| 600 | 90 | 0.5 | 150 | 106 | 2.79 | 41.10 | 55.89 | 0.23 | 92.1 | 99.3 |

Example 3

The experiment apparatus, the process procedure and the feed stock were the same as Example 2, with the exception that $Cs_{2.5}H_{0.5}PW_{12}O_{40}/SiO_2$ was used as the catalyst (hereinafter referred to as $PW/SiO_2$). The reaction conditions and results were listed in Table 2. As can be seen from Table 2, the reaction of cyclohexene and acetic acid resulted in a single-pass conversion of 95%, a single-pass selectivity to the ester product of 99%, and after a run time of 480 hours, the catalyst activity and the single-pass selectivity remained steady.

TABLE 2

Experimental data observed with the esterification of acetic acid and cyclohexene catalyzed by $Cs_{2.5}H_{0.5}PW_{12}O_{40}/SiO_2$

| | reaction conditions | | | | on-line analytic results | | | | | |
|---|---|---|---|---|---|---|---|---|---|---|
| run time h | temperature degrees Celsius | pressure MPa | acetic acid feeding rate mL/h | cyclohexene feed stock feeding rate mL/h | cyclohexene m % | acetic acid m % | acetic acid cyclohexyl ester m % | heavier polymers m % | conversion of cyclohexene % | selectivity to ester % |
| 24 | 60 | the normal pressure | 120 | 106 | 7.99 | 35.74 | 56.14 | 0.13 | 80.3 | 99.6 |

TABLE 2-continued

Experimental data observed with the esterification of acetic acid and cyclohexene catalyzed by $Cs_{2.5}H_{0.5}PW_{12}O_{40}/SiO_2$

| | reaction conditions | | | | on-line analytic results | | | | | |
|---|---|---|---|---|---|---|---|---|---|---|
| run time h | temperature degrees Celsius | pressure MPa | acetic acid feeding rate mL/h | cyclohexene feed stock feeding rate mL/h | cyclohexene m % | acetic acid m % | acetic acid cyclohexyl ester m % | heavier polymers m % | conversion of cyclohexene % | selectivity to ester % |
| 48 | 60 | the normal pressure | 120 | 106 | 7.50 | 35.39 | 56.98 | 0.13 | 81.5 | 99.6 |
| 72 | 60 | the normal pressure | 120 | 106 | 7.46 | 35.36 | 57.05 | 0.13 | 81.6 | 99.6 |
| 96 | 70 | 2 | 120 | 106 | 4.66 | 33.35 | 61.81 | 0.18 | 88.5 | 99.5 |
| 120 | 70 | 2 | 120 | 106 | 4.62 | 33.35 | 61.82 | 0.22 | 88.6 | 99.4 |
| 144 | 70 | 5 | 120 | 106 | 4.54 | 33.26 | 62.02 | 0.18 | 88.8 | 99.5 |
| 168 | 80 | 5 | 120 | 106 | 3.93 | 32.87 | 62.94 | 0.26 | 90.3 | 99.3 |
| 192 | 80 | 5 | 120 | 106 | 3.73 | 32.75 | 63.22 | 0.29 | 90.8 | 99.2 |
| 216 | 80 | 5 | 120 | 106 | 3.85 | 32.84 | 63.01 | 0.29 | 90.5 | 99.2 |
| 240 | 90 | 5 | 120 | 106 | 3.20 | 32.37 | 64.13 | 0.30 | 92.1 | 99.2 |
| 264 | 90 | 5 | 120 | 106 | 2.92 | 32.16 | 64.62 | 0.30 | 92.8 | 99.2 |
| 288 | 90 | 5 | 120 | 106 | 3.00 | 32.25 | 64.41 | 0.34 | 92.6 | 99.1 |
| 312 | 150 | 10 | 120 | 106 | 6.73 | 35.08 | 57.72 | 0.47 | 83.4 | 98.6 |
| 336 | 150 | 10 | 120 | 106 | 6.57 | 35.03 | 57.82 | 0.58 | 83.8 | 98.3 |
| 360 | 150 | 10 | 120 | 106 | 2.55 | 31.98 | 65.05 | 0.42 | 93.7 | 98.9 |
| 384 | 150 | 10 | 150 | 106 | 1.73 | 40.45 | 57.42 | 0.40 | 95.1 | 98.8 |
| 408 | 200 | 20 | 150 | 106 | 1.84 | 40.53 | 57.24 | 0.40 | 94.8 | 98.8 |
| 432 | 200 | 20 | 150 | 106 | 1.87 | 40.55 | 57.18 | 0.40 | 94.7 | 98.8 |
| 456 | 200 | 20 | 150 | 106 | 1.87 | 40.55 | 57.18 | 0.40 | 94.7 | 98.8 |
| 480 | 200 | 20 | 150 | 106 | 1.91 | 40.58 | 57.11 | 0.40 | 94.6 | 98.8 |

Example 4

The experiment apparatus, the process procedure and the feed stock were the same as Example 2, with the exception that the catalyst was a phosphorus modified H-beta molecular sieve catalyst (obtained by a method wherein a H-beta molecular sieve having a silica alumina ratio of 50 was modified by 85% phosphoric acid, and then kneaded with alumina and then extruded, dried at a temperature of 120 degrees Celsius, calcinated at a temperature of 500 degrees Celsius, with a phosphorus content of 2%). The reaction conditions and results were listed in Table 3. As can be seen from Table 3, the reaction of cyclohexene and acetic acid resulted in a single-pass conversion of 90%, a single-pass selectivity to the ester product of greater than 99%, and after a run time of 480 hours, the catalyst activity and the single-pass selectivity remained steady.

TABLE 3

Experimental data observed with the esterification of acetic acid and cyclohexene catalyzed by the H-beta molecular sieve catalyst

| | reaction conditions | | | | on-line analytic results | | | | | |
|---|---|---|---|---|---|---|---|---|---|---|
| run time h | temperature degrees Celsius | pressure MPa | acetic acid feeding rate mL/h | cyclohexene feed stock feeding rate mL/h | cyclohexene m % | acetic acid m % | acetic acid cyclohexyl ester m % | heavier polymers m % | conversion of cyclohexene % | selectivity to ester % |
| 24 | 70 | the normal pressure | 150 | 106 | 8.61 | 45.32 | 45.87 | 0.19 | 75.6 | 99.3 |
| 48 | 70 | the normal pressure | 150 | 106 | 8.30 | 45.07 | 46.47 | 0.16 | 76.5 | 99.4 |
| 72 | 70 | the normal pressure | 150 | 106 | 8.68 | 45.32 | 45.89 | 0.11 | 75.4 | 99.6 |
| 96 | 70 | the normal pressure | 150 | 106 | 8.65 | 45.35 | 45.81 | 0.19 | 75.5 | 99.3 |
| 120 | 70 | the normal pressure | 150 | 106 | 8.72 | 45.42 | 45.65 | 0.21 | 75.3 | 99.2 |
| 144 | 80 | 2 | 150 | 106 | 6.64 | 43.93 | 49.17 | 0.26 | 81.2 | 99.1 |
| 168 | 80 | 2 | 150 | 106 | 6.74 | 43.97 | 49.09 | 0.20 | 80.9 | 99.3 |
| 192 | 80 | 2 | 150 | 106 | 6.78 | 43.99 | 49.03 | 0.20 | 80.8 | 99.3 |
| 216 | 80 | 2 | 150 | 106 | 6.88 | 44.05 | 48.90 | 0.17 | 80.5 | 99.4 |
| 240 | 80 | 2 | 150 | 106 | 6.67 | 43.89 | 49.26 | 0.17 | 81.1 | 99.4 |

TABLE 3-continued

Experimental data observed with the esterification of acetic acid and cyclohexene catalyzed by the H-beta molecular sieve catalyst

| | reaction conditions | | | | on-line analytic results | | | | | |
|---|---|---|---|---|---|---|---|---|---|---|
| run time h | temperature degrees Celsius | pressure MPa | acetic acid feeding rate mL/h | cyclohexene feed stock feeding rate mL/h | cyclohexene m % | acetic acid m % | acetic acid cyclohexyl ester m % | heavier polymers m % | conversion of cyclohexene % | selectivity to ester % |
| 264 | 90 | 5 | 150 | 106 | 4.70 | 42.53 | 52.50 | 0.28 | 86.7 | 99.1 |
| 288 | 90 | 5 | 150 | 106 | 4.73 | 42.55 | 52.44 | 0.28 | 86.6 | 99.1 |
| 312 | 120 | 5 | 150 | 106 | 4.80 | 42.58 | 52.38 | 0.24 | 86.4 | 99.2 |
| 336 | 120 | 10 | 150 | 106 | 4.52 | 42.35 | 52.91 | 0.22 | 87.2 | 99.3 |
| 360 | 120 | 10 | 150 | 106 | 4.66 | 42.50 | 52.56 | 0.28 | 86.8 | 99.1 |
| 384 | 150 | 10 | 150 | 106 | 3.46 | 41.93 | 53.91 | 0.70 | 90.2 | 97.8 |
| 408 | 150 | 10 | 150 | 106 | 3.39 | 41.95 | 53.86 | 0.80 | 90.4 | 97.5 |
| 432 | 150 | 10 | 150 | 106 | 3.28 | 41.78 | 54.26 | 0.67 | 90.7 | 97.9 |
| 456 | 150 | 10 | 150 | 106 | 3.35 | 41.86 | 54.09 | 0.70 | 90.5 | 97.8 |
| 480 | 150 | 10 | 150 | 106 | 3.32 | 41.90 | 53.98 | 0.80 | 90.6 | 97.5 |

Example 5

The addition esterification product obtained from each of Examples 2 to 4 was collected, to conduct a separation by rectification experiment. The rectification was performed on a glass tower type rectification apparatus having a height of 2 m and a diameter of 40 mm, and the tower column was loaded with Φ3 mm stainless steel Dixon high-efficient rectification packing, the bottom was a 5 L glass flask, with a loading capacity of 4 L, and heated by an electric jacket, with a voltage regulator to adjust the heating at the bottom. The tower reflux was controlled by a reflux ratio regulator. The separation by rectification results were listed in Table 4.

TABLE 4

Experimental data observed with the addition esterification product separation by rectification

| | | | analytic results/m % | | | | |
|---|---|---|---|---|---|---|---|
| sample No. | temperature sections, degrees Celsius | weight/g | benzene | cyclohexene | acetic acid | acetic acid cyclohexyl ester | high-boiling materials |
| 0 | esterification product | 3800 | | 4.5 | 48.5 | 46.8 | 0.2 |
| 1 | 78 to 118 (unreacted feed stock) | 1971 | | 8.68 | 91.32 | 0 | 0 |
| 2 | 118 to 173 (transitional section) | 81 | | 0 | 53.1 | 46.9 | 0 |
| 3 | 173 to 175 (ester product section) | 1656 | | 0 | 0 | 99.64 | 0.36 |
| 4 | >176 residues | 91 | | 0 | 0 | 98.9 | 1.1 |

Examples 6 to 7 illustrate a process for producing acetic acid cyclohexyl ester by a reactive rectification.

Examples 6 to 7 were all performed on a reactive rectification model experiment apparatus with these specifications: the main part of the model apparatus was a stainless steel tower having a diameter (inner diameter) of 50 mm, a height of 3 m, the lower part of which communicated with a bottom having a volume of 5 L, inside the bottom there was installed a 10 KW electrical heating rod, which was used to via an intelligent controller through a silicon controlled rectifier (SCR) control the heating at the bottom. The tower top communicated with a condenser having a heat exchange area of 0.5 $m^2$, vapor from the tower top was condensed by this condenser into liquid and then introduced into a reflux tank having a volume of 2 L. Liquid in the reflux tank was partially refluxed by a reflux pump back to the reaction tower, partially withdrawn as lighter components. The operation parameters of the tower were controlled by and displayed on an intelligent type automatic control instrument. The tower reflux rate was controlled by a reflux control valve, the top withdrawal was controlled by a level controller at the reflux tank. The bottom withdrawal was controlled by a bottom blow-off valve which was controlled by a bottom level controller. Acetic acid and cyclohexene (from the process of Example 1) were respectively supplied into a 30 L storage tank, and through a dosing pump were pumped respectively into the corresponding preheater and preheated to a predetermined temperature and then introduced into the reaction tower, the feeding rate was controlled by the dosing pump and accurately metered by an electronic balance.

Example 6

A high temperature resistant sulfonic acid type ion exchange resin (with a trade name of Amberlyst 45, produced by the Rhom&Hass company) was by a multi-stage high speed grinder ground into powder having a particle size of less than 200 mesh (0.074 mm), there was added a porogenic agent, a lubricant, an antioxidant and a binder, mixed homogeneously with a high-speed mixer, and then with an internal mixer at 180 degrees Celsius mixed for 10 min, to completely plasticize the mass, and then injected into a mould and formed into a raschig ring type resin catalyst packing having a diameter of 5 mm, a height of 5 mm and a wall thickness of 1 mm. 1950 mL of the packing was loaded into the middle part of a model reaction tower (with a height of 1 m, corresponding to a theoretical plate number of 8), above and below which there was each loaded 1950 mL of a glass spring packing having a diameter of 3 mm and a length of 6 mm (with a loading height of 1 m, corresponding to a theoretical plate number of 10). Acetic acid and cyclohexene via a dosing pump were pumped respectively into a preheater and preheated and then introduced into the reaction tower, adjusting the heating at the bottom and the reflux rate at the tower top to continuously conduct the reaction, the steady-state reaction conditions and reaction results were listed in Table 5.

TABLE 5

Experimental data observed with the reactive rectification by the high temperature resistant sulfonic acid type ion exchange resin catalyst

| operation conditions | |
|---|---|
| operation pressure | the normal pressure |
| top temperature | 117 degrees Celsius |
| catalyst section temperature | 120 to 145 degrees Celsius |
| bottom temperature | 184 degrees Celsius |
| reflux ratio | 2 |

| mass | cyclohexene feed | acetic acid feed | top with-drawal | bottom with-drawal |
|---|---|---|---|---|
| position | catalyst bed at lower part | catalyst bed at upper part | tower top at reflux pump outlet | tower bottom at discharge outlet |
| flow rate g/h | 411 | 601 | 303 | 709 |
| temperature degrees Celsius | 75 | 75 | 40 | 184 |
| composition (ratio by mass) | | | | |
| cyclohexene | 100% | | 1.3% | |
| benzene | | | | |
| cyclohexane | | | | |
| acetic acid | | 100% | 98.7% | 0.42% |
| acetic acid cyclohexyl ester | | | | 99.30% |
| polymers | | | | 0.28% |

Calculation from the experimental data revealed a single-pass conversion of cyclohexene of 99%, a single-pass selectivity to acetic acid cyclohexyl ester of 99.72%.

Example 7

A Φ3 to 4 spherical $H_{0.5}Cs_{2.5}PW_{12}O_{40}/SiO_2$ catalyst (obtained by: $H_{0.5}Cs_{2.5}PW_{12}O_{40}$ powder and wide hole silica gel powder having a particle size of less than 200 mesh were on a mixer thoroughly mixed, and then, ball-formed on a coating machine by using silica sol as the binder, and then dried, calcinated) was sandwiched between titanium wire mesh corrugated plates, and produced into a cylindrical structured packing having a diameter of 50 mm and a height of 50 mm. The packing type catalyst L was loaded into the middle part of a model reaction tower (with a height of 1 m, corresponding to a theoretical plate number of 12), above and below which there was each loaded 1950 mL of a glass spring packing having a diameter of 4 mm and a height of 4 mm (with a loading height of 1 m, corresponding to a theoretical plate number of 15). Acetic acid and cyclohexene via a dosing pump were pumped respectively into a preheater and preheated and then introduced into the reaction tower, adjusting the heating at the bottom and the reflux rate at the tower top to continuously conduct the reaction, the steady-state reaction conditions and reaction results were listed in Table 6.

TABLE 6

Experimental data observed with the reactive rectification by the $H_{0.5}Cs_{2.5}PW_{12}O_{40}/SiO_2$ catalyst

| operation conditions | |
|---|---|
| operation pressure | 0.2 MPa |
| top temperature | 140 degrees Celsius |
| reaction section temperature | 140 to 170 degrees Celsius |
| bottom temperature | 208 degrees Celsius |
| reflux ratio | 2 |

| mass | cyclohexene feed | acetic acid feed | top with-drawal | bottom with-drawal |
|---|---|---|---|---|
| position | catalyst bed at lower part | catalyst bed at upper part | tower top at reflux pump outlet | tower bottom at discharge outlet |
| flow rate g/h | 616 | 601 | 158 | 1058 |
| temperature degrees Celsius | | | 40 | 208 |
| composition (ratio by mass) | | | | |
| cyclohexene | 100% | | 5.06% | |
| benzene | | | | |
| cyclohexane | | | | |
| acetic acid | | 100% | 94.94% | |
| acetic acid cyclohexyl ester | | | | 99.43% |
| polymers | | | | 0.57% |

Calculation from the experimental data revealed a single-pass conversion of cyclohexene of 98.7%, a single-pass selectivity to acetic acid cyclohexyl ester of 99.43%.

Examples 8 to 9 illustrate the experiment results observed with the acetic acid cyclohexyl ester hydrogenation.

Example 8

Acetic acid cyclohexyl ester having a purity of 99.6% was used as the hydrogenation feed stock.

40 g copper-zinc-aluminium based ester hydrogenation catalyst (synthesized at lab, with a composition of CuO 40.5%, ZnO 29.6%, $Al_2O_3$ 30.4%, by a method wherein to a copper, zinc, aluminium nitrate solution, there was added a NaOH solution till pH=9.0, and then centrifugal separated, washed, dried, tableted, calcinated) was loaded into a Φ20×2.5×800 mm jacketed stainless steel tube reactor at the middle part thereof, below and above which there were packed a predetermined amount of quartz sand, supplied with hydrogen gas (500 mL/min) to conduct a reduction under the conditions of 280 degrees Celsius and 6 MPa for 24 h, and then lowered to a predetermined temperature and pressure of the hydrogenation reaction. Acetic acid cyclohexyl ester via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 7. The results revealed that, when a copper-zinc-aluminium based ester hydrogenation catalyst was used, the single-pass conversion of the acetic acid cyclohexyl ester hydrogenation reaction was up to 99% or more, the single-pass selectivity to cyclohexanol was greater than 99.9%, and after a run time of 1000 h, the single-pass conversion and the single-pass selectivity did not drop.

TABLE 7

Experimental data observed with the acetic acid cyclohexyl ester hydrogenation catalyzed by the copper-zinc-aluminium based catalyst

| | reaction conditions | | | | | | reaction results | | | | | | single-pass | |
|---|---|---|---|---|---|---|---|---|---|---|---|---|---|---|
| run time h | temperature degrees Celsius | pressure MPa | ester feed g/h | hydrogen gas feed mL/min | space velocity h−1 | hydrogen/ester ratio | ethanol m % | acetic acid ethyl ester m % | cyclohexane m % | cyclohexanol m % | ethyl cyclohexyl ether m % | acetic acid cyclohexyl ester m % | conversion of cyclohexyl ester % | single-pass selectivity to cyclohexanol % |
| 24 | 200 | 6 | 20 | 400 | 0.5 | 7.62 | 23.17 | 1.21 | 0.04 | 51.06 | 1.99 | 22.53 | 77.00 | 99.93 |
| 48 | 200 | 6 | 20 | 400 | 0.5 | 7.62 | 23.14 | 1.27 | 0.10 | 50.99 | 2.06 | 22.43 | 77.10 | 99.81 |
| 72 | 200 | 6 | 20 | 400 | 0.5 | 7.62 | 23.27 | 1.21 | 0.15 | 51.19 | 1.95 | 22.23 | 77.30 | 99.73 |
| 96 | 220 | 6 | 20 | 400 | 0.5 | 7.62 | 25.74 | 1.94 | 0.14 | 57.47 | 2.69 | 12.02 | 87.70 | 99.76 |
| 120 | 220 | 6 | 20 | 400 | 0.5 | 7.62 | 25.96 | 2.00 | 0.10 | 58.14 | 2.66 | 11.14 | 88.60 | 99.83 |
| 144 | 220 | 6 | 20 | 400 | 0.5 | 7.62 | 26.17 | 2.06 | 0.13 | 58.68 | 2.70 | 10.26 | 89.50 | 99.79 |
| 168 | 235 | 6 | 20 | 400 | 0.5 | 7.62 | 27.59 | 2.30 | 0.15 | 62.04 | 2.95 | 4.97 | 94.90 | 99.77 |
| 192 | 235 | 6 | 20 | 400 | 0.5 | 7.62 | 27.77 | 2.27 | 0.30 | 62.14 | 3.00 | 4.54 | 95.35 | 99.54 |
| 216 | 235 | 6 | 20 | 400 | 0.5 | 7.62 | 27.59 | 2.42 | 0.21 | 62.17 | 3.02 | 4.58 | 95.30 | 99.68 |
| 240 | 250 | 6 | 20 | 400 | 0.5 | 7.62 | 28.98 | 1.93 | 0.09 | 64.91 | 2.33 | 1.75 | 98.20 | 99.87 |
| 264 | 250 | 6 | 20 | 400 | 0.5 | 7.62 | 28.98 | 1.99 | 0.20 | 65.12 | 2.15 | 1.56 | 98.40 | 99.70 |
| 288 | 250 | 6 | 20 | 400 | 0.5 | 7.62 | 29.04 | 1.93 | 0.18 | 64.98 | 2.31 | 1.56 | 98.40 | 99.74 |
| 312 | 265 | 6 | 20 | 400 | 0.5 | 7.62 | 29.20 | 1.87 | 0.15 | 65.11 | 2.40 | 1.27 | 98.70 | 99.77 |
| 336 | 265 | 6 | 20 | 400 | 0.5 | 7.62 | 29.14 | 1.81 | 0.13 | 64.98 | 2.29 | 1.66 | 98.30 | 99.81 |
| 360 | 265 | 6 | 20 | 400 | 0.5 | 7.62 | 29.14 | 1.87 | 0.21 | 65.18 | 2.14 | 1.46 | 98.50 | 99.68 |
| 384 | 300 | 6 | 20 | 400 | 0.5 | 7.62 | 28.83 | 1.69 | 0.23 | 64.24 | 1.99 | 3.02 | 96.90 | 99.66 |
| 408 | 300 | 6 | 20 | 400 | 0.5 | 7.62 | 28.70 | 1.78 | 0.25 | 64.14 | 2.00 | 3.12 | 96.80 | 99.62 |
| 432 | 300 | 6 | 20 | 400 | 0.5 | 7.62 | 28.75 | 1.72 | 0.24 | 64.07 | 2.05 | 3.17 | 96.75 | 99.64 |
| 456 | 250 | 3 | 20 | 400 | 0.5 | 7.62 | 24.97 | 3.42 | 0.64 | 55.96 | 5.35 | 9.66 | 90.12 | 98.97 |
| 480 | 250 | 3 | 20 | 400 | 0.5 | 7.62 | 25.04 | 3.27 | 0.65 | 55.68 | 5.41 | 9.95 | 89.82 | 98.95 |
| 504 | 250 | 3 | 20 | 400 | 0.5 | 7.62 | 24.84 | 3.29 | 0.12 | 55.74 | 5.50 | 10.51 | 89.25 | 99.81 |
| 528 | 250 | 15 | 20 | 400 | 0.5 | 7.62 | 30.44 | 0.72 | 0.13 | 65.82 | 1.82 | 1.07 | 98.90 | 99.81 |
| 552 | 250 | 15 | 20 | 400 | 0.5 | 7.62 | 30.41 | 0.78 | 0.16 | 65.95 | 1.72 | 0.97 | 99.00 | 99.76 |
| 576 | 250 | 15 | 20 | 400 | 0.5 | 7.62 | 30.50 | 0.72 | 0.15 | 65.95 | 1.80 | 0.88 | 99.10 | 99.78 |
| 600 | 250 | 6 | 10 | 400 | 0.25 | 15.24 | 29.88 | 1.33 | 0.18 | 66.24 | 1.50 | 0.88 | 99.10 | 99.74 |
| 624 | 250 | 6 | 10 | 400 | 0.25 | 15.24 | 29.86 | 1.36 | 0.17 | 66.21 | 1.58 | 0.83 | 99.15 | 99.75 |
| 648 | 250 | 6 | 10 | 400 | 0.25 | 15.24 | 29.78 | 1.42 | 0.16 | 66.21 | 1.55 | 0.88 | 99.10 | 99.76 |
| 672 | 250 | 6 | 40 | 400 | 1 | 3.81 | 22.17 | 0.83 | 0.18 | 48.52 | 1.34 | 26.95 | 72.51 | 99.64 |
| 696 | 250 | 6 | 40 | 400 | 1 | 3.81 | 22.51 | 0.97 | 0.18 | 49.57 | 1.36 | 25.41 | 74.08 | 99.64 |
| 720 | 250 | 6 | 40 | 400 | 1 | 3.81 | 22.48 | 0.94 | 0.19 | 49.39 | 1.37 | 25.64 | 73.84 | 99.64 |
| 744 | 250 | 6 | 20 | 2000 | 0.5 | 38.09 | 30.90 | 0.48 | 0.21 | 67.43 | 0.60 | 0.39 | 99.60 | 99.70 |
| 768 | 250 | 6 | 20 | 2000 | 0.5 | 38.09 | 30.86 | 0.54 | 0.37 | 67.43 | 0.50 | 0.29 | 99.70 | 99.45 |
| 792 | 250 | 6 | 20 | 2000 | 0.5 | 38.09 | 30.93 | 0.51 | 0.36 | 67.46 | 0.55 | 0.19 | 99.80 | 99.48 |
| 816 | 250 | 6 | 20 | 400 | 0.5 | 7.62 | 28.92 | 1.87 | 0.35 | 64.92 | 1.80 | 2.14 | 97.80 | 99.48 |
| 840 | 250 | 6 | 20 | 400 | 0.5 | 7.62 | 28.83 | 1.93 | 0.28 | 64.92 | 1.80 | 2.24 | 97.70 | 99.58 |
| 864 | 250 | 6 | 20 | 400 | 0.5 | 7.62 | 28.86 | 1.93 | 0.30 | 64.98 | 1.78 | 2.14 | 97.80 | 99.55 |
| 888 | 250 | 6 | 20 | 400 | 0.5 | 7.62 | 28.98 | 1.87 | 0.35 | 64.98 | 1.87 | 1.95 | 98.00 | 99.48 |
| 912 | 250 | 6 | 20 | 400 | 0.5 | 7.62 | 28.98 | 1.75 | 0.34 | 64.71 | 1.88 | 2.34 | 97.60 | 99.49 |
| 936 | 250 | 6 | 20 | 400 | 0.5 | 7.62 | 28.86 | 1.69 | 0.21 | 64.38 | 1.94 | 2.92 | 97.00 | 99.68 |
| 960 | 250 | 6 | 20 | 400 | 0.5 | 7.62 | 29.08 | 1.63 | 0.18 | 64.78 | 1.90 | 2.44 | 97.50 | 99.72 |
| 984 | 250 | 6 | 20 | 400 | 0.5 | 7.62 | 28.83 | 1.69 | 0.20 | 64.38 | 1.88 | 3.02 | 96.90 | 99.69 |
| 1008 | 250 | 6 | 20 | 400 | 0.5 | 7.62 | 28.92 | 1.75 | 0.25 | 64.64 | 1.90 | 2.53 | 97.40 | 99.62 |

Example 9

Acetic acid cyclohexyl ester having a purity of 99.6% was used as the hydrogenation feed stock.

40 g copper-chromium based ester hydrogenation catalyst (commercially available from Taiyuan Xinjida Chemical Ltd., with a trade name of C1-XH-1, with a CuO content of 55%, as tablet having a diameter of 5 mm, crashed into particles of 10 to 20 mesh) was loaded into a Φ20×2.5×800 mm jacketed stainless steel tube reactor at the middle part thereof, below and above which there were packed a predetermined amount of quartz sand, supplied with hydrogen gas (500 mL/min) to conduct a reduction under the conditions of 280 degrees Celsius and 6 MPa for 24 h, and then the system was lowered to a predetermined temperature and pressure of the reaction. Acetic acid cyclohexyl ester via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 8. The results revealed that, when a copper-chromium based ester hydrogenation catalyst was used, the single-pass conversion of the acetic acid cyclohexyl ester hydrogenation reaction was up to 98% or more, the single-pass selectivity to cyclohexanol was greater than 99.9%, and after a run time of 500 h, the single-pass conversion and selectivity did not drop.

TABLE 8

Experimental data observed with the acetic acid cyclohexyl ester hydrogenation catalyzed by the copper-chromium based ester catalyst

| | reaction conditions | | | | | | reaction results | | | | | | single-pass conversion | |
|---|---|---|---|---|---|---|---|---|---|---|---|---|---|---|
| run time h | temperature degrees Celsius | pressure MPa | ester feed g/h | hydrogen gas feed mL/min | space velocity h−1 | hydrogen/ester ratio | ethanol m % | acetic acid ethyl ester m % | high boiling materials m % | cyclohexanol m % | ethyl cyclohexyl ether m % | acetic acid cyclohexyl ester m % | of cyclohexyl ester % | single-pass selectivity to cyclohexanol % |
| 24 | 230 | 6 | 20 | 400 | 0.5 | 7.62 | 26.37 | 0.97 | 0.47 | 57.52 | 1.49 | 13.19 | 86.50 | 99.22 |
| 48 | 230 | 6 | 20 | 400 | 0.5 | 7.62 | 26.24 | 1.03 | 0.69 | 57.32 | 1.33 | 13.38 | 86.30 | 98.83 |
| 72 | 250 | 6 | 20 | 400 | 0.5 | 7.62 | 27.91 | 1.33 | 0.77 | 61.42 | 1.45 | 7.12 | 92.70 | 98.79 |
| 96 | 250 | 6 | 20 | 400 | 0.5 | 7.62 | 28.15 | 1.45 | 0.46 | 62.29 | 1.69 | 5.95 | 93.90 | 99.28 |
| 120 | 320 | 20 | 20 | 400 | 0.5 | 7.62 | 28.43 | 1.39 | 0.63 | 62.83 | 1.46 | 5.26 | 94.60 | 99.04 |
| 144 | 320 | 20 | 20 | 400 | 0.5 | 7.62 | 28.64 | 2.05 | 0.78 | 64.72 | 1.37 | 2.44 | 97.50 | 98.83 |
| 168 | 260 | 6 | 20 | 400 | 0.5 | 7.62 | 28.20 | 2.29 | 0.50 | 64.73 | 1.25 | 3.02 | 96.90 | 99.25 |
| 192 | 260 | 6 | 20 | 400 | 0.5 | 7.62 | 28.37 | 2.26 | 0.62 | 64.83 | 1.33 | 2.58 | 97.35 | 99.07 |
| 216 | 260 | 10 | 20 | 400 | 0.5 | 7.62 | 29.15 | 1.18 | 0.19 | 64.81 | 1.02 | 3.64 | 96.26 | 99.71 |
| 240 | 260 | 10 | 20 | 400 | 0.5 | 7.62 | 28.79 | 1.69 | 0.10 | 65.33 | 0.98 | 3.12 | 96.80 | 99.86 |
| 264 | 260 | 6 | 10 | 400 | 0.25 | 15.24 | 28.98 | 1.99 | 0.70 | 65.12 | 1.65 | 1.56 | 98.40 | 98.96 |
| 288 | 260 | 6 | 10 | 400 | 0.25 | 15.24 | 29.04 | 1.93 | 0.62 | 64.98 | 1.87 | 1.56 | 98.40 | 99.08 |
| 312 | 260 | 4 | 20 | 400 | 0.5 | 7.62 | 28.58 | 1.87 | 0.66 | 63.77 | 1.90 | 3.22 | 96.70 | 99.01 |
| 336 | 260 | 4 | 20 | 400 | 0.5 | 7.62 | 28.52 | 1.81 | 0.33 | 63.64 | 2.09 | 3.61 | 96.30 | 99.50 |
| 360 | 260 | 6 | 20 | 800 | 0.5 | 15.24 | 28.61 | 1.27 | 0.23 | 64.04 | 0.78 | 5.07 | 94.80 | 99.65 |
| 384 | 260 | 6 | 20 | 800 | 0.5 | 15.24 | 28.58 | 1.45 | 0.18 | 64.52 | 0.69 | 4.58 | 95.30 | 99.72 |
| 408 | 260 | 6 | 20 | 600 | 0.5 | 11.43 | 28.33 | 1.42 | 0.23 | 63.88 | 0.68 | 5.46 | 94.40 | 99.65 |
| 432 | 260 | 6 | 20 | 600 | 0.5 | 11.43 | 28.37 | 1.44 | 0.24 | 63.97 | 0.70 | 5.28 | 94.58 | 99.63 |
| 456 | 260 | 6 | 20 | 600 | 0.5 | 11.43 | 28.28 | 1.48 | 0.26 | 63.88 | 0.66 | 5.44 | 94.42 | 99.60 |
| 480 | 260 | 6 | 20 | 600 | 0.5 | 11.43 | 28.26 | 1.42 | 0.26 | 63.71 | 0.67 | 5.67 | 94.18 | 99.60 |
| 504 | 260 | 6 | 20 | 600 | 0.5 | 11.43 | 28.24 | 1.47 | 0.24 | 63.80 | 0.65 | 5.60 | 94.25 | 99.63 |

Example 10

This example illustrates the experiment results observed with the separation by rectification of an acetic acid cyclohexyl ester hydrogenation product.

4000 g of each reaction product of Examples 8 to 9 was collected, to conduct a separation by rectification experiment. The rectification was performed on a glass tower of 2 m height, and the tower column was loaded with Φ3 mm stainless steel Dixon high-efficient rectification packing, the bottom was a 5 L glass flask, heated by an electric jacket, with a voltage regulator to adjust the heating at the bottom. The tower reflux was controlled by a reflux ratio regulator. The separation by rectification results were listed in Table 9.

The Twelfth Embodiment

Example 1

This example illustrates a process for producing cyclohexene by a benzene selective hydrogenation.

Benzene and hydrogen gas at a ratio by molar of 1:3 were supplied into a hydrogenation reactor loaded with ruthenium based catalyst particles, under the conditions wherein the reaction temperature was 135 degrees Celsius, the reaction pressure was 4.5 MPa, the residence time was 15 min, to conduct a benzene hydrogenation reaction, after separating hydrogen gas from the reaction product, the liquid product was collected. The reaction ran continuously for 1000 h.

TABLE 9

Experimental data observed with the acetic acid cyclohexyl ester hydrogenation product separation by rectification

| | reaction conditions | | | analytic results | | | | | |
|---|---|---|---|---|---|---|---|---|---|
| | temperature | | fraction | | acetic acid | | | | acetic acid |
| fraction No. | degrees Celsius | degrees Celsius | weight g | ethanol m % | ethyl ester m % | cyclohexane | cyclohexanol m % | ethyl cyclohexyl ether | cyclohexyl ester |
| 0 (distillation feed stock) | | | 4000 | 29.30 | 0.66 | | 63.30 | 2.50 | 2.98 |
| 1 (ethanol product) | 79 | 81 | 1139.9 | 95.93 | | | | | |
| 2 (transitional fraction) | 81 | 155 | 50.5 | 76.24 | | | 18.81 | 0.99 | |
| 3 (alcohol ketone product) | 155 | 162 | 2549.6 | | | | 96.15 | 3.85 | |
| 4 (bottom residue) | >162 | | 200.2 | | 13.18 | | 27.07 | 0.2 | 59.55 |
| loss | | | 59.8 | | | | | | |
| total | | | 4000 | | | | | | |

Upon completion of the experiment, the collected liquid product was subject to vapor phase chromatography analysis, showing a composition of: benzene 53.3%, cyclohexene 35.4%, cyclohexane 11.3%.

Example 2

100 mL of a macroporous hydrogenous strong-acid ion exchange resin (synthesized at lab according to a classical literature method, wherein a styrene solution containing 15% divinylbenzene was subject to a suspension copolymerization and produced into base spherical particles, and then sulfonated by concentrated sulfuric acid, with a measured exchange capacity of 5.2 mmol $H^{+/}$g on dry basis) was loaded into a Φ32×4×1000 mm jacketed stainless steel tube reactor at the middle part thereof, below and above which there were packed a predetermined amount of quartz sand. Acetic acid and a cyclohexene feed stock (with a composition of: cyclohexene 75 m %, cyclohexane 25 m %; obtained by an extractive rectification of the reaction product of Example 1, with N,N-dimethyl acetamide as the extractant) were pumped via a dosing pump at a predetermined flow rate respectively into the reactor to conduct a reaction, to the outer jacket of the reaction tube there was supplied hot water to control the reaction temperature, with a counterbalance valve at the reactor outlet to control the reactor pressure. The reactor outlet product was sampled by an on-line sampling valve for on-line chromatography analysis, on the basis of the product composition, there was calculated the single-pass conversion of cyclohexene and the single-pass selectivity to acetic acid cyclohexyl ester. The reaction conditions and results were listed in Table 1.

As can be seen from Table 1, when a strong-acid ion exchange resin catalyst was used for the reaction of cyclohexene and acetic acid, there were obtained a single-pass conversion of cyclohexene of greater than 90%, a single-pass selectivity to the ester product of greater than 99%, and after a run time of 600 hours, the catalyst activity and the single-pass selectivity remained steady.

Example 3

The experiment apparatus and the process procedure were the same as Example 2, with the exception that the catalyst was a phosphorus modified H-beta molecular sieve catalyst (obtained by a method wherein a H-beta molecular sieve having a silica alumina ratio of 50 was modified by 85% phosphoric acid, and then kneaded with alumina and then extruded, dried at a temperature of 120 degrees Celsius, calcinated at a temperature of 500 degrees Celsius, with a phosphorus content of 2%); and the cyclohexene feed stock had a composition of benzene 60 m %, cyclohexene 40 m % (obtained by an extractive rectification of the reaction product of Example 1, with N,N-dimethyl acetamide as the extractant). The reaction conditions and results were listed in Table 2. As can be seen from Table 2, the reaction of cyclohexene and acetic acid resulted in a single-pass conversion of greater than 80%, and a single-pass selectivity to the ester product of greater than 99%, and after a run time of 480 hours, the catalyst activity and the single-pass selectivity remained steady.

Examples 4 to 5 illustrate a process for producing acetic acid cyclohexyl ester by a reactive rectification.

Examples 4 to 5 were all performed on a reactive rectification model experiment apparatus with these specifications: the main part of the model apparatus was a stainless steel tower having a diameter (inner diameter) of 50 mm and a height of 3 m, the lower part of which communicated with a bottom having a volume of 5 L, inside the bottom there was installed a 10 KW electrical heating rod, which was used to via an intelligent controller through a silicon controlled rectifier (SCR) control the heating at the bottom. The tower top communicated with a condenser having a heat exchange area of 0.5 $m^2$, vapor from the tower top was condensed by this condenser into liquid and then introduced into a reflux tank having a volume of 2 L. Liquid in the reflux tank was partially refluxed by a reflux pump back to the reaction tower, partially withdrawn as lighter components. The operation parameters of the tower were controlled by and displayed on an intelligent type automatic control instrument. The tower reflux rate was controlled by a reflux control valve, the top withdrawal was controlled by a level controller at the reflux tank. The bottom withdrawal was controlled by a bottom blow-off valve which was controlled by a bottom level controller. Acetic acid and a cyclohexene feed stock were respectively supplied into a 30 L storage tank, and through a dosing pump were pumped respectively into the corresponding preheater and preheated to a predetermined temperature and then introduced into the reaction tower, the feeding rate was controlled by the dosing pump and accurately metered by an electronic balance.

Example 4

A high temperature resistant sulfonic acid type ion exchange resin (with a trade name of Amberlyst 45, produced by the Rhom&Hass company) was by a multi-stage high speed grinder ground into powder having a particle size of less than 200 mesh (0.074 mm), there was added a porogenic agent, a lubricant, an antioxidant and a binder, mixed homogeneously with a high-speed mixer, and then with an internal mixer at 180 degrees Celsius mixed for 10 min, to completely plasticize the mass, and then injected into a mould and formed into a raschig ring type resin catalyst packing having a diameter of 5 mm, a height of 5 mm and a wall thickness of 1 mm. 1950 mL of the packing was loaded into the middle part of a model reaction tower (with a height of 1 m, corresponding to a theoretical plate number of 8), above and below which there was each loaded 1950 mL of a glass spring packing having a diameter of 3 mm and a length of 6 mm (with a loading height of 1 m, corresponding to a theoretical plate number of 10). A cyclohexene feed stock and acetic acid via a dosing pump were pumped respectively into a preheater and preheated and then introduced into the reaction tower, adjusting the heating at the bottom and the reflux rate at the tower top to continuously conduct the reaction, the steady-state reaction conditions and reaction results were listed in Table 3.

Example 5

A Φ3 to 4 spherical $H_{0.5}Cs_{2.5}PW_{12}O_{40}/SiO_2$ catalyst (obtained by: $H_{0.5}Cs_{2.5}PW_{12}O_{40}$ powder and wide hole silica gel powder having a particle size of less than 200 mesh were on a mixer thoroughly mixed, and then, ball-formed on a coating machine by using silica sol as the binder, and then dried, calcinated) was sandwiched between titanium wire mesh corrugated plates, and produced into a cylindrical structured packing having a diameter of 50 mm and a height of 50 mm. The packing type catalyst L was loaded into the middle part of a model reaction tower (with a height of 1 m, corresponding to a theoretical plate number of 12), above and below which there was each loaded 1950 mL of a glass spring packing having a diameter of 4 mm and a height of 4 mm (with a loading height of 1 m, corresponding to a theoretical plate number of 15). A cyclohexene feed stock and acetic acid via a dosing pump were pumped respectively into a preheater and preheated and then introduced into the reaction tower, adjusting the heating at the bottom and the reflux rate at the tower top to continuously conduct the reaction, the steady-state reaction conditions and reaction results were listed in Table 5.

Examples 6 to 7 illustrate a process for hydrogenating acetic acid cyclohexyl ester.

Example 6

The hydrogenation feed stock was acetic acid cyclohexyl ester having a purity of 99.6%.

40 g copper-zinc-aluminium based ester hydrogenation catalyst (synthesized at lab, with a composition of CuO 40.5%, ZnO 29.6%, $Al_2O_3$ 30.4%, by a method wherein to a copper, zinc, chromium nitrate solution, there was added a NaOH solution till pH=9.0, and then centrifugal separated, washed, dried, tableted, calcinated) was loaded into a Φ20×2.5×800 mm jacketed stainless steel tube reactor at the middle part thereof, below and above which there were packed a predetermined amount of quartz sand, supplied with hydrogen gas (500 mL/min) to conduct a reduction under the conditions of 280 degrees Celsius and 6 MPa for 24 h, and then lowered to a predetermined temperature and pressure of the hydrogenation reaction. Acetic acid cyclohexyl ester via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 5. Table 5 revealed that, when a copper-zinc-aluminium based catalyst was used, the single-pass conversion of the acetic acid cyclohexyl ester hydrogenation reaction was up to 99.0% or more, the single-pass selectivity to cyclohexanol was greater than 99.9%, and after a run time of 1000 h, the single-pass conversion and the single-pass selectivity did not drop.

Example 7

The hydrogenation feed stock was acetic acid cyclohexyl ester having a purity of 99.6%. 40 g copper-chromium based ester hydrogenation catalyst (commercially available from Taiyuan Xinjida Chemical Ltd., with a trade name of C1-XH-1, with a CuO content of 55%, as tablet having a diameter of 5 mm, crashed into particles of 10 to 20 mesh) was loaded into a Φ20×2.5×800 mm jacketed stainless steel tube reactor at the middle part thereof, below and above which there were packed a predetermined amount of quartz sand, supplied with hydrogen gas (500 mL/min) to conduct a reduction under the conditions of 280 degrees Celsius and 6 MPa for 24 h, and then the system was lowered to a predetermined temperature and pressure of the reaction. Acetic acid cyclohexyl ester via a dosing pump was pumped into the reactor, hydrogen gas was via a mass flow controller introduced into the reaction system to conduct a hydrogenation reaction, to the outer jacket of the reaction tube there was supplied heat conducting oil to control the reaction temperature, with a counterbalance valve at the reactor outlet to control the reactor pressure. The reaction product was sampled via an on-line sampling valve at the back of the reactor for on-line chromatography analysis. The reaction conditions and results were listed in Table 6. Table 6 revealed that, when a copper-zinc-aluminium based catalyst was used, the single-pass conversion of the acetic acid cyclohexyl ester hydrogenation reaction was up to 98.0% or more, the single-pass selectivity to cyclohexanol was greater than 99.9%, and after a run time of 500 h, the single-pass conversion and selectivity did not drop.

TABLE 1

Experimental data observed with the esterification of acetic acid and cyclohexane/cyclohexene catalyzed by the strong-acid ion exchange resin

| run time h | reaction conditions: temperature degrees Celsius | pressure MPa | acetic acid feeding rate mL/h | cyclohexane/cyclohexene feeding rate mL/h | single-pass conversion of cyclohexene % | single-pass selectivity to ester % |
|---|---|---|---|---|---|---|
| 24 | 70 | the normal pressure | 120 | 140 | 83.2 | 99.3 |
| 48 | 70 | the normal pressure | 120 | 140 | 83.5 | 99.2 |
| 72 | 70 | 1 | 120 | 140 | 83.5 | 99.0 |
| 96 | 80 | 1 | 120 | 140 | 88.1 | 99.3 |
| 120 | 80 | 1 | 120 | 140 | 87.2 | 99.2 |
| 144 | 80 | 2 | 120 | 140 | 88.3 | 99.4 |
| 168 | 90 | 2 | 120 | 140 | 91.3 | 99.4 |
| 192 | 90 | 3 | 120 | 140 | 91.7 | 99.3 |
| 216 | 90 | 5 | 120 | 140 | 91.4 | 99.1 |
| 240 | 90 | 5 | 180 | 140 | 92.9 | 99.3 |
| 264 | 90 | 5 | 180 | 140 | 92.7 | 99.3 |
| 288 | 100 | 10 | 180 | 140 | 92.0 | 99.4 |
| 312 | 100 | 10 | 360 | 280 | 82.9 | 99.5 |
| 336 | 100 | 15 | 360 | 280 | 82.7 | 99.5 |
| 360 | 150 | 20 | 360 | 280 | 77.9 | 98.5 |
| 384 | 150 | 20 | 360 | 280 | 78.0 | 98.7 |
| 408 | 90 | 10 | 180 | 140 | 92.5 | 99.5 |
| 432 | 90 | 0.5 | 150 | 140 | 90.6 | 99.4 |

TABLE 1-continued

Experimental data observed with the esterification of acetic acid and cyclohexane/cyclohexene catalyzed by the strong-acid ion exchange resin

| run time h | reaction conditions: temperature degrees Celsius | pressure MPa | acetic acid feeding rate mL/h | cyclohexane/cyclohexene feeding rate mL/h | single-pass conversion of cyclohexene % | single-pass selectivity to ester % |
|---|---|---|---|---|---|---|
| 456 | 90 | 0.5 | 150 | 140 | 90.1 | 99.3 |
| 480 | 90 | 0.5 | 150 | 140 | 90.3 | 99.2 |
| 504 | 90 | 0.5 | 150 | 140 | 90.1 | 99.3 |
| 528 | 90 | 0.5 | 150 | 140 | 90.3 | 99.5 |
| 552 | 90 | 0.5 | 150 | 140 | 89.9 | 99.5 |
| 576 | 90 | 0.5 | 150 | 140 | 89.8 | 99.3 |
| 600 | 90 | 0.5 | 150 | 140 | 90.1 | 99.4 |

TABLE 2

Experimental data observed with the esterification reaction of acetic acid and cyclohexene/benzene catalyzed by the H-beta molecular sieve catalyst

| run time h | reaction conditions: temperature degrees Celsius | pressure MPa | acetic acid feeding rate mL/h | cyclohexene/benzene feeding rate mL/h | single-pass conversion of cyclohexene % | single-pass selectivity to ester % |
|---|---|---|---|---|---|---|
| 24 | 70 | the normal pressure | 90 | 120 | 72.3 | 99.5 |
| 48 | 70 | the normal pressure | 90 | 120 | 72.2 | 99.3 |
| 72 | 70 | the normal pressure | 90 | 120 | 72.5 | 99.1 |
| 96 | 70 | the normal pressure | 90 | 120 | 72.4 | 99.4 |
| 120 | 70 | the normal pressure | 90 | 120 | 72.3 | 99.3 |
| 144 | 80 | 2 | 90 | 120 | 76.2 | 99.2 |
| 168 | 80 | 2 | 90 | 120 | 77.4 | 99.1 |
| 192 | 80 | 2 | 90 | 120 | 77.6 | 99.1 |
| 216 | 80 | 2 | 90 | 120 | 78.0 | 99.2 |
| 240 | 80 | 2 | 90 | 120 | 78.1 | 99.2 |
| 264 | 90 | 5 | 90 | 120 | 81.2 | 99.3 |
| 288 | 90 | 5 | 90 | 120 | 81.6 | 99.2 |
| 312 | 120 | 5 | 90 | 120 | 82.4 | 98.9 |
| 336 | 120 | 10 | 90 | 120 | 82.2 | 99.0 |
| 360 | 120 | 10 | 90 | 120 | 82.6 | 99.1 |
| 384 | 150 | 10 | 90 | 120 | 85.2 | 96.8 |
| 408 | 150 | 10 | 90 | 120 | 85.6 | 96.7 |
| 432 | 150 | 10 | 90 | 120 | 85.9 | 96.9 |
| 456 | 150 | 10 | 90 | 120 | 86.3 | 96.8 |
| 480 | 150 | 10 | 90 | 120 | 86.6 | 96.5 |

TABLE 3

Experimental data observed with the reactive rectification by the high temperature resistant sulfonic acid type ion exchange resin catalyst

| operation conditions | |
|---|---|
| operation pressure | 0.3 MPa |
| top temperature | 118 degrees Celsius |
| catalyst section temperature | 140 to 146 degrees Celsius |
| bottom temperature | 200 degrees Celsius |
| reflux ratio | 5 |

TABLE 3-continued

Experimental data observed with the reactive rectification by the high temperature resistant sulfonic acid type ion exchange resin catalyst

| mass | cyclohexene feed | acetic acid feed | top with-drawal | bottom with-drawal |
|---|---|---|---|---|
| position | catalyst bed at lower part | catalyst bed at upper part | tower top at reflux pump outlet | tower bottom at discharge outlet |

TABLE 3-continued

Experimental data observed with the reactive rectification by the high temperature resistant sulfonic acid type ion exchange resin catalyst

| | | | | |
|---|---|---|---|---|
| flow rate g/h | 1027 | 601 | 921 | 707 |
| temperature degrees Celsius | | | 40 | 225 |
| composition (ratio by mass) | | | | |
| cyclohexene | 40.0% | | 0.55% | |
| benzene | 19.0% | | 21.17% | |
| cyclohexane | 41.0% | | 45.71% | |
| acetic acid | | | 32.57% | 0.84% |
| acetic acid cyclohexyl ester | | | | 98.6% |
| polymers | | | | 0.56% |

Calculation from the experimental data revealed a single-pass conversion of cyclohexene of 98.8%, a single-pass selectivity to acetic acid cyclohexyl ester of 98.0%.

TABLE 4

Experimental data observed with the reactive rectification by the $H_{0.5}Cs_{2.5}PW_{12}O_{40}/SiO_2$ catalyst

| operation conditions | |
|---|---|
| operation pressure | 0.3 MPa |
| top temperature | 102 degrees Celsius |

TABLE 4-continued

Experimental data observed with the reactive rectification by the $H_{0.5}Cs_{2.5}PW_{12}O_{40}/SiO_2$ catalyst

| | |
|---|---|
| reaction section temperature | 145 to 180 degrees Celsius |
| bottom temperature | 209 degrees Celsius |
| reflux ratio | 5 |

| mass | cyclohexene feed | acetic acid feed | top with-drawal | bottom with-drawal |
|---|---|---|---|---|
| position | catalyst bed at lower part | catalyst bed at upper part | tower top at reflux pump outlet | tower bottom at discharge outlet |
| flow rate g/h | 1540 | 601 | 1084 | 1056 |
| temperature degrees Celsius | | | 40 | 209 |
| composition (ratio by mass) | | | | |
| cyclohexene | 40.0% | | 0.36% | |
| benzene | 19.0% | | 27.03% | |
| cyclohexane | 41.0% | | 58.21% | |
| acetic acid | | 100% | 14.39% | |
| acetic acid cyclohexyl ester | | | | 99.62% |
| polymers | | | | 0.38% |

Calculation from the experimental data revealed a single-pass conversion of cyclohexene of 99.35%, a single-pass selectivity to acetic acid cyclohexyl ester of 99.6%.

TABLE 5

Experimental data observed with the acetic acid cyclohexyl ester hydrogenation by the copper-zinc-aluminium based ester hydrogenation catalyst

| | reaction conditions | | | | | | reaction results | | | | | | |
|---|---|---|---|---|---|---|---|---|---|---|---|---|---|
| run time h | temperature degrees Celsius | pressure MPa | ester feed g/h | hydrogen gas feed mL/min | space velocity $h^{-1}$ | hydrogen/ester ratio by molar | ethanol m % | cyclohexanol m % | acetic acid cyclohexyl ester m % | lighter impurities m % | heavier impurities m % | single-pass conversion of cyclohexyl ester % | single-pass selectivity to cyclohexanol % |
| 24 | 200 | 6 | 20 | 400 | 0.5 | 7.62 | 23.23 | 51.12 | 22.47 | 1.29 | 1.89 | 76.79 | 99.81 |
| 48 | 200 | 6 | 20 | 400 | 0.5 | 7.62 | 23.12 | 50.95 | 22.45 | 1.36 | 2.12 | 76.93 | 99.79 |
| 72 | 200 | 6 | 20 | 400 | 0.5 | 7.62 | 23.25 | 51.15 | 22.26 | 1.36 | 1.98 | 77.06 | 99.68 |
| 96 | 220 | 6 | 20 | 400 | 0.5 | 7.62 | 25.62 | 57.26 | 12.27 | 2.13 | 2.72 | 87.81 | 99.65 |
| 120 | 220 | 6 | 20 | 400 | 0.5 | 7.62 | 25.88 | 58.06 | 11.13 | 2.22 | 2.71 | 89.07 | 99.75 |
| 144 | 220 | 6 | 20 | 400 | 0.5 | 7.62 | 26.2 | 58.71 | 10.28 | 2.13 | 2.68 | 89.82 | 99.76 |
| 168 | 235 | 6 | 20 | 400 | 0.5 | 7.62 | 27.51 | 62.1 | 4.99 | 2.54 | 2.86 | 95.50 | 99.73 |
| 192 | 235 | 6 | 20 | 400 | 0.5 | 7.62 | 27.61 | 63.1 | 3.77 | 2.62 | 2.9 | 97.11 | 99.40 |
| 216 | 235 | 6 | 20 | 400 | 0.5 | 7.62 | 27.5 | 62.5 | 4.28 | 2.6 | 3.12 | 96.46 | 99.55 |
| 240 | 250 | 6 | 20 | 400 | 0.5 | 7.62 | 28.89 | 65.05 | 1.68 | 2.07 | 2.31 | 98.31 | 99.78 |
| 264 | 250 | 6 | 20 | 400 | 0.5 | 7.62 | 28.9 | 65.22 | 1.82 | 2.05 | 2.01 | 98.18 | 99.71 |
| 288 | 250 | 6 | 20 | 400 | 0.5 | 7.62 | 29.12 | 65.05 | 1.61 | 2.05 | 2.17 | 98.12 | 99.73 |
| 312 | 265 | 6 | 20 | 400 | 0.5 | 7.62 | 29.2 | 65.11 | 1.27 | 2.02 | 2.4 | 98.41 | 99.73 |
| 336 | 265 | 6 | 20 | 400 | 0.5 | 7.62 | 29.12 | 64.82 | 1.02 | 2.92 | 2.12 | 99.21 | 97.99 |
| 360 | 265 | 6 | 20 | 400 | 0.5 | 7.62 | 29.21 | 64.9 | 1.55 | 2.04 | 2.3 | 98.04 | 99.60 |
| 384 | 300 | 6 | 20 | 400 | 0.5 | 7.62 | 28.91 | 64.21 | 3.12 | 1.87 | 1.89 | 96.33 | 99.59 |
| 408 | 300 | 6 | 20 | 400 | 0.5 | 7.62 | 28.8 | 64.02 | 3.23 | 1.93 | 2.02 | 96.30 | 99.56 |
| 432 | 300 | 6 | 20 | 400 | 0.5 | 7.62 | 28.6 | 63.95 | 3.32 | 2.01 | 2.12 | 96.44 | 99.54 |
| 456 | 250 | 3 | 20 | 400 | 0.5 | 7.62 | 24.86 | 55.85 | 9.75 | 4.12 | 5.42 | 92.10 | 98.70 |
| 480 | 250 | 3 | 20 | 400 | 0.5 | 7.62 | 24.92 | 55.46 | 11.05 | 2.96 | 5.61 | 89.89 | 98.62 |
| 504 | 250 | 3 | 20 | 400 | 0.5 | 7.62 | 24.84 | 55.74 | 10.51 | 3.41 | 5.5 | 90.85 | 99.74 |
| 528 | 250 | 15 | 20 | 400 | 0.5 | 7.62 | 30.2 | 65.63 | 1.42 | 0.83 | 1.92 | 96.69 | 99.73 |
| 552 | 250 | 15 | 20 | 400 | 0.5 | 7.62 | 30.27 | 65.86 | 1.04 | 0.98 | 1.85 | 97.18 | 99.69 |
| 576 | 250 | 15 | 20 | 400 | 0.5 | 7.62 | 30.25 | 65.86 | 1.13 | 0.86 | 1.9 | 97.04 | 99.71 |
| 600 | 250 | 6 | 10 | 400 | 0.25 | 15.24 | 29.78 | 66.15 | 1.03 | 1.52 | 1.52 | 98.09 | 99.70 |
| 624 | 250 | 6 | 10 | 400 | 0.25 | 15.24 | 29.85 | 66.25 | 0.82 | 1.51 | 1.57 | 98.28 | 99.71 |
| 648 | 250 | 6 | 10 | 400 | 0.25 | 15.24 | 29.81 | 66.15 | 0.95 | 1.6 | 1.49 | 98.19 | 99.73 |
| 672 | 250 | 6 | 40 | 400 | 1 | 3.81 | 22.21 | 48.49 | 26.93 | 1.02 | 1.35 | 72.02 | 99.58 |

TABLE 5-continued

Experimental data observed with the acetic acid cyclohexyl ester hydrogenation by the copper-zinc-aluminium based ester hydrogenation catalyst

| reaction conditions | | | | | | | reaction results | | | | | | |
|---|---|---|---|---|---|---|---|---|---|---|---|---|---|
| run time h | temperature degrees Celsius | pressure MPa | ester feed g/h | hydrogen gas feed mL/min | space velocity $h^{-1}$ | hydrogen/ester ratio by molar | ethanol m % | cyclohexanol m % | acetic acid cyclohexyl ester m % | lighter impurities m % | heavier impurities m % | single-pass conversion of cyclohexyl ester % | single-pass selectivity to cyclohexanol % |
| 696 | 250 | 6 | 40 | 400 | 1 | 3.81 | 22.47 | 49.52 | 25.42 | 1.17 | 1.42 | 73.81 | 99.57 |
| 720 | 250 | 6 | 40 | 400 | 1 | 3.81 | 22.51 | 49.42 | 25.53 | 1.14 | 1.4 | 73.59 | 99.57 |
| 744 | 250 | 6 | 20 | 2000 | 0.5 | 38.09 | 30.98 | 67.39 | 0.32 | 0.69 | 0.62 | 97.50 | 99.65 |
| 768 | 250 | 6 | 20 | 2000 | 0.5 | 38.09 | 30.79 | 67.38 | 0.34 | 0.97 | 0.52 | 97.84 | 99.26 |
| 792 | 250 | 6 | 20 | 2000 | 0.5 | 38.09 | 30.89 | 67.32 | 0.31 | 0.94 | 0.54 | 97.73 | 99.32 |
| 816 | 250 | 6 | 20 | 400 | 0.5 | 7.62 | 28.88 | 64.82 | 2.23 | 2.25 | 1.82 | 97.74 | 99.34 |
| 840 | 250 | 6 | 20 | 400 | 0.5 | 7.62 | 28.81 | 64.82 | 2.36 | 2.25 | 1.76 | 97.66 | 99.47 |
| 864 | 250 | 6 | 20 | 400 | 0.5 | 7.62 | 28.91 | 65.01 | 2.13 | 2.19 | 1.76 | 97.84 | 99.47 |
| 888 | 250 | 6 | 20 | 400 | 0.5 | 7.62 | 28.96 | 64.95 | 2.01 | 2.27 | 1.81 | 97.94 | 99.34 |
| 912 | 250 | 6 | 20 | 400 | 0.5 | 7.62 | 28.91 | 64.67 | 2.4 | 2.11 | 1.91 | 97.40 | 99.36 |
| 936 | 250 | 6 | 20 | 400 | 0.5 | 7.62 | 28.85 | 64.35 | 2.92 | 1.93 | 1.95 | 96.69 | 99.59 |
| 960 | 250 | 6 | 20 | 400 | 0.5 | 7.62 | 29.12 | 64.76 | 2.36 | 1.84 | 1.92 | 97.09 | 99.65 |
| 984 | 250 | 6 | 20 | 400 | 0.5 | 7.62 | 28.77 | 64.21 | 3.07 | 1.97 | 1.98 | 96.59 | 99.54 |
| 1008 | 250 | 6 | 20 | 400 | 0.5 | 7.62 | 28.91 | 64.61 | 2.58 | 2.01 | 1.89 | 97.12 | 99.52 |

TABLE 6

Experimental data observed with the acetic acid cyclohexyl ester hydrogenation by the copper-chromium based ester hydrogenation catalyst

| reaction conditions | | | | | | | reaction results | | | | | | |
|---|---|---|---|---|---|---|---|---|---|---|---|---|---|
| run time h | temperature degrees Celsius | pressure MPa | ester feed g/h | hydrogen gas feed mL/min | space velocity $h^{-1}$ | hydrogen/ester ratio by molar | ethanol m % | cyclohexanol m % | acetic acid cyclohexyl ester m % | lighter impurities m % | heavier impurities m % | single-pass conversion of cyclohexyl ester % | single-pass selectivity to cyclohexanol % |
| 24 | 230 | 6 | 20 | 400 | 0.5 | 7.62 | 26.28 | 57.45 | 13.27 | 0.98 | 2.02 | 85.51 | 99.22 |
| 48 | 230 | 6 | 20 | 400 | 0.5 | 7.62 | 26.2 | 57.25 | 13.37 | 1.08 | 2.1 | 85.52 | 98.91 |
| 72 | 250 | 6 | 20 | 400 | 0.5 | 7.62 | 27.85 | 61.35 | 7.12 | 1.36 | 2.32 | 92.06 | 98.79 |
| 96 | 250 | 6 | 20 | 400 | 0.5 | 7.62 | 28.11 | 61.25 | 7.01 | 1.46 | 2.17 | 91.85 | 99.32 |
| 120 | 320 | 20 | 20 | 400 | 0.5 | 7.62 | 28.39 | 62.75 | 5.42 | 1.41 | 2.03 | 93.75 | 99.24 |
| 144 | 320 | 20 | 20 | 400 | 0.5 | 7.62 | 28.61 | 64.65 | 2.41 | 2.15 | 2.18 | 97.86 | 98.88 |
| 168 | 260 | 6 | 20 | 400 | 0.5 | 7.62 | 28.15 | 64.71 | 3.04 | 2.32 | 1.78 | 97.72 | 99.27 |
| 192 | 260 | 6 | 20 | 400 | 0.5 | 7.62 | 28.26 | 64.75 | 2.67 | 2.29 | 2.03 | 98.03 | 99.08 |
| 216 | 260 | 10 | 20 | 400 | 0.5 | 7.62 | 29.11 | 64.79 | 3.52 | 1.25 | 1.33 | 95.54 | 99.70 |
| 240 | 260 | 10 | 20 | 400 | 0.5 | 7.62 | 28.65 | 65.25 | 3.2 | 1.73 | 1.17 | 96.77 | 99.83 |
| 264 | 260 | 6 | 10 | 400 | 0.25 | 15.24 | 28.92 | 65.06 | 1.55 | 2.01 | 2.46 | 98.53 | 98.94 |
| 288 | 260 | 6 | 10 | 400 | 0.25 | 15.24 | 29.02 | 64.92 | 1.5 | 1.99 | 2.57 | 98.40 | 99.08 |
| 312 | 260 | 4 | 20 | 400 | 0.5 | 7.62 | 28.49 | 63.71 | 3.24 | 1.89 | 2.67 | 96.64 | 99.02 |
| 336 | 260 | 4 | 20 | 400 | 0.5 | 7.62 | 28.41 | 63.58 | 3.59 | 1.88 | 2.54 | 96.23 | 99.49 |
| 360 | 260 | 6 | 20 | 800 | 0.5 | 15.24 | 28.59 | 64.01 | 4.94 | 1.32 | 1.14 | 94.34 | 99.62 |
| 384 | 260 | 6 | 20 | 800 | 0.5 | 15.24 | 28.55 | 64.44 | 4.55 | 1.47 | 0.99 | 95.02 | 99.68 |
| 408 | 260 | 6 | 20 | 600 | 0.5 | 11.43 | 28.29 | 63.75 | 5.57 | 1.45 | 0.94 | 93.95 | 99.64 |
| 432 | 260 | 6 | 20 | 600 | 0.5 | 11.43 | 28.33 | 63.88 | 5.3 | 1.48 | 1.01 | 94.27 | 99.62 |
| 456 | 260 | 6 | 20 | 600 | 0.5 | 11.43 | 28.21 | 63.81 | 5.5 | 1.52 | 0.96 | 94.18 | 99.61 |
| 480 | 260 | 6 | 20 | 600 | 0.5 | 11.43 | 28.19 | 63.66 | 5.68 | 1.46 | 1.01 | 93.93 | 99.58 |
| 504 | 260 | 6 | 20 | 600 | 0.5 | 11.43 | 28.18 | 63.75 | 5.65 | 1.49 | 0.93 | 94.01 | 99.64 |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A process for producing a hydrogenation catalyst, wherein the hydrogenation catalyst comprises components (a), (b), (c), and (d), wherein the component (a) is copper oxide, the component (b) is zinc oxide, the component (c) is a metal oxide, wherein the metal is one or more selected from the group consisting of aluminum, gallium, tin, titanium, zirconium, chromium, molybdenum, tungsten, manganese, rhenium, lanthanide metals and actinide metals, and the component (d) is one or more alkaline earth metal hydroxides, wherein a weight ratio of the component (a):the component (b):the component (c):the component (d) is 5 to 60:10 to 50:5 to 60:0.2 to 2, the process comprises:

(1) producing a composite metal oxide by a coprecipitation method, wherein the composite metal oxide comprises the component (a), the component (b), and the component (c), wherein a weight ratio of the component (a):the component (b):the component (c) is 5 to 60:10 to 50:5 to 60; and (2) impregnating the component (d) into the composite metal oxide to obtain a mixture, and then filtered, dried and calcined such that the weight ratio of the component (a):the component (b):the component (c):the component (d) is 5 to 60:10 to 50:5 to 60:0.2 to 2.

2. A process for co-producing cyclohexanol and alkanol, comprising:

reacting a carboxylic acid cyclohexyl ester with hydrogen gas in the presence of a hydrogenation catalyst to produce cyclohexanol and alkanol at the same time, wherein the carboxylic acid has formula of R—COOH, and R is hydrogen or a $C_{1-6}$ straight or branched alkyl, wherein the hydrogenation catalyst comprises components (a), (b), (c), and (d), wherein the component (a) is copper oxide, the component (b) is zinc oxide, the component (c) is a metal oxide, wherein the metal is one or more selected from the group consisting of aluminum, gallium, tin, titanium, zirconium, chromium, molybdenum, tungsten, manganese, rhenium, lanthanide metals and actinide metals, and the component (d) is one or more alkaline earth metal hydroxides, and wherein a weight ratio of the component (a):the component (b):the component (c):the component (d) is 5 to 60:10 to 50:5 to 60:0.2 to 2.

3. A process for co-producing cyclohexanol and alkanol, comprising:

(1) reacting a cyclohexene source with at least one carboxylic acid in the presence of an addition esterification catalyst to conduct an addition esterification reaction, to produce a first product stream comprising carboxylic acid cyclohexyl ester in line with Manner (2) or a combination of Manner (1) and Manner (2), wherein the at least one carboxylic acid has formula of R—COOH, and R is hydrogen or a $C_{1-6}$ straight or branched alkyl; and (2) reacting the first product stream with hydrogen gas in the presence of a hydrogenation catalyst to conduct a hydrogenation reaction to produce a second product stream comprising cyclohexanol and alkanol at the same time; and Step (A) or a combination of Step (A) and Step (B), wherein (A) reacting benzene with hydrogen gas in the presence of a partial hydrogenation catalyst to conduct a partial hydrogenation reaction to obtain a cyclohexene-containing hydrogenation product as the cyclohexene source; and (B) subjecting the hydrogenation product obtained from Step (A) to a further separation to obtain a mixture of cyclohexene and benzene or a mixture of cyclohexene and cyclohexane as the cyclohexene source, wherein according to Manner (1), the addition esterification reaction is conducted in one or more addition esterification reactor, while according to Manner (2), the addition esterification reaction is conducted in one or more reactive rectification tower.

4. The process according to claim 3, wherein the addition esterification catalyst is one or more selected from the group consisting of strong-acid ion exchange resins, heteropolyacids, and zeolite molecular sieves.

5. The process according to claim 3, wherein the hydrogenation catalyst comprises components (a), (b), (c), and (d), wherein the component (a) is copper oxide, the component (b) is zinc oxide, the component (c) is a metal oxide, wherein the metal is one or more selected from the group consisting of aluminum, gallium, tin, titanium, zirconium, chromium, molybdenum, tungsten, manganese, rhenium, lanthanide metals and actinide metals, and the component (d) is one or more alkaline earth metal hydroxides, and wherein a weight ratio of the component (a):the component (b):the component (c):the component (d) is 5 to 60:10 to 50:5 to 60:0.2 to 2.

6. The process according to claim 3, wherein a molar ratio of the carboxylic acid to cyclohexene in the cyclohexene source is 0.2 to 20:1, according to Manner (1), the reactor is a tank reactor, a fixed bed reactor, a fluidized bed reactor, a boiling bed reactor or any combination thereof in parallel, the reaction temperature is from 50 to 200 degrees Celsius, the reaction pressure is from the normal pressure to 10 MPa, and when the addition esterification reaction is conducted in a continuous manner, the liquid feed space velocity is from 0.5 to 20 $h^{-1}$, when the addition esterification reaction is conducted in a batchwise manner, the reaction duration is from 0.1 to 10 h, according to Manner (2), the reactor is a reactive rectification tower, the theoretical plate number thereof is from 10 to 150, the operation pressure is from −0.0099 MPa to 5 MPa, the temperature in the addition esterification catalyst bed loading area is from 40 to 200 degrees Celsius, the reflux ratio is from 0.1:1 to full reflux, the addition esterification catalyst is disposed onto 5 to 30 plates located between a position corresponding to ⅓ of the theoretical plate number and a position corresponding to ⅔ of the theoretical plate number, and relative to the total packed volume of the addition esterification catalyst, the liquid feed space velocity is from 0.1 to 20 $h^{-1}$, wherein a carboxylic acid cyclohexyl ester stream or a mixed stream of carboxylic acid and carboxylic acid cyclohexyl ester obtained from Manner (2) as the addition esterification product is introduced into Step (2).

7. The process according to claim 3, wherein Step (2) is carried out in a tank reactor, a fixed bed reactor, a boiling bed reactor, a fluidized bed reactor or any combination thereof connected in parallel, at a reaction temperature from 200 to 300 degrees Celsius, under a reaction pressure from 4 to 10 MPa, at a molar ratio of hydrogen gas to carboxylic acid cyclohexyl ester in the first product stream from 5 to 100:1, in a continuous manner at a liquid feed space velocity from 0.2 to 2 $h^{-1}$ or in a batch manner for a reaction duration is from 1 to 5 h.

8. A process for producing cyclohexanone, comprising:

producing cyclohexanol using the process according to claim 3, and using the obtained cyclohexanol to produce cyclohexanone.

9. A process for producing caprolactam, comprising:

producing cyclohexanone using the process according to claim 8, and using the obtained cyclohexanone to produce caprolactam.

10. The process according to claim 1, wherein, in the hydrogenation catalyst, the weight ratio of the component (a):the component (b):the component (c):the component (d) is 30 to 45:20 to 35:20 to 50:0.5 to 1.5.

11. The process according to claim 4, wherein the heteropolyacid is one or more selected from the group consisting of a heteropolyacid having a keggin structure, a heteropolyacid having a Dawson structure, a heteropolyacid having an Anderson structure, a heteropolyacid having a Silverton structure, acid salts of the heteropolyacid, the heteropolyacid/carrier and acid salts of the heteropolyacid/carrier.

12. The process according to claim 3, wherein Step (1) is conducted in line with a combination wherein Manner (1) firstly and then Manner (2) is conducted.

* * * * *